US006207369B1

(12) United States Patent
Wohlstadter et al.

(10) Patent No.: US 6,207,369 B1
(45) Date of Patent: *Mar. 27, 2001

(54) MULTI-ARRAY, MULTI-SPECIFIC ELECTROCHEMILUMINESCENCE TESTING

(75) Inventors: Jacob N. Wohlstadter; James Wilbur, both of Rockville; George Sigal, Gaithersburg; Mark Martin, Rockville; Liang-Hong Guo, Laurel, all of MD (US); Alan Fischer, Cambridge, MA (US); Jon Leland, Silver Spring; Mark A. Billadeau, Mt. Airy, both of MD (US)

(73) Assignee: Meso Scale Technologies, LLC, Gaithersburg, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/715,163

(22) Filed: Sep. 17, 1996

Related U.S. Application Data

(63) Continuation-in-part of application No. 08/611,804, filed on Mar. 6, 1996, now Pat. No. 6,066,448, which is a continuation-in-part of application No. 08/402,076, filed on Mar. 10, 1995, now abandoned, and a continuation-in-part of application No. 08/402,277, filed on Mar. 10, 1995, now abandoned.

(51) Int. Cl.[7] ....................... G01N 33/543; G01N 33/551
(52) U.S. Cl. .............................. 435/6; 204/400; 204/403; 422/50; 422/52; 422/55; 422/61; 422/82.05; 422/82.07; 422/82.08; 435/287.1; 435/287.2; 435/288.7; 435/808; 435/810; 435/968; 435/975; 436/164; 436/172; 436/518; 436/524; 436/534; 436/805

(58) Field of Search ....................... 422/50, 52, 55, 422/61, 82.05, 82.07, 82.08, 99; 204/400, 403; 435/6, 287.1, 287.2, 288.7, 810, 808, 968, 975; 436/164, 172, 518, 524, 534, 805

(56) References Cited

U.S. PATENT DOCUMENTS 4,280,815  *  7/1981  Oberhardt et al. ............. 23/230 B
4,652,333       3/1987  Carney .

(List continued on next page.)

FOREIGN PATENT DOCUMENTS

WO 90/05301    5/1990   (WO) .
WO 90/14221   11/1990   (WO) .

(List continued on next page.)

OTHER PUBLICATIONS

Abbott and Whitesides, 1994, Potential–Dependent Wetting of Aqueous Solutions on Self–Assembled Monolayers Formed from 15–(ferrocenylcarbonyl) pentadecanethiol on Gold, *Langmuir* 10: 1493–1497.*

(List continued on next page.)

*Primary Examiner*—Christopher L. Chin
(74) *Attorney, Agent, or Firm*—Kramer Levin Naftalis & Frankel LLP

(57) ABSTRACT

Materials and methods are provided for producing patterned multi-array, multi-specific surfaces for use in diagnostics. The invention provides for electrochemiluminescence methods for detecting or measuring an analyte of interest. It also provides for novel electrodes for ECL assays. Materials and methods are provided for the chemical and/or physical control of conducting domains and reagent deposition for use multiply specific testing procedures.

13 Claims, 47 Drawing Sheets

U.S. PATENT DOCUMENTS

| | | |
|---|---|---|
| 4,663,230 | 5/1987 | Tennent . |
| 4,823,759 | 4/1989 | Guire et al. . |
| 4,891,321 | 1/1990 | Hubscher . |
| 5,061,445 * | 10/1991 | Zodski et al. ................... 422/52 |
| 5,068,088 | 11/1991 | Hall et al. . |
| 5,093,268 * | 3/1992 | Leventis et al. ................ 436/172 |
| 5,098,771 | 3/1992 | Friend . |
| 5,110,693 | 5/1992 | Friend et al. . |
| 5,124,075 | 6/1992 | Yasada et al. . |
| 5,147,806 * | 9/1992 | Kamin et al. ................... 436/149 |
| 5,165,909 | 11/1992 | Tennent et al. . |
| 5,171,560 | 12/1992 | Tennent . |
| 5,189,549 | 2/1993 | Leventis et al. . |
| 5,194,133 | 3/1993 | Cluck et al. . |
| 5,221,605 | 6/1993 | Bard et al. . |
| 5,238,808 | 8/1993 | Bard et al. . |
| 5,240,863 | 8/1993 | Shibue et al. . |
| 5,247,243 * | 9/1993 | Hall et al. ...................... 324/71.1 |
| 5,296,191 | 3/1994 | Hall et al. . |
| 5,304,326 | 4/1994 | Goto et al. . |
| 5,310,687 | 5/1994 | Bard et al. . |
| 5,324,457 | 6/1994 | Zhang et al. . |
| 5,340,716 | 8/1994 | Ullman et al. . |
| 5,418,171 | 5/1995 | Kimura et al. . |
| 5,466,416 * | 11/1995 | Ghaed et al. ................... 422/52 |
| 5,468,606 | 11/1995 | Bogart et al. . |
| 5,492,840 | 2/1996 | Malmgvist . |
| 5,632,957 * | 5/1997 | Heller et al. .................. 422/68.1 |

FOREIGN PATENT DOCUMENTS

| | | |
|---|---|---|
| WO 92/14139 | 8/1992 | (WO) . |
| WO 96/06946 | 3/1996 | (WO) . |

OTHER PUBLICATIONS

Abbott et al., 1992, "Manipulation of the Wettability of Surfaces on the 0.1 – to 1–μm Scale Through Micromatching and Molecular Self–Assembly", *Science* 257: 1380–1382.*

Abbott et al., 1994, "Using Micromachining, Molecular Self–Assembly, and Wet Etching to Fabricate 0.1–1μm–Scale Structures of Gold and Silicon", *Chemistry of Materials* 6: 596–602.*

Adalsteinsson et al., 1979, Preparation and Magnetic Filtration of Polyacrylamide Gels Containing Covalently Immobilized Proteins and a Ferrofluid *J. Mol. Catal.* 6: 199–225.*

Bain and Whitesides, 1989, "Modeling Organic Surfaces with Self–Assembled Monolayers", *Angew. Chem.* 101: 522–528.*

Bains, 1992, "Setting a Sequence to Sequence a Sequence", *Bio/Technology* 10: 757–758.*

Chaudhury and Whitesides, 1992, "How to Make Water Run Uphill", *Science* 256: 1539–1541.*

Chaudhury and Whitesides, 1992, "Correlation between Surface Free Energy and Surface Constitution", *Science* 255: 1230–1232.*

Deaver, D. R., 1995, "A New Non–Isotopic Detection System for Immunoassay", *Nature* 377: 758–760.*

DiMillia et al., 1994, "Wetting and Protein Adsorption of Self–Assembled (sic) Monolayers of Alkanethiolates Supported on Transparent Films of Gold," *Journal of the American Chemical Society* 116: 2225–2226.*

Dresselhaus, M. S.; Dresselhaus, G.; Eklund, P.C.; "Science of Fillerines and Carbon Nanotubes", Academic Press, San Diego, CA 1996.*

Ferguson et al., 1993, "Monolayers on Disordered Substrates: Self–Assembly of Alkyldichlorosilanes on Surface–Modified Polyethylene and Polydimethylsiloxane", *Macromolecules* 26: 5870–5875.*

Ferguson et al., 1991, "Contact Adhesion of Thin Gold Films on Elastomeric Supports: Cold Welding Under Ambient Conditions", *Science* 253: 776–778.*

Gershon & Khilko, 1995, "Stable Chelating Linkage for Reversible Immobilization of Oligohistidine Tagged Proteins in the Biacore Surface Plasmon Resonance Detector", *J. of Immunol. Methods*: 65–76.*

Haapakka, 1982, "The Mechanism of the Cobalt(II)–Catalyzed Electrogenerated Chemiluminescence of Luminol in Aqueous Alkaline Solution", *Anal. Chim Acta* 141:263–268.*

Haneko, 1987, Liquid Crystal TV Displays, Principles & Applications of Liquid Crystal Displays, KTK Scientific Publishers, Tokyo, D. Reidel Publishing.*

Hickman et al., 1991, "Molecular Self–Assembly of Two–Terminal Voltameric Microsensors with Internal References", *Science* 252: 688–691.*

Hydrogels in Medicine and Pharmacy, vol. I–III; Peppas, N.A. Edition, CRC Press, Boca Raton, Florida, 1987.*

Itaya & Bard, 1978, "Chemically Modified Polymer Electrodes: Synthetic Approach Employing Poly(methacryl chloride) Anchors", *Anal. Chem.* 50(11): 1487–1489.*

Kaneko, 1987, *Liquid Crystal TV Displays: Principles and Applicants of Liquid Crystal Displays* (KTK Scientific Publishers, Tokyo; D. Reidel Publishing Company, Dordrecht) Chapter 2: 3–32.*

Kim et al., 1995, "Polymer Microstructures Formed by Moulding in Capillaries", *Nature* 376: 581–584.*

Knight et al., 1994, "Occurance, Mechanisms and Analytical Applications of Electrogenerated Chemiluminescence", *Analyst* 119: 879–890.*

Kumar and Whitesides, 1993, "Feature of gold having micrometer to centimeter dimensions can be formed through a combination of stamping with an elastomeric stamp and an alkanetiol 'ink' followed by chemical etching", *Appl. Phys. Lett.* 63: 2002–2004.*

Kumar et al., 1994, "Patterning Self–Assembled Monolayers: Applications in Materials Science", *Langmuir* 10: 1498–1511.*

Laibinis et al., 1989, "Orthogonal Self–Assembled Monolayers: Alkanethiols on Gold and Alkane Carboxylic Acids on Alumina", *Science* 245: 845–847.*

Leland and Powell, 1990, "Electrogenerated Chemiluminescence: An Oxidative–Reduction Type ECL Reaction Sequence Using Tripropyl Amine", *J. Electrochem. Soc.* 137: 3127–3131.*

Martin and Nieman, 1993, "Glucose quantitation using an immobilized glucose dehydrogenase enzyme reactor and a trist (2,2'–bipyridyl) ruthenium (ii) chemiluminescent sensor" *Analytica Chimica Acta* 281: 475–481.*

"Methods in Enzymology, Immobilized Enzymes & Cells, Pt. B.," Morback, K. Ed., Elsevier Applied Science: London, 1988.*

Nielsen, P. E., 1995, "DNA Analogues With Nonphosphodiester Backbones", *Annu. Rev. Biophys. Biomol. Street* 24: 167–183.*

Obeng et al., 1991, "Electrogenerated Chemiluminescence. 53. Electrochemistry and Emissiion from Adsorbed Monolayers of a Tris(bipyridyl)ruthenium(II)–Based Surfactant on Gold and Tin Oxide Electrodes", *Langmuir* 7: 195–201.*

Olah et al., 1980, "Polymer Films on Electrodes. 4. Nafion–Coated Electrodes and Electrogenerated Chemiluminescence of Surface–Attached Ru(bpy)$3^{2+}$", *J. Am. Chem. Soc.* 102: 6641–6642.*

Pale–Grosdemange et al., 1991, "Formation of Self–Assembled Monolayers by Chemisorption of Derivatives of Oligo (ethylene Glycol) of Structure HS(CH2)11(OCH2CH2)m OH on Gold" *Journal of the American Chemical Society* 113: 12–20.*

Pollack et al., 1980, "Enzyme Immobilization by Condensation Copolymerization into Cross–Linked Polyacrylamide Gels", *J. Am. Chem. Soc.* 102(20): 6324–36.*

Polyethylene glycol chemistry: Biotechnical & Biomedical Applications, Harris, T.M. Ed., 1992 Plinum Press.*

Prime and Whitesides, 1993, "Adsorption of Proteins Onto Surfaces Containing End–Attached Oligo (ethylene oxide): A Model System Using Self–Assembled Monolayers" *J. Amer. Chem. Soc.* 115: 10714–721.*

Prime and Whitesides, 1991, "Self–Assembled Organic Monolayers; Model Systems for Studying Adsorption of Proteins at Surfaces", *Science* 252: 1164–1167.*

Sassenfeld, 1990, "Engineering Proteins for Purification", *Tibtech* 8: 88–93.*

Soane, D. S., Polymer Applications for Biotechnology: Soane, D. S. editor, Simon & Schuster, Englewood Cliffs, NJ.*

"Solid Phase Biochemistry: Analytical & Synethic Aspects" Souten, W.H., Ed., T. Wiley & Sons: NY, 1983.*

Spinke et al., 1993, "Molecular Recognition at Self–Assembled Monolayers: Optimization of surface functionalization", *J. Chem. Phys.* 99: 7012–7019.*

Spinke et al., 1993, "Molecular Recognition at Self–Assembled Monolayers: The Construction of Multicomponent Multilayers", *Langmuir* 9: 1821–1825.*

Strezoska et al., 1991, "DNA sequencing by hybridization: 100 bases read by a non–gel based method", *Proc. Natl. Acad. Sci. USA* 88: 10089–10093.*

Sundberg et al., 1995, "Spatially–Addressable Immobilization of Macromolecules on Solid Supports", *J. Am. Chem. Soc.* 117: 12050–12057.*

Tampion, J. and Tampion, M. D. "Immobilized Cells: Principles & Applications", Cambridge Univ. Press, NY 1987.*

Wilber, et al., 1995, "Scanning Force Microscopies Can Image Patterned Self–Assembled Monolayers", *Langmuir* 11: 825–831.*

Xu et al., 1994, "Electrogenerated Chemiluminescence. 55. Emission from Adsorbed Ru(bby)$3^{2+}$ onGraphite, Platinum, and Gold", *Langmuir* 10: 2409–2414.*

Yang, H. J. et al., 1994, "Electrochemiluminescence: A New Diagnostic and Research Tool", *BioTechnology* 12: 193–194.*

Zhang et al., 1988, "Electrogenerated Chemiluminescent Emission from an Organized (L–B) Monolayer of a Ru(bpy)$3^{2+}$–BasedSurfactant on Semiconductor and Metal Electrodes" *J. Phys. Chem.* 92: 55665569.*

* cited by examiner

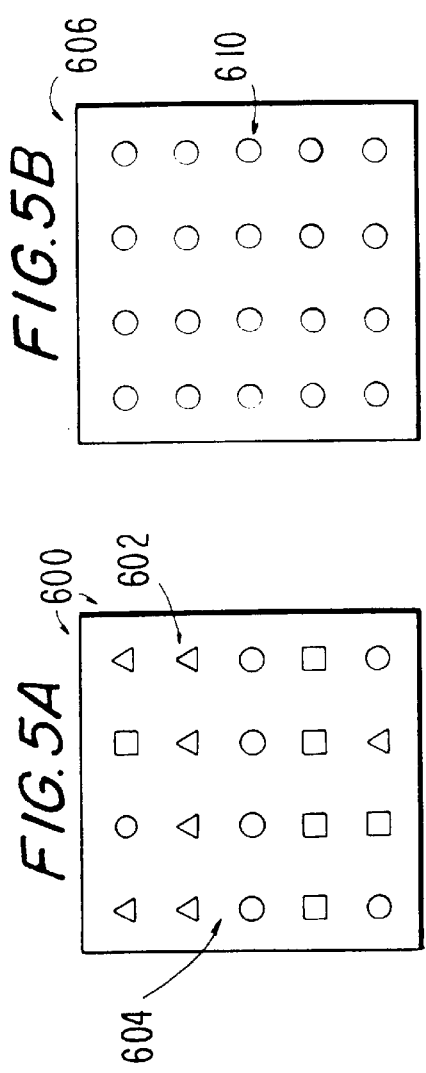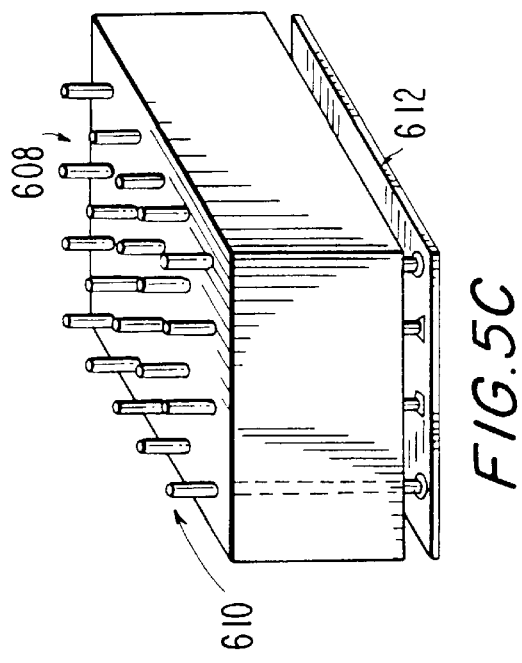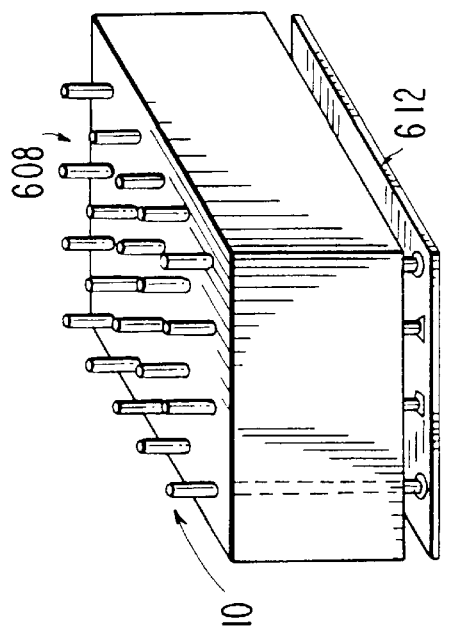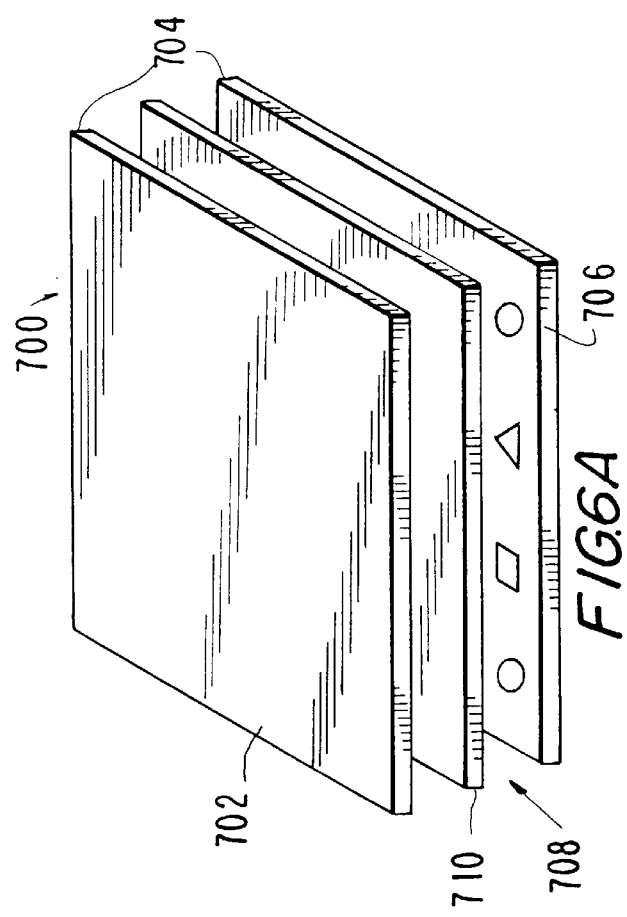

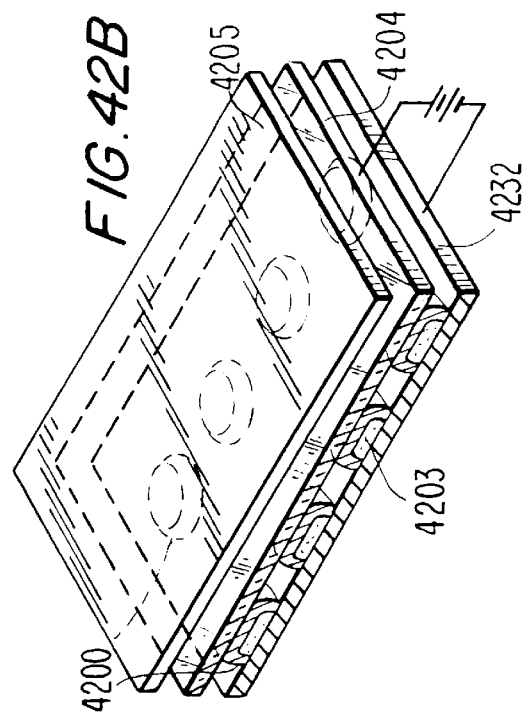
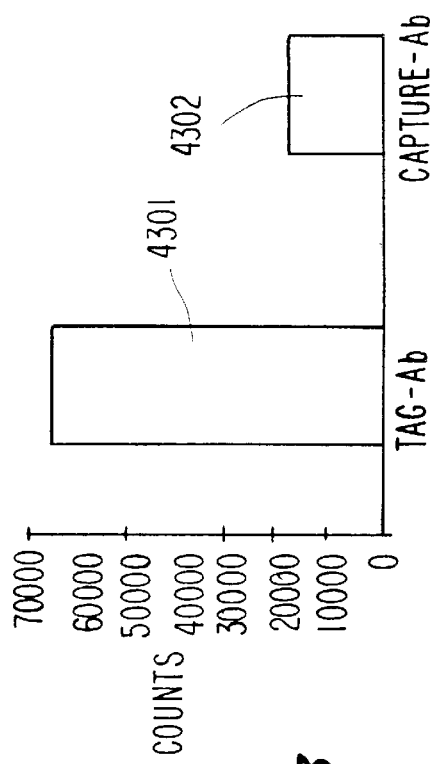
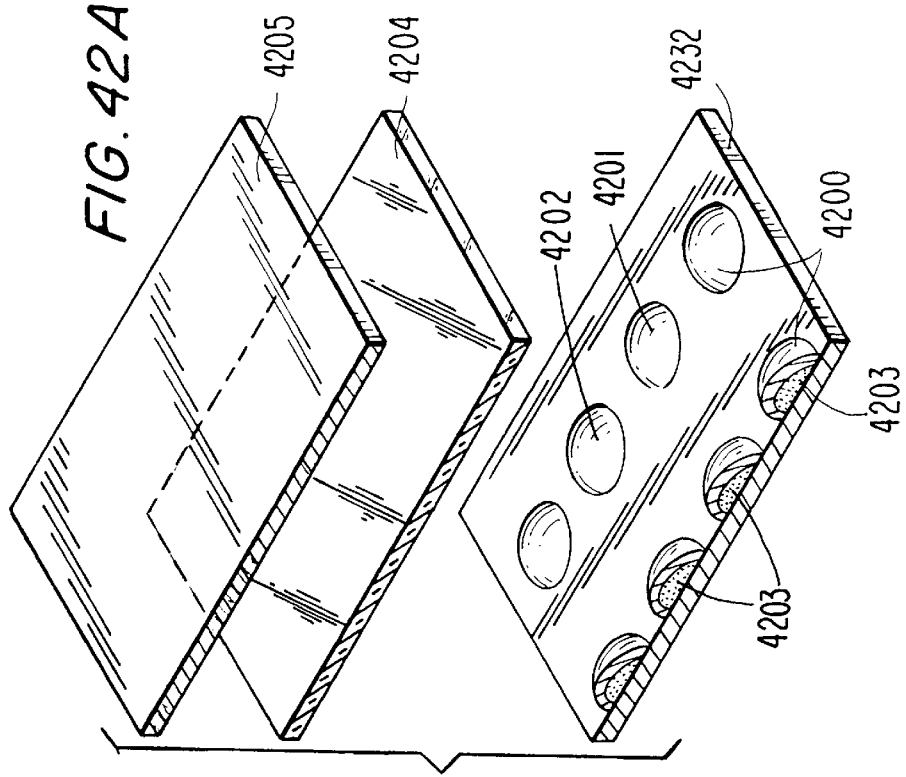

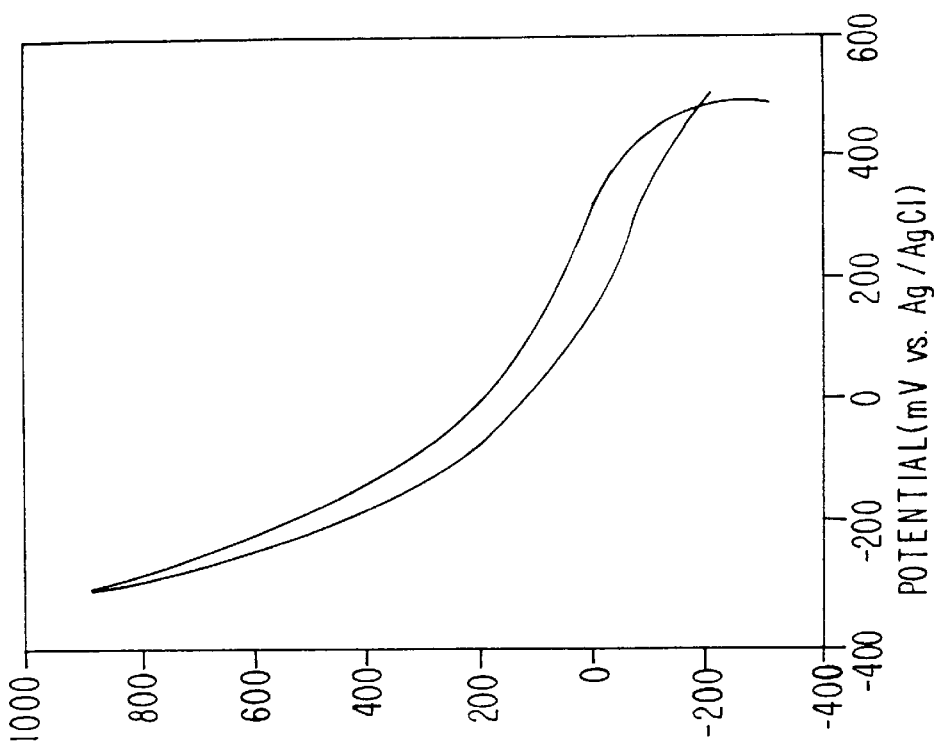
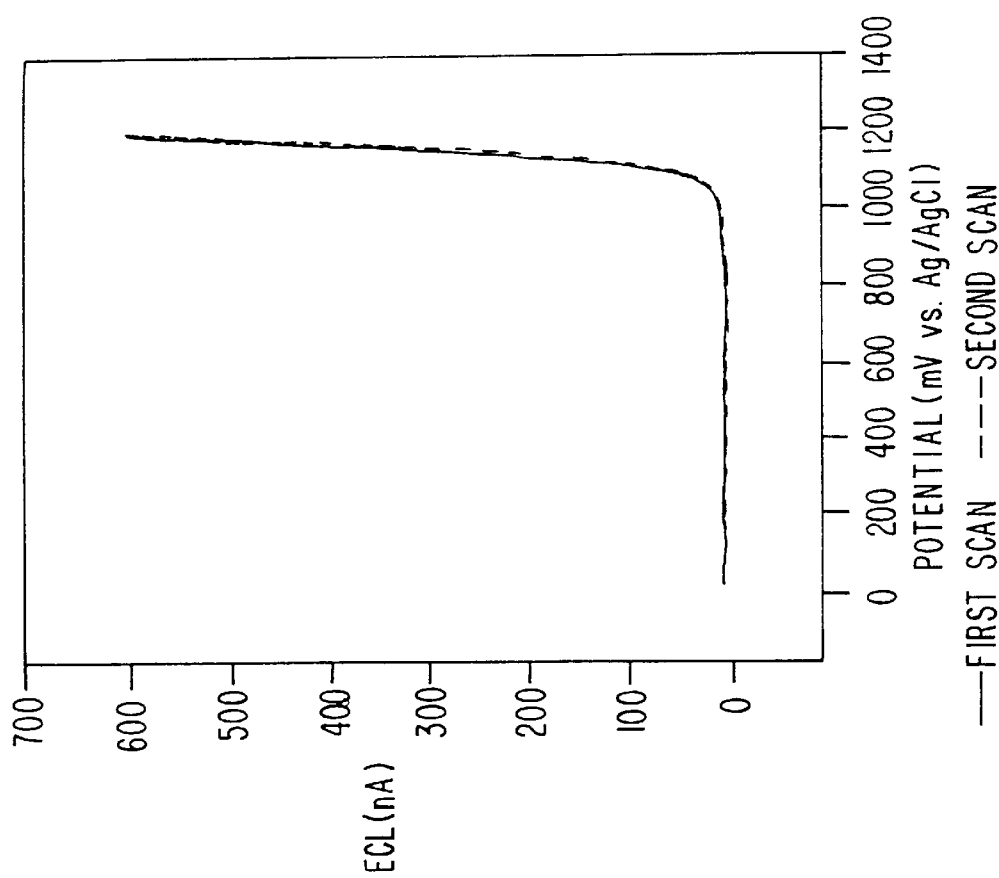

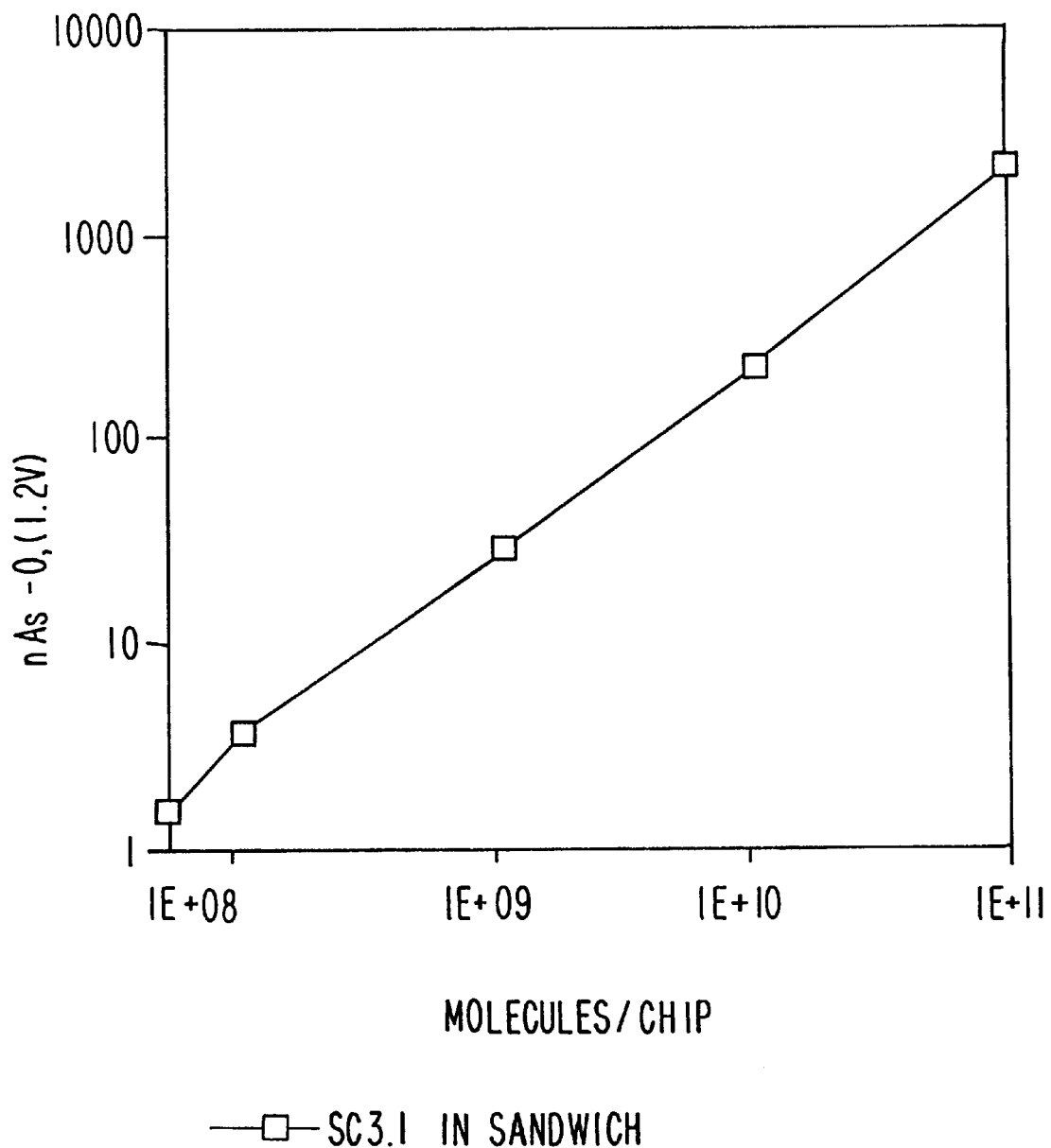

MULTI-ARRAY, MULTI-SPECIFIC ELECTROCHEMILUMINESCENCE TESTING

This application is a continuation-in-part of application Ser. No. 08/611,804 filed Mar. 6, 1996, now U.S. Pat. No. 6,066,448, which is a continuation-in-part of applications Ser. Nos. 08/402,076 filed Mar. 10, 1995, now abandoned and 08/402,277 filed Mar. 10, 1995, now abandoned each of which is incorporated by reference herein in its entirety.

TABLE OF CONTENTS
1. INTRODUCTION
2. BACKGROUND OF THE INVENTION
   2.1. Diagnostic Assays
   2.2. Electrochemiluminescence
   2.3. Commercial ECL Assays
   2.4. Objects Of The Invention
3. SUMMARY OF THE INVENTION
4. DESCRIPTION OF THE FIGURES
5. DETAILED DESCRIPTION OF THE INVENTION
   5.1. Preparation Of A Binding Surface
   5.2. Binding Reagents
   5.3. Voltage Waveform
   5.4. Addressable Electrode And Methods For Using The Same
   5.5. Light Detection
   5.6. Analysis Of ECL Signals
   5.7. Preparation Of Electrodes For Multi Arrays
   5.8. Cassettes
   5.9. Apparatus For Conducting ECL Reactions
   5.10. ECL Assays That May Be Conducted
   5.11. PMAMS For Use With Other Analytic Methods And/Or ECL
   5.12. Electrochromic ECL Display
   5.13. PMAMS For Use In Other Chemical Reactions
   5.14. ECL Assays Employing The Capture Of Particles On Porous Electrodes
   5.15. ECL Assays Employing PMAMS On Electrodes
   5.16. ECL Assays Employing PMAMS On A Porous Substrate
   5.17. ECL Assays Employing PMAMS On Composite Electrodes
   5.18. ECL Assays Employing PMAMS On A Porous Electrode
   5.19. Methods For Increasing Signal To Background
6. EXAMPLES
   6.1. Preparation Of An MAB PMAMS Surface By Micro-Stamping
   6.2. Preparation Of An MAB And Nucleic Acid PMAMS Surface By Micro-Stamping
   6.3. Preparation Of A PMAMS Surface By Etching
   6.4. Sandwich Assay On A PMAMS Surface
   6.5. Assay On A First And Second PMAMS Surface
   6.6. Nucleic Acid Assay On A PMAMS Surface
   6.7. Competitive Assay On A PMAMS Surface With A Photomultiplier Detector
   6.8. Competitive Assay On A PMAMS Surface With A CCD Detector
   6.9. Preparation Of An MAB PMAM Surface By Micro Stamping With An $SH(CH_2)_{10}CH_3$ Alkane Thiol
   6.10. Preparation Of An MAB And Nucleic Acid PMAMS Surface By Micro-Stamping With An $SH(CH_2)_{10}CH_3$ Alkane Thiol
   6.11. Preparation Of A PMAMS Surface Using A Streptavidin-Biotin Linker
   6.12. Preparation Of An MAB Single Surface
   6.13. Assay Conducted On An MAB Single Surface
   6.14. Preparation Of A Single Surface With Working And Counterelectrodes
   6.15. Assay Conducted On A Single With Working And Counterelectrodes
   6.16. Preparation Of A Surface With Counterelectrodes
   6.17. Assay Conducted On A Single Surface With The Working And Counterelectrodes On Different Surfaces
   6.18. Fabrication Of A CC (Dispersed) Fibril MAT By Vacuum Filtration
   6.19. Fabrication Of A Fibril Mat On A Metal Mesh Support By Evaporation
   6.20. Immobilization Of Avidin On Fibrils Bearing NHS-Ester Functional Groups
   6.21. Immobilization Of Monoclonal Antibody (Anti-AFP) On Carbon Fibrils
   6.22. Cyclic Voltammograms Of Fibril Mats: Comparison Of Fibril Mat With Gold Foil Electrode
   6.23. Electrochemical Properties Of Fibril Mat Electrodes: Comparison Of Anodic Peak Current With Thickness Of The Mat
   6.24. Non-Specific Binding Of Protein To Fibrils
   6.25. Reduction Of Non-Specific Binding Of Proteins To Fibrils With Detergents/Surfactants
   6.26. ECL Of Free TAG In Solution With Fibril Mat Electrode
   6.27. ECL Of Adsorbed Labeled Antibody With Fibril Mat Electrode
   6.28. ECL Using Fibril Mat Electrode For Sandwich Assay
   6.29. ECL Detection Of TAG1-Labeled Avidin On A Polyacrylamide Surface
   6.30. ECL Sandwich Immunoassay On A Polyacrylamide Surface
   6.31. Multiple ECL Sandwich Immunoassay On Polyacrylamide Surfaces Supported On An Electrode
   6.32. Multiple ECL Competitive Immunoassays On Polyacrylamide Surfaces Supported On An Electrode
   6.33. Multiple ECL Assays For Binding Of Cells On Polyacrylamide Surfaces Supported On An Electrode
   6.34. Multiple ECL Assays For Binding Of Analytes To Cells On Polyacrylamide Surfaces Supported On An Electrode
   6.35. Multiple ECL Competitive Hybridization Assays On Polyacrylamide Surfaces Supported On An Electrode
   6.36. Multiple ECL Hybridization Sandwich Assays On Polyacrylamide Surfaces Supported On An Electrode
   6.37. Multiple Assays Of Different Types On A Polyacrylamide Surfaces Supported On An Electrode
   6.38. Highly Reversible ECL
   6.39. Quasi-Reversible ECL
   6.40. Irreversible ECL
   6.41. An ECL Sandwich Immunoassay Using A Primary Antibody Immobilized On A Patterned Gold Electrode
   6.42. Preparation Of Aerosil-200 Silica Particles Coated With Streptavidin 6.43. Formation Of A Fibril Mat On A Support Of Stainless Steel Filter Paper For Use In Particle-based ECL Assay 6.44. A Particle-based ECL Assay For AFP Using Streptavidin-Coated Beads Captured On A Fibril Mat 6.45. A Particle-based ECL Assay For ATP Using Streptavidin-Coated Silica Beads Captured On A Fibril Mat 6.46. ECL Emitted From Fluorescent Dye-Labeled Latex Beads Captured On A Fibril Mat Electrode 6.47. An ECL Sandwich Immunoassay For AFP Using Biotin-Streptavidin Capture To Immobilize A Capture Antibody On A Gold Electrode 6.48. The Detection Of Nucleic Acid Hybridization To A Probe Immobilized On A Gold Electrode 6.49. Preparation Of Sheets Of A Composite Electrode Containing Fibrils And EVA 6.50. Oxidation Of Fibril-Polymer Composite By Chromic Acid 6.51. Derivatization Of A Fibril-Polymer Composite With A Mixture Of Sulfuric And Nitric Acids 6.52. Preparation Of A Fibril Composite Electrode With Exposed Hydroxyl Groups 6.53. Immobilization Of Streptavidin On Oxidized Fibril-Polymer Composites 6.54. Immobilization Of Proteins On Fibril-Polymer Composites Via SMCC Activation 6.55. Immobilization Of Streptavidin On A Composite Electrode Presenting Exposed Hydroxyl Groups 6.56. Assay For AFP On A Composite Electrode Of EVA And Fibrils 6.57. ECL Assay For TSH A Composite Electrode Of EVA And Fibrils 6.58. DNA Hybridization Assay On A Fibril Polymer Composite 6.59. Measurement Of The Surface Area Of A Fibril-Composite Electrode 6.60. Preparation Of NHS Ester-Functionalized Fibrils 6.61. Conjugation Of Streptavidin To NHS Ester Fibrils 6.62. Fabrication Of A Ultra Thin Fibril Mat (UTFM) On A Nylon Membrane Filter 6.63. A Nucleic Acid Hybridization Assay On A Bilayer Ultra Thin Fibril Mat Electrode 6.64. A Sandwich Immunoassay For AFP On A Bilayer Ultra Thin Fibril Mat Electrode 6.65. Forming Conductive Films Of Gold On Nonconductive Filter Membranes 6.66. A Sandwich Immunoassay For A On Ultra Thin Fibril Mat Electrode Formed On A Gold-Coated Nylon Filter Membrane 6.67. AFP Assay On Two Different Electrodes: Voltammetric Resolution Of Signal And Background

7. INCORPORATION OF REFERENCES

What is claimed is:

ABSTRACT

1. INTRODUCTION

The present invention provides for a patterned multi-array, multi-specific surface (PMAMS) for electrochemiluminescence based tests, as well as methods for making and using PMAMS.

2. BACKGROUND OF THE INVENTION

2.1. Diagnostic Assays

There is a strong economic need for rapid sensitive diagnostic technologies. Diagnostic technologies are important in a wide variety of economic markets including health care, research, agricultural, veterinary, and industrial marketplaces. An improvement in sensitivity, time required, ease of use, robustness, or cost can open entirely new diagnostic markets where previously no technology could meet the market need. Certain diagnostic technologies may possess high sensitivity but are too expensive to meet market needs. Other techniques may be cost effective but not robust enough for various markets. A novel diagnostic technique which is capable of combining these qualities is a significant advance and opportunity in the diagnostics business.

There are a number of different analytical techniques used in diagnostic applications. These techniques include radioactive labeling, enzyme linked immunoassays, chemical colorimetric assays, fluorescence labeling, chemiluminescent labeling, and electrochemiluminescent labeling. Each of these techniques has a unique combination of sensitivity levels, ease of use, robustness, speed and cost which define and limit their utility in different diagnostic markets. These differences are in part due to the physical constraints inherent to each technique. Radioactive labeling, for example, is inherently non-robust because the label itself decays and the disposal of the resulting radioactive waste results in economic, safety and environmental costs for many applications.

Many of the sensitive diagnostic techniques in use today are market-limited primarily because of the need for skilled technicians to perform the tests. Electrochemiluminescent procedures in use today, for example, require not only skilled technicians but repeated washing and preparatory steps. This increases both the costs and the need for waste disposal. Novel diagnostics which simplify the testing procedures as well as decrease the cost per test will be of great importance and utility in opening new markets as well as improving performance in existing markets.

2.2. Electrochemiluminescence

Electrochemiluminescence ("EdL") is the phenomena whereby an electrically excited species emits a photon (see, e.g., Leland and Powell, 1990 *J. Electrochem. Soc.* 137(10):3127–3131). Species from which ECL can be induced are termed ECL labels and are also referred to herein as TAGs. Commonly used ECL labels include: organometallic compounds where the metal is from, for example, the noble metals of group VIII, including Ru-containing and Os-containing organometallic compounds such as the $Ru(2,2'\text{-bipyridine})_3^{2+}$ moiety (also referred to as "Rubpy" or TAG1), disclosed, e.g., by Bard et al. (U.S. Pat. No. 5,238,808). "TAG1" and "Rubpy" also refer to derivatives of $Ru(2,2'\text{-bipyridine})_3^{2+}$. Fundamental to ECL-based detection systems is the need for an electrical potential to excite the ECL label to emit a photon. An electrical potential waveform is applied across an electrode surface, typically a metal surface, and a counterelectrode (see e.g., U.S. Pat. Nos. 5,068,088, 5,093,268, 5,061,445, 5,238,808, 5,147,806, 5,247,243, 5,296,191, 5,310,687, 5,221,605). The ECL is promoted to an excited state as a result of a series of chemical reactions triggered by the electrical energy received from the working electrode. A molecule which promotes ECL of the TAG is advantageously provided, such as oxalate or, more preferably, tripropylamine (see U.S. Pat. No. 5,310,687).

The excitation of a TAG in an ECL reaction typically involves diffusion of the TAG molecule to the surface of an electrode. Other mechanisms for the excitation of a TAG molecule by an electrode include the use of electrochemical mediators in solution (Haapakka, 1982, Anal Chim. Acta, 141:263) and the capture of beads presenting TAG molecules on an electrode (PCT published applications WO 90/05301 and WO 92/14139). Alternatively, ECL has been observed from TAG that was adsorbed directly on the surface of working electrodes (U.S. Pat. No. 5,324,457), e.g., by non-specific adsorption (Xu et al., 1994, Langmuir, 10:2409–2414), by incorporation into L-B films (Zhang et al., 1988, J. Phys. Chem., 92:5566), by incorporation into self-assembled monolayers (Obeng et al., 1991, Langmuir, 7:195), and by incorporation into thick (micrometer) films (Rubenstein et al., 1981, J. Am. Chem. Soc., 102:6641). Similarly, Xu et al. (PCT published application WO 96/06946) have observed ECL from TAG molecules intercalated into DNA strands when such strands were adsorbed onto gold electrodes by interaction with aluminum centers immobilized on a self-assembled monolayer of alkanethiolates.

Various apparatus well known to the art are available for conducting and detecting ECL reactions. For example, Zhang et al. (U.S. Pat. No. 5,324,457) discloses exemplary electrodes for use in electrochemical cells for conducting ECL. Leventis et al. (U.S. Pat. No. 5,093,268) discloses electrochemical cells for use in conducting ECL reactions. Kamin et al. (U.S. Pat. No. 5,147,806) discloses apparatus for conducting and detecting ECL reactions, including voltage control devices. Zoski et al. (U.S. Pat. No. 5,061,445) discloses apparatus for conducting and detecting ECL reactions, including electrical potential waveform diagrams for eliciting ECL reactions, digital to analog converters, control apparatus, detection apparatus and methods for detecting current generated by an ECL reaction at the working electrode to provide feedback information to the electronic control apparatus.

2.3. Commercial ECL Assays

The light generated by ECL labels can be used as a reporter signal in diagnostic procedures (Bard et al., U.S. Pat. No. 5,221,605). For instance, an ECL label can be covalently coupled to a binding agent such as an antibody or nucleic acid probe. The ECL label/binding agent complex can be used to assay for a variety of substances (Bard et al., U.S. Pat. No. 5,238,808). The use of ECL in assays is reviewed in detail by, for example, Knight et al., 1994, Analyst, 119:879–890. In brief, the ECL technique may be used as a method of detecting in a volume of a sample an analyte of interest present in the sample in relatively small concentrations.

To date, all commercial ECL assays are carried out on centimeter scale electrode surfaces. The centimeter scale electrodes strike a balance between the enhanced magnitude of an ECL signal resulting from larger electrodes and the desirability of decreasing the total sample volume necessary for each assay. However, even centimeter scale electrodes fail to achieve the sensitivity required for many assays. In an attempt to overcome this problem, all commercial ECL systems further enhance sensitivity by using coated magnetic beads to capture ECL analytes or reagents. The beads are then moved adjacent to a working electrode for enhanced sensitivity.

However, the currently available technology has many limitations (primarily cost and complexity) that restrict its use in low cost assays employing disposable cartridges as well as its use in high throughput systems that perform multiple assays concurrently.

Leventis et al. (U.S. Pat. No. 5,093,268) has proposed a method of assaying more than one different analyte simultaneously by the use of different ECL labels for each analyte, each emitting photons at different wavelengths for each different analyte in a single assay. However, this technique is limited, for example, by the unavailability of a sufficient number of effective ECL labels radiating at different wavelengths and the need to optimize the chemical conditions for each ECL label. These practical constraints have prevented the commercialization of such multi-wavelength, multi-analyte ECL detection systems.

Commercial methods for conducting ECL assays also require that the assay cell, including the electrodes, must be cleaned by any one of a number of methods, including the use of dilute acids, dilute bases, detergent solutions, and so forth as disclosed, for example, by U.S. Patent No. 5,147,806.

2.4. Objects Of The Invention

It is therefore an object of the present invention to provide a novel, cost effective electrode and disposable for conducting ECL assays.

It is a further object of the present invention to provide a novel and cost effective system for conducting a plurality of ECL assays, either sequentially or simultaneously and in a preferred embodiment, providing built-in control standards for improved accuracy.

It is a further object of the present invention to provide a cassette comprising one or more supports suitable for conducting a plurality of simultaneous or sequential ECL assays that is also disposable.

It is a further and related object of this invention to reduce the time and cost of conducting individual assays for analytes of interest in biological samples.

It is still a further and related object of this invention to provide methods and apparatus for conducting a plurality of simultaneous assays for a plurality of analytes of interest in a single biological sample.

3. SUMMARY OF THE INVENTION

The invention relates to a cassette for conducting ECL reactions and assays comprising one or more binding domains immobilized on a support. The support may act as an electrode for generating electrochemiluminescence. Alternatively, one or more electrodes may be on additional supports, and said electrodes may be brought into proximity to the first support so as to generate ECL. The cassette may have one or more electrodes or one or more electrode/counterelectrode pairs. The cassette may also comprise a second support capable of being placed adjacent to the first support to provide sample containing means therebetween, and/or serve as an electrode. The binding domains are patterned on a support surface and are prepared so as to bind analytes or reagents of interest.

The invention further relates to novel, disposable electrodes amenable to use in a disposable format. These electrodes can be comprised of various forms of carbon such as glassy carbon, carbon black or carbon (graphitic) nanotubes.

The invention further relates to composite electrodes, i.e. electrodes comprised of more than one material. These electrodes can be tailored to control performance, cost and manufacturability to make them amenable to use in a disposable format.

The invention further relates to assays in which particles are used as solid-phase supports for binding reagents. Said particles are captured on a porous electrode by filtration and analytes are detected. Kits based on pre-prepared conducting filters with particles are described.

The invention further relates to electrodes that can be used to resolve two or more ECL signals. Methods for the modification of electrodes are also described.

The invention further relates to an apparatus for measuring electrochemiluminescence of a sample that provides support or cassette handling means, voltage control means adapted to apply a controlled voltage waveform effective to trigger electrochemiluminescence, photon detector means for detecting electrochemiluminescence from the sample and sample handling means.

The invention further relates to methods for using the cassettes for measuring electrochemiluminescence in a sample by contacting the plurality of binding domains of a cassette with a sample which contains a plurality of analytes of interest, under ECL assay conditions, and then applying a voltage waveform effective to trigger electrochemiluminescence and detecting or measuring of the triggered electrochemiluminescence.

The invention also provides for kits comprising components including cassettes suitable for simultaneously measuring a plurality of electrochemiluminescence reactions, support surfaces and upon which a plurality of domains are immobilized assay, media for conduct of the ECL assay conducting chemical reactions.

The invention is also in rapid disposable electrochemiluminescence assays. Commercial ECL assays are performed using a flow cell with a working and counter electrode. A disposable electrode, as disclosed herein, does not require washing and/or cleaning to eliminate carry-over and regenerate a uniform electrode surface as does a permanent flow cell electrode.

The invention also provides for increased kinetics through the use of porous electrodes. Formatted and/or porous disposable electrodes are used to rapidly produce assay results.

Assay results with disposable electrodes may be achieved in less than an hour. In preferred embodiments ECL assay results from disposable electrodes may be achieved in less than 30 minutes and in some cases less than 15 minutes. In the most preferred embodiments, the assay results can be achieved in less than 5 minutes or in the most advantageous case, than 1 minute. In multi-assay formats of the invention more than one ECL assay result may be achieved in such time periods or less. Kits for rapid disposable ECL systems are disclosed.

Additionally, the invention provides for portable ECL diagnostic instruments. Cartridges or kits for portable ECL diagnostics may use the novel disposable electrodes and reagent packs. PMAMS and electrodes for ECL assays may be packaged as kits for use in portable ECL instrument readers. Such kits and ECL instrument readers may be used to achieve assay results in short time periods. Assay results may be achieved in the very short time periods discussed above.

4. DESCRIPTION OF THE FIGURES

FIG. 1 illustrates a cassette according to the invention wherein a plurality of binding domains are present on an electrode.

FIG. 1A illustrates two supports forming a cassette according to the invention wherein a plurality of binding domains 14 are present on support 10 and a plurality of corresponding electrodes 16 is present on support 12 so that approximation of the supports places an electrode pair adjacent to each binding domain.

FIG. 2 illustrates two supports forming a cassette according to the invention wherein a plurality of binding domains 30 on support 26 are adjacent to each of single electrodes 32 so that approximating supports 26 and 28 places each of counterelectrodes 38 adjacent to each of binding domains 30.

FIG. 3 illustrates two supports forming a cassette according to the invention wherein a plurality of binding domains 48 have electrode counterelectrode pairs 50 adjacent thereto on support 44. Support 46 may optionally be placed adjacent to support 44 so that support 46 provides sample containing means adjacent to binding domains 48 and electrodes 50.

FIG. 4 illustrates two supports forming a cassette according to the invention wherein a plurality of binding domains 64 on support 60 are contacted with a sample suspected of containing an analyte. Support 62 has regions 66 containing reaction medium for detecting or measuring an analyte of interest or for carrying out a desired reaction so that approximating support 60 and support 62 causes binding domains 64 and regions 66 to contact one another.

FIG. 5A illustrates a top view of patterned binding domains for a multi-array, multi-specific binding surface. Geometric shapes, triangles, squares and circles, represent binding domains specific for different analytes. The binding domains may be hydrophobic or hydrophilic. The surrounding surface may have the opposite property (hydrophilic or hydrophobic) of the binding domains to minimize spreading of binding reagents or analyte from the binding domains.

FIG. 5B illustrates a top view of a microfluidics guide for delivering binding reagents and/or analytes to discrete binding domains. Each dot illustrates a cross section of a microfluidics guide (e.g., a capillary).

FIG. 5C illustrates a side view of a microfluidics guide showing the approximation of registered or aligned microfluidic guides for delivering binding reagents and/or analytes to a multi array of patterned binding domains. Each microfluidic guide may deliver a different binding reagent to a discrete binding domain.

FIG. 6A illustrates the approximation of a multi-array of electrodes in register with a surface having patterned multi-array, multi-specific binding domains. A removable electrode protection barrier is shown between the electrode array and the binding surface array. The entire assembly comprises a cassette for conducting a plurality of ECL reactions.

FIG. 6B illustrates the approximation of an array of registered or aligned addressable working and counterelectrodes. The electrodes may be shape complementary with the binding domain or of other shapes (e.g., interdigitating).

Figure 7:
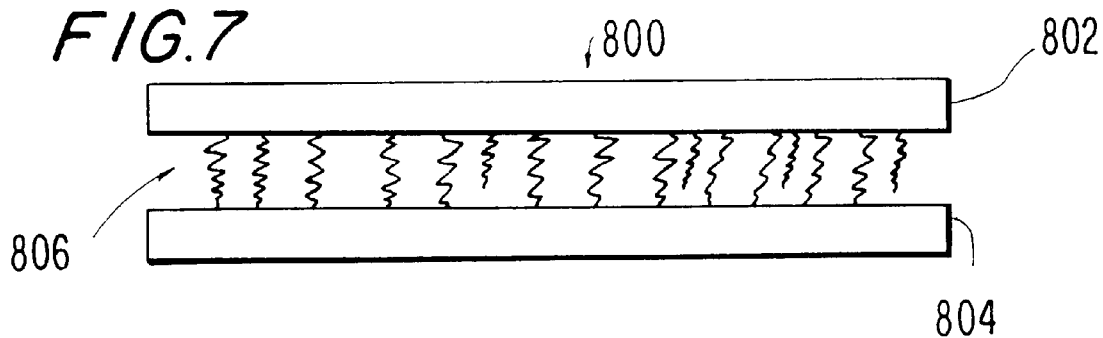

FIG. 7 illustrates the side view of an approximated array of registered or aligned addressable working and counter-electrodes and the complementary binding surface wherein conducting polymers are grown from the surfaces of the electrodes across the gap between the electrode array and the binding domains so as to extend the potential field around the ECL label of the sample to increase the efficiency of the ECL reaction.

Figure 8:
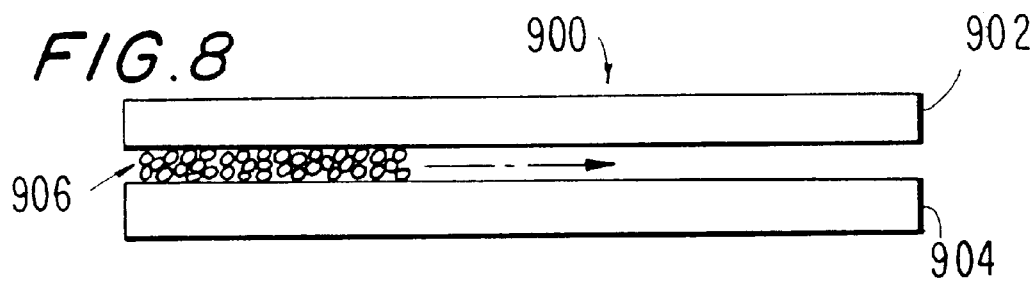

FIG. 8 illustrates the side view of an approximated array of registered or aligned addressable working and counter-electrodes and the complementary binding surface with conducting particles interspersed between both components to extend the potential field. By extending the potential field around the ECL label of the sample the efficiency of the ECL reaction is enhanced. The conducting particles can be magnetic to permit ready manipulation.

Figure 9:
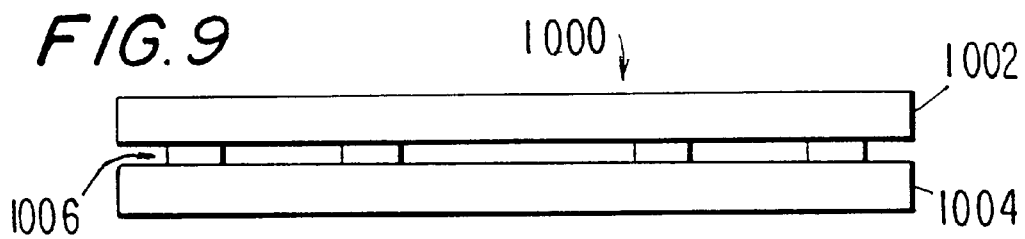

FIG. 9 illustrates the side view of an approximated array of registered or aligned addressable working and counter-electrodes and the complementary binding surface wherein the electrodes have fine projections extending into the gap between the electrode surface and the binding domains in order to extend the potential field around the ECL label of the sample, to increase the efficiency of the ECL reaction.

Figure 10:
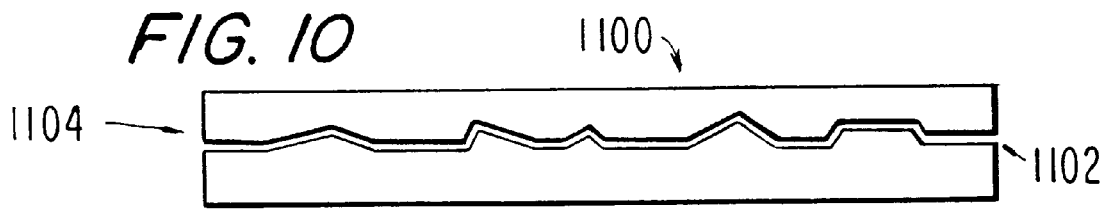

FIG. 10 illustrates the side view of an approximated array of registered or aligned addressable working and counter-electrodes and the complementary binding surface where the surfaces are not parallel, but are instead conformed one to the other in a complementary fashion.

Figure 11:
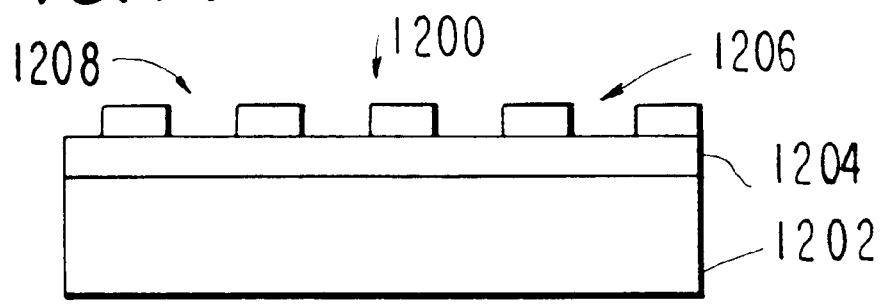

FIG. 11 illustrates the side view of a support having a metallic layer thereon to provide a single electrode and binding surface assembly in the form of a cassette. An array of self-assembled monolayers ("SAMs") is patterned on the metallic layer.

Figure 12:
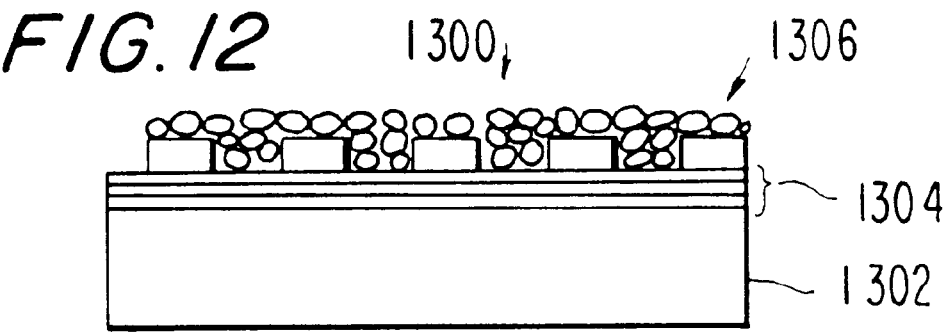

FIG. 12 illustrates the side view of a support having a metallic layer thereon to provide a single electrode and binding surface assembly in the form of a cassette. An array of SAMs is patterned on the metallic layer and conducting microparticles are shown interspersed among the patterned SAMs so as to extend the potential field around the ECL label of the sample, to increase the efficiency of the ECL reaction.

Figure 13:
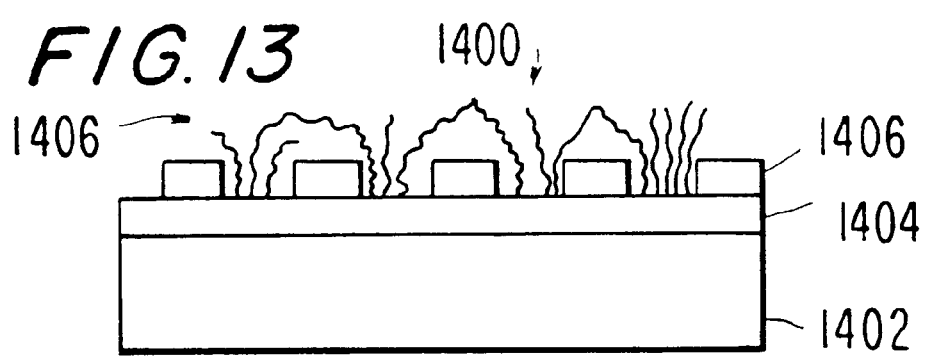

FIG. 13 illustrates the side view of a support having a metallic layer thereon to provide a single electrode and binding surface assembly in the form of a cassette. An array of self assembled monolayers or SAMs is patterned on the metallic layer and the growth of a conducting polymer and/or fiber from the ECL label so as to extend the potential field around the ECL label of the sample to increase the efficiency of the ECL reaction, is illustrated.

Figure 14:
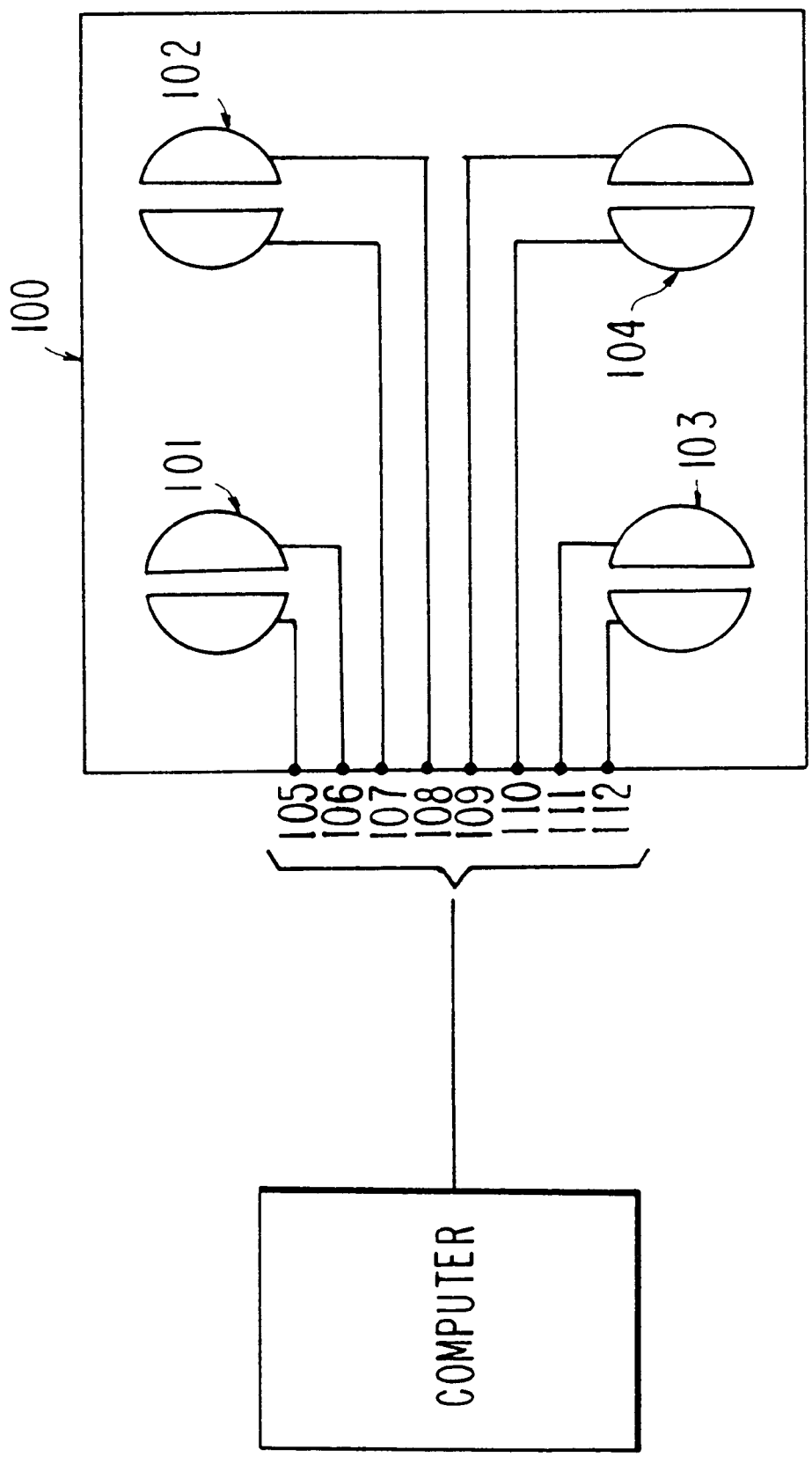

FIG. 14 is a diagram of a support having an array of electrode pairs controlled by a computer.

Figure 15:
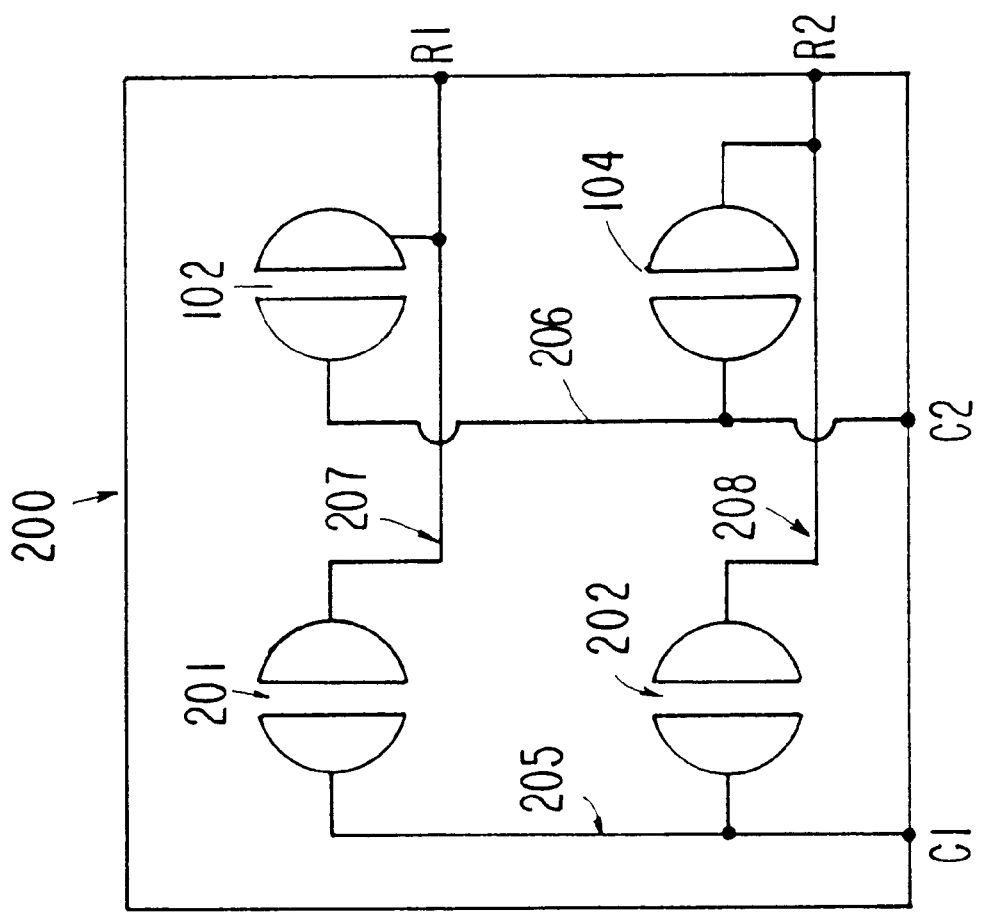

FIG. 15 is a diagram of a support having an array of electrode pairs.

Figure 16:
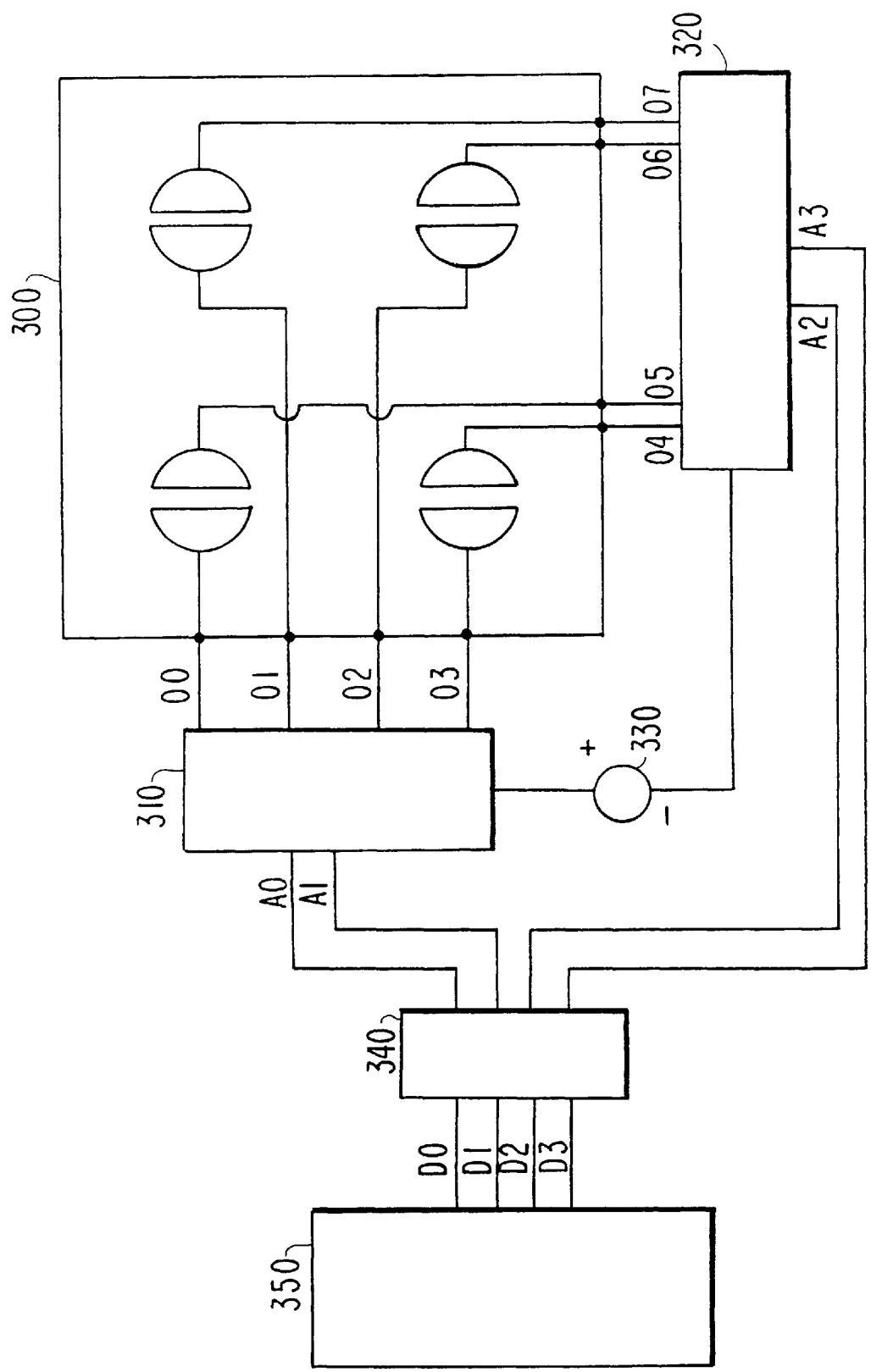

FIG. 16 is a diagram of a support having an array of electrode pairs and computer system for controlling the energization of each electrode pair.

Figure 17:
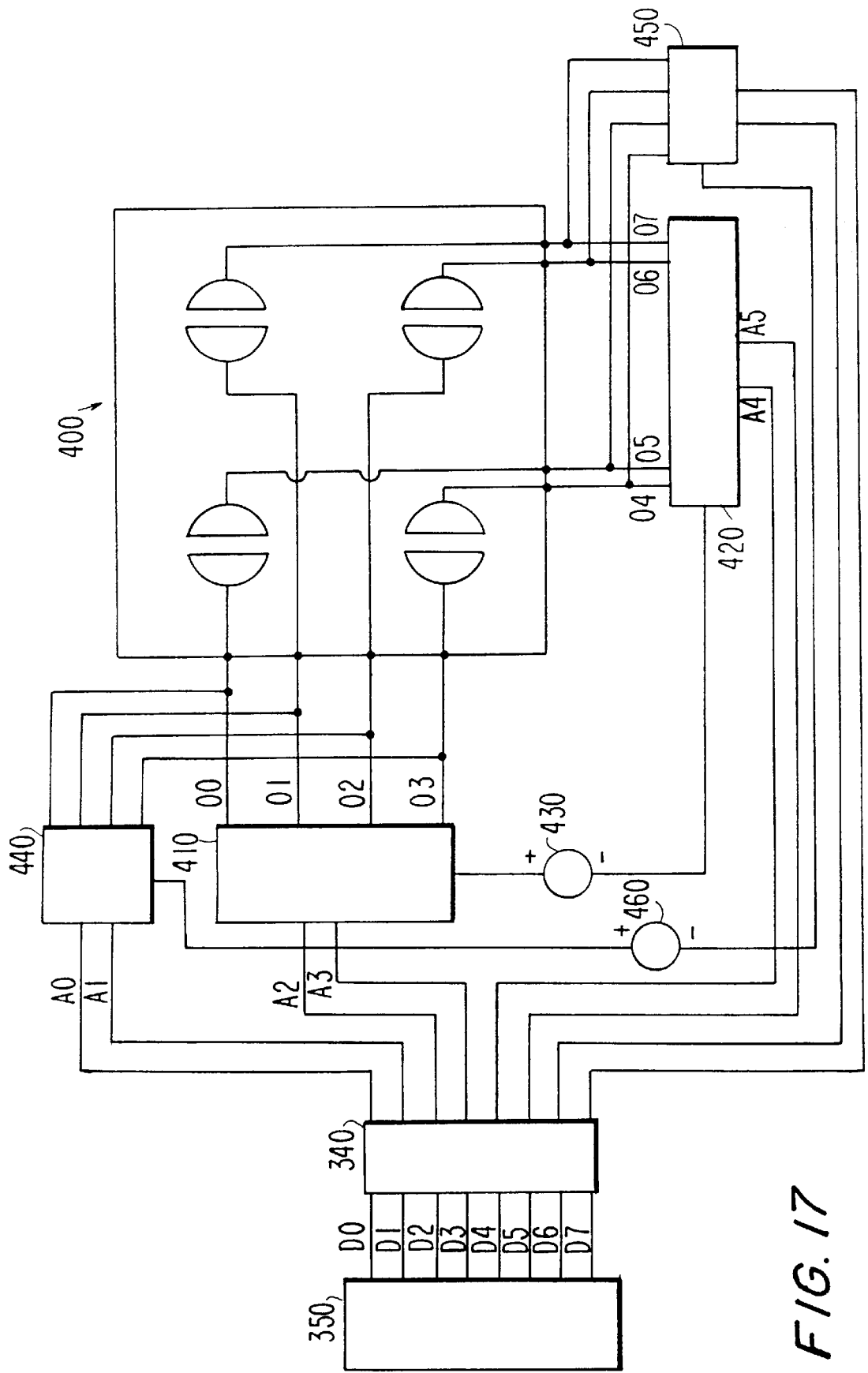

FIG. 17 is a diagram of a support having an array of electrode pairs and a computer system with a plurality of voltage sources and multiplexers for controlling the energization of each electrode pair.

Figure 18:
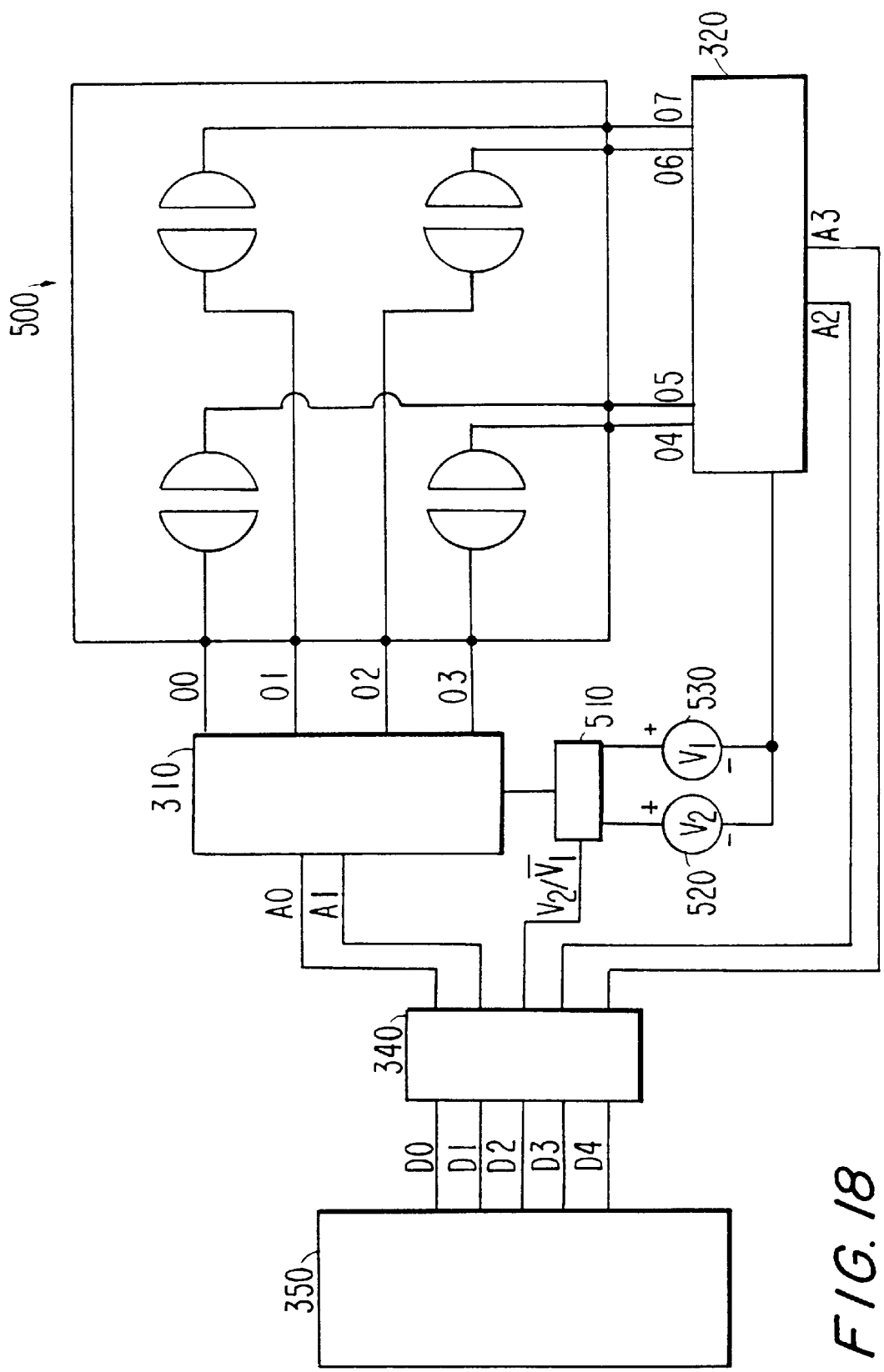

FIG. 18 is a diagram of a support having an array of electrode pairs and a computer system with a plurality of switched voltage sources for controlling the energization of each electrode pair.

FIGS. 19 (a)–(e) are plan views of several alternative electrode-counterelectrode pair combinations.

Figure 20:
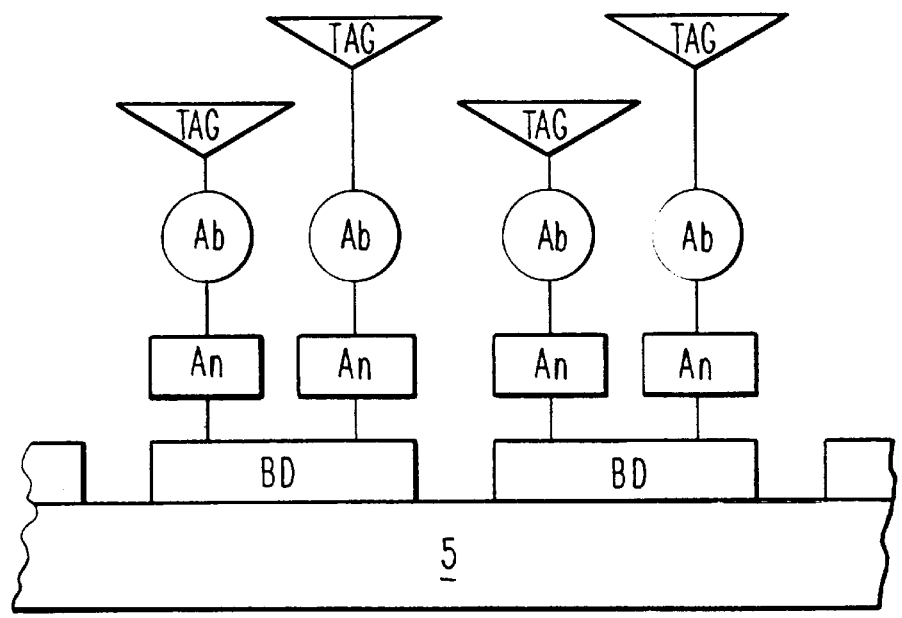

FIG. 20 illustrates a support with a completed sandwich assay.

Figure 21:
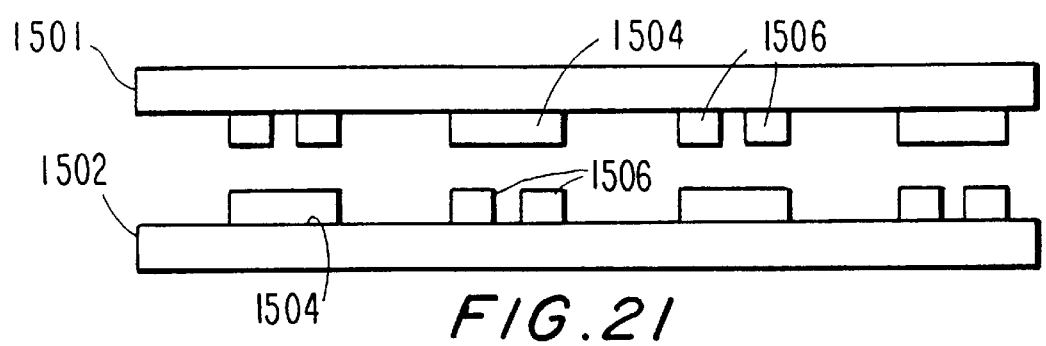

FIG. 21 illustrates two opposing PMAMS surfaces on supports.

Figure 22A:
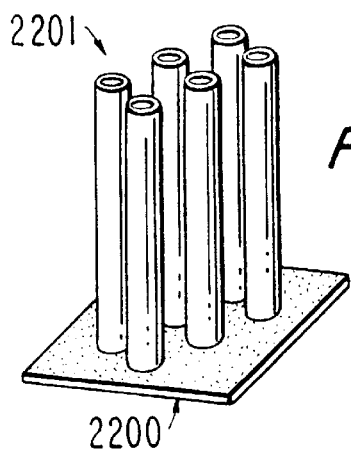

FIG. 22A illustrates an array of microfluidics guides (2201) and a fibril mat (2200).

Figure 22B:
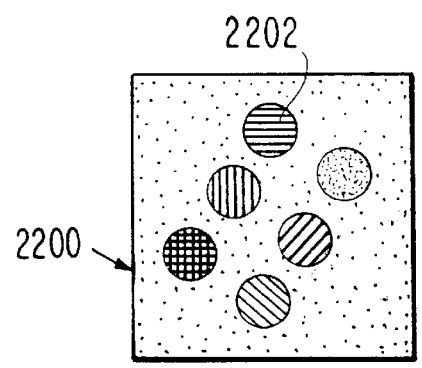

FIG. 22B illustrates binding domains (2202) on a fibril mat (2200).

Figure 23A:
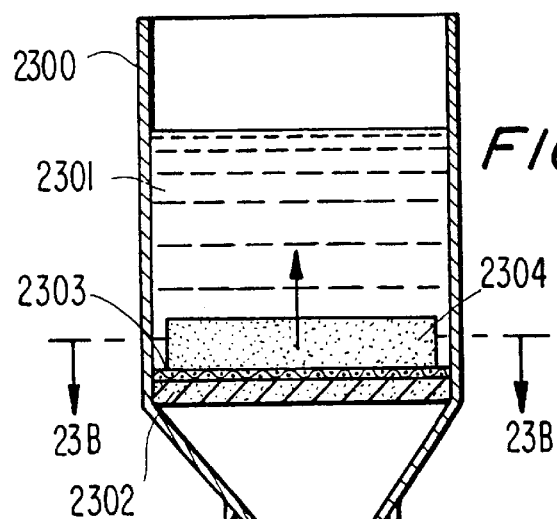

FIG. 23A illustrates an apparatus for forming a fibril mat by vacuum filtration.

Figure 23B:
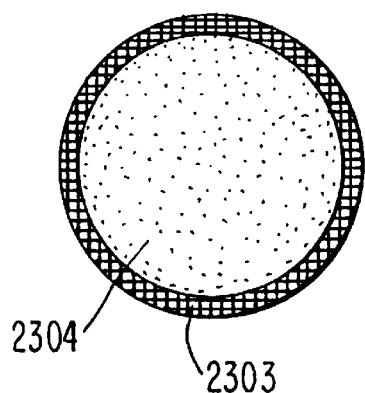

FIG. 23B illustrates a fibril mat (2304) on a filter membrane (2303).

Figure 24:
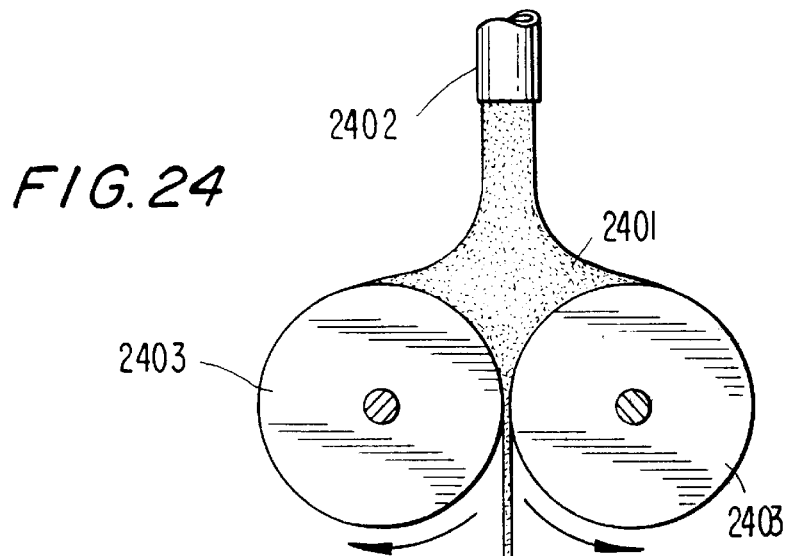

FIG. 24 illustrates the use of rollers to produce fibril mats.

Figure 25:
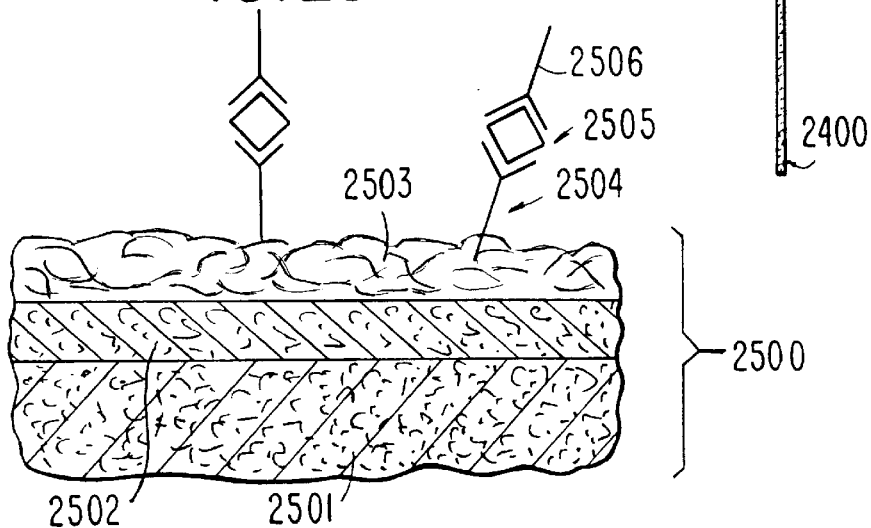

FIG. 25 shows a schematic of a multi-layer fibril mat, in which the upper layer has binding domains used for assays.

Figure 26:
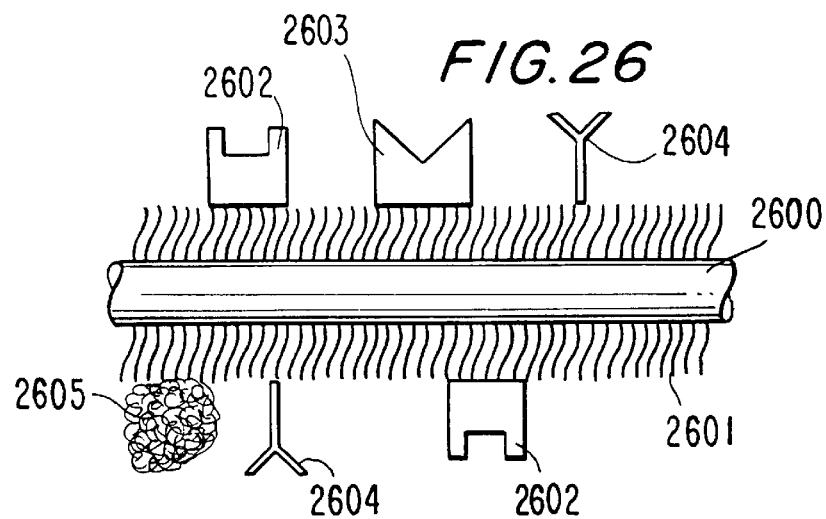

FIG. 26 shows a schematic of a fibril derivatized with moieties that enhance non-specific binding, and several species, both biological and non-biological are bound to the surface.

Figure 27:
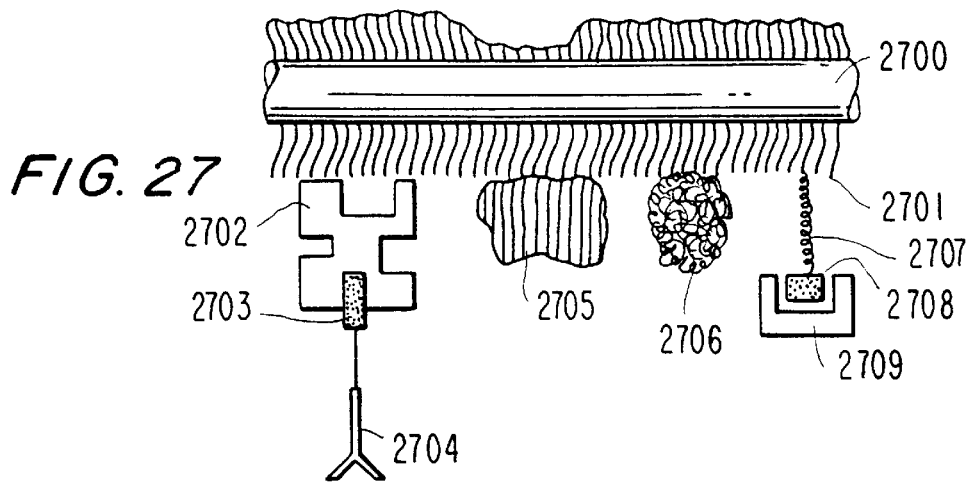

FIG. 27 shows a schematic of a fibril derivatized with moieties that enhance non-specific binding and several species bound to a derivatized fibril with some species additionally bound to ligands.

Figure 28:
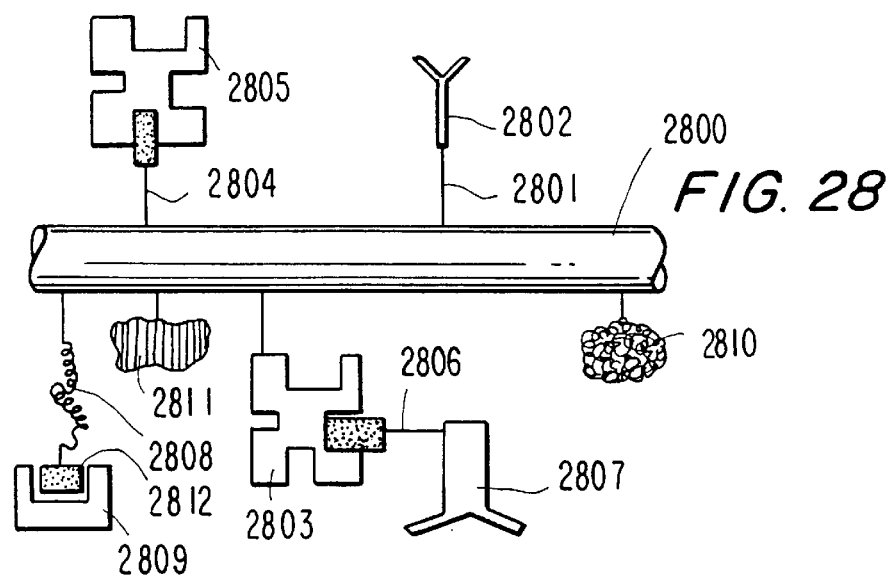

FIG. 28 illustrates several species covalently attached to a fibril and some species are further bound to additional entities.

Figure 29:
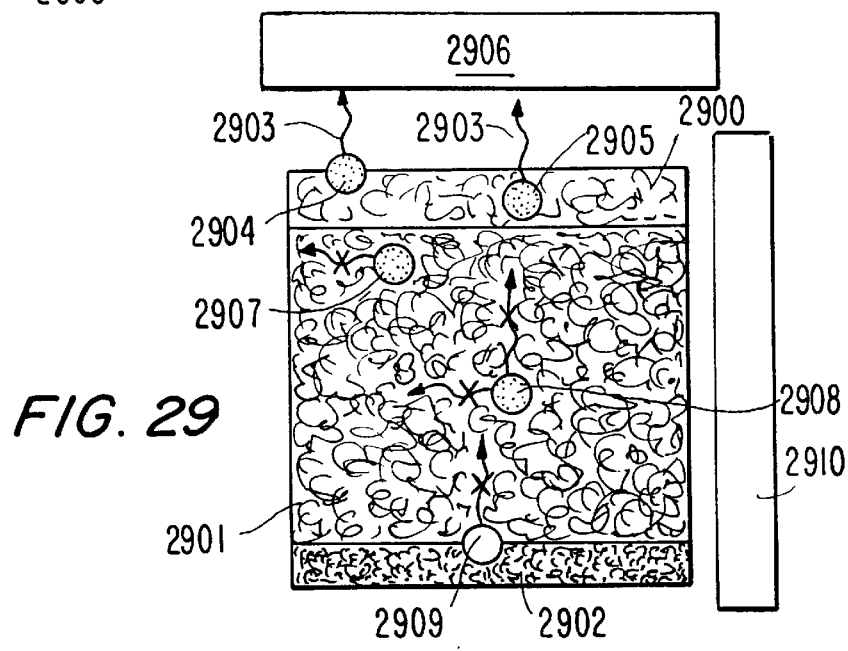

FIG. 29 illustrates the use of a multilayer fibril mat as an optical filter that, depending on the position of a source of light on or within the mat, may allow light to pass and/or may absorb and/or scatter light.

Figure 30A:
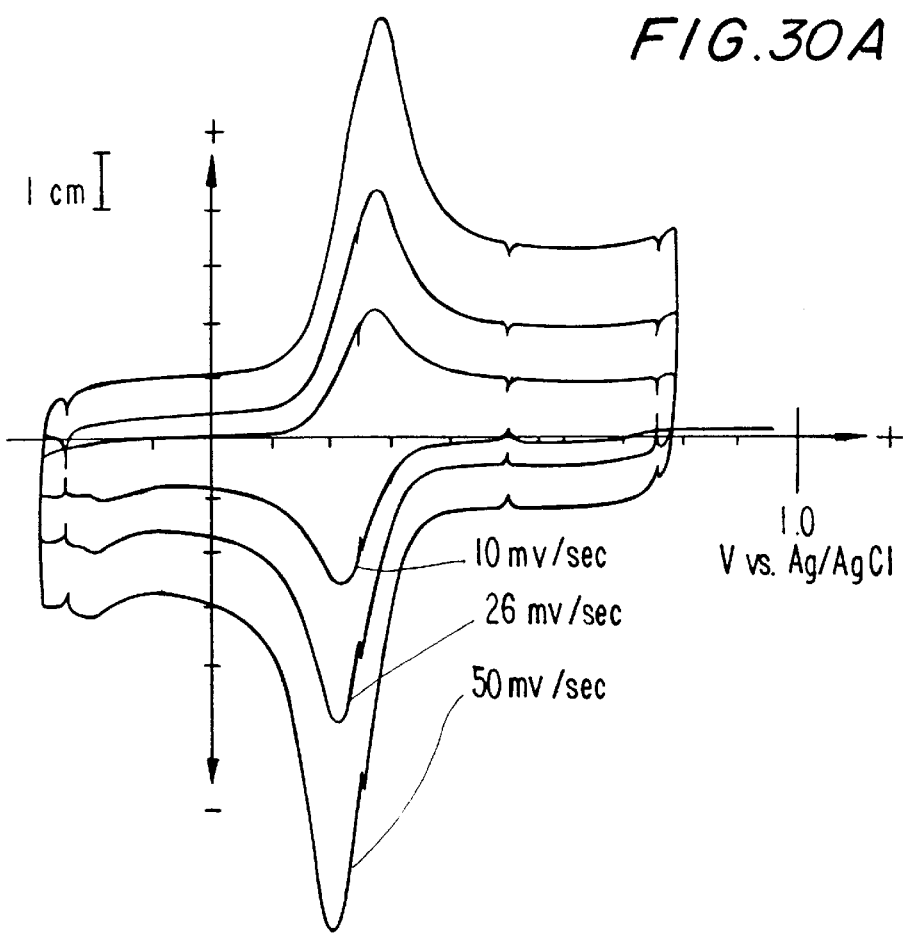

FIG. 30A illustrates cyclic voltammograms from electrochemical measurements on carbon fibril mat electrodes.

Figure 30B:
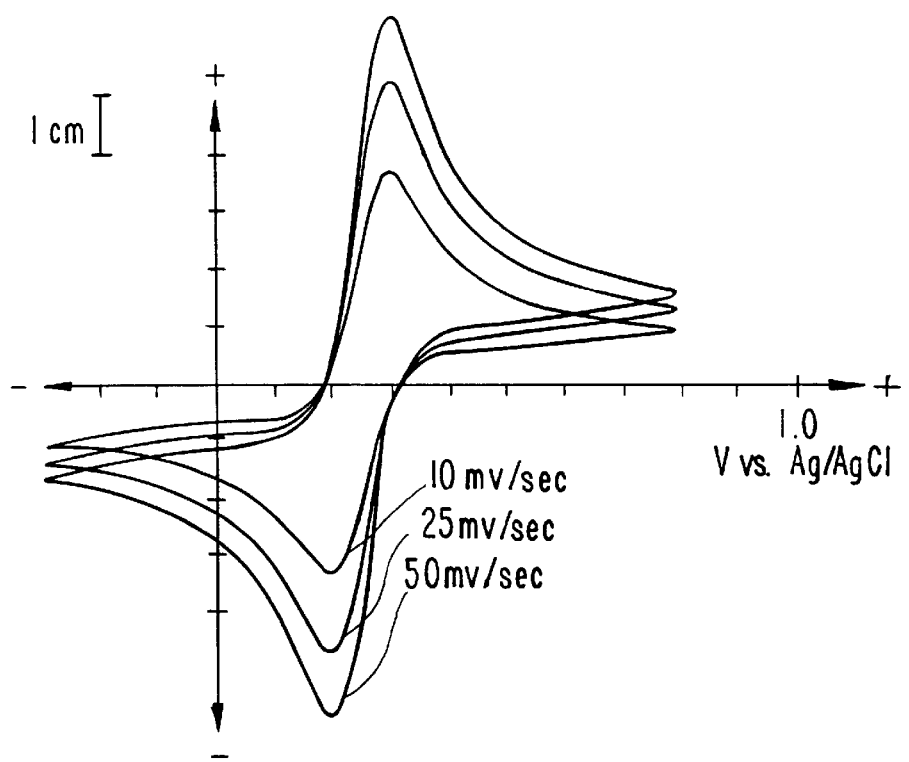

FIG. 30B illustrates cyclic voltammograms from electrochemical measurements on gold foil electrodes.

Figure 31:
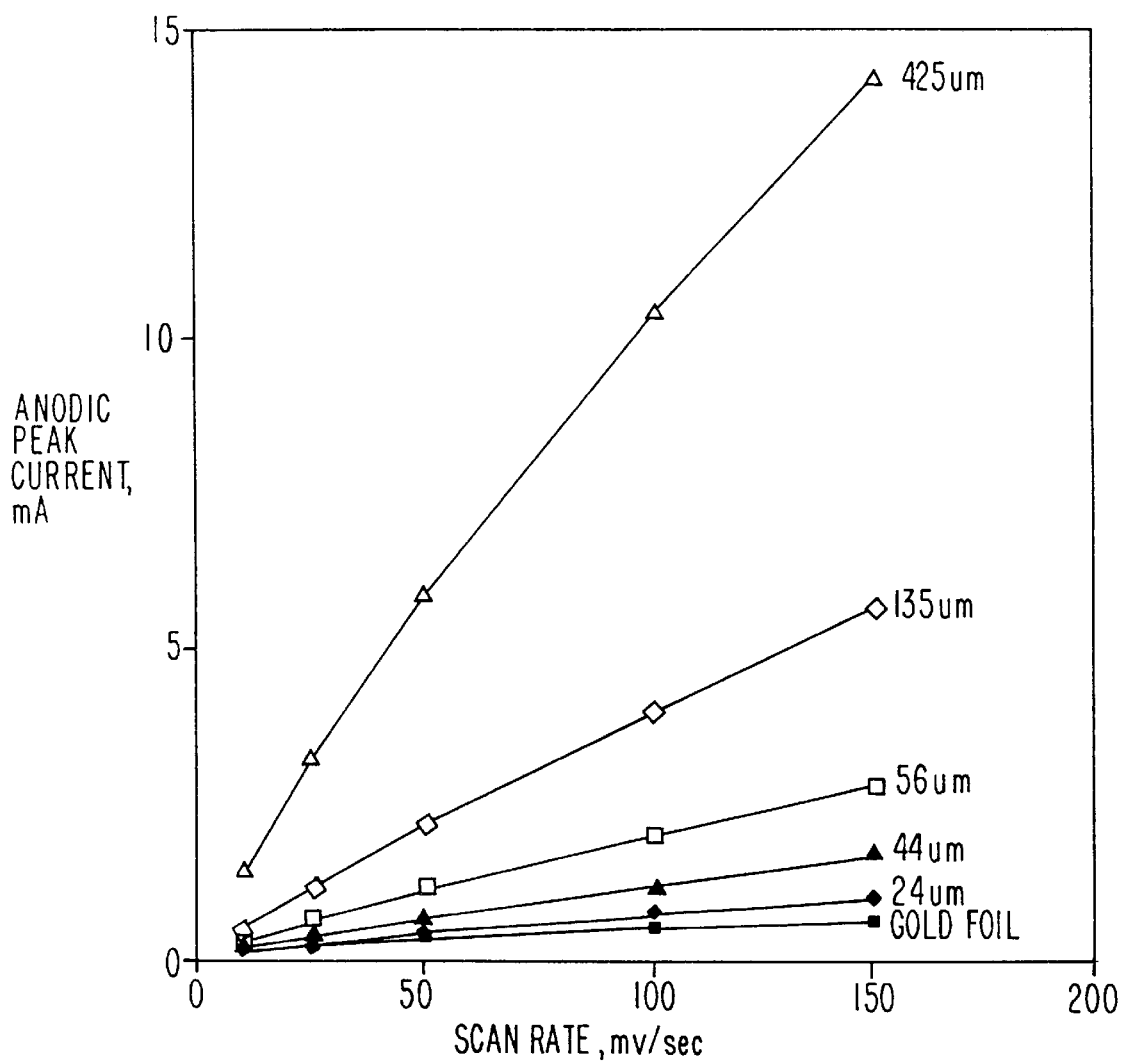

FIG. 31 compares an electrochemical property of fibril mats as a function of the thickness of the mat and the scan rate.

Figure 32:
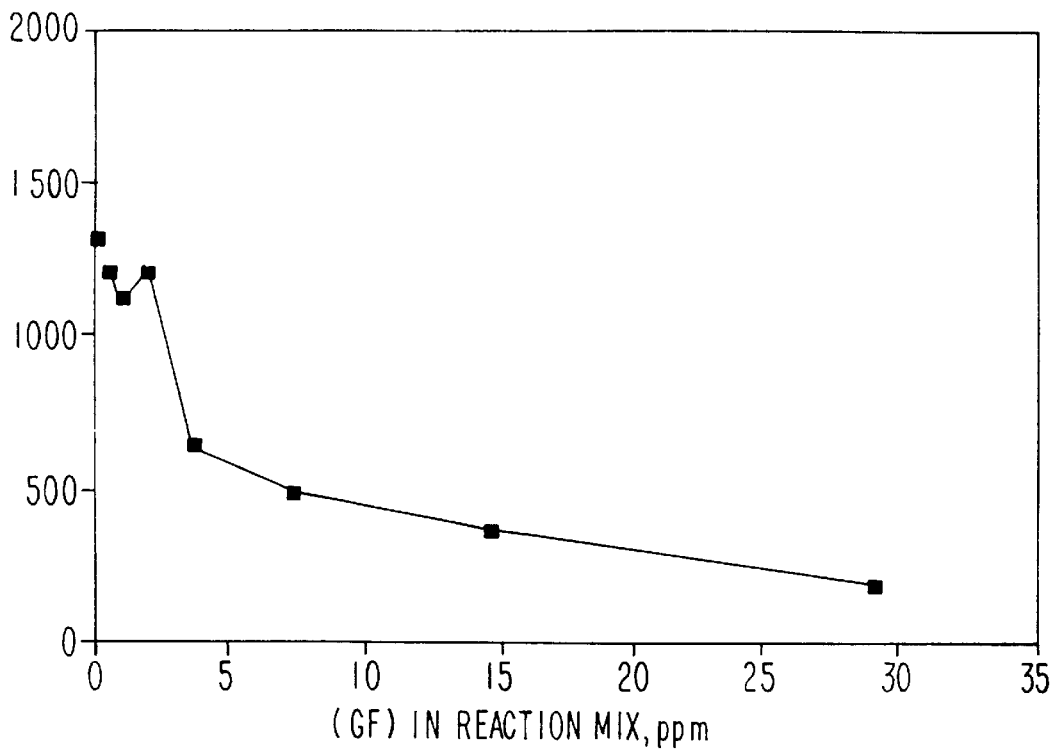

FIG. 32 shows a plot that illustrates that non-specific binding on fibrils generally increases as the concentration of fibrils in a protein solution increases.

Figure 33:
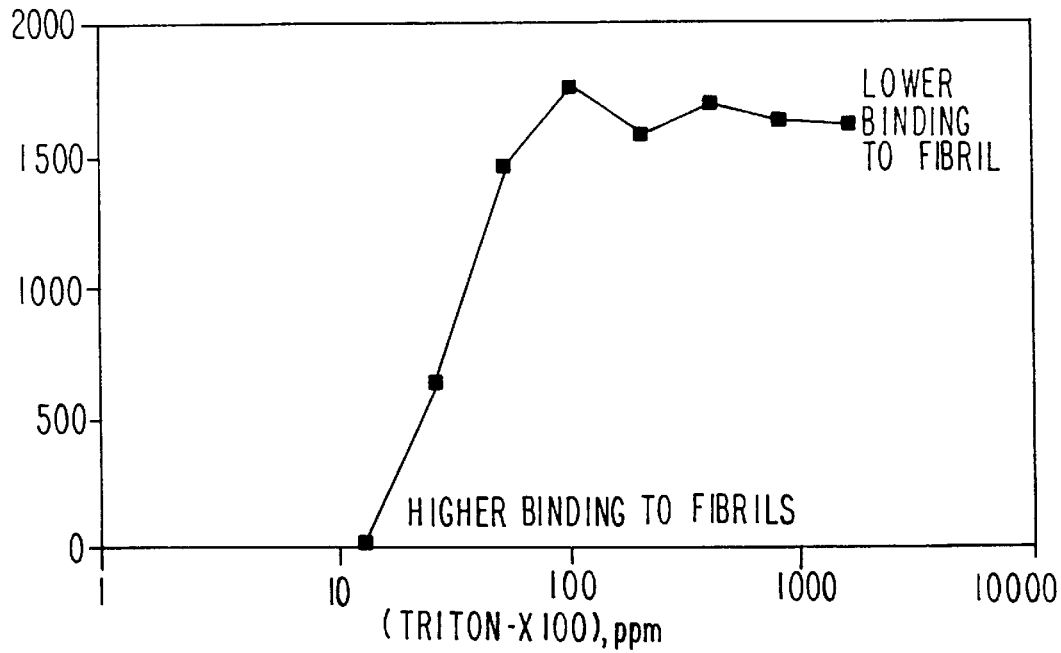

FIG. 33 demonstrates that the use of surfactants can reduce non-specific binding between ECL-TAG1-labeled protein and carbon fibrils.

Figure 34:
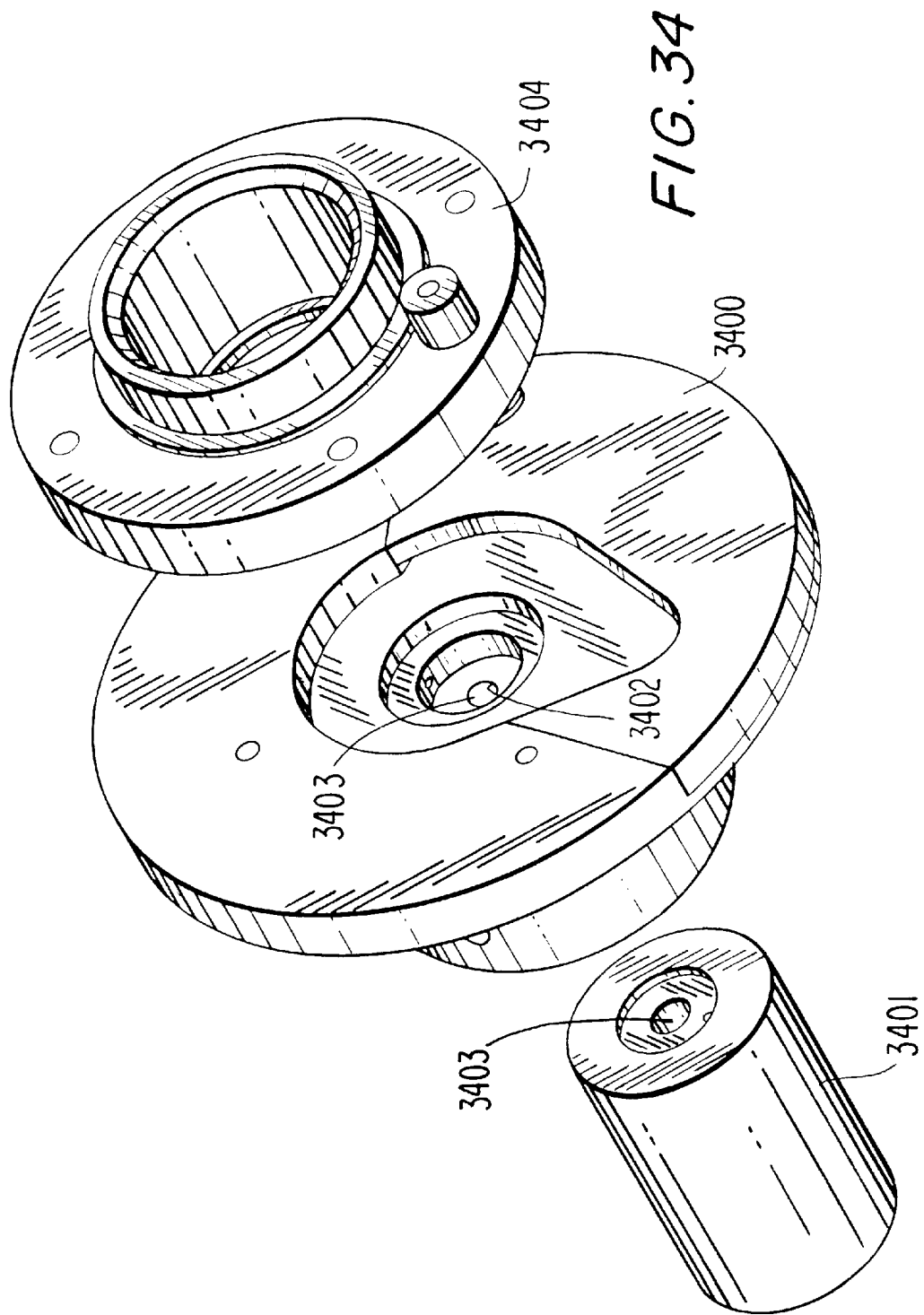

FIG. 34 shows a schematic of a top view of an experimental cell used to measure electrochemical properties and ECL on a fibril mat electrode.

Figure 35:
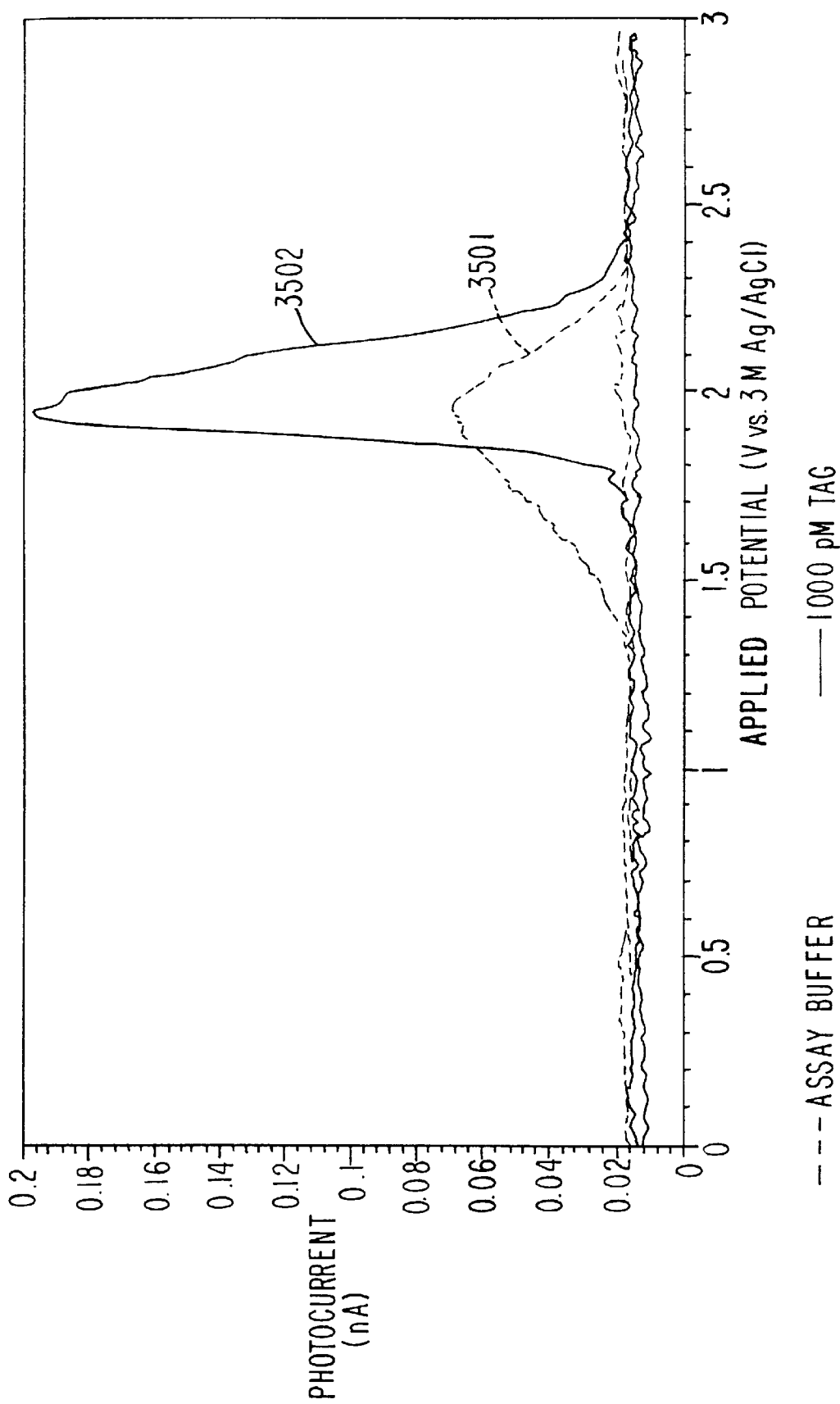

FIG. 35 shows an ECL signal obtained using a fibril mat as an electrode and 1000 pM TAG1 (solid line) in solution and a signal from assay buffer (no TAG1) (dashed line).

Figure 36:
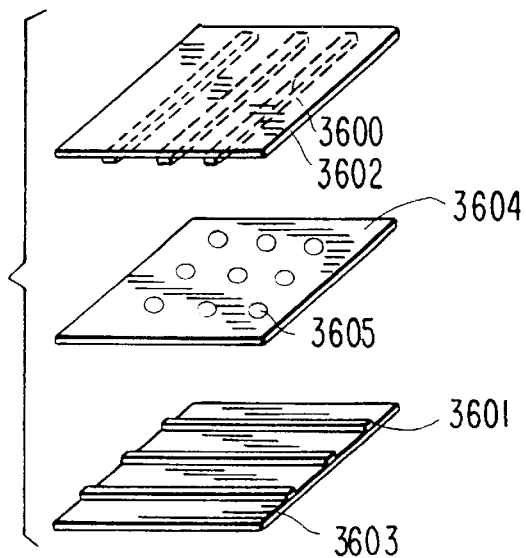

FIG. 36 shows a schematic of a two surface PMAMS device, in which two arrays of supported electrodes are separated by a patterned dielectric layer.

Figure 37:
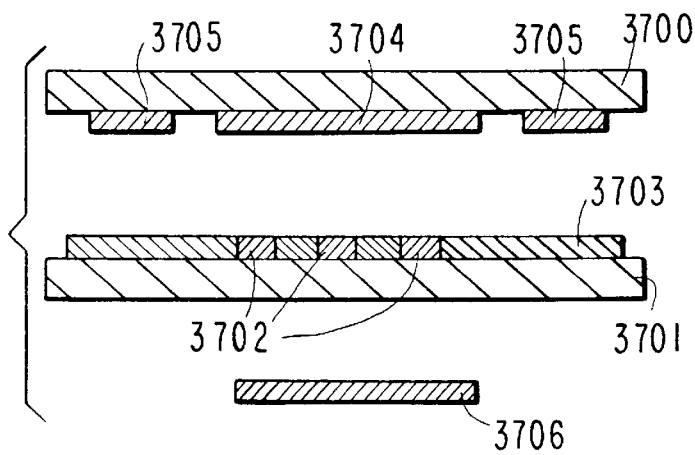

FIG. 37 illustrates an apparatus with a plurality of binding domains (3702) on one support and an electrode and counterelectrode on another support.

Figure 38:
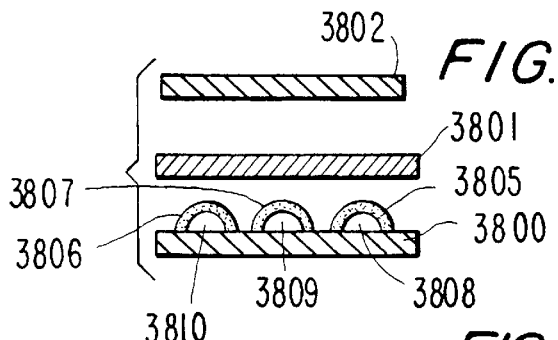

FIG. 38 shows a cassette where binding domains are presented on the surfaces of distinct objects supported on the counter electrode.

Figure 39:
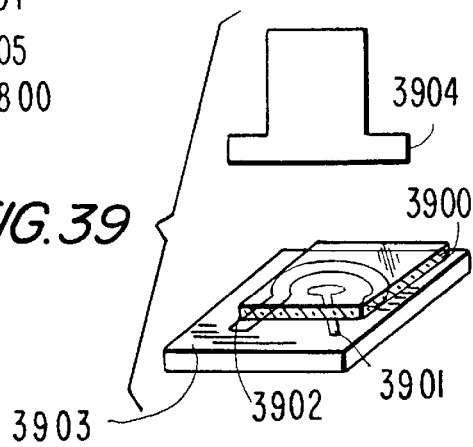

FIG. 39 shows a gel in contact with a working and counterelectrode.

Figure 40:
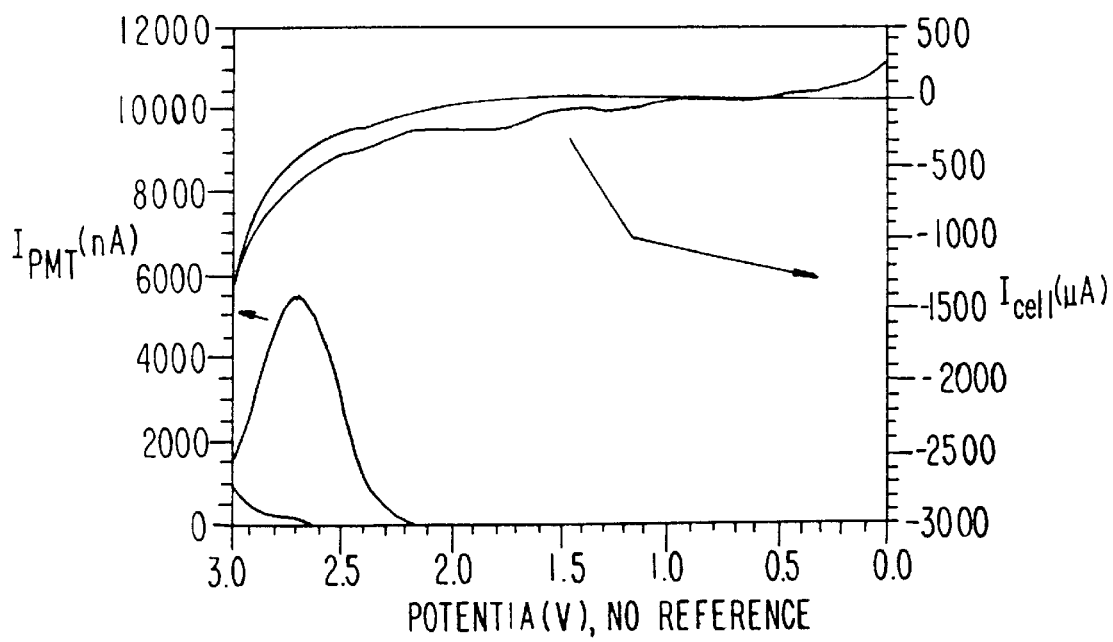

FIG. 40 shows a graph of ECL intensity and a cyclic voltammogram from an ECL labeled gel in contact with a working and counterelectrode.

Figure 41:
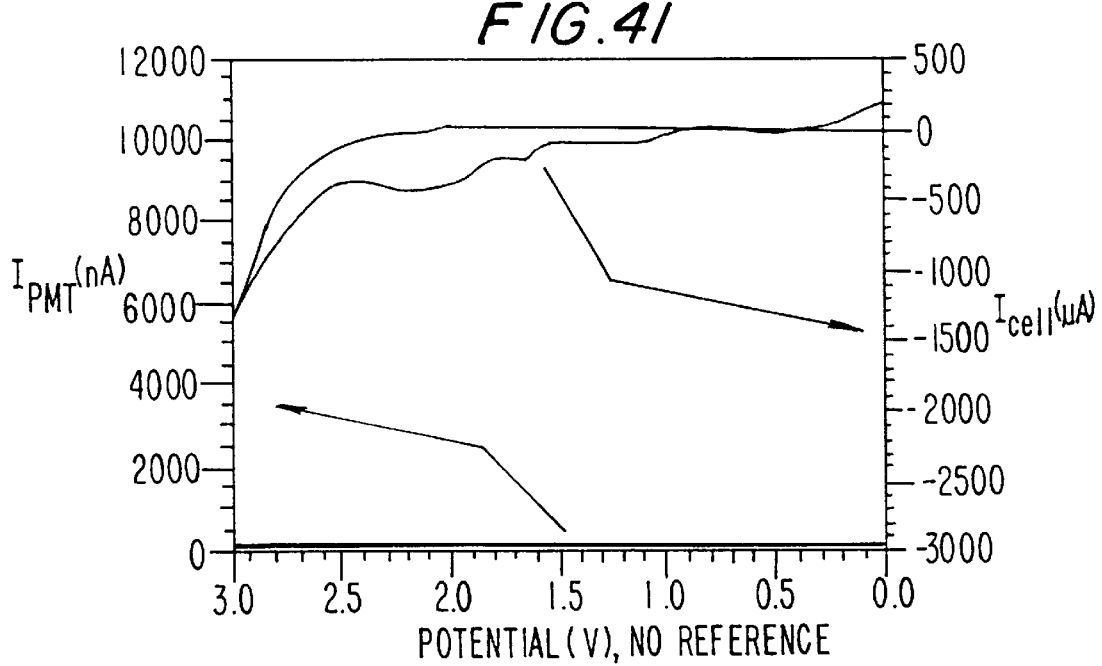

FIG. 41 shows a graph of ECL intensity and a cyclic voltammogram from a non-ECL labeled gel in contact with a working and counterelectrode.

FIG. 42 shows a schematic for a two-surface cassette used for ECL.

FIG. 43 demonstrates that fibril mats can be used as electrodes for ECL of Antibody-TAG1 adsorbed to the mats.

Figure 44B:
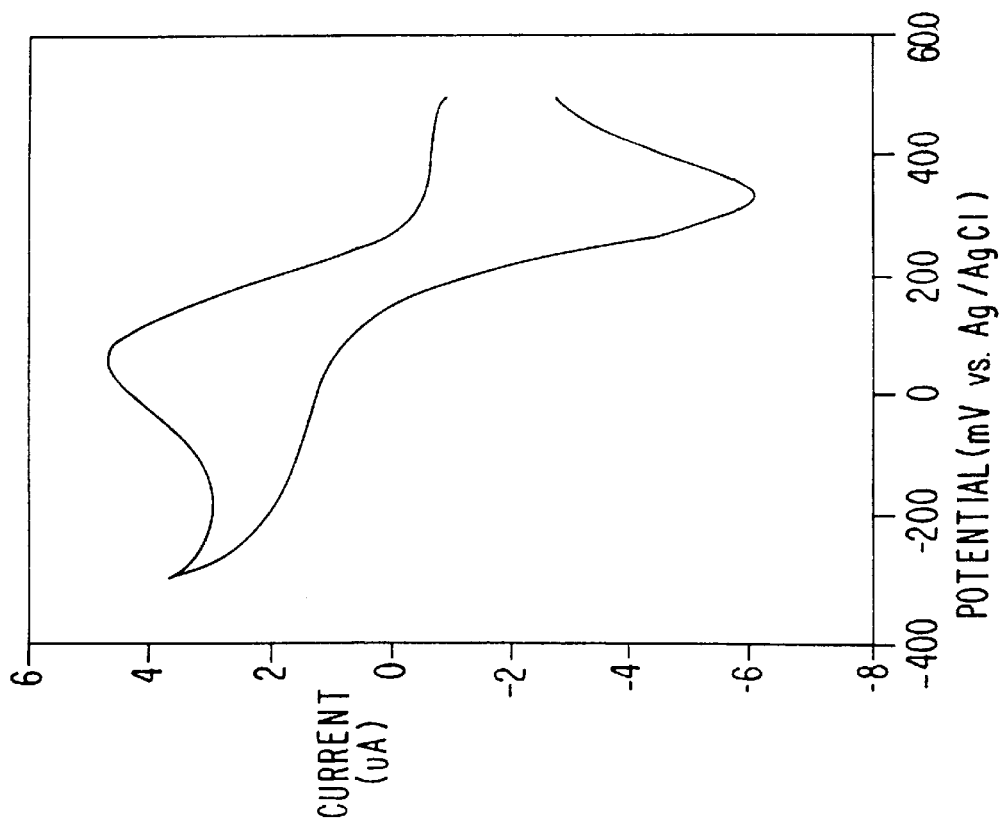
Figure 44A:
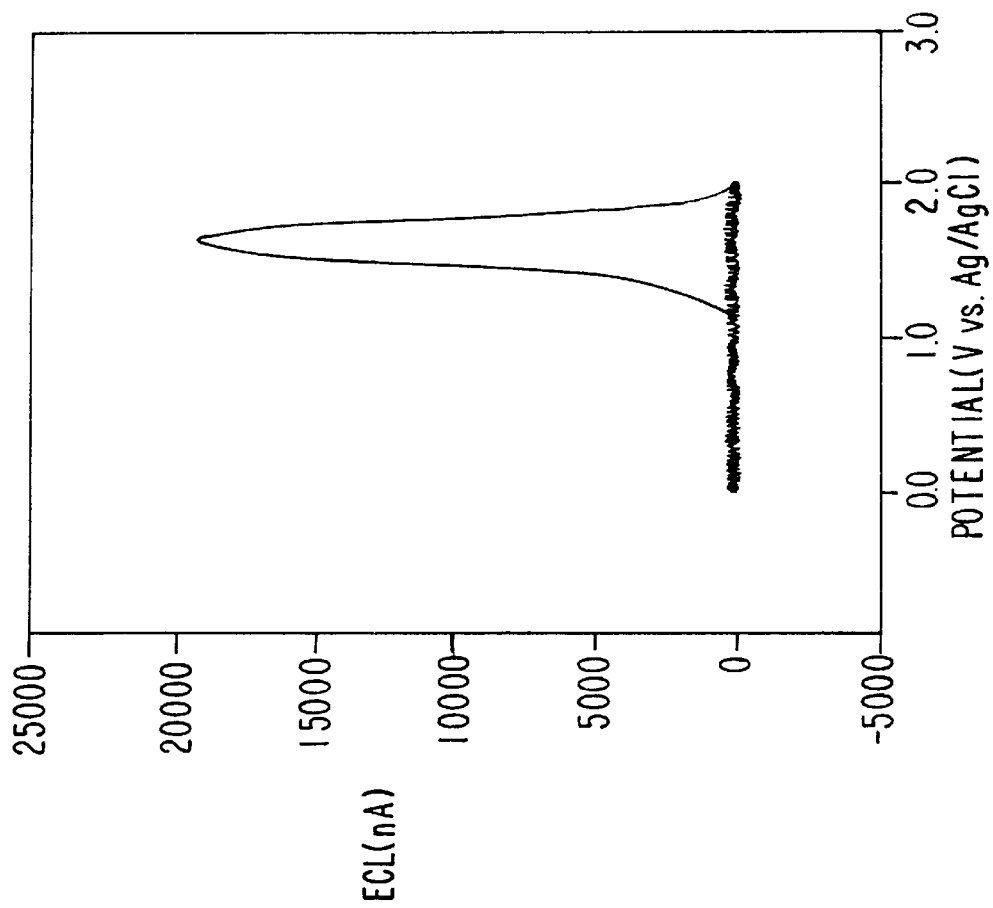

FIG. 44A shows ECL intensity of a TAG1 labeled protein immobilized on an electrode.

FIG. 44B shows the cyclic voltammogram of a coated electrode.

Figure 45B:
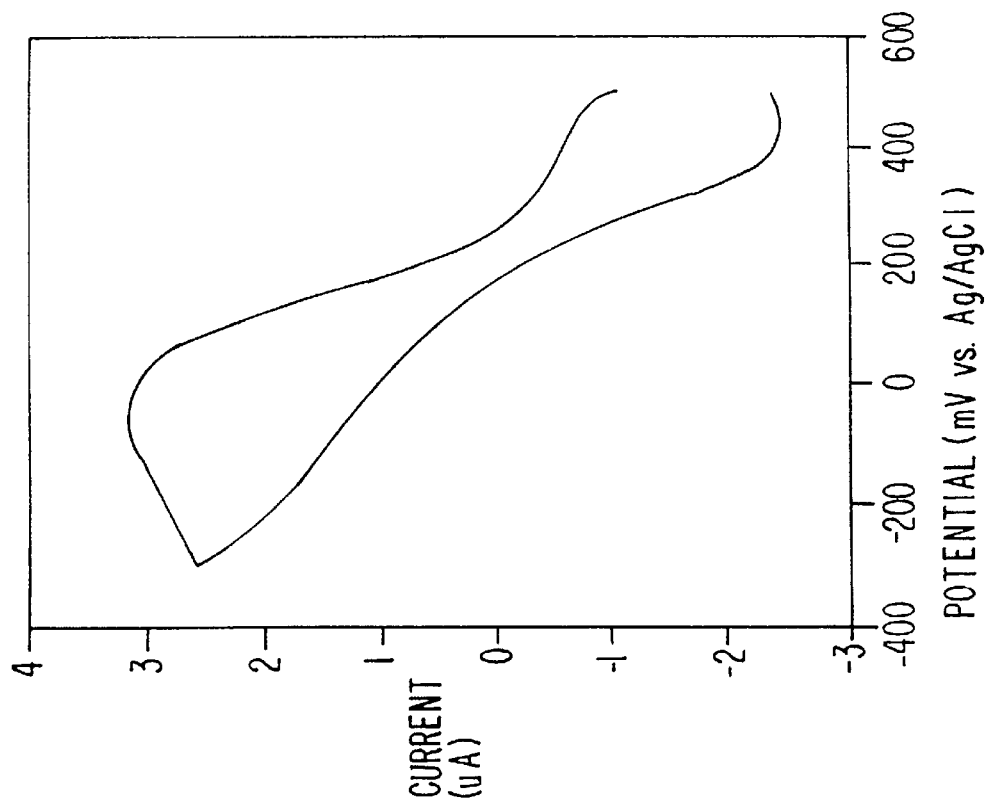
Figure 45A:
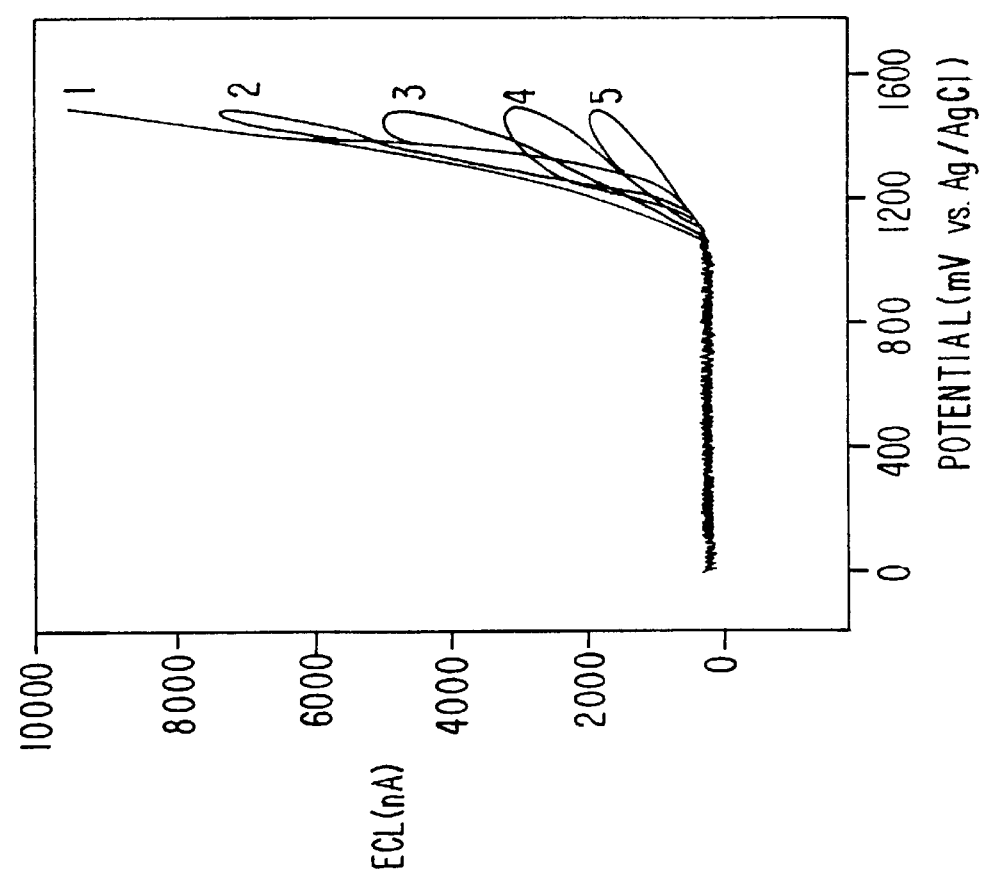

FIG. 45A shows quasi-reversible repetitive generation of ECL signal from an immobilized ECL TAG1 labeled protein.

FIG. 45B shows the cyclic voltammogram of a coated electrode indicating partial preservation of the coating.

FIG. 46A shows irreversible generation of ECL signal from an immobilized ECL TAG1 labeled protein.

FIG. 46B shows the cyclic voltammogram of a coated electrode indicating substantial loss of the coating.

Figure 47:
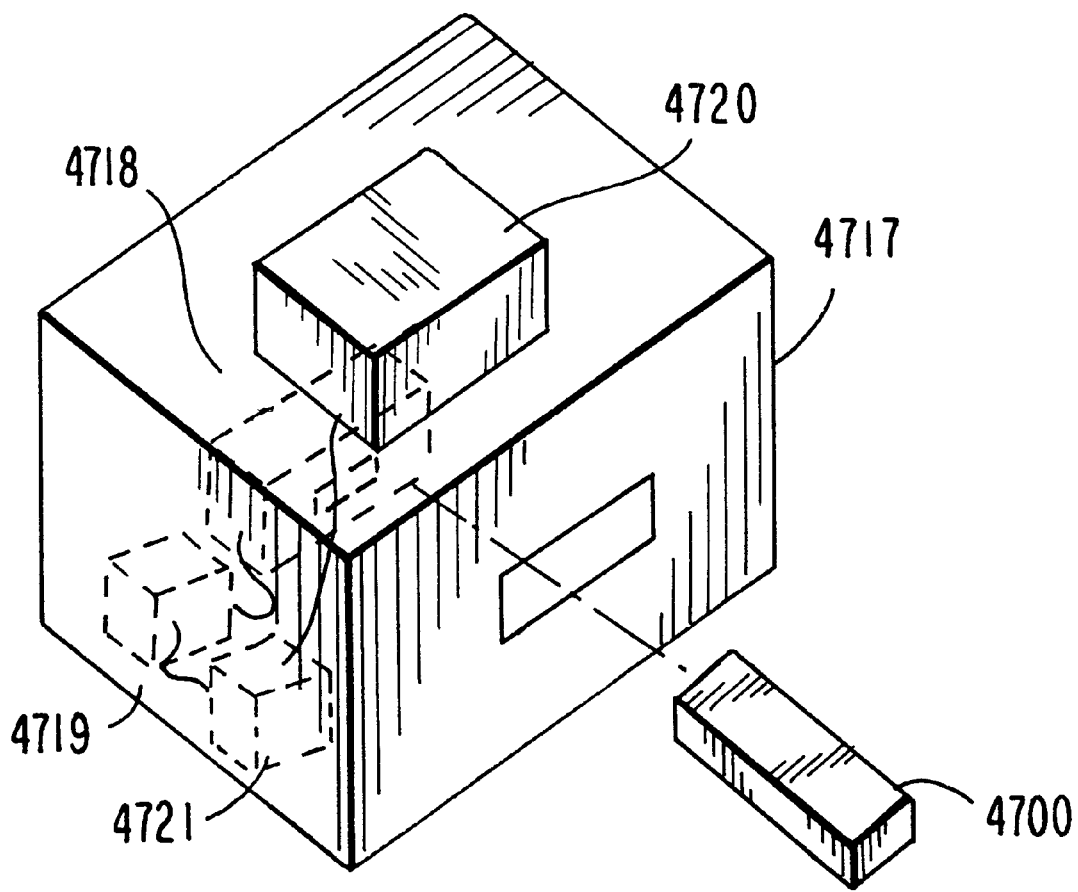

FIG. 47 shows a multi-array ECL apparatus and a microprocessor containing controller means for generating and analyzing ECL signals.

Figure 48:
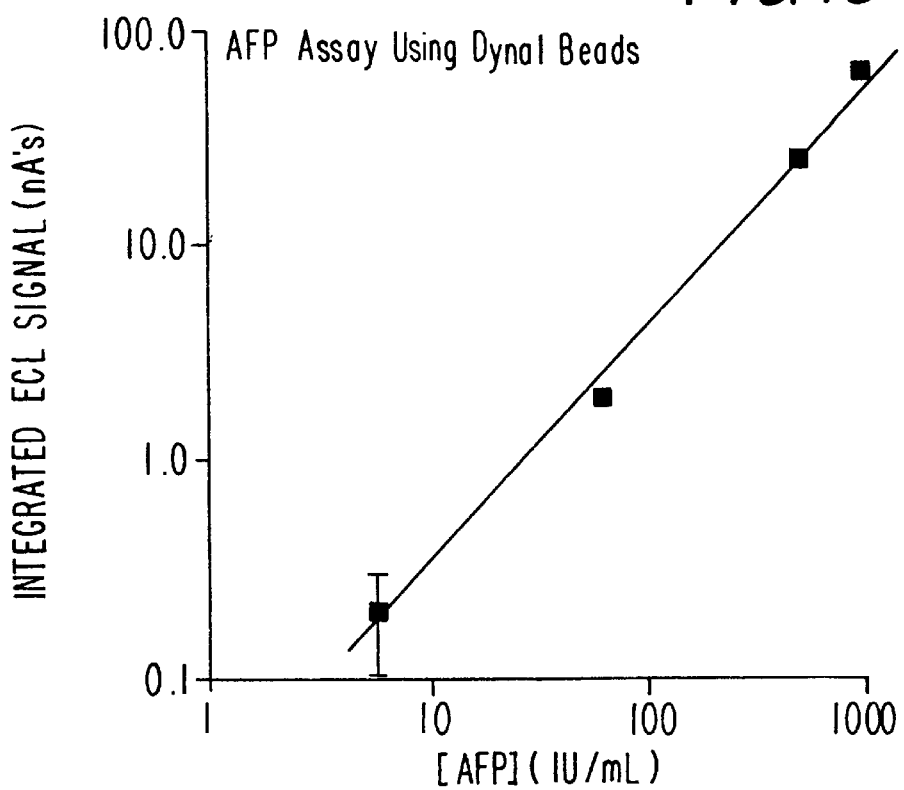

FIG. 48 shows the dose response for an AFP immunoassay that involves formation of a sandwich complex on streptavidin-coated Dynal beads, capture of the beads on a fibril mat electrode, and detection of the bound complex by ECL.

Figure 49:
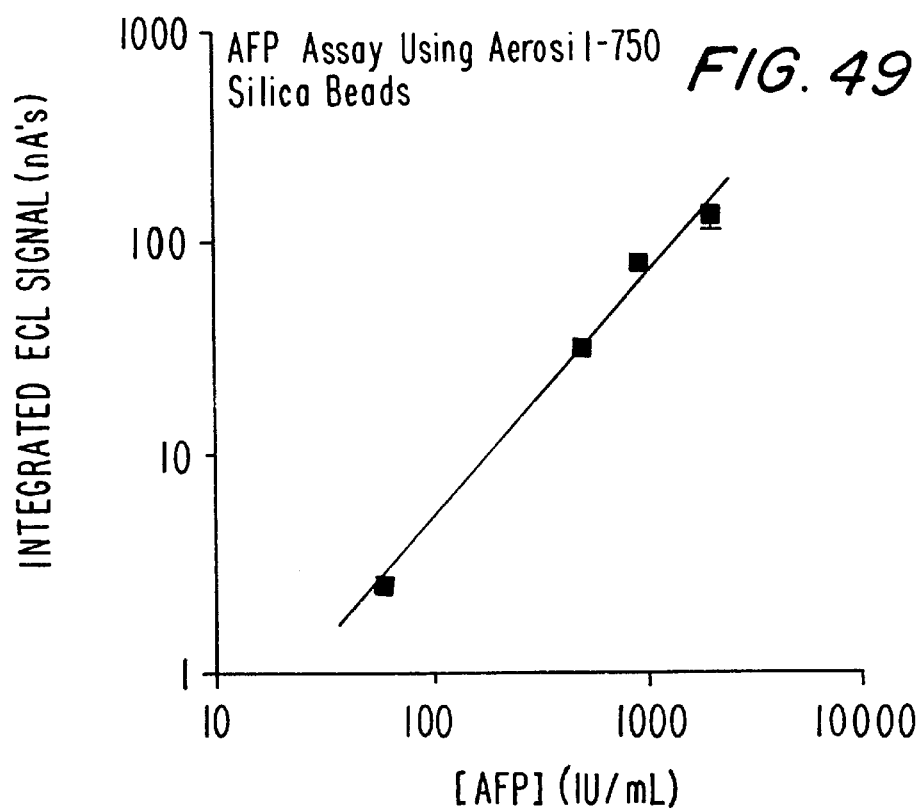

FIG. 49 shows the dose response for an AFP immunoassay that involves the formation of a sandwich complex on streptavidin-coated silica particles, the capture of the particles on a fibril mat electrode, and detection of the bound complex by ECL.

Figure 50:
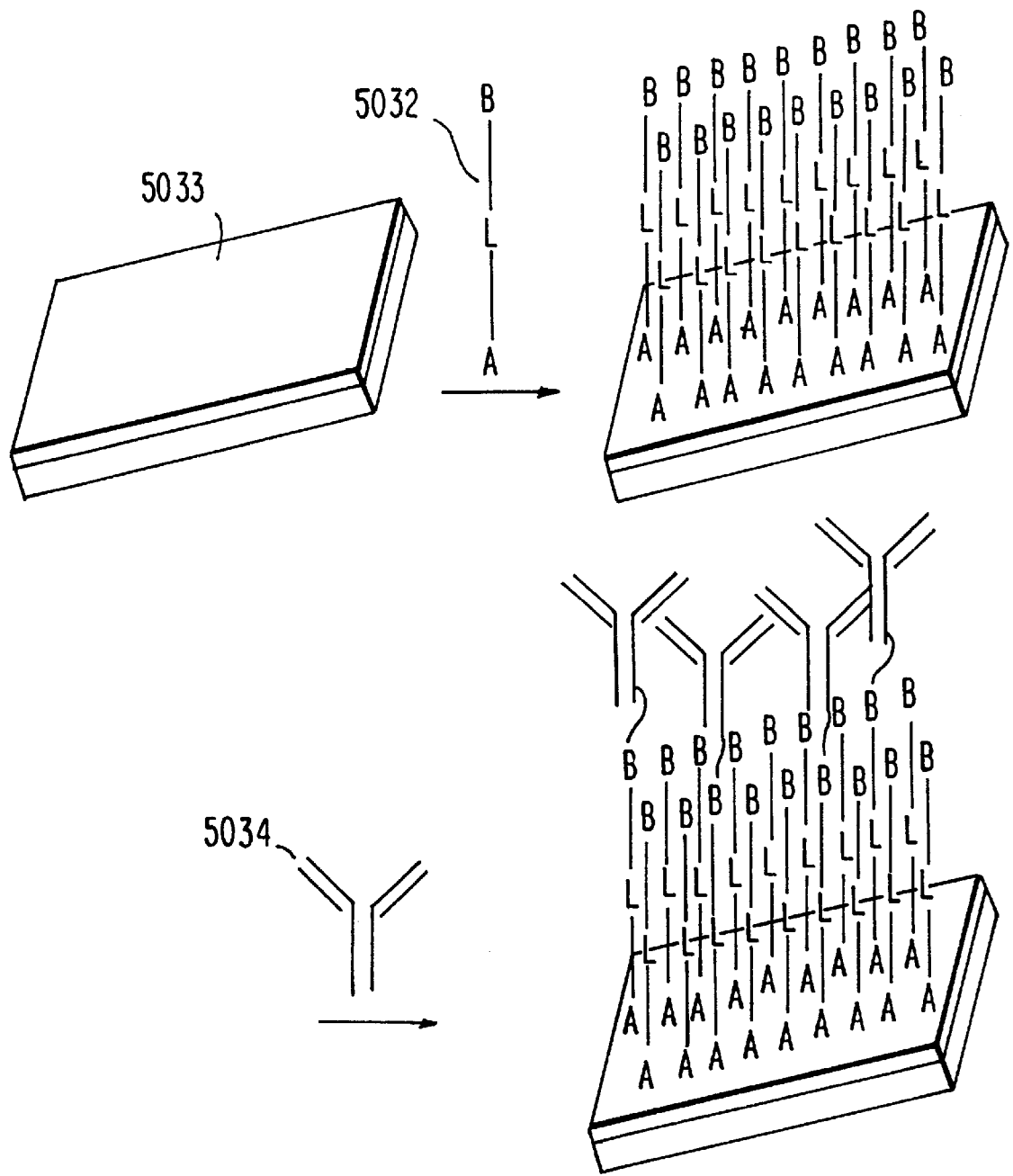

FIG. 50 shows a schematic describing the use of a SAM for immobilizing binding reagents on a surface.

Figure 51:
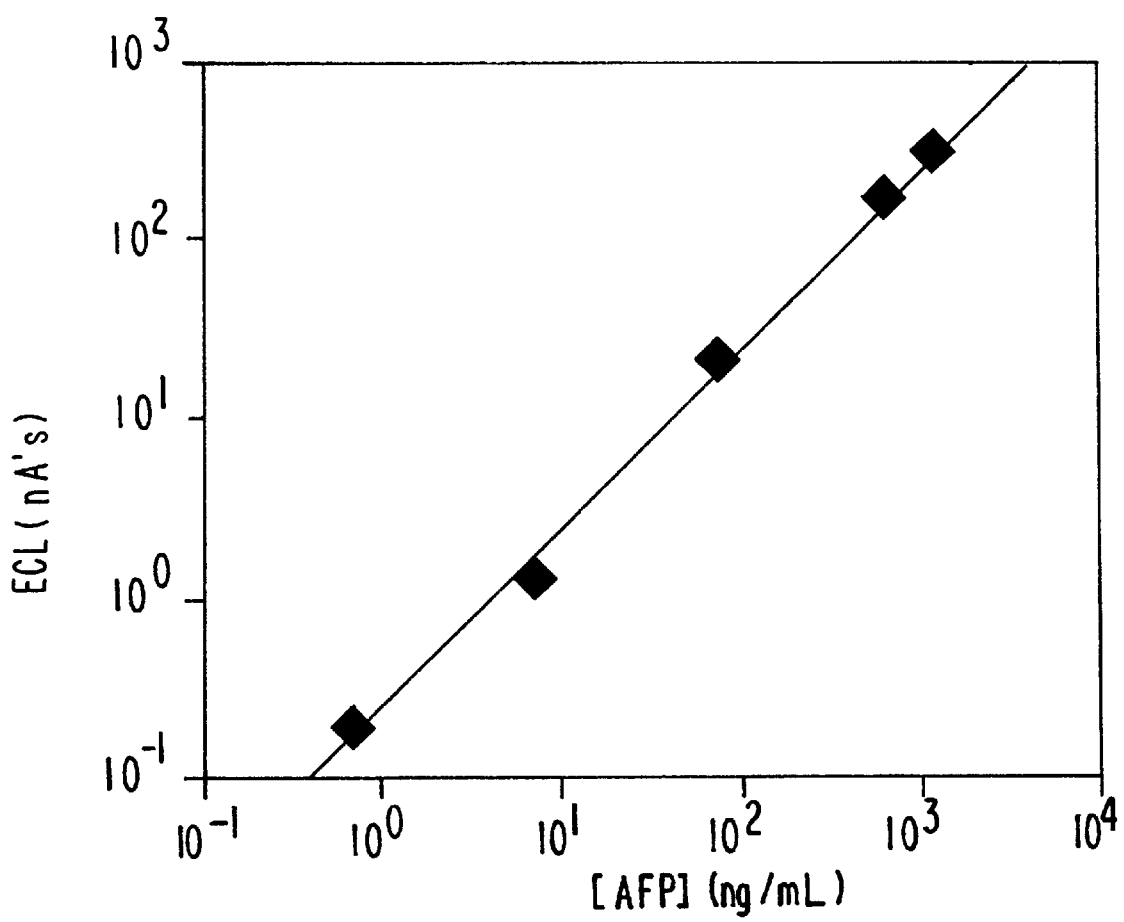

FIG. 51 shows the dose response for an AFP immunoassay that involves the formation of a sandwich complex on a streptavidin-coated SAM of alkanethiolates on a gold electrode, and detection of the bound complex by ECL.

Figure 52:
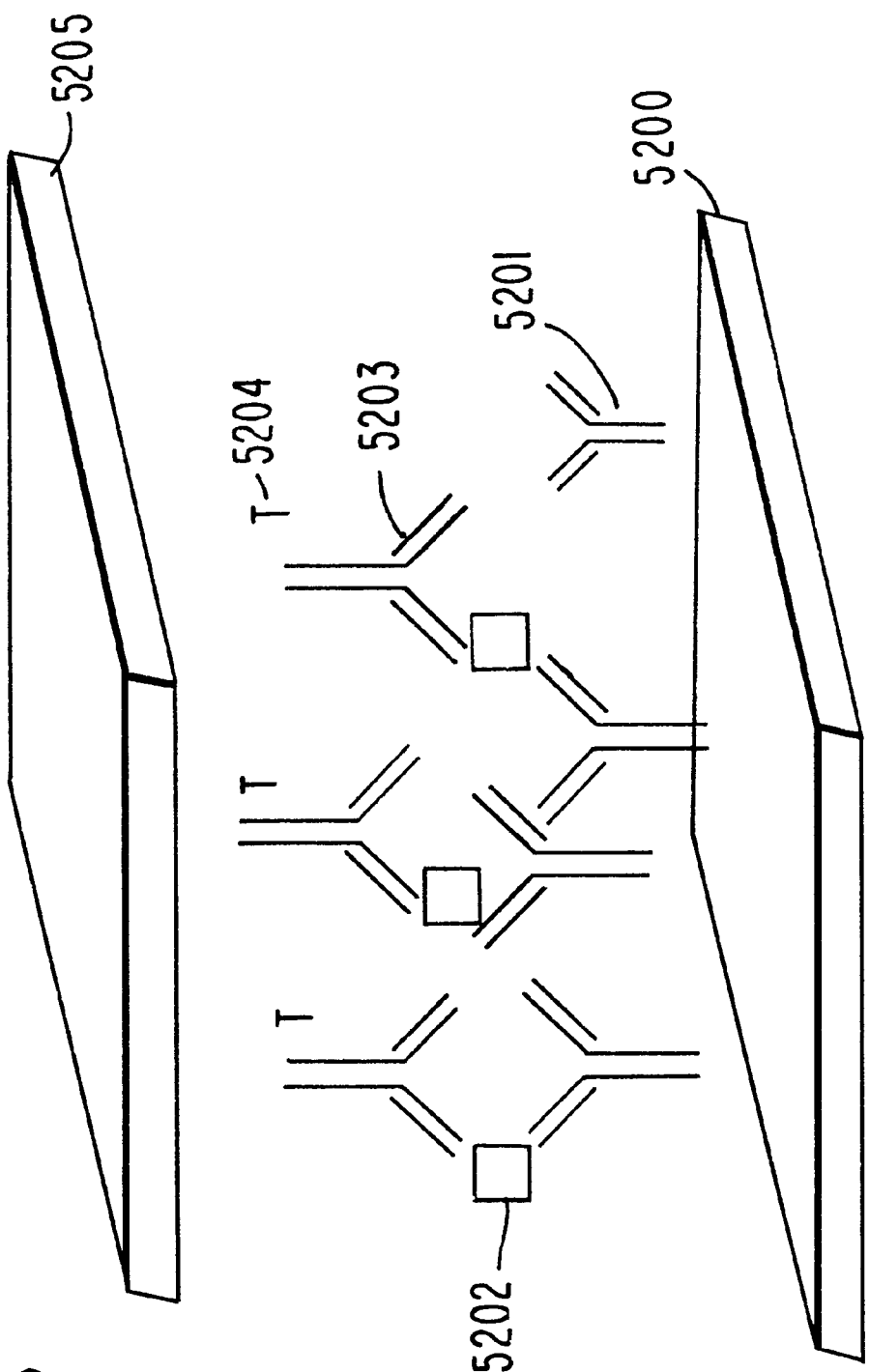

FIG. 52 illustrates the presentation of TAG moieties to the working electrode in a "Two Surface" assay.

Figure 53A:
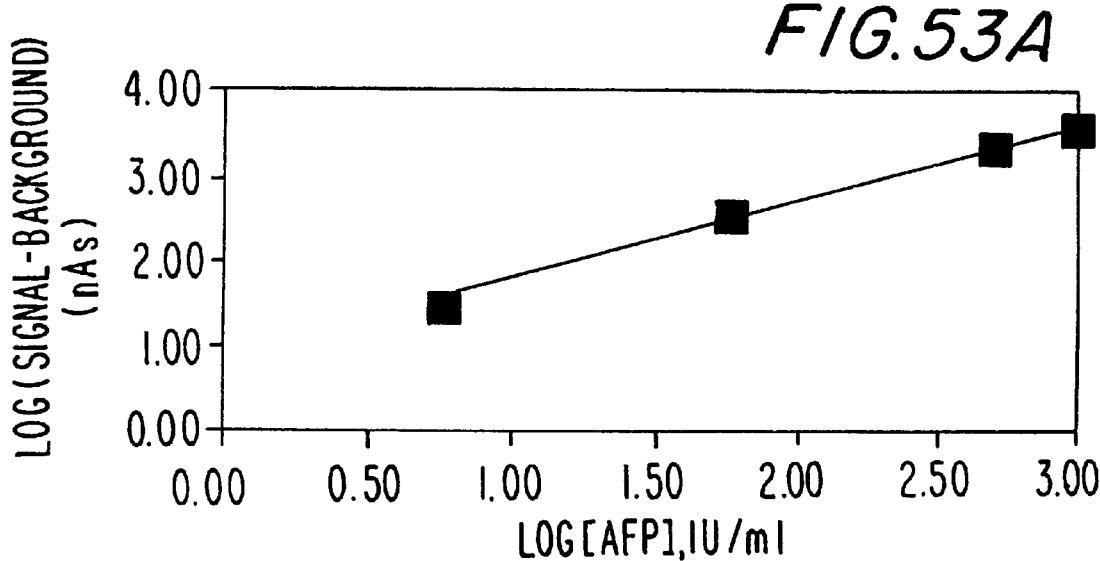
Figure 53B:
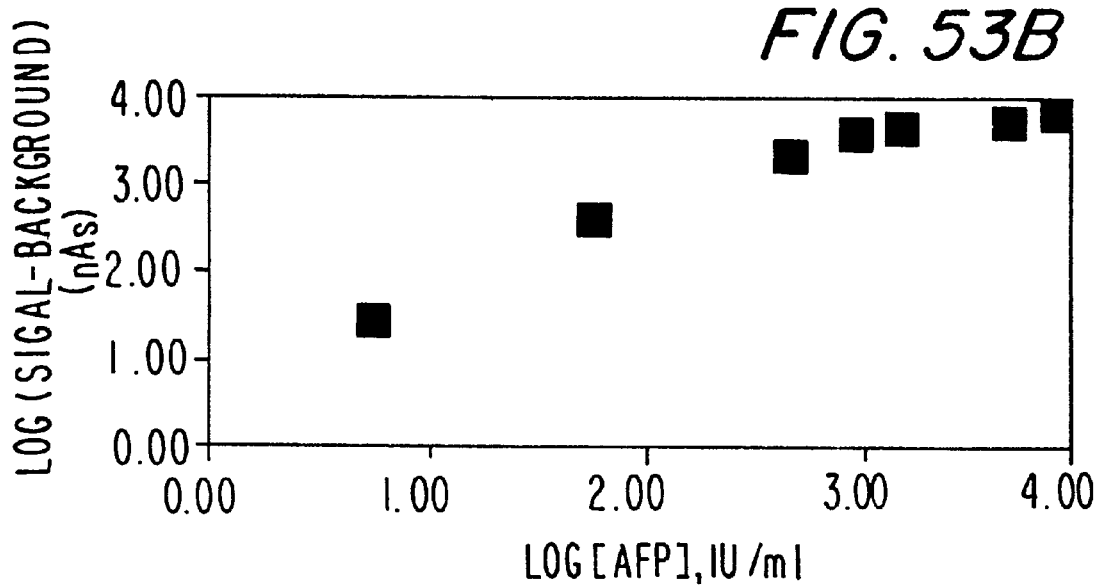

FIG. 53 shows the dose response for an AFP immunoassay that involves formation of a sandwich complex on a streptavidin-coated, oxidized, EVA-fibril composite and detection of the bound complex by ECL.

FIG. 54 shows the dose response for a nucleic acid hybridization assay that involves formation of a nucleic acid sandwich complex on a streptavidin-coated, oxidized, EVA-fibril composite and detection of the bound complex by ECL.

Figure 55:
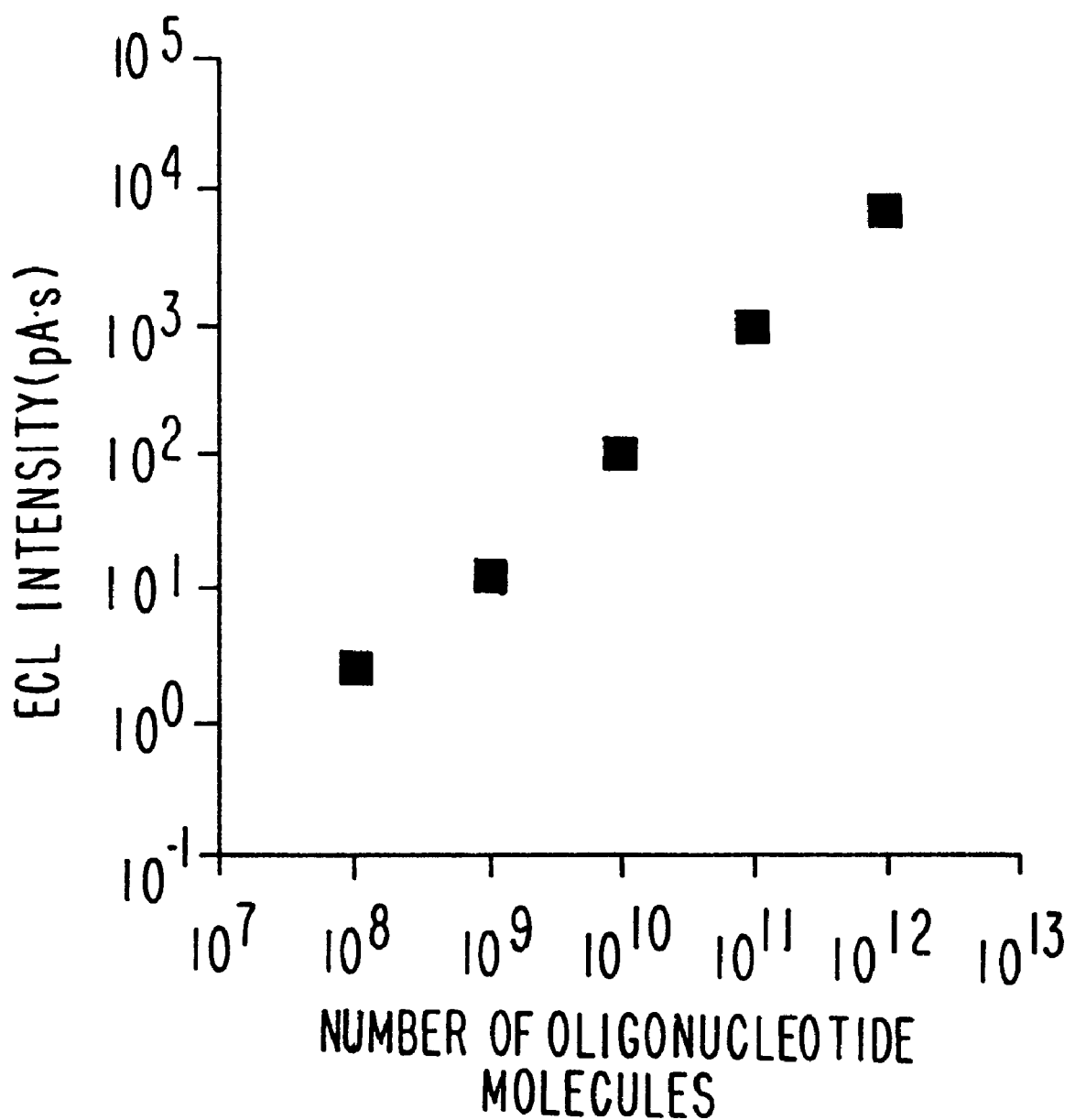

FIG. 55 shows the dose response for a DNA assay that involves hybridization of a biotin-labeled oligonucleotide to a TAG1 labeled oligonucleotide, capture of the complex on a streptavidin-coated fibril mat electrode and detection of the bound complex by ECL.

Figure 56:
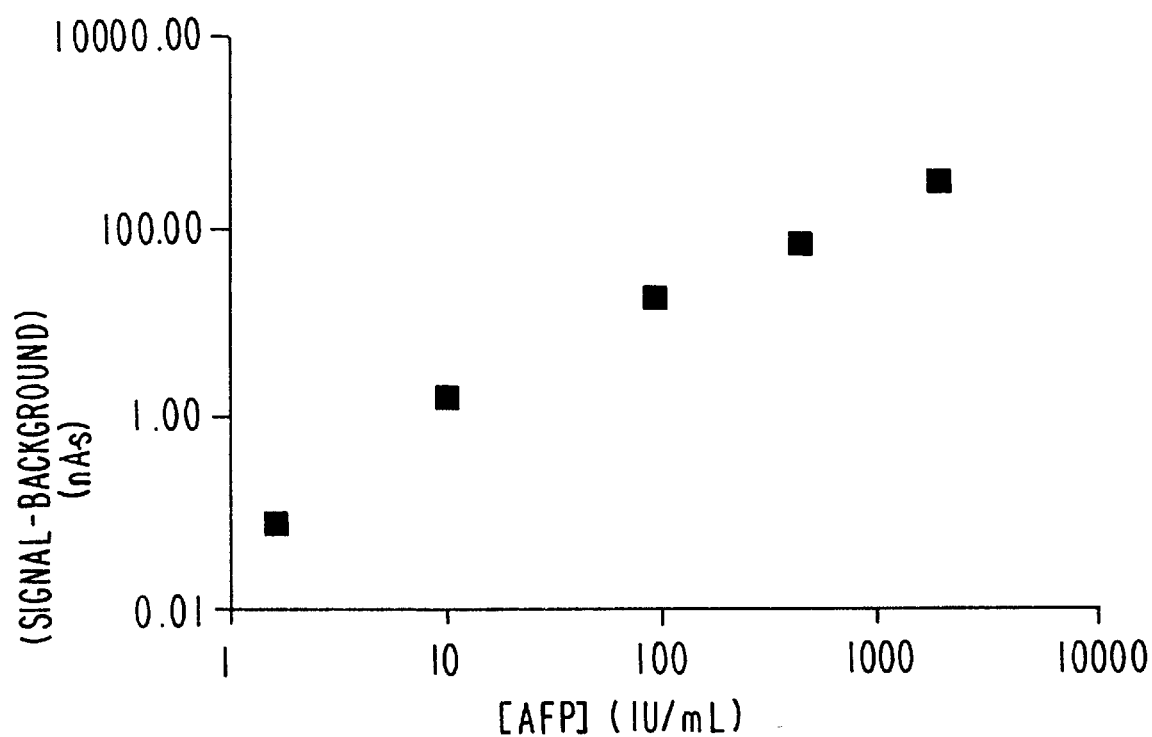

FIG. 56 shows the dose response for an AFP assay that involves the formation of a sandwich complex on a streptavidin-coated, UTFM on a nylon membrane and detection of the bound complex by ECL.

Figure 57:
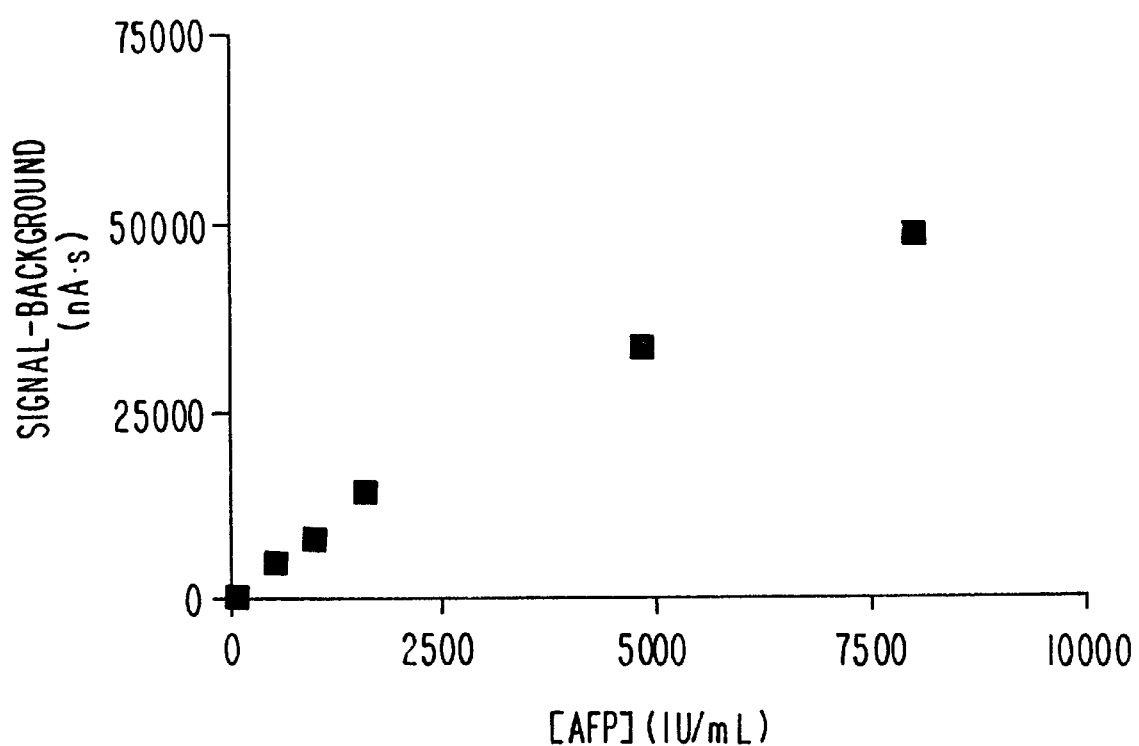

FIG. 57 shows the dose response for an AFP assay that involves the formation of a sandwich complex on a streptavidin-coated UTFM formed on a gold-coated nylon membrane and detection of the bound complex by ECL.

FIG. 58 illustrates an ECL signal in which the electrochemical potential for one or more components is shifted.

FIG. 59 illustrates an ECL signal in which the intensity of the ECL signal for one or more components of the sample is reduced relative to the ECL signal for other components of the sample.

Figure 60:
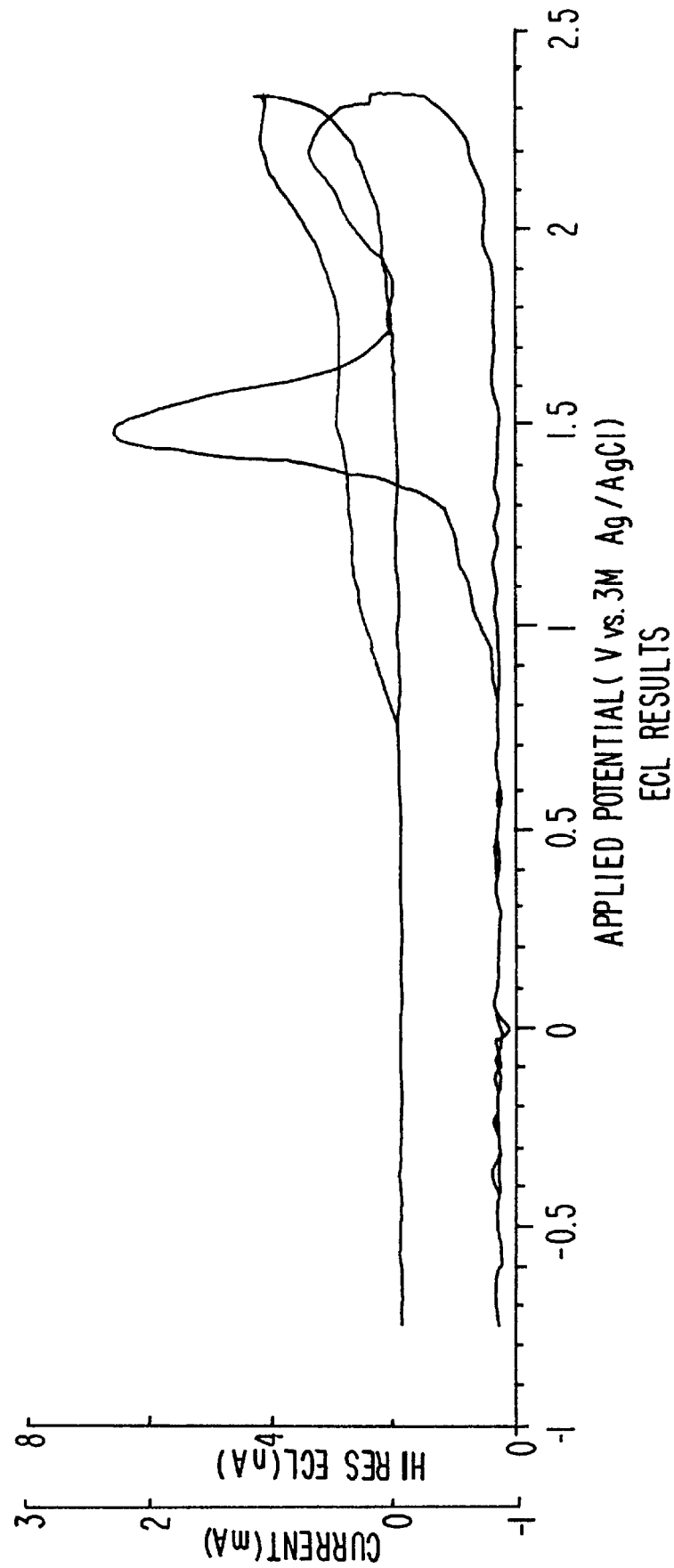

FIG. 60 shows an ECL trace of a sample that is ECL assay buffer.

Figure 61:
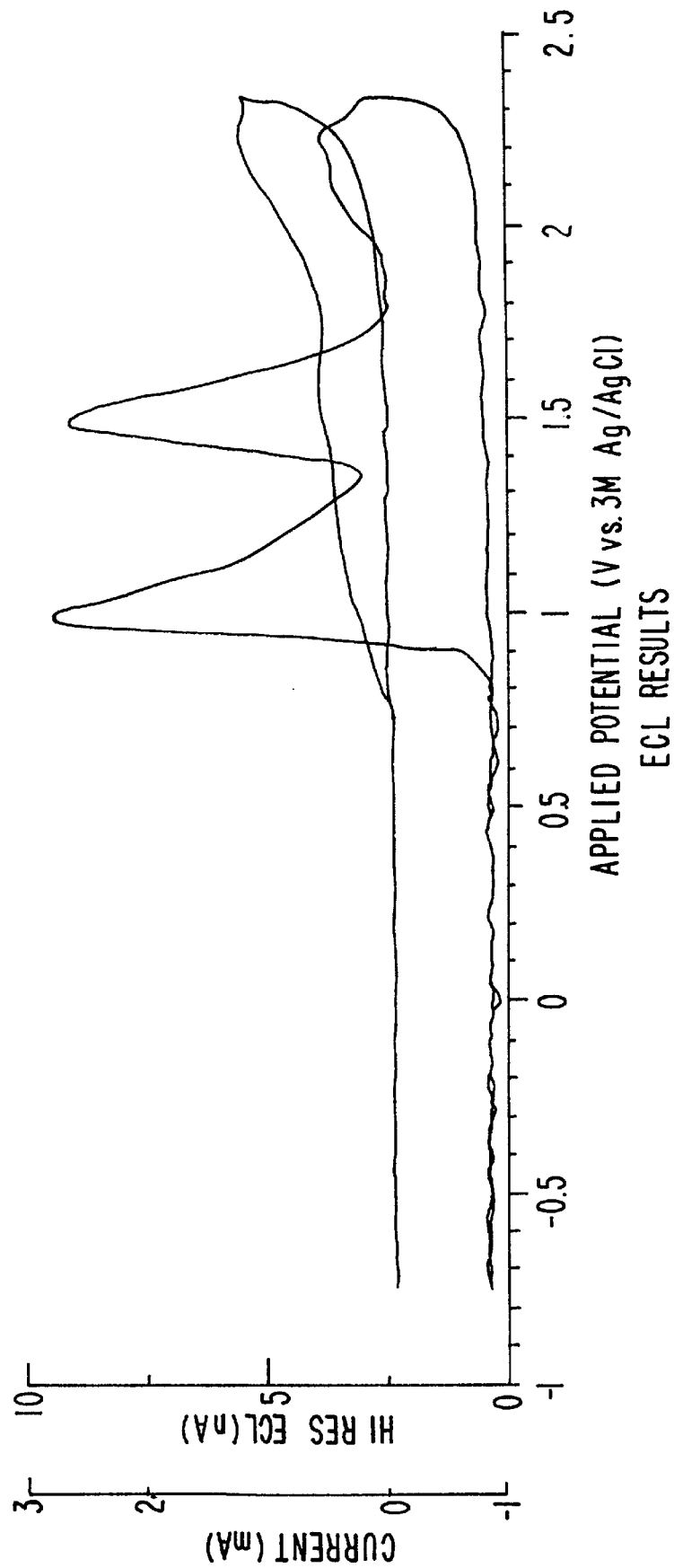
Figure 62:
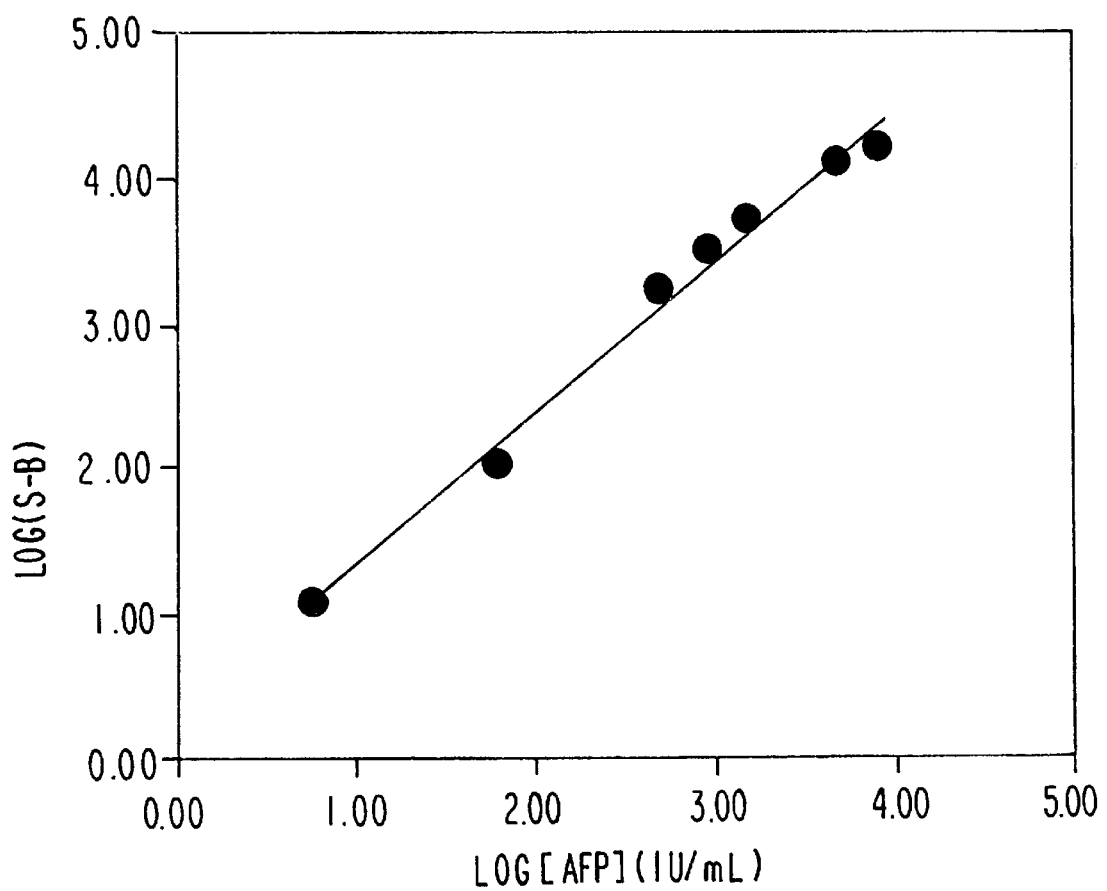
Figure 63:
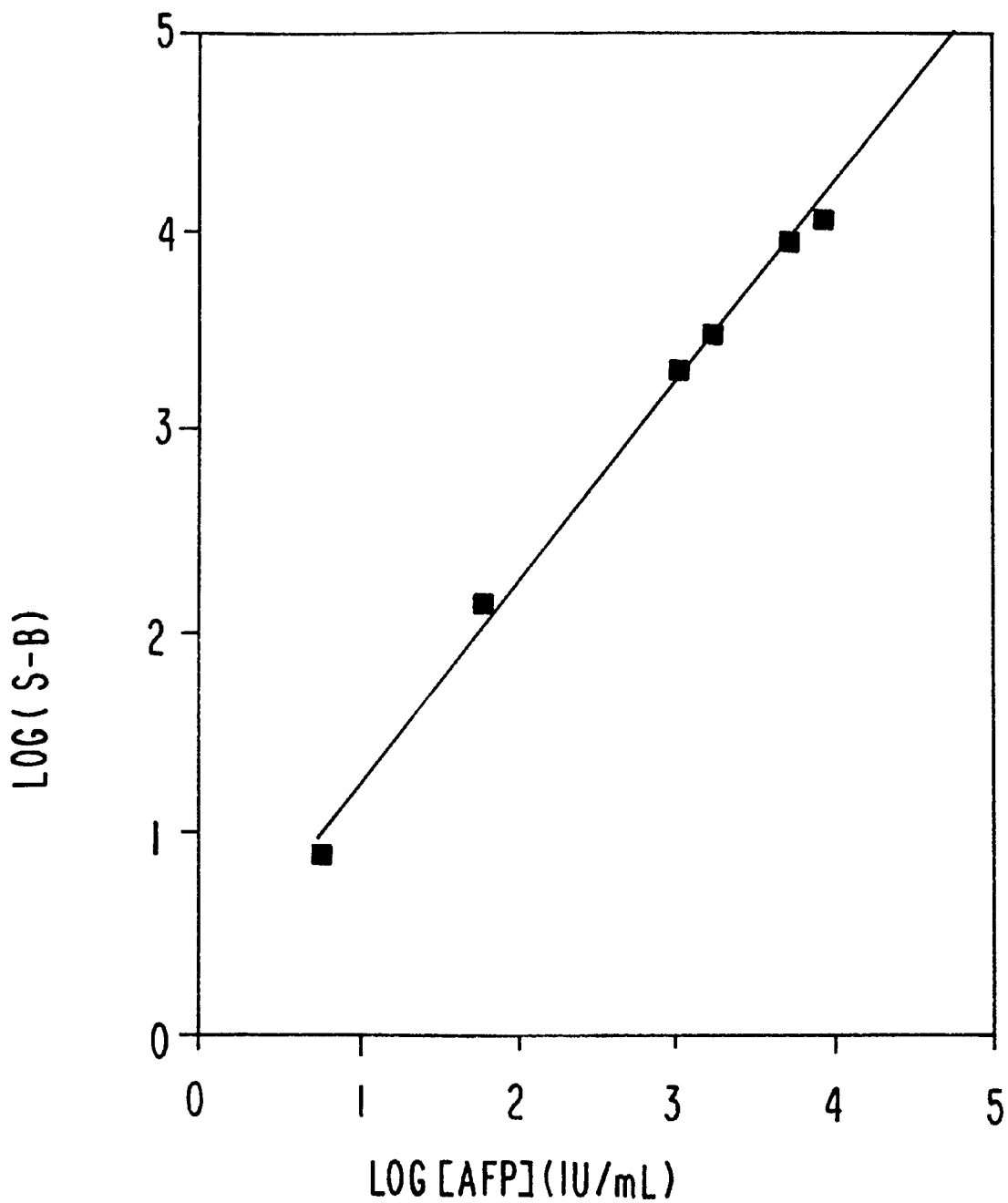
Figure 64:
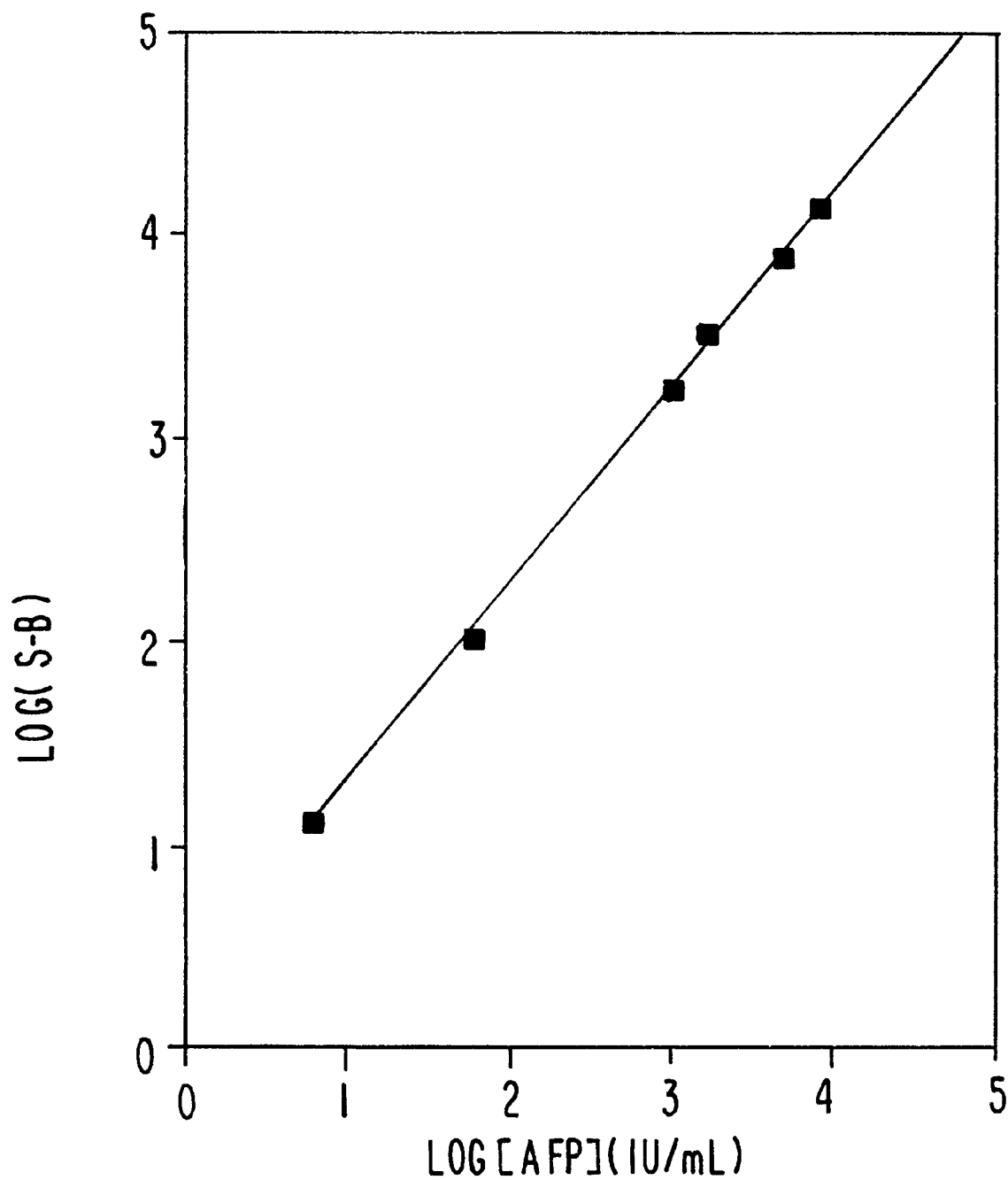
Figure 65:
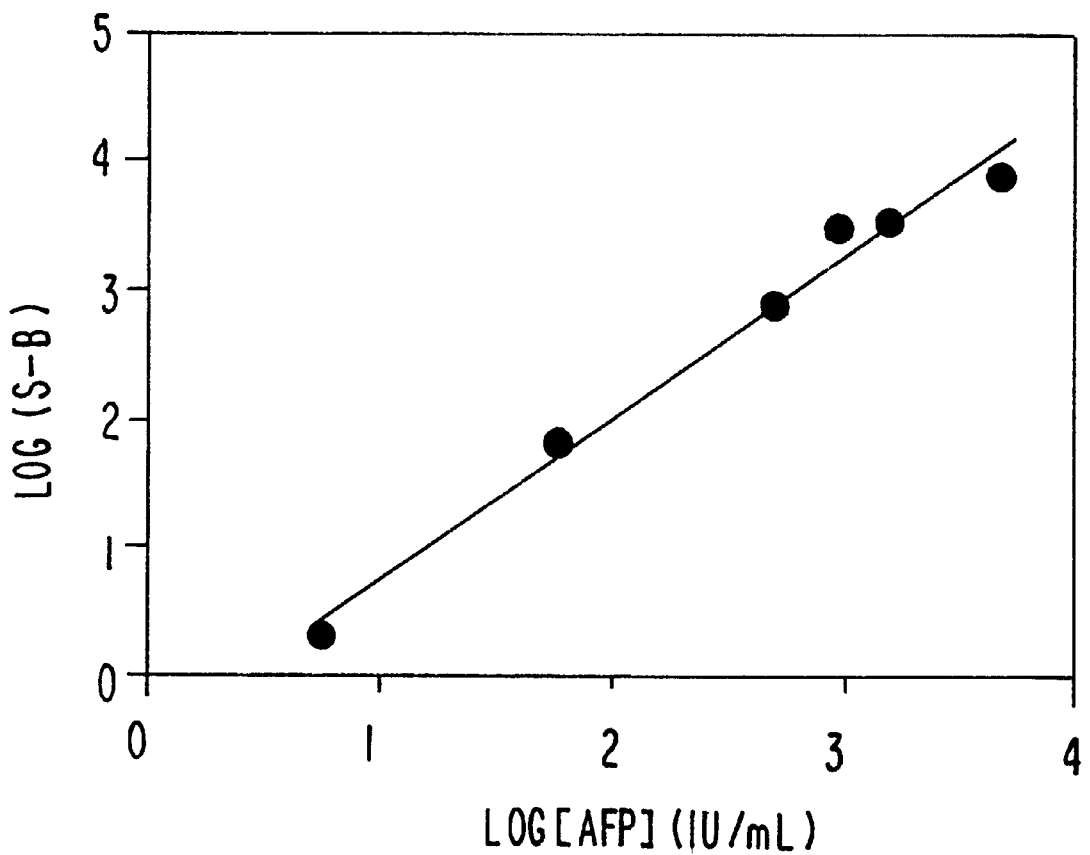
Figure 66:
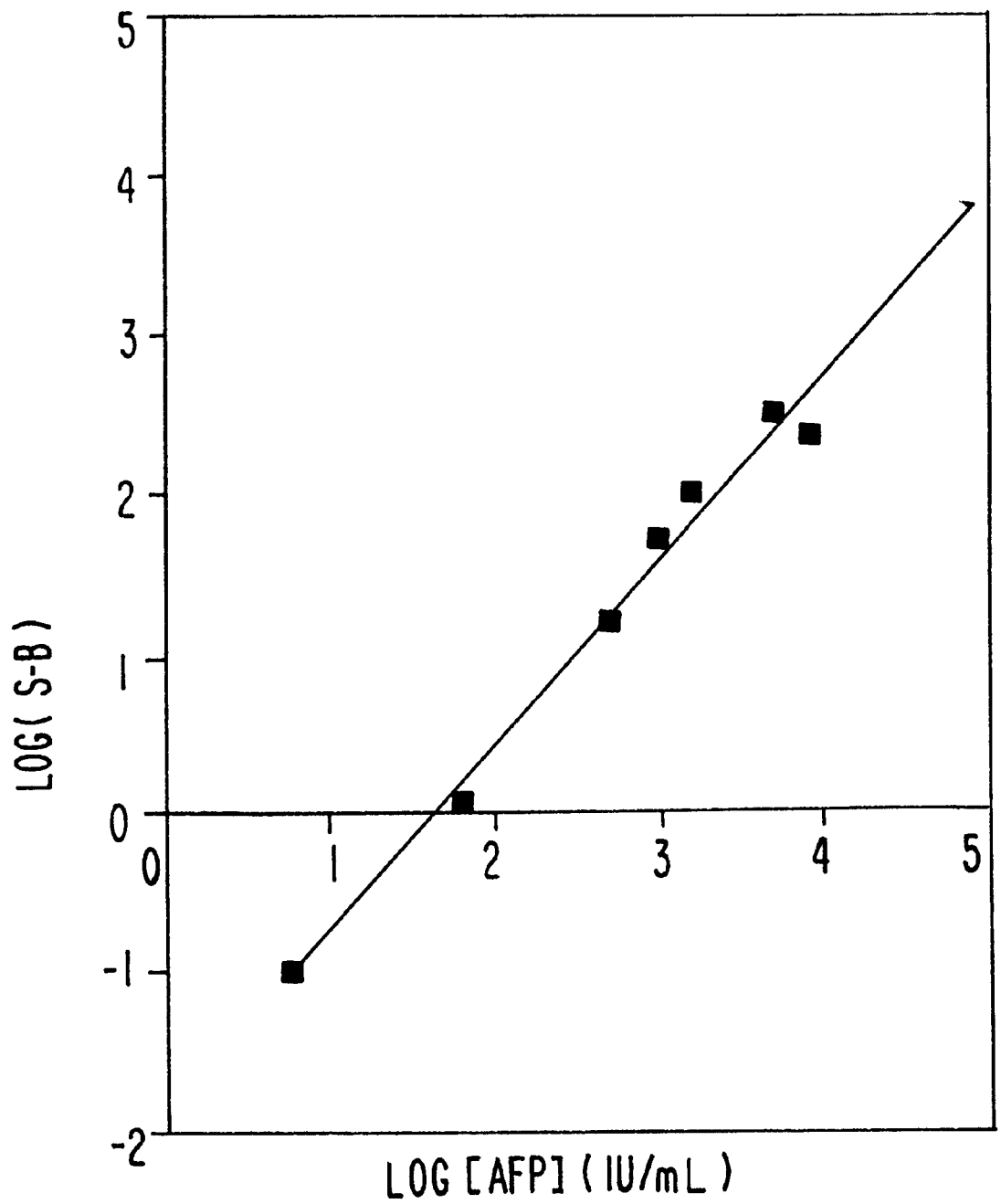
Figure 67:
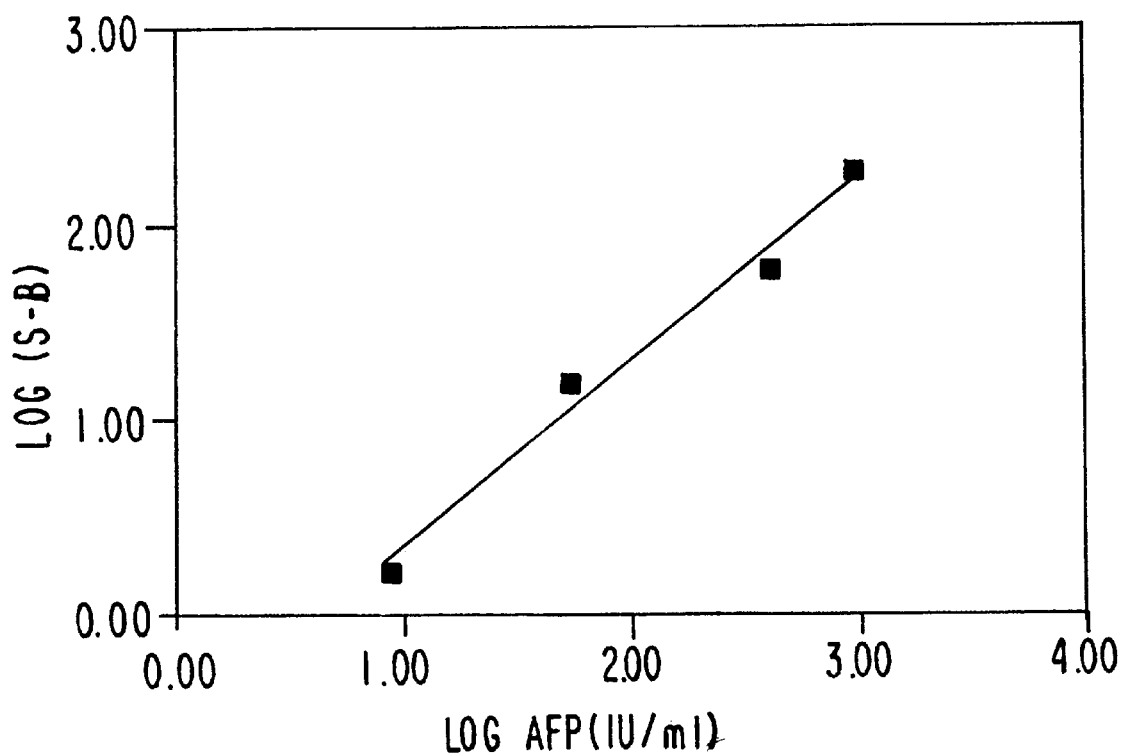
Figure 68:
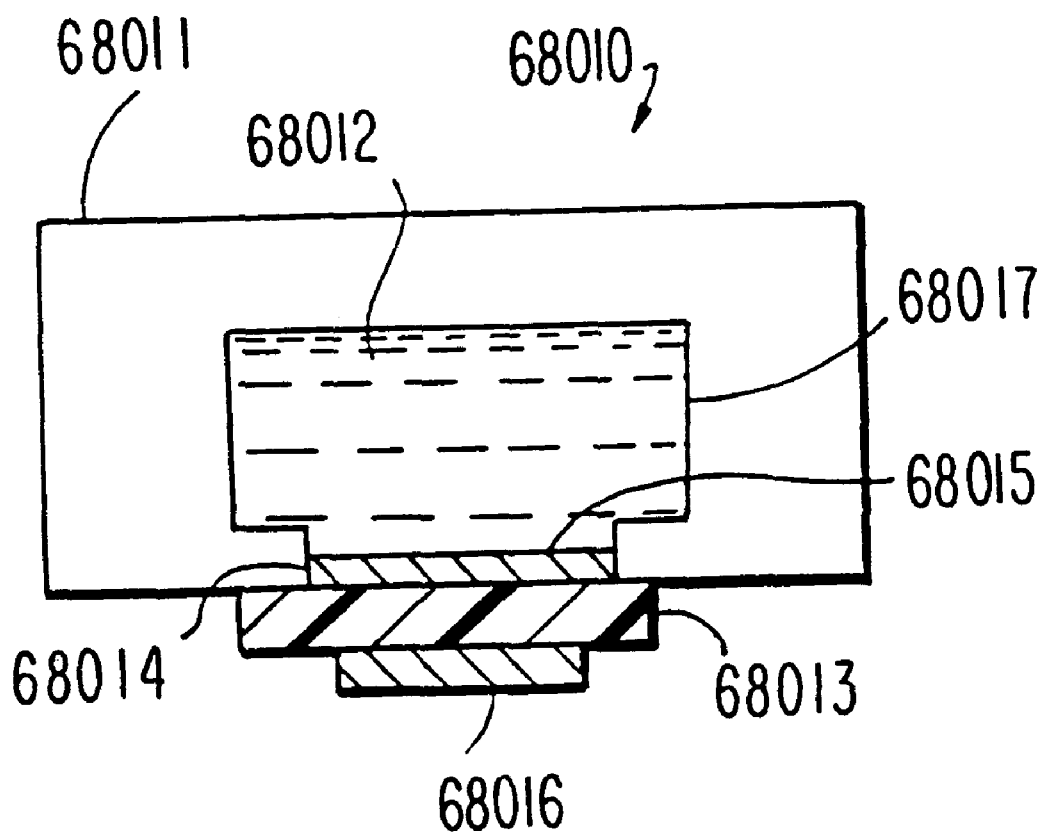
Figure 69:
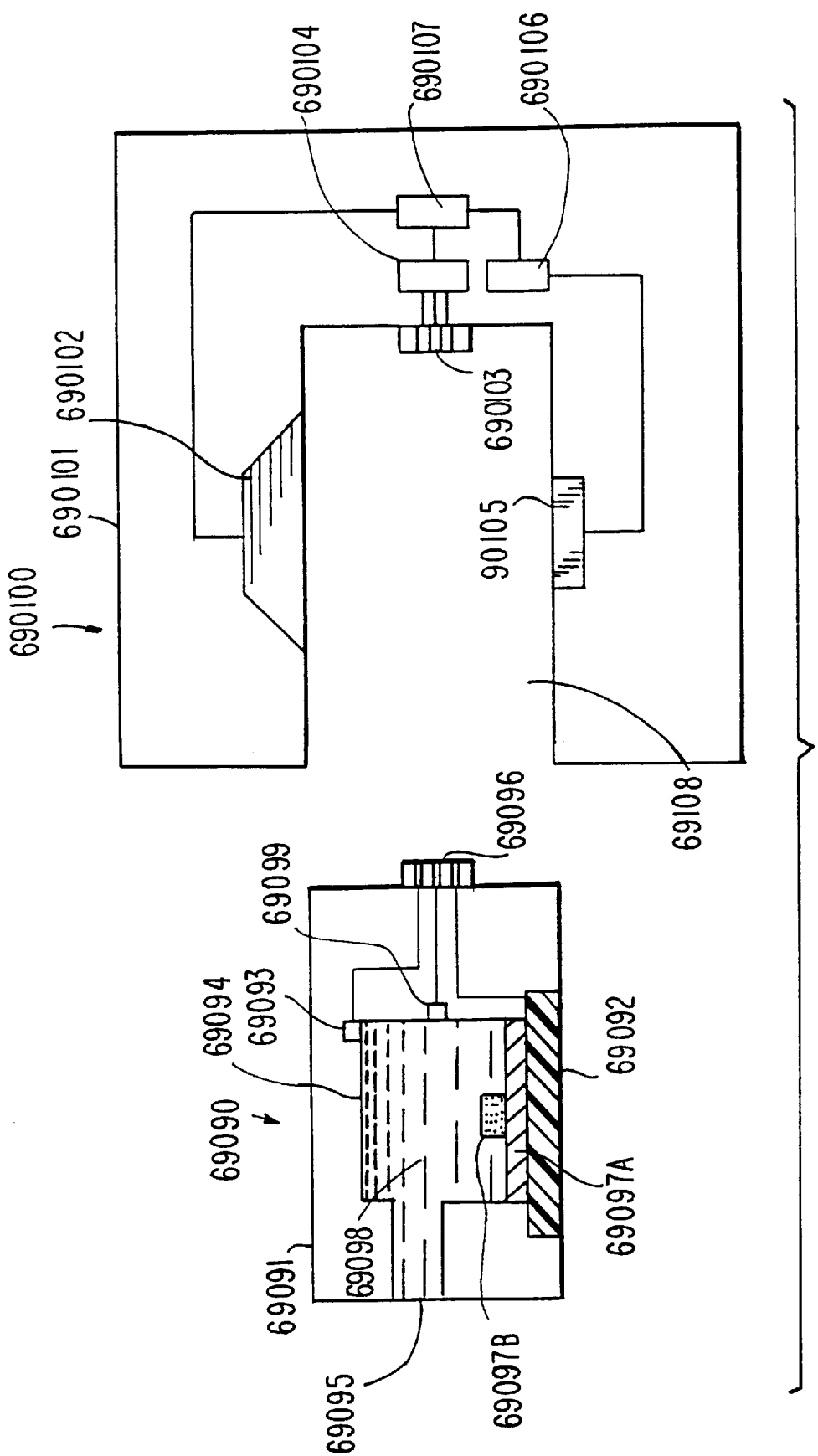

FIG. 61 shows an ECL trace of a sample that contains AFP.

5. DETAILED DESCRIPTION OF THE INVENTION

Accordingly, the invention includes in a broad aspect cassettes for conducting one or more electrochemiluminescence assays. The cassettes are formed of supports having thereon a plurality of binding domains able to specifically bind one or more analytes of interest. The binding domains are prepared as patterned, multi-array multi-specific surfaces ("PMAMS") on the support. The PMAMS offer a significant improvement from ECL assay methods previously known by, e.g., greatly increasing the density of assays that can be performed and allowing for a plurality of different assays that may be rapidly or simultaneously performed.

The cassette may include a plurality of electrodes able to selectively trigger ECL emission of light from ECL labeled reagents bound to the binding domains. FIG. 47 shows an multi-array ECL apparatus using a cassette 4700 which comprises a housing 4717, electrical connections to the electrode in the cassette 4718, a waveform generator or potentiostat 4719, a CCD camera for imaging the ECL emitted from the PMAMS 4720, and a microcomputer for controlling the waveform generator and analyzing the image received by the camera 4721.

Figure 1:
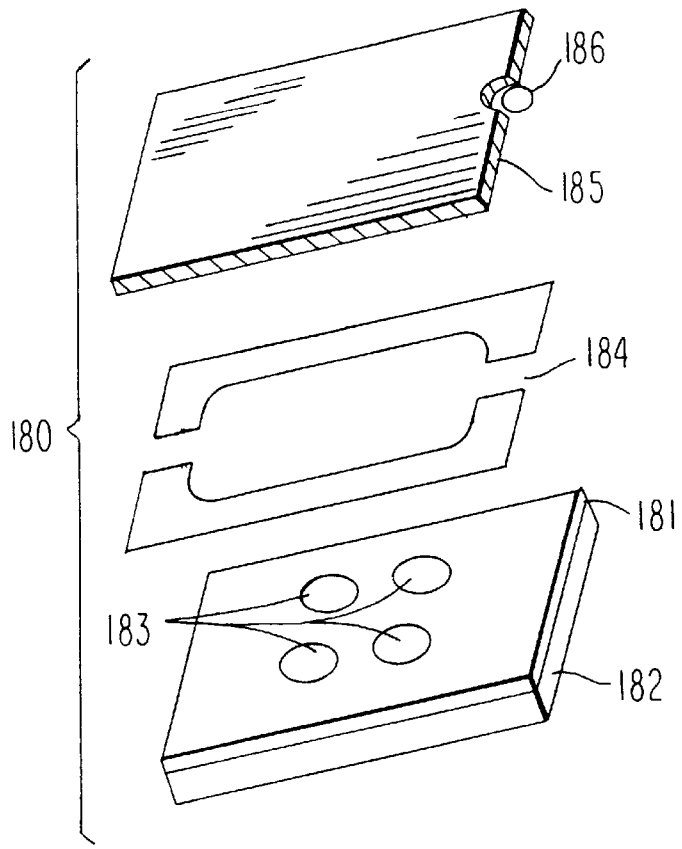
Figure 1A:
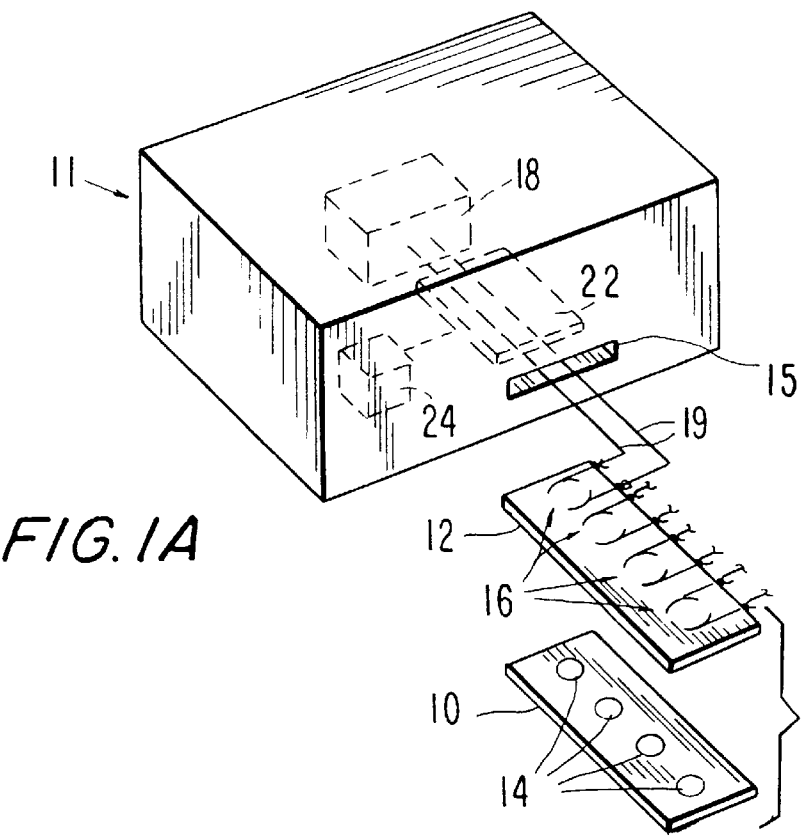

In the embodiment of the invention shown in FIG. 1, a cassette 180 comprises a working electrode comprising a conducting material 181 on a support material 182. A plurality of binding domains, i.e. a PMAMS 183 are present on the electrode 181. The cassette also includes a means for introducing samples and reagents (fluid channel 184) and a counter electrode 185. A reference electrode 186 may also be included.

In another embodiment, a plurality of working electrodes are used to simultaneously generate an ECL signal at a plurality of binding domains. In this embodiment, the ECL signal from each binding domain is identified without the use of light imaging equipment.

In certain embodiments of the invention, it is desirable to reproducibly immobilize a specified or predetermined amount of one or more reagents on a surface. Immobilization broadly applies to any method by which a reagent is attached to a surface, including but not limited to: covalent chemical bonds; non-specific adsorption; drying a reagent on a surface; electrostatic interactions; hydrophobic and/or hydrophilic interactions; confinement or entrainment in liquids or gels; biospecific binding, (e.g., ligand/receptor interactions or hybridization of oligonucleotides); metal/ligand bonds; chelation, and/or entanglement in polymers.

The amount of reagent immobilized on a surface may be predetermined in several ways. For example, the amount of reagent on a surface may be specified by one or more volume and/or area elements in which the reagent is present. It may also be specified by the number of individual molecules of a reagent that are immobilized on a surface. The amount of reagent may be specified in terms of the density of a particular reagent in a given region. The amount of reagent may be specified as a percentage of a surface bearing a particular reagent, either with regard to the total area of the surface, or relative to the amounts of other reagents present on the surface. The amount of reagent may also be defined as the quantity of reagent that must be present on a particular surface to give sufficient ECL intensity so as to make an assay achieve a desired specificity. In a specific example, a 1 cm$^2$ area of a gold surface may be coated with a monolayer of alkanethiols.

Reagents may also be reproducibly immobilized on coated surfaces. The coating may serve to enhance immobilization for some reagents and/or reduce or prohibit immobilization for other reagents. The surface may be completely coated or the surface may be partially coated (i.e. a patterned coating). The coating may be uniform in composition, or it may contain elements of different composition. In a specific example, the coating may be a patterned monolayer film that immobilizes immunoglobulin G via covalent chemical bonds in some areas, and prevents its immobilization in others.

The coating may also serve to predetermine the amount(s) of one or more reagents immobilized on the surface in subsequent steps or processes. Alternatively, the amount of a particular reagent may be controlled by limiting the amount of reagent that is deposited.

Having a surface that has reagents (or a coating) immobilized in a quantitative, reproducible fashion gives the ability to reproducibly and quantitatively measure an ECL signal from a sample, thus allowing calibration.

Broadly, the assays conducted using cassettes according to the invention are assays that benefit from the use of a plurality of discrete binding domains. For example, use of such cassettes allows rapid and/or concurrent detection or measurement of a wide variety of analytes of interest. In a preferred embodiment, the assays according to the invention are also those that benefit from the use of an ECL labeled reagent, analyte or binding surface. An ECL assay according to the invention comprises contacting a plurality of binding domains with a sample suspected of containing an analyte of interest and triggering an ECL emission from a bound ECL label, wherein the ECL label is on the analyte or a competitor of the analyte, on a reagent that binds to the analyte or on the plurality of binding domains.

The invention provides for ECL assay methods for detecting or measuring an analyte of interest, comprising (a) contacting one or more binding domains immobilized on an electrode, in which said contacting is with a sample comprising molecules leveled to an ECL label, (b) applying a voltage waveform effective to trigger ECL at said binding domains, and (c) measuring or detecting ECL.

The term sample is used in the broadest sense. It includes a quantity of any substance to be used in the methods of the invention. By way of non-limiting examples it may include a portion of a material to be assayed containing an analyte-of-interest, a pre-processed or prepared part thereof or a quantity of reagents to be used in the method of the invention.

The invention also provides ECL assay methods for detecting or measuring an analyte of interest, comprising (a) contacting one or more binding domains, said binding domains being immobilized on a surface of one or more supports, in which said contacting is with a sample comprising molecules linked to an electrochemiluminescent label; (b) bringing an electrode into proximity to said binding domains; and (c) applying a voltage waveform effective to trigger ECL at said binding domains; and detecting or measuring ECL.

In another embodiment, the invention provides ECL assay methods for (a) contacting one or more binding domains, said plurality of binding domains (i) being immobilized on a surface of one or more supports, and (ii) being spatially aligned with and in proximity to a plurality of electrode and counterelectrode pairs, in which said contacting is with a sample comprising molecules linked to an electrochemiluminescent label; (b) bringing an electrode and counterelectrode into proximity to said binding domains; (c) applying a voltage waveform effective to trigger electrochemiluminescence at said binding domains; and (d) detecting or measuring electrochemiluminescence.

The invention provides a method of detecting in a volume of a multicomponent, liquid sample a plurality of analytes of interest which may be present in the sample at various concentrations.

Broadly a plurality of analytes may be detected from a multicomponent sample in less than $10^{-3}$ molar concentrations. Preferably a plurality of analytes may be detected at less than $10^{-12}$ molar concentrations from a multicomponent sample.

The invention provides for detection from a multicomponent sample which may be performed as heterogeneous assays, i.e., assays in which a plurality of unbound labeled reagents are separated from a plurality of bound labeled reagents prior to exposure of the bound labeled reagents to electrochemical energy, and homogeneous assays, i.e., assays in which a plurality of unbound labeled reagents and bound labeled reagents are exposed to electrochemical energy together.

In the assays of the present invention, the electromagnetic radiation used to detect a particular analyte is distinguishable from the electromagnetic radiation corresponding to other analytes by identifying its position and/or location as one or more features of a pattern, said pattern corresponding to the pattern of the binding domains in the PMAMS.

In the homogeneous assays of the present invention, the electromagnetic radiation emitted by the bound labeled reagents either as an increase or as a decrease in the amount of electromagnetic radiation emitted by the bound labeled reagents in comparison to the unbound reagents, or by detection of electromagnetic radiation emitted from sources corresponding in space to one or more features of a pattern corresponding to the pattern of the binding domains in the PMAMS.

In a specific example of the method of the invention shown in FIG. 20, a sandwich assay is conducted on a support (5) with a plurality of binding domains (BD) on its surface that are specific for binding a particular analyte (An). When a sample suspected of containing the analyte is applied to the binding domains, the analyte is bound to the binding domains. Antibodies (Ab), which are suitable for selectively binding analyte (An) and have been labeled with an ECL moiety (TAG) to form Ab-TAG, are then applied to the analyte on the binding domains. After excess, unbound Ab-TAG is washed off the binding domains, a potential waveform suitable for triggering electrochemiluminescence is applied to the TAG by electrodes (not shown) to trigger an ECL emission from any TAG on the binding domains. The ECL signal is detected by light detection means and recorded by digital computer means.

Further embodiments, features and variations of the invention are provided as described hereinbelow.

5.1. Preparation Of A Binding Surface

To better understand the invention, a more detailed description of the preparation of binding domains on a support is provided. A patterned array of binding domains on a surface that are specific for a plurality of analytes is referred to herein as a patterned, multi-array multi-specific surface or PMAMS. PMAMS are prepared on a support, for example, by patterning of self-assembled monolayers ("SAMs") (Ferguson et al, 1993, Macromolecules 26(22):5870–5875; Prime et al., 1991, Science 252:1164–1167; Laibinis et al., 1989, Science 245:845–847; Kumar et al., 1984, Langmuir 10(5):1498–1511; Bain et al., 1989, Angew. Chem. 101:522–528). Surface patterning methods also include the use of physical etching (e.g., micromachining) (Abbott et al., 1992, Science 257:1380–1382; Abbott, 1994, Chem. Mater. 6(5):596–602), microlithography (Laibinis et al., 1989, Science 245:845–847), attachment of chemical groups to the surface through the use of photoactivatable chemistries (Sundberg et al., 1995, J. Am. Chem. Soc. 117(49):12050–12057), and micro-stamping techniques (Kumar et al., 1994, Langmuir 10(5):1498–1511; Kumar et al., 1993, Appl. Phys. Lett. 63(14):2002–2004). Other surface patterning methods include procedures for the spatially controlled dispensing of fluids or particles (e.g., micropen deposition (e.g., using a microfluidic guide to deliver onto a surface using X-Y translation)), microcapillary filling (Kim et al., 1995, Nature 376:581), Ink-Jet technology, or syringe dispensers. Combinations of these techniques may be used to provide complex surface patterns. In FIG. 5A, a support 600 is shown with shape independent binding domains that are represented, simply for illustration purposes, as geometric shapes 602 to indicate that different binding specificities may be present on a single support. Surface 604 between binding domains may be alternatively hydrophobic or hydrophilic to confine deposition of binding reagent to form binding domains. Binding domains and/or the surface(s) between binding domains may be alternatively prone and resistant to nonspecific binding, and/or they may be prone and resistant to the attachment of binding reagents via covalent or non-covalent interactions. In the case where non-specific binding through hydrophobic interactions is not the desired method for attachment of binding chemistries to the surface, detergent may be added to prevent incidental non-specific binding from occurring.

The binding domains are broadly from 0.1 $\mu$m to 10 mm in width or diameter or widest dimension depending upon the geometry of the domain. The surfaces are selectively derivatized to have specific binding components exposed to e.g., the ECL assay solution. Additionally, non-specific interactions at the binding domains are decreased while maintaining a specific binding moiety by incorporating moieties such as polyethyleneglycols on the exposed surface of the discrete binding domains (Prime et al., 1993, J. Chem Soc. 115:10714–10721; Prime et al., 1991 Science 252:1164–1167; Pale-Grosdemange et al., 1991, J. Am. Chem. Soc. 113:12–20).

The PMAMS may contain broadly from 2 to $10^8$ binding domains. Preferably, the number of binding domains is from 50 to 500. In still other embodiments, the number of binding domains is from 25 to 100. In still other embodiments, the number of binding domain is from 2 to 20.

The support may be a variety of materials including but not limited to glass, plastic, ceramic, polymeric materials, elastomeric materials, metals, alloys, composite foils, semiconductors, insulators, silicon and/or layered materials, etc. Derivatized elastomeric supports can be prepared, e.g., as described by Ferguson et al., 1993, Macromolecules 26:5870–5875; Ferguson et al., 1991, Science 253:776–778; Chaudhury et al., 1992, Science 255:1230–1232.

The surface of the support on which PMAMS are prepared may contain various materials, e.g., meshes, felts, fibrous materials, gels, solids (e.g., formed of metals) elastomers, etc. The support surface may have a variety of structural, chemical and/or optical properties. For example, the surface may be rigid or flexible, flat or deformed, transparent, translucent, partially or fully reflective or opaque and may have composite properties, regions with different properties, and may be a composite of more than one material. The surface may have patterned surface binding regions and/or patterned regions where catalyses may occur according to the invention on one or more surfaces, and/or an addressable array of electrodes on one or more surfaces. The surfaces of the supports may be configured in any suitable shapes including planar, spheroidal, cuboidal, and cylindrical. In a specific embodiment, the support bearing a PMAMS is a dipstick.

The support bearing a PMAMS may contain carbon, e.g., particulate carbon, graphite, glassy carbon, carbon black, or may contain one or more carbon fibers. These fibers may be amorphous or graphitic carbon.

A support bearing a PMAMS may contain "carbon fibrils", "carbon nanotubes", "graphitic nanotubes", "graphitic fibrils", "carbon tubules", "fibrils" and "buckeytubes", all of which terms are used to describe a broad class of carbon materials (see Dresselhaus, M. S.; Dresselhaus, G.; Eklund, P. C.; "Science of Fullerenes and Carbon Nanotubes", Academic Press, San Diego, Calif., 1996, and references cited therein). We use the terms "fibrils" and "carbon fibrils" throughout this application to include this broad class of carbon-based materials.

Individual carbon fibrils as disclosed in U.S. Pat. Nos. 4,663,230, 5,165,909, and 5,171,560 are particularly advantageous. They may have diameters that range from about 3.5 nm to 70 nm, and length greater than $10^2$ times the diameter, an outer region of multiple essentially continuous layers of ordered carbon atoms and a distinct inner core region. Simply for illustrative purposes, a typical diameter for a carbon fibril may be approximately between about 7 and 25 nm, and a typical range of lengths may be 1 $\mu$m to 10 $\mu$m. Carbon fibrils may also have a single layer of carbon atoms.

Carbon materials can be made to form aggregates. For example, as disclosed in U.S. Pat. No. 5,110,693 and references therein, two or more individual carbon fibrils may form microscopic aggregates of entangled fibrils. These aggregates can have dimensions ranging from 5 nm to several cm. Simply for illustrative purposes, one type of microscopic aggregate ("cotton candy or CC") resembles a spindle or rod of entangled fibers with a diameter that may range from 5 nm to 20 $\mu$m with a length that may range from 0.1 $\mu$m to 1000 $\mu$m. Again for illustrative purposes, another type of microscopic aggregate of fibrils ("birds nest, or BN") can be roughly spherical with a diameter that may range from 0.1 $\mu$m to 1000 $\mu$m. Larger aggregates of each type (CC and/or BN) or mixtures of each can be formed (vide infra).

Fibrils that can be used in a support include but are not limited to individual fibrils, aggregates of one or more fibrils, suspensions of one or more fibrils, dispersions of fibrils, mixtures of fibrils with other materials (e.g., oils, paraffins, waxes, polymers, gels, plastics, adhesives, epoxies, teflon, metals, organic liquids, organic solids, inorganic solid, acids, bases, ceramics, glasses, rubbers, elastomers, biological molecules and media, etc.) as well as combinations thereof.

The fibrils may be magnetic in some cases and non-magnetic in others. The extent to which fibrils can be made magnetic or non-magnetic is controlled by the process used to produce the fibrils. Examples of such process are disclosed in U.S. Pat. Nos. 4,663,230, 5,165,909, and 5,171,560. PMAMS are located on, in, or in proximity to the supports described supra.

PMAMS can be generated from different types of surface binding groups. Self-assembling monolayers that can be used to form a monolayer on a surface to which they bind, include but are not limited to alkane thiols (which bind gold and other metals), alkyltrichlorosilane (e.g., which bind silicon/silicon dioxide), alkane carboxylic acids (e.g., which bind aluminum oxides) as well as combinations thereof. The monolayer may be formed first and then linking chemistry used to attach binding reagents. Derivatization after self-assembly produces a more perfect two-dimensional crystalline packing of the monolayer on a support surface with fewer pin holes or defects. The monolayer can be derivatized with the binding reagents before or after self-assembly. Regular defects in the monolayer may be desirable, and can be obtained by derivatization prior to self-assembly of the monolayer or the support surface. If the derivatized group (e.g., exposed binding group) on the binding reagent is sterically large, it may create a close-packed surface at the exposed end, but with regular gaps at the metal surface. This is useful for allowing charge to flow through these regular gaps to the ECL labeled moieties bound to the portion contacting the sample solution.

The preparation of incomplete monolayers is known in the art. Other procedures for the preparation of incomplete monolayers include but are not limited to: the formation of monolayers from dilute solutions of binding reagent, the termination of the monolayer forming reaction before completion, the damaging of more complete monolayers with radiation (e.g., ionic particles), light or chemical reagents. In one embodiment, repeated stamping without re-inking the stamp can give a range of defective monolayers (Wilbur et al., 1995, Langmuir, 11:825)

PMAMS can be generated on the surface of matrices. Matrices may be highly conducting, e.g., metal electrodes or conducting polymer films; or matrices may be insulators; or semi-conducting and/or of medium conductivity. The matrix material may be an ionic conductor or a porous material. Such porous materials may be utilized as support material and/or a conductive material and/or a filter material and/or a channelling material (e.g., allowing passage of fluids, ionic species etc.).

The porous material may be combined with additional materials. For example, composite structures may be fabricated of porous materials with additional porous materials, conductive materials, semiconductive materials, channelling structures and/or solutions (e.g., ionic fluids). Such composites may be laminar structures, sandwich structures, and/or interspersed composites. A solid matrix may be used which is a porous material supported on a metal electrode. Alternatively, a porous material is sandwiched between conducting materials, semiconducting materials or a combination of semiconducting and conducting materials. One or more binding domains may be contained on one continuous slab of the porous material and/or may be located on a plurality of discrete objects on the support each with one or more binding domains. The porous material (e.g., gel) surface may be flat, hemispherical or take on any regular or irregular shape and/or may have a variety of physical properties (e.g., elastomeric, rigid, low density, high density, gradient of densities, dry, wet etc.) and/or optical properties (e.g., transparent, translucent, opaque, reflective, refractive etc.) and or electrical properties (e.g. conductive, semiconductive, insulating, variably conductive, for example wet vs. dry etc.). The porous material may be a composite of more than one materials.

A pattern of channels may be formed in the matrix. The porous material layers may be from 5 microns to 2000 microns thick. The porous material layers may also be thicker than 2 mm.

The pores may extend partially and/or fully through the material or may be part of a network of pores. These pores may have dimensions ranging broadly from 50 Å to 10000 μm. In a preferred embodiment, the material has some pores with dimensions ranging from 200 Å to 500 Å and some pores with dimensions ranging from 0.5 μm to 100 μm.

The porosity of the material may be constant throughout the material or may increase or decrease as a function of the position in the material. The material may have a wide variety of pores of different size distributed in a disorganized and/or random manner.

For example, the material may have some pores that are large enough to pass objects as large as biological cells, some pores that can pass biological media as large as proteins or antibodies, some pores that can pass only small (<1000 molecular weight) organic molecules, and/or combinations thereof.

The porosity of the material may be such that one or more molecules, liquids, solids, emulsions, suspensions, gases, gels and/or dispersions can diffuse into, within and/or through the material. The porosity of the material is such that biological media can diffuse (actively or passively) or be forced by some means into, within and/or through the material. Examples of biological media include but are not limited to: whole blood, fractionated blood, plasma, serum, urine, solutions of proteins, antibodies or fragments thereof, cells, subcellular particles, viruses, nucleic acids, antigens, lipoproteins, liposaccharides, lipids, glycoproteins, carbohydrates, peptides, hormones or pharmacological agents. The porous material may have one or more layers of different porosity such that biological media may pass through one or more layers, but not through other layers.

The porous material may be able to support a current due to the flow of ionic species. In a further refinement, the porous material is a porous water-swollen gel, for example polyacrylamide or agar. A variety of other gel compositions are available (for example see Soane, D. S. *Polymer Applications for Biotechnology;* Soane, D. S., Ed.; Simon & Schuster: Englewood Cliffs, N.J., 1992 or *Hydrogels in Medicine and Pharmacy,* Vol. I–III; Peppas, N. A. Ed.; CRC Press: Boca Raton, Fla., 1987). Binding domains can be attached to matrices by covalent and non-covalent linkages. (Many reviews and books on this subject have been written; some examples are Tampion J. and Tampion M. D. *Immobilized Cells: Principles and Applications* Cambridge University Press: NY, 1987; *Solid Phase Biochemistry: Analytical and Synthetic Aspects* Scouten, W. H. Ed., John Wiley and Sons: NY, 1983; *Methods in Enzymology, Immobilized Enzymes and Cells, Pt. B* Mosbach, K. Ed., Elsevier Applied Science: London, 1988; *Methods in Enzymology, Immobilized Enzymes and Cells, Pt. C* Mosbach, K. Ed., Elsevier Applied Science: London, 1987; *Methods in Enzymology, Immobilized Enzymes and Cells, Pt. C* Mosbach, K. Ed., Elsevier Applied Science: London, 1987; see also *Hydrogels in Medicine and Pharmacy, supra*). For example, a protein can be attached to a cross linked copolymer of polyacrylamide and N-acryloylsuccinimide by treatment with a solution of the protein. The binding domains may also be integrated into a porous matrix in a step prior to polymerization or gelation. In one embodiment, binding domains may be attached to uncrosslinked polymers by using a variety of coupling chemistries. The polymers may then be crosslinked (for example using chemistries which include amide bonds, disulfides, nucleophilic attack on epoxides, etc.) (see for example: Pollack et al., 1980, J. Am. Chem. Soc. 102(20):6324–36). Binding domains may be attached to monomeric species which are then incorporated into a polymer chain during polymerization (see Adalsteinsson, O., 1979, J. Mol. Catal. 6(3): 199–225). In yet another embodiment, binding domains may be incorporated into gels by trapping of the binding domains in pores during polymerization/gelation or by permeation of the binding domains into the porous matrix and/or film. Additionally, binding domains may be adsorbed onto the surface of porous matrices (e.g., polymer gels and films) by nonspecific adsorption caused for example by hydrophobic and/or ionic interactions. Biotin may be advantageously used as a linking or binding agent. Avidin, streptavidin or other biotin binding agents may be incorporated into binding domains.

PMAMS can be generated on porous materials (e.g., gels) with varying pore size and solvent content. For example, polyacrylamide gels varying in pore size can be made by varying the concentration of acrylamide and the degree of crosslinking.

On such PMAMS with pore sizes smaller than the analyte, binding reactions will occur substantially on the surface of the gel. In this case, filtration and/or electrophoresis through the gel can be used to concentrate analytes at the surface of the gel and modulate the kinetics (e.g., increase the rate) of the binding reaction. Faster kinetics is advantageous in rapid assays (e.g., short times to results) and may generate increased sensitivity in a shorter time period.

On PMAMS with pore sizes larger than the analyte, binding reactions can occur on the surface as well as in the bulk of the gel. In this case, filtration can be used and/or electrophoresis can be used to increase the kinetics of binding and remove unbound species from the surface.

PMAMS formed on gels can be stored wet and/or they may be stored in a dried state and reconstituted during the assay. The reagents necessary for ECL assays can be incorporated in the gel before storage (by permeation into the gel or by incorporation during formation of the gel) and/or they can be added during the assay.

Patterned binding domains of a PMAMS can be generated by application of drops or microdrops containing each binding domain in the matrix in a liquid form to a substrate. Solidification and/or gelling of the liquid can then be caused by a variety of well known techniques (polymerization, crosslinking, cooling below the gelling transition, heat). Agents that cause solidification or gelation may be included in the drops, so that at some time after dispensing, the drops solidify and/or gel. A subsequent treatment (e.g., exposure to light, radiation and/or redox potential) may be used to cause solidification and/or gelation. In other embodiments such drops or microdrops may be slurries, pre-polymeric mixtures, particulate groups, and/or substantially solid drops. Additionally vapor phase deposition may be utilized.

Patterning can also be achieved by forming a layered structure of matrices each containing one or more binding domains. For example, agarose linked (by standard chemistries) to an antibody could be poured into a container and allowed to gel by cooling. Subsequent layers containing other antibodies could then be subsequently poured on the first layer and allowed to gel. The cross section of this layered structure gives a continuous surface presenting a plurality of distinct binding domains. Such cross sections may be stacked and another cross section may be cut to create a PMAMS surface with even greater density of binding domains. Alternatively, lines of a matrix containing a given binding element are laid down adjacent to one another and/or stacked. Such structures may also be cut in cross-section and utilized as a PMAMS surface.

Patterning can also be achieved by taking advantage of the ability of some matrices to achieve separation. For example, a mixture of nucleic acid probes could be separated by electrophoresis in a polyacrylamide slab generating a surface presenting a plurality of distinct binding domains.

Microfluidics guides may also be used to prepare the PMAMS binding domains on a support. A partial list of microfluidic guides includes hollow capillaries, capillaries made of and/or filled with a matrix (e.g., a porous or solvent swollen medium), solid supports which can support a thin film or drop of liquid. The capillary may be solid and reagents flow along the outside surface of the capillary, a reagent fluid reservoir may be exposed to a porous matrix tip which is brought into contact with a PMAMS surface. For example, the reagent reservoir may be continuously or periodically refilled so that a given porous matrix tip may reproducibly deposit reagents (e.g., alkane thiols to form monolayers and/or binding reagents etc.) a plurality of times. Additionally, varying the porosity of the tip can be utilized to control reagent flow to the surface. Different or identical binding reagents may be present in a plurality of capillaries and/or multiple distinct binding agents may be present in a given capillary. The capillaries are brought into contact with the PMAMS (e.g., patterned SAM) surface so that certain regions are exposed to the binding reagents so as to create discrete binding domains. Different binding reagents, each present in a different microfluidic guide are delivered concurrently from the fluidic guide array onto a metal surface, SAM, etc, as desired. Microfluidic guides can also be used to ink a microstamp with a desired molecule prior to application to the support surface. For example, individual microfluidic guides can be used to apply different binding reagents linked to a moiety that promotes adsorption to the surface of the support (e.g., a free thiol on a hydrocarbon linker, which promotes adsorption to gold), to form a PMAMS. Thus, for example, a microstamp inked via the use of microfluidic guides with antibodies of different specificities that have incorporated a linker with a free thiol, can be used to apply such antibodies in desired areas on a gold surface to form discrete binding domains of a PMAMS.

Microfluidic guide also refers to microprinting devices which deliver microdrops of fluid by ejection of the drop through a small orifice (e.g., an Ink-Jet printer). The ejection drops in these devices may be caused by different mechanisms including heating, electrostatic charge, and/or pressure from a piezo device. Patterning of more than one liquid can be achieved through the use of multiple orifices and/or one orifice and appropriate valving.

In one method for preparation of a PMAMS, microfluidic guides are used to deliver (preferably concurrently) directly onto discrete regions on a surface, drops containing the desired binding reagents, to form discrete binding domains. The binding reagents may contain a functional chemical group that forms a bond with a chemical group on the surface to which it is applied. In another variation, binding reagents in the drop are nonspecifically adsorbed or bound to the surface (e.g., dried on the surface).

Alternatively, drop(s) deposited on a surface contain reagents that can form a matrix. This matrix may be a solid, polymer or a gel. The formation of the matrix may be by evaporation of solvent. It may be by polymerization of monomeric species. It may be by cross-linking of preformed polymers. It may be by modulating temperature (e.g., cooling and/or heating). It may be by other methods. For example, a polymeric species may be cooled through a cooling transition or by addition of a reagent that causes gelling. The formation of the solid matrix may be induced by generation of reactive species at an electrode (including the substrate), by light (or other radiation) by addition of reagents that induce solidification or gelling, by cooling or heating. Additionally, the surface may contain catalysts capable of initiating matrix formation (e.g. gelling or polymerization).

In a preferred technique, patterned hydrophilic/hydrophobic regions to prevent spreading of applied fluids or gels can be used. Such a fluid or gel may contain binding reagents to be linked to a surface on a support to form a binding domain of the PMAMS. In this case, use of such a hydrophilic/hydrophobic border aids in confining the produced binding domain to a discrete area. Alternatively, the fluid contains reagents which can form a matrix on the surface and binding reagents are contained within a defined region when deposited on a surface. For example, hydrophilic/hydrophobic border aids may be utilized to confine the drop to a defined region. Additionally, either the hydrophilic or hydrophobic areas may present groups which can be incorporated (e.g., covalently or non-covalently bound) into the matrix, allowing for a more stable adhesion of the matrix to the substrate (Itaya and Bard, 1978, Anal. Chem. 50(11):1487–1489). In another technique, the fluid or gel that is applied is the sample containing the analyte of interest, and the sample is applied to a prepared PMAMS. In one preferred example, capillaries containing hydrophilic solutions can be used to deposit a solution onto discrete areas, creating hydrophilic domains surrounded by hydrophobic regions. Alternatively, hydrophobic binding domains surrounded by hydrophilic regions can be used with a hydrophobic fluid containing binding reagents or analyte (s)). Hydrophobic and hydrophilic are relative terms, with respect to each other and/or with respect to the sample to be applied, i.e., such that the spread or wetting of a fluid or gel sample applied to the binding domains is controlled. Further, controlled solution deposition from the microfluidics array may be accomplished using physical surface features (e.g., wells or channels on the surface). A microfluidics guide can be included in a cassette, or more preferably, used to apply specific reagents to a support prior to use.

More than one linking chemistry may be applied to the same support surface and/or a surface with both hydrophilic and hydrophobic binding domains can be created using multiple stamps. For example, an area where a hydrophilic binding domain is desired at position 1 and a hydrophobic binding domain is desired at position 2 can be prepared as follows. A first hydrophilic stamp is made which has a disk at position 1 and a larger ring at position 2. A second hydrophobic stamp is made with a disk at position 2 which fits inside the ring monolayer left by stamp 1. Finally, the surface is washed with a hydrophobic solution of monolayer components.

In particular, a PMAMS is generated by micro-contact printing, i.e., stamping. The monolayer so applied is composed of a surface-binding group, e.g., for a gold surface, a thiol group with an alkane (e.g., $(CH_2)_n$)) spacer is preferred. A spacer group is linked (preferably covalently bound) to a linking group A. "A" can be, e.g., avidin, streptavidin or biotin or any other suitable binding reagent with an available complementary binding partner "B". The A:B linkage may be covalent or non-covalent and some linkage chemistries known to the art that can be used are disclosed by, e.g., Bard et al. (U.S. Pat. Nos. 5,221,605 and 5,310,687). "B" is further linked to a binding reagent such as an antibody, antigen, nucleic acid, pharmaceutical or other suitable substance for forming a binding domain that can bind to one or more analytes of interest in a sample to be tested. B may also be linked to an ECL TAG or label. Linking group B may be delivered to the SAM by means of a capillary or microfluidics guide array (FIGS. 5A–5C) able to place a plurality of "B" reagents with different binding surface specificities on the monolayer "A" linkage. A and B can also be linked before or prior to being attached to the monolayer. As discussed, in FIG. 5A, shape independent binding domains are represented, simply for illustration purposes as geometric shapes 602 to indicate that different binding specificities may be present on a single support 600. FIG. 5B provides a top view of a microfluidic guide (e.g., capillary) array 606. The dots 610 are the guides in cross section. FIG. 5C provides a side view of a microfluidic guide array 608. The lines emerging from the top and bottom are individual microfluidic guides 610. The geometric shapes 612 on the lower aspect represent specific binding domains formed upon delivery of binding reagent from each individual capillary.

By way of example, after the first stamping discussed supra, the bare surface (e.g., gold) regions may be reacted with a second alkane thiol which does not have linking chemistry A and is of the opposite hydrophobicity/hydrophilicity of the first monolayer above. In this way, specific linking domains are prepared on a surface.

A binding reagent that is specific or for one analyte of interest may be used for each binding domain or a binding reagent may be used that specifically binds to multiple analytes of interest.

In yet another variation, a support surface may be stamped multiple times by materials (e.g., binding reagents, ECL labels, SAMs) having different linking chemistries and/or binding moieties as shown by FIG. 5A above.

The binding reagents that are patterned can be stable and/or robust chemical groups (e.g., that survive the conditions to which they are subjected) which are later linked to less stable or robust binding groups. Multiple binding linkages may be utilized so as to optimize the conditions of each step in the preparation of a PMAMS surface and/or simplify the manufacturing of PMAMS surfaces. For example, a first PMAMS surface may be fabricated in a generic fashion and then modified to create different PMAMS surfaces. In another example, a generic PMAMS surface may be reacted with a solution mixture of binding reagents which themselves contain binding domains which direct them to particular regions (e.g., binding domains) on the PMAMS surface. For example, a pattern of binding domains each presenting a different oligo(nucleotide) sequence is linked to the surface. This surface is then treated with a solution containing a mixture of secondary binding reagents, each linked to a oligo (nucleotide) sequence complementary to a sequence on the surface. In this way, patterning of these secondary binding elements can be achieved. Preferably, the oligo (nucleotide) sequences are 6–30 mers of DNA. Certain sets of 6–30 mer sequences may contain substantially similar sequence complementarity so that the approximate binding constants for hybridization are similar within a given set and discernably different from less complementary sequences. In another embodiment, the secondary binding elements are proteins (for example, antibodies).

Methods described to inhibit wetting or spread of applied reagents or sample on a surface as described in Section 5.13 infra, can also be used in the preparation of PMAMS (and/or in sample application). Applied potential (e.g., from the electrode/counterelectrode pair) may be used to further control the deposition and/or spreading of reagents and/or samples (see, e.g., Abbott et al., 1994, Langmuir 10(5):1493–1497).

The PMAMS binding reagents may be located on materials that contain carbon, e.g. particulate carbon, carbon black, carbon felts, glassy carbon and/or graphitic carbon. In some embodiments, they may be located on carbon fibers, e.g. carbon fiber, or carbon fibrils. The binding reagents may be located on individual carbon fibrils or they may be located on aggregates of one or more fibrils. In many embodiments, the PMAMS binding reagents may be located on suspensions or dispersion of these carbon materials, mixtures of carbon materials with other materials as well as combinations thereof.

The PMAMS binding reagents may be located on a plurality of individual fibrils and/or aggregates of fibrils localized on or in or in proximity to a support. In one example, the binding reagents are localized on dispersed individual fibrils or fibril aggregates. These fibrils or aggregates of fibrils may be localized spatially into distinct domains on a support, and may constitute binding domains. In another example, the binding reagents may be located on aggregates of carbon particles.

In another example, individual such binding domains or a plurality of such binding domains are located in spatially distinct regions of the support. By way of a non-limiting example, individual such binding domains or collections of binding domains may be located in depressions, pits and/or holes in the support. In still another example, individual binding domains or a plurality of domains may be located in drops of water, gels, elastomers, plastics, oils, etc. that are localized on the surface of the support. In yet another example, individual binding domains may be localized on the support by a coating (which may be patterned) that has different binding affinities for different binding reagents and/or binding reagent/fibril ensembles.

Binding domains located on a plurality of individual fibrils and/or aggregates of fibrils may be prepared on a support by means of one or more microfluidic guides (e.g., a capillary). Different or identical binding reagents may be present in or on a plurality of microfluidic guides and/or multiple distinct binding agents may be present in or on a given microfluidic guide. The capillaries may be brought into contact with the support (spotting) and/or may deliver the reagents while either the microfluidic guide and/or the surface is being scanned or translated relative to the other (i.e., a penlike method of writing). The microfluidic guide may deliver the binding reagents located on the fibrils to the support so that certain regions of the support are exposed to the fibril-binding reagent complex(es) so as to create a discrete binding domain(s). In a preferred aspect, different binding reagents, each present in a different microfluidic guide are delivered concurrently from the guide array onto the support. In one example, binding reagents and/or the fibrils on which they are localized are derivatized with a chemical functional group that forms a bond (e.g., covalent or non-covalent interaction) to the surface of the support. In some embodiments, the binding reagents and fibrils are non-specifically bound or adsorbed to the surface. In yet another aspect, the binding reagents localized on the fibrils may be delivered to depressions, pits and/or holes in the surface of the support. In another example, the binding reagents are delivered to a surface that is coated with a material that has a stronger or weaker binding affinity for certain binding reagents or binding reagent/fibril ensembles and so creates domains of the reagents that are localized spatially and distinctly from other binding reagents The binding reagents are localized on one or more individual fibrils or aggregates of fibrils that are magnetic. In such a case, a magnetic support may attract the binding reagents localized on magnetic fibrils to the support.

The support may contain several distinct regions that are magnetic and are surrounded by regions that are not magnetic.

Binding reagents localized on magnetic fibrils may be localized on magnetic regions of the support. In one example, the support may contain one or more distinct regions that are magnetic and are surrounded by regions that are not magnetic, and the strength of the magnetic field in the magnetic regions can be modulated or switched. In this aspect, use of such a modulated or switchable magnetic field aids in affixing or releasing the binding reagents localized on fibrils from the surface of the support and so may serve to stir or mix said domains.

There are broadly from 2 to $10^8$ binding domains and preferably from 25 to 500 domains.

The binding domains may be located on the working electrode and/or the counter electrode.

The different embodiments described herein for different types of PMAMS, supports, and electrodes and configurations thereof may also be practiced in combination with each other.

The PMAMS supports may be preserved (e.g., through protective surface coatings, drying the surface, robust packaging under vacuum or inert atmosphere, refrigeration and related methods) for later use.

5.2. Binding Reagents

The binding domains of the invention are prepared so as to contain binding reagents that specifically bind to at least one analyte (ligand) of interest. Binding reagents in discrete binding domains are selected so that the binding domains have the desired binding specificity. Binding reagents may be selected from among any molecules known in the art to be capable of, or putatively capable of, specifically binding an analyte of interest. The analyte of interest may be selected from among those described in Section 5.10 infra, "ECL Assays That May Be Conducted." Thus, the binding reagents include but are not limited to receptors, ligands for receptors, antibodies or binding portions thereof (e.g., Fab, (Fab)'$_2$), proteins or fragments thereof, nucleic acids, oligonucleotides, glycoproteins, polysaccharides, antigens, epitopes, cells and cellular components, subcellular particles, carbohydrate moieties, enzymes, enzyme substrates, lectins, protein A, protein G, organic compounds, organometallic compounds, viruses, prions, viroids, lipids, fatty acids, lipopolysaccharides, peptides, cellular metabolites, hormones, pharmacological agents, tranquilizers, barbiturates, alkaloids, steroids, vitamins, amino acids, sugars, nonbiological polymers, biotin, avidin, streptavidin, organic linking compounds such as polymer resins, lipoproteins, cytokines, lymphokines, hormones, synthetic polymers, organic and inorganic molecules, etc. Nucleic acids and oligonucleotides can refer to DNA, RNA and/or oligonucleotide analogues including but not limited to: oligonucleotides containing modified bases or modified sugars, oligonucleotides containing backbone chemistries other than phosphodiester linkages (see, for example, Nielsen, P. E. (1995) Annu Rev. Biophys. Biomcl. Street. 24 167–183), and/or oligonucleotides, that have been synthesized or modified to present chemical groups that can be used to form attachments to (covalent or non-covalent) to other molecules (where we define a nucleic acid or oligo (nucleotide) as containing two or more nucleic acid bases and/or derivatives of nucleic acid bases).

The PMAMS of the invention may have a plurality of discrete binding domains that comprises at least one binding domain that contains binding reagents that are identical to each other and that differ in specificity from the binding reagents contained within other binding domains, to provide for binding of different analytes of interest by different binding domains. By way of example, such a PMAMS comprises a binding domain containing antibody to thyroid stimulating hormone (TSH), a binding domain containing an oligonucleotide that hybridizes to hepatitis C virus (HCV), a binding domain containing an oligonucleotide that hybridizes to HIV, a binding domain containing an antibody to an HIV protein or glycoprotein, a binding domain that contains antibody to prostate specific antigen (PSA), and a binding domain that contains antibody to hepatitis B virus (HBV), or any subset of the foregoing.

A PMAMS may have a plurality of binding domains that comprises at least one binding domain that contains within it binding reagents that differ in binding specificity, so that a single binding domain can bind multiple analytes of interest. By way of example, such a PMAMS comprises a binding domain that contains both antibody to a T cell antigen receptor and antibody to a T cell surface antigen such as CD4.

A PMAMS may have a plurality of binding domains that comprises (i) at least one binding domain that contains binding reagents that are identical to each other and that differ in specificity from at least one of the binding reagents contained within the other binding domains; and (ii) at least one binding domain that contains within it binding reagents that differ in binding specificities. By way of example, a PMAMS is made that has (a) at least one binding domain that contains binding reagents of a single identity, e.g., antibody to a T cell antigen receptor, e.g., a, p T cell antigen receptor or γ, δ T cell antigen receptor), thus allowing this at least one binding domain to bind all cells expressing this T cell antigen receptor; and (b) at least one binding domain that contains two different binding reagents, e.g., antibody to T cell antigen receptor and antibody to CD4, thus allowing this at least one binding domain to bind CD4$^+$ T lymphocytes expressing that T cell antigen receptor (i.e., a subpopulation of T lymphocytes).

In another embodiment, at least one binding domain contains binding reagents which are different molecules but which have the same binding specificities (e.g., binding reagents such as epidermal growth factor and antibody to the epidermal growth factor receptor).

A plurality of binding reagents can be chosen so that even though the binding reagents are different and have different binding specificities, they recognize the same analyte (in an alternative embodiment, different analytes are recognized). For example, where the analyte is an analyte that has numerous binding moieties (e.g., a cell, which has different cell surface antigens), different binding reagents that bind to different binding moieties will recognize the same analyte. As another example, antibodies to different cell surface antigens on a single cell will recognize the same cell. As yet another example, antibodies to different epitopes of a single antigen can be used as binding reagents to recognize the antigen.

A plurality of binding reagents can be chosen so that a plurality of binding domains may be formed where such binding domains recognize the same analyte but with different affinities. The use of such a PMAMs allows for the detection of an analyte over a greater range of concentrations (e.g., a high affinity binding domain may be saturated with analyte under conditions that do not saturate a lower affinity binding domain).

In still a further embodiment, only binding reagent(s) that specifically bind a single analyte of interest are present in one or more binding domains. Alternatively, binding reagents that specifically bind more than one analyte of interest are present in one or more binding domains (e.g., a cross-reactive antibody). In a particular design, binding reagents can be used that bind a class of analytes, e.g., with similar characteristics.

Binding domains may also be incorporated into a PMAMS that contain binding reagents that are specific for a desired standard analyte and that are utilized as an internal standard (e.g., a binding domain which can be contacted with a sample containing a defined quantity of an analyte to which the binding reagents bind). Multiple binding domains containing binding reagents specific for the same analyte(s) can also be incorporated into a PMAMS so as to allow statistical averaging of analytical results. The binding reagents may not only be specific for the same analyte, but may be identical, thus recognizing the same binding moiety on the analyte. Thus, a plurality of binding domains (e.g., within a range of 2 to $10^8$) can be prepared that specifically bind to the same binding moiety, so that the ECL readings can be statistically averaged to control for variation and improve accuracy. The plurality of binding domains on a PMAMS may be specific for a control analyte or an analyte of interest, or both, on a single support.

As another example, one or more discrete binding domains may be prepared with a known initial concentration number of ECL labels. The built-in ECL layer serves as a control to monitor, e.g., label degradation and temperature effects.

A binding reagent may be used that is an enzyme specific for a substrate (said substrate being the analyte of interest), in which a product of the enzymatic reaction upon the substrate is a reporter agent (an agent that is detectable), e.g., a product that triggers an ECL reaction, a fluorescent molecule, a substance that changes color upon contact with appropriate enzyme (e.g., a chromogenic substrate for horseradish peroxidase), etc. In an example of such an embodiment, the enzyme used as a binding reagent is glucose dehydrogenase (GDH), which can be used to detect or measure glucose in a sample. An ECL label is situated within or near to the binding domain containing the GDH. NADH is produced by the action of the enzyme upon glucose, NADH being capable of reacting with the ECL labels to promote ECL (Martin et al., 1993, Anal. Chim. Acta 281:475).

Binding domains containing binding reagents which increase background binding (i.e., that bind to a binding moiety present on the analyte of interest as well as on other analytes in the sample) can be used to increase signal to noise ratios during the detection or measurement of electrochemiluminescence. By way of example, where the analyte of interest is a specific cellular subpopulation (e.g., CD4$^+$ cells) and the sample is a fluid sample (e.g., blood) that contains cells from a patient, antibody to sialic acid can be used as a binding reagent to increase background binding to virtually all cells in the sample (since sialic acid is a component of virtually all cell surface glycoproteins), and an antibody to a cell surface antigen specific to the cellular subpopulation (e.g., antibody to CD4) can then be used as a binding reagent (in the same or different binding domain as that containing the antibody to sialic acid).

5.3. Voltage Waveform

The voltage waveform (change in electrical potential/time) impressed upon the electrodes and counter-electrodes of ECL cells must be sufficient to trigger an ECL reaction. This voltage waveform usually is in the form of a uniform voltage sweep starting at a first voltage, moving steadily to a second voltage, moving back through the first voltage to a third voltage and then back again to the first voltage. For example, the waveform may start at a first voltage in a range from −0.5 through 0.5 volts, up to a second voltage in a range from 1 through 2.5 volts and moving back through the first voltage to a third voltage ranging from 0.0 to −1 volts. As another example, in simpler waves, the voltage can be modified from 0.0 to +3.5 to 0.0. The voltage waveforms may incorporate linear ramps, step functions, and/or other functions. The voltage waveforms may incorporate periods of time when the voltage remains fixed at one potential. The applied potential may be controlled relative to one or more reference electrodes, or, no reference electrodes may be used. Additionally, negative potential may be used. Thus, the voltages used to induce ECL emissions from the cassette of the present invention will be readily selected for optimal ECL signal intensity and specificity for the ECL label and assay medium.

In some applications, the voltage is preferably varied as the light emitted from the binding domain is measured. This is particularly important to determine the threshold value of the electrical field necessary to cause the binding domain to emit light. In this case, the electrical potential applied at the binding domain starts at a value believed to be below the threshold required to emit light, and a first measurement is made of the light emitted. If no light is measured, or the light is below a predetermined threshold, the electrical potential applied across the electrode pair is increased under computer control, such as by a computer controlled voltage source and another light measurement is made. This process can be repeated until the predetermined appropriate amount of light is received. In this way, the voltage applied may be used as the assay signal.

The voltage waveform may contain an AC component. The use of such a waveform allows for better signal to noise in the detection of the ECL signal, e.g., by filtering out signals that differ in frequency from the voltage input).

The ordinary artisan who is familiar with the voltage and current settings as disclosed, for example, by U.S. Pat. Nos. 5,324,457 and 5,068,088 will readily be able to select the optimum operating voltages and voltage sweep for triggering ECL emission.

The potential required for generating ECL may be generated by illumination of the working electrode surface if the working electrode is a semiconductor or contains another moiety that generates electrical current in response to light.

5.4. Addressable Electrodes And Methods For Using The Same

Numerous methods may be used for addressing the plurality of electrode/counterelectrode pairs. Several illustrative such techniques are illustrated in FIGS. 14–18. Shown in those figures by way of example are four electrode/counterelectrode pairs 101, 102, 103, 104 and a waveform generator which typically is a digital computer and which preferably is the same computer used for processing the ECL detected by the detection means.

In FIG. 14, each electrode/counterelectrode pair 101–104 is individually addressed by a pair of lines connected to the waveform generator. By way of example, lines 105, 106 access electrode/counterelectrode pair 101. An appropriate waveform may be applied by the waveform generator at any given time to any one or more of the pairs of lines connected to the various electrode/counterelectrode pairs.

To reduce the number of connections required to address the electrode pairs, alternatives to the direct connection scheme of FIG. 14 are provided. For example, a row-and-column accessing scheme is illustrated in FIG. 15 for electrically energizing some or all of the electrodes. In this scheme, one of the electrodes 201, 202 in each column of the plurality of electrode/counterelectrode pairs is connected to a common electrical conductor 205 on support 200, and each of the counterelectrodes in each row of the plurality of electrode/counterelectrode pairs is connected to conductor 207, 208 on the support 200. Conductors 205, 206 connect to connections C1, C2, respectively, at the edge of support 200 and conductors 207, 208 connect to connections R1, R2, respectively. Each of these connections is then connected by a separate line to the waveform generator. As a result, in the configuration of FIG. 15, the number of required connections and signal lines from the waveform generator has been reduced from 8 to 4.

To enable rapid and sequential energizing of each electrode pair, a computer controlled switching device is beneficial. The configuration of FIG. 16 shows a plurality of electrodes connected to a first multiplexer 310. A plurality of counterelectrodes are connected to a second multiplexer 320. The first multiplexer is also connected to a first pole of a voltage source 330 that typically supplies the time varying electrical potential described infra. The second multiplexer is also connected to a second pole of the voltage source. Using addressing lines A0–A3 electrically connected to each of the multiplexers and connected to latch 340, a computer processor 350 can direct the multiplexers to selectively connect any or all of the first electrodes to the first pole of the voltage source, and any or all of the second electrodes to the second pole of the voltage source.

As shown in FIG. 17, a plurality of voltage sources are connected through separate sets of multiplexers to each of the electrodes. If a first electrical potential or range of electrical potentials is required at a particular electrode pair, the multiplexers 410, 420 associated with the voltage source 430 providing that potential are addressed by the computer processor 350, typically through a latch 340, thereby connecting that particular voltage source to the electrode pair in question. If a different electrical potential or range of electrical potentials is required for another electrode pair, the multiplexers 440, 450 associated with that different voltage source 460 are addressed by the computer processor, thereby connecting that voltage source through the associated multiplexers 440, 450 to the electrode pair.

If the electrode array in this embodiment has at least a portion of the electrode pairs independently driveable, as shown in FIG. 14, or 15, for example, one electrode pair can be driven by one voltage source while another electrode pair is simultaneously driven with another voltage source. Alternatively, the two voltage sources of FIG. 17 can be replaced with a single voltage source connected to both sets of multiplexers in parallel, allowing two electrode pairs to be driven from the same voltage source.

Instead of a duplicate set of multiplexers for each voltage source as shown in FIG. 17, a plurality of voltage sources 520, 530 can be provided as shown in FIG. 18. These voltage sources can be connected through a computer controlled electrical switch 510 or switches to a single set of multiplexers 310, 320. As shown in FIG. 18, the computer would direct switch 510 to connect a particular voltage source to the multiplexers, and would also direct the multiplexers (by signalling their address lines A0–A3) to connect the selected voltage source to the particular electrode pair desired.

Alternatively, the electrical potential applied to each of the electrode pairs in any embodiment can be varied. This is of particular benefit when a cassette having a plurality of different binding domains is used. Such a cassette may require a different range of applied electrical potential at different binding domains. Several different embodiments capable of varying the electrical potential applied to each electrode are contemplated.

Advantageously, a computer controlled voltage source may be used. A computer controlled voltage source is one that can be addressed by a computer to select a particular electrical potential to be supplied. Alternatively it can be programmed to sequentially apply a particular range of electrical potentials over a predetermined time. In such a system, address lines electrically connected to the computer and the voltage source would allow the computer to program the voltage source to produce the particular electrical potential to be applied to the electrode pair to be energized.

Additional methods for addressing the plurality of electrode pairs may also be used. For example, a plurality of reference electrodes may be placed in proximity to each of the plurality of electrode and counterelectrode pairs in order to sense the voltage applied thereto. In this way, additional control of the voltage waveform may be maintained.

FIG. 36 shows another embodiment of the invention; arrays of electrodes (3600, 3601) are supported on each of two surfaces (3602, 3603) separated by a pattern of gaps in an insulator 3604 (for example a plastic sheet with punched holes 3605. Each electrode may pass over a plurality of gaps. If a potential is applied between one electrode on each surface, current can only pass through a gap contacting both electrodes, thus limiting the location of any electrochemistry or ECL which may occur. In the preferred embodiment shown in the figure, the electrodes (3600, 3601) are arrays of lines on a support. The two sets of electrodes on the two surfaces are oriented perpendicular to each other. Gaps in the insulating sheet are located only at the intersection of the electrodes from each surface.

This embodiment has the advantage over individually addressed electrode pairs that less electrical leads are required.

In an alternate embodiment, the insulator 3604 is omitted and the surfaces are placed in close proximity so that only a narrow gap exists between the two surfaces. In this embodiment, a potential applied between are electrode on each surface will preferentially cause current to pass at the intersection of the electrode (i.e., where the distance between the electrodes is minimal) thus limiting the location of any electrochemistry or ECL which may occur.

5.5. Light Detection

The light generated by the triggered ECL emission is detected by an appropriate light detector or detectors positioned adjacent to the apparatus of the invention. The light detector may be, for example, film, a photomultiplier tube, photodiode, avalanche photo diode, charge coupled device ("CCD") or other light detector or camera. The light detector may be a single detector to detect sequential emissions or may be plural to detect and spatially resolve simultaneous emissions at single or multiple wavelengths of emitted light. The light emitted and detected may be visible light or may be emitted as non-visible radiation such as infrared or ultraviolet radiation. The detector or detectors may be stationary or movable. The emitted light or other radiation may be conducted to the detector or detectors by means of lenses, mirrors and fiberoptic light guides or light conduits (single, multiple, fixed, or moveable) positioned on or adjacent to the binding surface of the cassette or the detector may receive the light directly. In addition, the supports, PMAMS and electrode surfaces themselves can be utilized to guide or allow transmission of light.

The PMAMS may be formed on the surface of an array of light detectors so that each detector only receives light from one binding domain. The array of light detectors may be a CCD chip, and the binding domains may be attached (using standard coupling chemistries) to the surface of the semiconductor device.

Drops deposited on the binding domains, or on a near, second surface, can be used as microlenses to direct or control emitted light. Alternatively, a light detector can be oriented directly in front of the cassette; and various light focusing devices, such as parabolic reflectors or lenses may be employed instead of a light conduit to direct light from any of a plurality of binding domains to the detector. The light emitted from at least two discrete binding domains may be measured simultaneously or sequentially.

Error due to thermal drift, aging of the apparatus, or the electrical noise inherent in light detectors may be controlled by a "chopper" means between the light measuring device and the binding domain being measured. The chopper can be any one of the common mechanical choppers well known to those of ordinary skill in the art, such as a spinning disk with slots or cutouts that allow light to pass. Alternatively, the light can be chopped by an LCD shutter, an array of LCD shutters, a solid state light valve or valves or the like. Alternatively, a planar array of LCD shutters or solid-state light valves such as those known in the art of optical computing may be used. These devices are preferably located between the plane of the cassette, and the light conduit (or conduits) or light focusing devices that direct light from the binding domains to the light detector. In an embodiment, a shutter is located above each of the binding domains. When using an LCD shutter or light valve, the shutters may be modulated at different frequencies to simultaneously provide different chopping rates for different light emitting binding domains. Using this technique, a plurality of different light signals may be superimposed and simultaneously measured by a single detector. An electronic band pass filter electrically connected to the light detector may then be used to separate the electrical single signal into several electrical components, each corresponding to one of the plurality of individual light components. By chopping the light, as above, or using other mechanism well known to the art, an AC light waveform is created that allows the DC noise component to be electronically filtered out.

Also, the ECL signal may be calibrated by comparison to results previously determined with standard reagents to correct for signal modulation due to reagent depletion.

5.6. Analysis Of ECL Signals

Signals arising from a given binding domain can have a range of values, and these values correlate with quantitative measurement to provide an 'analog' signal. In another technique a 'digital' signal is obtained from each domain to indicate that an analyte is either present or not present.

Statistical analysis is used for both techniques, and is particularly useful for translating a plurality of digital signals so as to provide a quantitative result. Some analytes, however, require a digital present/not present signal indicative of a threshold concentration. 'Analog' and/or 'digital' formats may be utilized separately or in combination. Other statistical methods can be utilized with PMAMS. For instance it is possible to create concentration gradients of PMAMS on a surface (Chaudhury et al., 1992, *Science* 256:1539–1541). This technique is used to determine concentrations through statistical analysis of binding over the concentration gradient. Multiple linear arrays of PMAMS with concentration gradients may be produced with a multiplicity of different specific binding reagents. The concentration gradients may consist of discrete binding domains presenting different concentrations of the binding reagents.

The presence of control assay systems on the binding surface of the cassette is also important to assure the uniformity of each analysis to control for signal variation (e.g., variations due to degradations, fluctuations, aging of the cassettes and other components, thermal shifts, noise in electronic circuitry and noise in the photodetection device, etc.). For example, multiple redundant binding domains (containing identical binding reagents or different binding reagents that are specific for the same analyte) for the same analyte may be utilized. In another example, analytes of known concentration are utilized or control domains of a PMAMS are covalently linked to a known quantity of an ECL label or a known quantity of ECL label in solution is used.

The assays conducted according to the invention will rapidly and efficiently collect large amounts of data that can be stored, e.g., in the form of a database consisting of a collection of clinical or research information. The data collected may also be used for rapid forensic or personal identification. For example, the use of a plurality of nucleic acid probes when exposed to a human DNA sample can be used for a signature DNA fingerprint that can readily be used to identify clinical or research samples.

5.7. Preparation Of Electrodes For Multi Arrays

The electrodes may be broadly from 0.001 to 10 mm in width or diameter. In a preferred range the electrodes are from 0.01 to 1 mm in dimension (width or diameter or widest dimension depending upon the geometry of the electrodes).

Preferably, the electrodes are fabricated from suitable conductive materials, such as transparent metal films or semiconductors (e.g., gold or indium-tin oxide, respectively), as is well known to the art, for example, for the fabrication of liquid crystal displays and the like. In the assembled form of the cassette, sufficient space remains between the first and second supports to contain an analytic sample as, for example, a thin film or a wetted surface.

The electrodes may be fabricated from materials that contain carbon, e.g. particulate carbon, carbon black, carbon felts, glassy carbon, carbon fibers, carbon fibrils and/or aggregates of the above.

One or more individual fibrils and/or one or more aggregates of fibrils may be processed to form a larger aggregate (U.S. Pat. No. 5,124,075). In one embodiment, this larger aggregate is a mat or mesh. Hereinafter, the term "fibril mat" will be used to describe a mat or mesh of fibrils which the fibrils may be entangled interwoven. Fibril mats can have a surface area between 50 and 400 $M^2$/gram.

By way of example, a fibril mat may be used as a working electrode, a counter electrode or a reference electrode in analytical and/or preparative electrochemistry. In one example, the fibril mat is used as an electrode for electrochemiluminescence (ECL).

The binding domains of the PMAMS may be supported by an electrode, e.g. a fibril mat or an electrode formed from carbon black. The PMAMS of the invention has a plurality of discrete binding domains, of which two or more may be identical to each other or may differ. The fibril mat supports one or more binding domains.

One or more microfluidic guides may be used to prepare a plurality of binding domains on a fibril mat. Different or identical binding reagents may be present in a plurality of microfluidic guides and/or multiple distinct binding agents may be present in a microfluidic guide.

In FIGS. 22A and 22B a plurality of microfluidic guides 2201, preferably in an array, are used to deliver, preferably concurrently, onto regions of the fibril mat 2200, drops containing the desired binding reagents, to form discrete binding domains 2202. The binding reagents form a bond with moieties present on the fibril mat. The binding reagents may adsorb non-specifically to the mat or dry on the surface.

The desired binding reagents are delivered to the fibril mat while suction filtration is applied to the mat. In this instance, the suction filtration draws none, some or all of the binding reagents into or through the mat, and in doing so, reduces the amount of lateral spreading of the binding reagents on the surface of the mat during the patterning process.

Fibril mats are prepared by compressing suspensions of carbon fibrils onto a substrate through which the liquid of the suspension may pass (e.g., a filter). Examples of filters that may be used to form fibril mats include filter paper, filters formed from polymeric (e.g., nylon) membranes, metal micromeshes, ceramic filters, glass filters, elastomeric filters, fiberglass filters and/or a combination of two or more of such filter materials. One of skill in the art of filtration would recognize that these materials are merely examples of the many possible materials suitable for filtration of suspensions of solids.

FIGS. 23A and 23B illustrates an embodiment, in which fibril mats may be fabricated by suction filtration. A dispersion and/or suspension of carbon fibrils 2301 is filtered using a filter 2300 equipped optionally with a filter membrane 2303 and/or a filter support 2302. The suspension is filtered using suction applied by a vacuum source 2305 to the filter by, for example, a filter flask 2306. A fibril mat 2304 collects on either or both the filter membrane 2303 and/or the filter support 2302. The fibril mat 2304, with or without the filter membrane 2303 may be removed from the filter.

In another embodiment, suspensions of fibrils are forced through a filter by use of pressure. In one example, pressure is exerted on a confined suspension of fibrils by compressing a confined layer of air and/or liquid above the suspension with a piston. In a specific example, the suspension of fibrils is confined in a syringe, the piston is a syringe plunger, and the filter is a disposable syringe filter (many such filters are well known to one of skill in the art).

Suspensions of fibrils are forced through a filter by capillary action or filtered by wicking of the suspension into or through a filter.

In another embodiment, individual fibrils or aggregates of fibrils are crosslinked covalently into mats. Fibrils derivatized with photosensitive moieties that polymerize when exposed to light are irradiated with light.

In another embodiment, individual fibrils or aggregate of fibrils are sprayed onto a substrate. It is possible to use electrospray.

The filter may be used to trap the fibrils in its pores and so form a mat in which the filter acts as a support. In FIG. 24, a fibril mat 2400 may be prepared by passing a slurry of fibrils 2401, delivered by a source 2402, between two large rollers 2403. In this process, which may be analogous to processes found in the fabrication of paper or polymer sheets, the rollers force the liquid from the suspension and a large, continuous mat of fibrils is produced from which smaller mats may be cut.

Fibril mats may be freestanding (e.g., unsupported) or supported.

The rate of filtration can be varied to achieve desired properties in the mat. For example, properties that may be varied include uniformity or non-uniformity of structure, the extent of entanglement of the fibrils or aggregates of fibrils, the thickness, the porosity of the mat, and/or combinations thereof.

Suspensions of carbon fibrils are confined and the liquid in which the fibrils are suspended is removed. In one example, the liquid in which the fibrils are suspended is allowed to evaporate. In another example, the liquid is removed by heating. In yet another example, the suspension is subjected to centrifugation, and the resulting liquid (e.g., the supernatant) is removed. In another example, the liquid is removed by evacuation.

The suspension may be placed on one or more of the filters described supra, and the suspension dried by evaporation. The suspension may be dried by heating or baking in an oven or the liquid may be removed by freezing and extracting the liquid. In yet another example, the liquid is removed by evacuation with a pump. Many other methods which are well known to one skilled in the art are available for removing liquids from a suspension.

Suspensions of fibrils suitable for forming fibril mats by filtration may be formed by dispersing one or more carbon fibrils in an appropriate liquid, quasi-solid or gel. Examples of appropriate liquids include but are not limited to water, ethanol, methanol, hexane, methylene chloride, buffered solutions, surfactants, organic solvents, solutions of containing biological media (e.g., as proteins, antibodies or fragments thereof, cells, subcellular particles, viruses, nucleic acids, antigens, lipoproteins, liposaccharides, lipids, glycoproteins, carbohydrates, peptides, hormones or pharmacological agents, solutions of small molecules, polymer precursors, solutions of acids or bases, oils and/or combinations thereof).

A suspension of fibrils may be prepared by dispersing carbon fibrils in an aqueous solution by means of sonication. In another embodiment, surfactant and or detergent may be added.

The fibril mat may have broadly a thickness between 0.01 $\mu$m and 10,000 $\mu$m.

In preferred embodiments, the fibril mat has a thickness between 1 $\mu$m and 100 $\mu$m. In particularly preferred embodiments, fibril mats range from 10 mm to 200 mm in width or diameter.

The fibril mat may be washed repeatedly and refiltered to remove residual materials remaining from the suspension.

Fibril mats prepared by filtration or evaporation are heated (e.g., in an oven) to remove residual liquid from the suspension not removed by filtration.

Successive filtration steps may be used to form mats of fibrils composed of one or more distinct layers that are either in contact with or in close proximity to one or more other layers. Layers may be distinguished by several properties, including but not limited to differences in the porosity, the density, the thickness, the distribution of sizes of individual fibrils and/or microscopic aggregates of fibrils, the type, number and/or size of fibril aggregates, the chemical derivatization of the fibrils (vide infra), and/or the presence of other matter attached to the fibrils.

FIG. 25, a multi-layered fibril mat 2500 is prepared by successive filtration steps. A 0.5 $\mu$m to 100 $\mu$m thick layer 2501 of plain fibrils forms the first layer; a 0.5 to 10 $\mu$m thick layer of fibrils 2502 that incorporate moieties such as poly-(ethyleneglycols) that resist adsorption of proteins and other molecules forms the second layer; a 0.5 to 5 $\mu$m thick layer 2503 that incorporates one or more binding domains (vide supra) forms the third layer. The binding domains contain one or more antibodies 2504, which may bind an analyte 2505. This antibody/analyte complex may bind a labeled antibody 2506. The label may be an ECL label. In other embodiments, the label may be one or more of a plurality of labels described elsewhere in this application. Such a multilayer mat may be freestanding or supported on one of a plurality of possible supports described above.

Multilayer mats may be formed in which there are combinations of layers, in which some or all of the layers may be different.

The filter used to form the fibril mat, the fibrils, and/or the fibril mat may be coated. In particular embodiments, the coatings are metallic. These coatings may be patterned such that certain portions are coated, and other portions are not. In one example, the coating is applied by electrodeposition. In another example, the coating is applied by electroless deposition. Other methods of metal deposition, e.g. thermal or electron bean depositions or sputtering, can also be used.

The filter is coated with a metal, and the fibril is derivatized with a chemical functional group that forms a bond with said metal. The filter is a metal screen or metal sheet.

The fibril mat may be flat or deformed, regular or irregular, round, oval, rectangular, or one of many shapes, rigid or flexible, transparent, translucent, partially or fully opaque and may have composite properties or regions of different individual or composite properties.

The mat may be a disk or a piece taken from a sheet.

A plurality of fibril mats may be fabricated, preferably concurrently, and preferably in an array. In one example, an array of microfluidic guides forms a plurality of fibril mats on a support as described above. In another example, an array of filters, or a patterned filter (e.g., with regions of different porosity) is used to prepare an array of fibril mats.

A mask with an array of holes (e.g., a screen) is used to cover certain portions of a filter or support, and a plurality of discrete fibril mats are made concurrently by either filtration and/or evaporation.

Fibril mats may have a density from 0.1 to 3.0 grams/cm$^2$. The mat may have variable density. For example, mechanical force or pressure may be applied to the mat at different times to increase or decrease the density.

Fibril mats may have pores. These pores may extend partially and/or fully through the mat or may be part of a network or pores. These pores may have dimensions ranging broadly from 50 Å to 1000 $\mu$m. In a preferred embodiment, the fibril mat has pores with dimensions ranging from 200 Å to 500 Å. The porosity of the mat may depend on the density of the mat, among other factors.

The porosity of the mat may be constant throughout the mat or may increase or decrease as a function of the position in the mat. The fibril mat may have a wide variety of pores of different size distributed in a disorganized and/or random manner.

The fibril mat may contain distinct regions of different porosity. For example, the fibril mat may have one or more layers, each having a different porosity. The fibril mats may have columns of different porosity that run through the mat.

The porosity of the mat may be varied by including different amounts of aggregates of carbon fibrils, where aggregates have different size, shape, composition, or combinations. In a particular example, a mat can be prepared from individual fibrils, CC fibrils (described supra) and BN fibrils (described supra), or different combinations. For example, the fibril mat may have some pores that are large enough to pass objects as large as biological cells, some pores that can pass biological media as large as proteins or antibodies, some pores that can pass only small (<1000 molecular weight) organic molecules, and/or combinations thereof.

The porosity of the mat may be such that one or more molecules, liquids, solids, emulsions, suspensions, gases, gels and/or dispersions can diffuse into, within and/or through the mat. The porosity of the fibril mat is such that biological media can diffuse (actively or passively) or be forced by some means into, within and/or through the mat. Examples of biological media include but are not limited to whole blood, fractionated blood, plasma, serum, urine, solutions of proteins, antibodies or fragments thereof, cells, subcellular particles, viruses, nucleic acids, antigens, lipoproteins, liposaccharides, lipids, glycoproteins, carbohydrates, peptides, hormones or pharmacological agents. The fibril mat may have one or more layers of different porosity such that material may pass through one or more layers, but not through other layers.

The fibril mat is supported by or on another material.

By way of example, the supporting material may be a metal, plastic, polymer, elastomer, gel, paper, ceramic, glass, liquid, wax, oil, paraffin, organic solid, carbon or a mixture of two or more of each. The material may be solid or liquid. If it is solid, it may contain one or a plurality of holes or pores. In specific examples, the support may be a metal mesh, a nylon filter membrane or a filter paper. The support may be a conductor, a semiconductor and/or an insulator. The fibril mat may incorporate another material, for example thin fibers, shards, or balls of metal to increase the conductivity of the mat. In another example, the fibril mat may incorporate other carbon, glass and/or metal fibers of varying size, shape and density to create a different porosity than can be achieved with fibrils alone. In another aspect, the mat may incorporate magnetic beads (for example, DYNAL beads). In the latter example, the beads may either serve to change a property of the mat, or may themselves be used as supports to immobilize binding domains.

In an embodiment disclosed in U.S. Pat. Nos. 5,304,326 and 5,098,771, fibrils may be dispersed in another material. For example, fibrils may be dispersed in oils, waxes, paraffin, plastics (e.g., ABS, polystyrene, polyethylene, acrylonitrile, etc.), ceramics, teflon, polymers, elastomers, gel, and/or combinations thereof. Dispersions of fibrils in other materials are conducting. Dispersions of fibrils in other materials may be molded, pressed, formed, cast, spun, weaved, and/or thrown so as to form objects of a desired shape and/or form.

Other carbon materials (e.g., particulate carbon, carbon fibers, graphitic carbon, buckminsterfullerenes, fullerenes, or combinations thereof) may be dispersed in another material. They can be derivatized with chemical functional groups that can be used to attach other materials to them. Materials may be attached covalently to these functional groups, or they may be adsorbed non-covalently.

Carbon fibrils may be prepared with chemical functional groups attached covalently to their surface. As described in International Publication No. WO 90/14221, these chemical functional groups include but are not limited to COOH, OH, $NH_2$ N-hydroxy succinimide (NHS)-esters, poly-(ethylene glycols), thiols, alkyl $((CH_2)n)$ groups, and/or combinations thereof. These and other chemical functional groups can be used to attach other materials to the surface of fibrils.

Certain chemical functional groups (e.g., COOH, $NH_2$, SH, NHS-esters) may be used to couple other small molecules to the fibrils. There are a plurality of possible combinations of such chemical functional groups and small molecules.

In many embodiments, NHS-ester groups are used to attach other molecules or materials bearing a nucleophilic chemical functional group (e.g., an amine). In a preferred embodiment, the nucleophilic chemical functional group is present on and/or in a biomolecule, either naturally and/or by chemical derivatization. Examples of suitable biomolecules include but are not limited to amino acids, proteins and functional fragments thereof, antibodies, binding fragments of antibodies, enzymes, nucleic acids, and combinations thereof. This is one of many such possible techniques and is generally applicable to the examples given here and many other analogous materials and/or biomolecules. In a preferred embodiment, reagents that may be used for ECL may be attached to the fibril via NHS-ester groups.

An antibody that can be used in an ECL assay can be attached to one or more fibrils or a fibril mat by covalent bonds (e.g., reaction with an NHS-ester), by reaction with an appropriate linker (vide supra), by non-specific binding, and/or by a combination thereof. Nucleic acids and/or cells can be attached to fibrils or fibril mats by covalent links to NHS-esters attached to the fibrils.

It may be desirable to control the extent of non-specific binding of materials to fibrils and/or fibril mats. Simply by way of non-limiting examples, it may be desirable to reduce or prevent the non-specific adsorption of proteins, antibodies, fragments of antibodies, cells, subcellular particles, viruses, serum and/or one or more of its components, ECL labels (e.g., $Ru^{II}$,(bpy)$_3$ and $Ru^{III}(bpy)_3$ derivatives), oxalates, trialkylamines, antigens, analytes, and/or combinations, thereof. In another example, it may be desirable to enhance the binding of biomolecules.

One or more chemical moieties that reduce or prevent non-specific binding may be present in, on, or in proximity to a carbon-containing electrode (e.g. carbon black) or one or more fibrils, one or more fibril aggregates, a dispersion of fibrils in another material and/or a fibril mat. Such moieties, e.g., PEG moieties and/or charged residues (e.g., phosphates, ammonium ions), may be attached to the electrode.

Materials used in the support, electrode and/or binding domain may be treated with surfactants to reduce non-specific binding. For example, fibrils or fibril mats may be treated with surfactants and/or detergents that are well known to one of ordinary skill in the art (for example, the Tween series, Triton, Span, Brij). The fibrils or fibril mats are washed, soaked, incubated with, sonicated in, and/or a combination thereof with solutions of surfactants and/or detergents. Solutions of PEGs and/or molecules which behave in similar fashion to PEG (e.g., oligo- or polysaccharides, other hydrophilic oligomers or polymers) ("Polyethylene glycol chemistry: Biotechnical and biomedical applications, Harris, J. M. Editor, 1992, Plenum Press) may be used instead of and/or in conjunction with surfactants and/or detergents.

Undesirable non-specific adsorption of certain entities such as those listed above may be blocked by competitive non-specific adsorption. This competitive binding species might be bovine serum albumin (BSA) immunoglobulin G (IgG).

Non-specific binding of the ECL-TAG may be reduced by chemical modification of the TAG. For example, the TAG may be modified so as to increase its hydrophilicity (e.g. by adding hydrophilic, polar, hydrogen bonding, and/or charged functional groups to the bipyridyl ligands in $Ru(bpy_3)$) and thus reduce non-specific binding of the TAG to other surfaces.

It may be desirable to immobilize biomolecules or other media to carbon-containing materials, e.g. carbon black, fibrils, a fibril mat, and/or carbon dispersed in another material. One may attach antibodies, fragments of antibodies, proteins, enzymes, enzyme substrates, inhibitors, cofactors, antigens, haptens, lipoproteins, liposaccharides, cells, sub-cellular components, cell receptors, viruses, nucleic acids, antigens, lipids, glycoproteins, carbohydrates, peptides, amino acids, hormones, protein-binding ligands, pharmacological agents, and/or combinations thereof. It may also be desirable to attach non-biological entities such as, but not limited to polymers, elastomers, gels, coatings, ECL tags, redox active species (e.g., tripropylamine, oxalates), inorganic materials, chelating agents, linkers etc.

One or more or a plurality of species may become bound non-specifically (e.g., adsorb) to the surface of a material comprised of carbon.

Biological molecules or other media can be attached to fibrils or fibril mats by non-specific adsorption. The extent of non-specific adsorption for any given fibril, fibril mat and/or biomolecule will be determined by certain properties of each. Certain chemical functional groups or biological moieties present on fibrils may reduce or enhance non-specific binding. The presence of hydrophobic and/or hydrophilic patches on the surface of a protein may enhance or reduce non-specific binding of the protein to fibrils or fibril mats. Hydrophilic and/or hydrophobic patches are utilized to control non-specific binding in controlled areas.

Carbon can be derivatized with alkyl ($CH_2$) chains and/or carboxylic acid groups to enhance non-specific binding of biological molecules or media or other materials.

FIG. 26 illustrates the above embodiment schematically in the case of a single fibril. A fibril 2600 is derivatized with alkyl chains 2601. Biomolecules 2602, 2603, and 2604 bind non-specifically to the alkyl chains. Polymer/elastomer 2605 is also bound.

Underivatized fibrils, fibril aggregates and/or fibril mats are used for immobilization of biomolecules, biological media, and other materials by non-specific binding.

The ECL TAG may contains charged residues that could be used to selectively attract a TAG-labeled moiety to a support and/or electrode. For example, a derivatized ECL TAG which has a net negative charge may have a relatively low affinity for an electrode at more reducing potentials and then have higher affinity for the electrode as the electrode potential becomes more oxidizing. The affinity of the ECL label and/or binding reagents to the electrode may be made to modulate. This modulation may be used to improve the kinetics of binding or improve the efficiency of a washing step.

In FIG. 28 molecules (both biological and non-biological) may be attached to fibrils by means of a covalent bond. Fibrils 2800 bearing an NHS-ester chemical functional groups may form covalent bonds 2801 to biomolecules or biological media 2802, 2803. These biological media may use an amino group to form a covalent bond by reaction with the NHS-ester group. Polymer 2808 is immobilized. One of ordinary skill in the art would recognize the generality of NHS-ester groups as coupling agents for molecules and would be able to select both the appropriate biomolecules and the appropriate reaction conditions to achieve immobilization.

A pair of moieties and/or molecules "M1" and "S1", of which one or more is attached to a fibril, exhibit a mutual affinity or binding capacity. M1/S1 may be antibody/antigen, antibody/hapten, enzyme/substrate, enzyme/cofactor, enzyme/inhibitor, lectin/carbohydrate, receptor/hormone, receptor/effector, nucleic acid/nucleic acid, protein/nucleic acid, virus/ligand, cell/cellular receptor, etc. Many combinations of "binding pairs" M1/S1 and would be able to select combinations appropriate to achieve the desired binding. Either or both M1 and S1 may be attached to one or more fibrils.

FIGS. 27 and 28 illustrate some of the many possible configurations that are possible with this embodiment. In FIG. 27, a fibril 2700 derivatized with alkyl chains 2701 non-specifically binds a molecule 2702 that has a mutual affinity or binding capacity for another molecule 2703. Molecule 2703 is also attached to another molecule 2704. A blocking molecule 2705 may be non-specifically adsorbed to the fibril. A blocking polymer 2706 and/or a polymer 2707 which has a ligand (2708) that has an affinity for a molecule 2709 are non-specifically adsorbed.

In FIG. 28, a fibril 2800 is covalently linked via 2801 to biomolecules 2802 and 2803, and a linker molecule 2804. The linker molecule 2804 has a mutual affinity or binding capacity for another biomolecule 2805. Biomolecule 2803 has a mutual affinity or binding capacity for another linker molecule 2806, which is covalently linked to 2807. Polymer 2808 with a ligand 2812 that is specific for a binding partner 2809 is covalently linked to a fibril. Blocking molecules (e.g. BSA) 2811 and blocking polymers 2810 are covalently attached.

A fibril may be derivatized with biotin and/or a biotinylated linker and avidin and/or streptavidin may bind to this linker. Avidin and/or streptavidin may be bound to the fibril, and a biotinylated antibody and/or protein may bind.

Avidin and/or streptavidin may be immobilized on the fibrils by either non-specific binding, covalent bond, another or the same coupling pair, or a combination thereof. The use of (strept)avidin and biotin as "binding pairs" is a widely applied method of attaching biomolecules or biological media to other materials and is well known to those skilled in the art (Spinke et al., 1993, Langmuir 9:1821).

A binding pair may be a monoclonal antibody and an antigen that binds to this antibody.

Multiple binding pairs (e.g., M1/S1/M2) may form. M1 is a monoclonal antibody, S1 is an antigen to M1, and M2 is an antibody that binds to S1. This complex may constitute an antibody/antigen/antibody "sandwich" complex (such antibodies may or may not be monoclonal). M2 may be an antibody tagged with an ECL-active tag (vide supra), a fluorescent label, a radioactive label, an enzymic tag, and/or combinations thereof.

M1 may be a moiety that can complex with a metal, metal ion, or organometallic compound (a "chelating agent") and S1 is a metal, metal ion, or organometallic compound (a "chelate") that forms a complex with M1, and M2 is a moiety on a biological molecule that binds to the M1/S1 complex (Gershon and Khilko, 1995, Journal of Immunological Methods, 7371).

The fabrication of metallic electrode patterns and conductive elements to distribute electrical current to such electrodes on a surface is carried out by methods well known to the art (see, e.g., Leventis et al., U.S. Pat. No. 5,189,549). The preparation of metal films on transparent surfaces is used to produce liquid crystal displays and is readily adapted to the preparation of electrodes according to the invention. Haneko, 1987, Liquid Crystal TV Displays, Principles and Applications of Liquid Crystal Displays, KTK Scientific Publishers, Tokyo, D. Reidel Publishing. Transparent electrode surfaces may also be prepared, for example, according to the method of DiMilla et al., 1994, J. Am. Chem. Soc. 116(5):2225–2226. 0.5 nm of titanium and 5 nm of gold are deposited on transparent substrates (glass or plastic). A thin gold layer as prepared by the method of DiMilla, supra may be used to prepare a transparent electrical structure by the method of Kumar supra. Modifications of this procedure to increase the thickness of the conductor layers for improved current carrying capacity while preferably maintaining transparency are desirable and readily apparent to the ordinary artisan. Such techniques may be used to prepare electrode surfaces that are aligned with or in proximity with discrete binding domains of a PMAMS.

In addition, the films and/or monolayers may be composed of moieties which facilitate the transfer of electrical potential from the electrode surface to the ECL label, rather than using insulating moieties (e.g., alkyl chains) as taught by Zhang and Bard. For example, pi orbital overlap in extensively conjugated systems can be used for electron transfer. Such pi orbital electron transfer is provided by poly-pyrole or other conjugated rings or double bonded structures.

Oligonucleotides may be utilized to modulate electron transfer. For example, overlapping pi bonds in double stranded DNA may be utilized to increase electron transfer rates. Oligonucleotides bound to an electrode surface can be utilized as a binding agent in a binding domain. Upon binding a complementary oligonucleotide sequence a double strand with organized overlapping pi bonds is formed. In a particular embodiment, a first or primary immobilized (e.g., covalently linked to a support) oligonucleotide is ECL labeled. In another embodiment a secondary complementary oligonucleotide or oligonucleotide of partially complementary sequence to the primary oligonucleotide is ECL labeled. A tertiary oligonucleotide complementary to or partially complementary to the secondary oligonucleotide is labeled (e.g., a sandwich assay). Branched oligonucleotide chains may also be utilized. A variety of oligonucleotides and/or oligonucleotide mimics can be utilized (e.g., oligonucleotides with modified bases and/or modified backbones containing for example nitrogen and/or sulfur). Differential studies may be performed. Variable stability of pi overlap in oligonucleotides and/or oligonucleotide complexes may be monitored through modulation of electron transfer. The signal (e.g., ECL light generated and/or impedance measurements) generated from a pi bond stabilized ECL labeled double helical oligonucleotide pair may be correlated against the signal and/or expected signal from a more disordered single stranded oligonucleotide. The variation in ECL signal between a fully complementary ECL labeled double stranded oligonucleotide and a partially complementary ECL labeled double stranded oligonucleotide may be correlated. Additionally, oligonucleotide complexes of multiple oligonucleotides may be utilized. For example, triple helices may be employed.

Modulation of electron transfer rates may be measured using ECL detection as well as electronic means. ECL labels may be covalently linked to oligonucleotide strands and/or non-covalently associated (e.g., intercalated). DNA may be coupled to the electrode without the use of a linker (e.g., adsorption of 5' thiolated DNA on gold) or with a short (<10 atom) linker to ensure low resistance to electron transfer from the DNA to the electrode. A linking chain may be used that can efficiently transport electrons from the electrode to the DNA strand (e.g., a polyacetylene chain).

A mixed monolayer and/or film may be used in which at least one constituent of the monolayer or film, as the case may be, facilitates the transfer of electrical potential. Alternatively, a molecule or particle that facilitates the transfer of electrical potential is adsorbed to the monolayer or film. As examples of the foregoing, the pi conjugated monolayers and/or conducting micro-particles which adsorb to and/or are approximate to the electrode surface, may be used. Patterned regular gaps are created in the monolayer and or film. By utilizing controlled patterns of gaps in an ordered substantially perpendicular SAM composed of long chain alkane thiols (i.e., insulating) to which ECL labels have subsequently been attached, the effective potential imposed at the ECL labels can be controlled. For example, FIG. 11 shows a cassette 1200 formed of a single support 1202 with a metallic layer 1204, a SAM pattern 1206 and gaps 1208 between the SAM patterns.

ECL labeled proteins may be non-covalently linked to a monolayer surface. An ECL labeled protein may adsorb to the surface of a methyl terminated alkane thiol derivatized gold surface. The gold surface may act as the working electrode or the counter electrode. A plurality of binding domains may be incorporated on a single support as is illustrated in FIGS. 11–13. In preferred embodiments the binding domains contain labelled and/or unlabelled proteins and/or nucleic acids and/or cells and/or chemical species.

Alternatively, the length of the components of the monolayer (e.g., the length of the alkane chain in alkane thiol monolayers) may be varied to control the effective potential at the exposed surface of the monolayer.

Broadly, alkane thiols may have carbon chains of length between 1 carbon and 100 carbons. In a preferred embodiment the carbon length of the alkane thiol contains between 2 and 24 carbons. The carbon chain length of the alkane thiol is between 2 and 18 carbons. The carbon chain length is between 7 and 11 carbons. Such alkane thiols may have a variety of head groups exposed to the assay media including methyl groups, hydroxy groups, amines, carboxylic acids, oligo (ethylene glycols), phosphate groups, phosphoryl groups, biotin, nitrilotriacetic acid, glutathione, epoxides, dinitrophenyl, and/or NHS esters. Other head groups include ligands commonly used for the purification and immobilization of recombinant fusion proteins (e.g., Sassenfeld, 1990, TIBTECH 8:88–93). The binding domains may be derivatized to varying degrees to achieve varying densities of binding reagents. For example, different densities of activatable chemistries may be used and/or derivatization may be carried out to varying extents. Mixed chemistries may be utilized to create desired binding densities. Mixed monolayers may be utilized to control the density of activatable groups and/or binding reagents. The density of binding groups is controlled to optimize the ECL signal to noise ratio. The total number of binding sites within a binding domain(s) is controlled to optimize the intensity of the ECL light signal with respect to other ECL light signals from other binding domain(s) whether such ECL light signals are detected sequentially or simultaneously and/or with respect to the light detection means.

The voltage waveform may be applied so as to activate ECL labels associated with a binding domain(s) within a PMAMS one or more times. An electronic potential sufficient to activate ECL light generation may be applied multiple times to the same alkane thiol derivatized surface with bound ECL label to generate multiple ECL light signals. Electronic potential is applied sufficiently to generate ECL reversibly. Potential is applied so as to generate ECL quasi-reversibly. In a quasi-reversible series of voltage waveforms the binding domain within which ECL label associates (e.g., binds), may be chemically and/or physically altered. The voltage waveform series applied may yield irreversible ECL light generation.

Further, an electric potential sufficient to release the components of the monolayer may be applied. It is desirable to release such monolayer components where the volume above the electrode surface is small (e.g., another support or plate resting on the electrode surface). In this way as the monolayer is disrupted, even some ECL labels that are not efficiently excited may be excited by the electrode surface to generate the electrochemiluminescent signal and the ECL labels are restricted to a small volume restricting diffusion from the electrode. Various monolayer compositions may be utilized to control the degree of monolayer disruption for a given potential. Monolayers with components with strong inter-component affinity will be more resistive to monolayer disruption. Longer alkane chain thiols resist disruption more effectively than short alkane chain thiols. By varying the chain length the desired stability may be achieved.

Modification of the binding domains within a PMAMS may be used to modulate the ECL signal. A series of voltage waveforms is applied so as to generate a multiplicity of ECL signals. Said multiplicity of ECL signals may be utilized to gain extra and/or better results. Statistical analysis of the rate of modulation of the ECL signal may be correlated to the overall quality of one or more binding domains. Additionally, said multiplicity of ECL signals may be utilized to increase signal to noise by, for example, filtering certain ECL signals of a series. Further, multiple electronic potential waveform pulses may be utilized to reduce undesirable modulation of signal due to non-specific binding. Electronic potential may be applied to prevent non-specific binding of certain charged species. Additionally, electronic potential may be applied so as to promote the localization near a binding domain(s) of certain analytes or chemical species of interest. The voltage waveform applied supplies large over-potential (e.g., higher potential than is required to generate ECL). Over-potentials may be utilized to modulate ECL signals in a voltage wave series or in a single voltage wave pulse. Additionally, over-potentials may be utilized to modulate the ECL reaction kinetics and/or modulate the binding potential chemically and/or physically. Further, one or more voltage waveforms and/or other electronic probes known to those skilled in the art may be utilized to assess and/or correlate and/or extrapolate information on the quality and/or electronic properties of an electrode(s).

Preferably, the efficiency of the ECL reaction may be enhanced by extending the working electrode surface area by providing additional conducting means in contact with the electrodes. Projections or extensions from the electrode (e.g., wires or whiskers) of conducting materials or conducting particles may be used to increase the electrode surface area, such that the electrical field and more closely approaches the ECL label. Alternatively, indentations or wells in the electrode structures may serve the same purpose.

In particular, conductive particles may fill the gaps on the electrode surface and/or cover the support or monolayer so that the electrical field around the ECL label is increased in absolute magnitude, as shown by FIG. 12. These conductive particles extend the electrode surface area and thereby increase the efficiency of the ECL reaction. FIG. 12 shows a cassette 1300 having a support 1302 bearing a patterned SAM 1306 on a metallic layer 1304 and indicates conducting micro-particles filling in the gaps (e.g., 1208 in FIG. 11) and extending above the metallic surface between the SAM patterns. For magnetic conducting particles, a magnet or magnetic field may be used to draw the particles to the surface. The conductive particles may also be used as described to extend the electrical potential between the electrode surfaces and the binding domain of a PMAMS with two approximated supports. In FIG. 8, the cassette 900 consists of a first support 902 that has a multi array of electrodes, and a second support 904 that has a PMAMS. Conducting micro-particles 906 are positioned between the opposing surfaces in order to extend the electrical potential toward the ECL label on the binding domains (not shown).

Alternatively, conductive polymers are grown from the exposed gaps on the electrode surface to facilitate extending the electrical potential around the ECL label of the sample as shown by FIG. 13. FIG. 13 shows a cassette 1400 having a support 1402 bearing a metallic layer 1404 on a patterned SAM surface 1406. Conductive polymers 1408 are grown over the SAM surface to extend the electrical field provided by a multi array of electrodes (not shown) to binding domains (not shown) on the SAM surface. The conductive polymers may also be used as described to extend the electrical potential between the electrode surfaces and the binding domains of a PMAMS of two approximated supports as illustrated by FIG. 7. In FIG. 7, the cassette 800 consists of approximated supports 802 and 804. Conductive polymers 806 are grown between the opposed surfaces so as to extend the electrical potential toward the ECL label on the binding domain (not shown).

FIG. 9 illustrates a cassette 1000 formed with a first support 1002 having a multielectrode array, a second support 1004 having a PMAMS binding surface, wherein conductive projections (1006) (e.g., fine wire or other protrusions) of the working electrode extend the electrical field around the ECL label in the PMAMS binding domains.

The electrode pairs may be created in a variety of configurations. The simplest configurations, depicted in the figures accompanying this disclosure, are made of metal and/or metal oxide films and/or semiconductor films applied on a non-conducting planar surface. The electrodes of these electrode pairs preferably define between them a region of relatively constant width thereby providing a relatively constant electrical field.

Figures 19A, 19B, 19C, 19D, 19E:
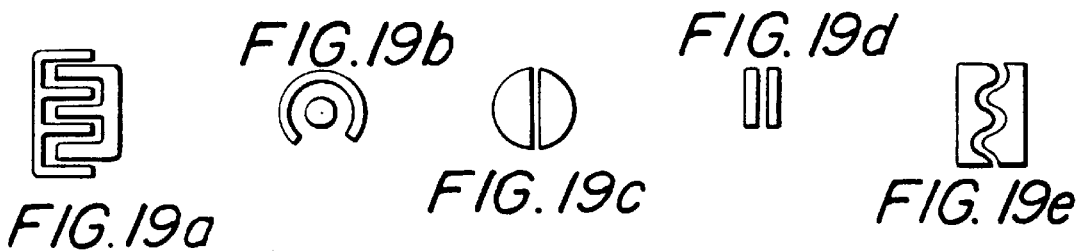

Other configurations of the electrodes are provided. Several of these configurations are shown in plane views in FIGS. 19(a)–(e). FIG. 19(a) shows an inter-digitated comb-like electrode pair. In this structure, each electrode has a plurality of digits extending from the conductor making a comb-like shape. The electrode and counterelectrode pair may be positioned adjacent to a binding domain, or a binding domain may be positioned between an electrode and counterelectrode. FIG. 19(b) shows a pair of concentric electrodes, one circular and one semicircular. FIG. 19(c) shows two semicircular electrodes with their straight edges facing each other. FIG. 19(d) shows a pair of rectangular electrodes. FIG. 19(e) shows a pair of interdigitated electrodes having complementary opposing curved surfaces to form a sinuous gap therebetween.

The electrode/counterelectrode pairs may also be formed into specific shapes complementary to shapes on the PMAMS binding surface for alignment purposes. Exemplary shapes are shown in FIG. 6B. A support 712 bearing electrode pairs 714–720 is shown. The electrode pairs may be, e.g., circular 714, interdigitated 716 triangular interdigitating 718 or multi electrode interdigitating 720.

In the embodiments shown in FIGS. 14–19 discussed supra, the electrode pairs are located on a single support. Alternatively, the electrode pairs are located on first and second opposing supports as shown by FIG. 2.

5.8. Cassettes

Cassettes contain one or more supports of the invention. Cassettes may include a plurality of binding domains and one or more working electrodes.

Figure 2:
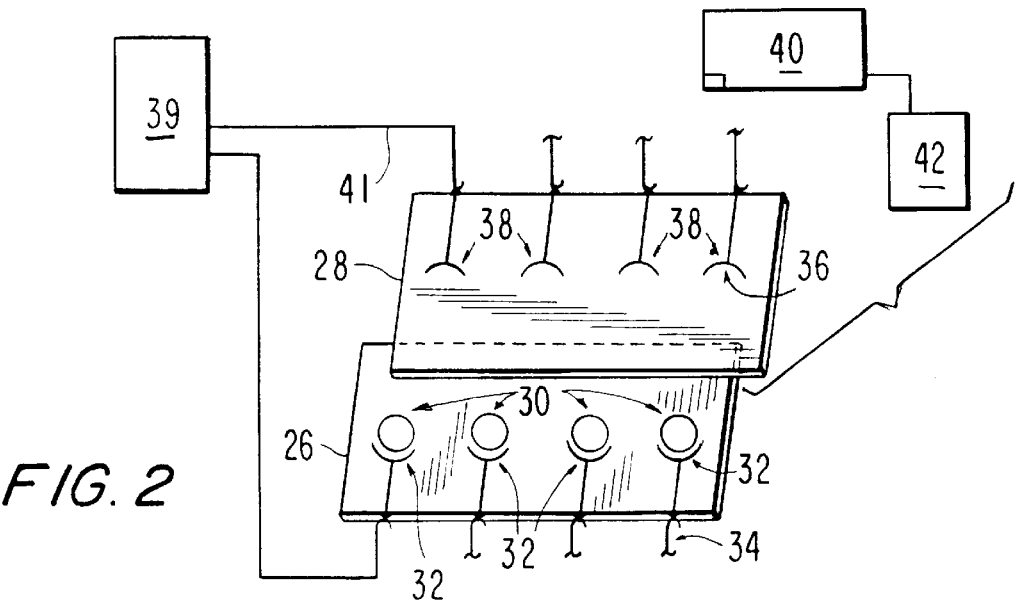

FIG. 2 depicts a cassette where each of plural binding domains 30 on support 26 are adjacent to a different one of plural electrodes 32. Counterelectrodes 38 are formed on a second support 28. An ECL assay is conducted as previously described by placing a sample on binding domains 30 and then moving together supports 26 and 28 so that counter-electrodes 38 are each adjacent to each of binding domains 30 and an ECL reaction may be triggered as described above by waveform generator means 39, via a lead 34, and an ECL signal detected and recorded by light detector means 40, wire 41, and digital computer means 42.

Figure 3:
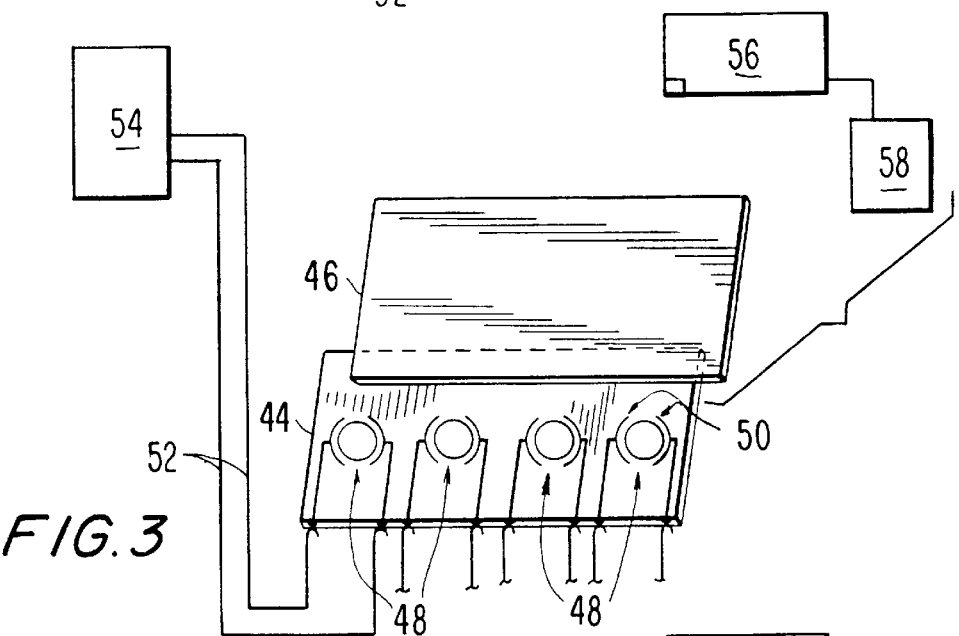

FIG. 3 illustrates a cassette where each of plural binding domains 48 has a different one of plural electrode/counterelectrode pairs 50 adjacent thereto on support 44. Support 46 may optionally be placed adjacent to support 44 so that support 46 forms a sample containing means adjacent to plural binding domains 48 and plural electrodes 50. Thus, an ECL reaction may be triggered via electrical connection 52 by waveform generator means 54, and an ECL signal detected by light detector means 56 and recorded and analyzed by digital computer means 58.

A cassette is provided that contains one or more pairs of supports as shown in FIG. 21, each pair of supports being situated so that the surface of a first support 1501 that contains binding domains faces the surface containing binding domains on the second support 1502, in which each surface contains electrodes 1504 and binding domains 1506; such that each binding domain on the first support faces and is aligned with an electrode on the second support, and each binding domain on the second support faces and is aligned with an electrode on the first support.

Figure 4:
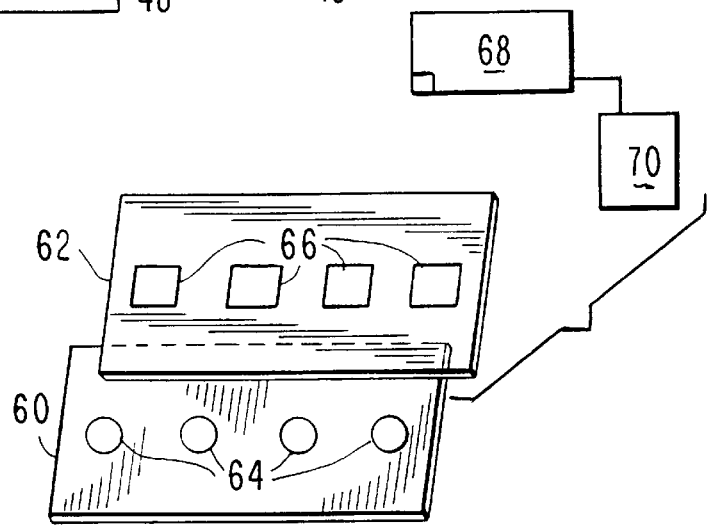

FIG. 4 illustrates a cassette wherein ECL electrodes are optional. Binding domains 64 on support 60 are contacted with a sample suspected of containing an analyte. Regions 66 on support 62 contain reaction medium for detecting or measuring an analyte of interest or for carrying out a desired reaction.

Support 60 and Support 62 are brought together so that binding domains 64 and regions 66 are contacted and the presence of an analyte or reaction product is determined by a reporter system, e.g. a calorimetric chemiluminescent or fluorescent signal that may be detected by photodetector means 68 and recorded and analyzed by digital computer means 70.

In a preferred embodiment, a cassette or apparatus of the invention comprises a means for sample delivery onto the plurality of discrete binding domains (see, e.g., element 1 on FIG. 1 of U.S. Pat. No. 5,147,806; element 1 on FIG. 1 of U.S. Pat. No. 5,068,088; each of which is incorporated by reference in its entirety). The means for sample delivery can be stationary or movable and can be any known in the art, including but not limited to one or more inlets, holes, pores, channels, pipes, microfluidic guides (e.g., capillaries), tubes, spigots, etc. Fluids can be moved through the system by a variety of well known methods, for example: pumps, pipettes, syringes, gravity flow, capillary action, wicking, electrophoresis, pressure, vacuum, etc. The means for fluid movement may be located on the cassette or on a separate unit. The sample can be placed on all of the binding domains together. Alternatively, a sample may be placed on particular binding domains by a capillary fluid transport means. Alternatively, samples may be placed on the support by an automatic pipetter for delivery of fluid samples directly to the PMAMS on a support, or into a reservoir in a cassette or cassette holder for later delivery directly to the binding surface.

Supports may be prepared from materials including but not limited to, glass, plastic, ceramic, polymeric materials, elastomeric materials, metals, carbon or carbon containing materials, alloys, composite foils, silicon and/or layered materials. Supports may have a wide variety of structural, chemical and/or optical properties. They may be rigid or flexible, flat or deformed, transparent, translucent, partially or fully reflective or opaque and may have composite properties, regions with different properties, and may be a composite of more than one material.

Reagents for conducting assays may be stored on the cassette and/or in a separate container. Reagents may stored in a dry and/or wet state. In one embodiment, dry reagents in the cassette are rehydrated by the addition of a test sample. In a different embodiment, the reagents are stored in solution in "blister packs" which are burst open due to pressure from a movable roller or piston. The cassettes may contain a waste compartment or sponge for the storage of liquid waste after completion of the assay. In one embodiment, the cassette includes a device for preparation of the biological sample to be tested. A filter may be included for removing cells from blood. In another example, the cassette may include a device such as a precision capillary for the metering of sample.

The plurality of binding domains and the plurality of electrodes/counterelectrodes on the supports are typically placed in registered proximity to one another by mechanical means, e.g., by using guide posts, alignment pins, hinges (between each support) or guide edges. Optical guide means may be used to position both supports and electronic means utilizing optical guide marks defined on the supports. Other systems using electrical or magnetic registration means are also available.

The supports of the cassette may be configured so as to protect the electrode pairs from contact with the sample until required to trigger an ECL reaction. For example, the electrodes may be kept separate from a binding domain surface until electrode contact with the sample is required by using various mechanical means such as a removable electrode protective means.

A cassette or apparatus of the invention comprises reference electrodes, e.g., Ag/AgCl or a saturated calomel electrode (SCE).

The supports may be held together by clips, adhesive, rivets, pins or any other suitable mechanical attachment. They may also be held together by the surface tension of a liquid sample or by a compression means removably placed on opposite sides of the two supports.

The cassette may also comprise more than two supports, with, for example, alternating layers of binding domains and electrodes or multiple supports comprising both a binding surface and an electrode surface on a single support. This will form a three dimensional array of ECL analysis cells. All of the foregoing components of the cassette are transparent, except, optionally, some areas between the binding domains. For example, multiple transparent binding surfaces, electrode surfaces, and supports may be stacked.

The first and second supports may be flat and opposed to define a sample-holding volume therebetween. Alternatively, the first and second support layers may be configured in other suitable shapes including spheroidal, cuboidal, cylindrical, provided that the two supports, and any other components thereof, conform in shape. For example, FIG. 10 shows a cassette 1100 formed from two adjacent non-planar supports 1102 and 1104. Each support has a surface complementary to the other in conformation.

Either support may have a PMAMS surface or a multi electrode array or both. One or both of the supports may be elastomeric so as to conform to the shape of the other support. The supports or the cassettes may also be prepared in a precut format, or dispensed in a suitable length from a roll dispenser. The cassette may further include sample receiving means such as a sample-holding volume and sample distribution grooves, channels, indentations and the like.

FIG. 37 shows a cassette where binding domains (3702) in and/or on a matrix (3703) are presented on a surface (3701). A second surface (3700) supporting a working electrode (3704) and a counter electrode (3705) is placed so that the binding domains are in close proximity to the working electrode. Under conditions which lead to light generation from ECL label bound to the binding domains, light may be detected through either or both surfaces. An array of light detectors (3706, e.g., a CCD array, an intensified CCD array, or an avalanche photodiode array) is used to simultaneously measure the plurality of light signals from each of the binding domains. The light detector array images the light generated from binding domains. Lenses, reflectors and/or optical guides may be utilized to enhance imaging. In other examples, light detected from zones or regions of light detectors (e.g., a light detecting pixel(s)) is correlated to a binding domain(s). Image analysis may be used to aid in the correlation of detected light with binding domains. In one favored embodiment, the surface is elastomeric or compliant and therefore capable of making intimate contact with the electrode surfaces. The binding domains are linked to polymers capable of carrying ionic currents from the counter electrode to the working electrode. In a more favored embodiment, the objects are water-swollen polymers capable of carrying an ionic current from the counter electrode to the working electrode.

FIG. 38 shows a cassette where binding domains (3805, 3806, 3807) are presented on the surfaces of distinct objects (3808, 3809, 3810) supported on the counter electrode (3800). A working electrode (3801) is placed in proximity to the surface of the objects. Under conditions which lead to ECL from TAGged groups bound to the binding domains, light may be detected through either or both of the electrodes (if one or both of the electrodes is transparent or semitransparent) and/or from the side. An array of light detectors (3802) is used to simultaneously measure the plurality of light signals from each of the binding domains. The objects may be elastomeric and/or compliant and are therefore capable of forming intimate contact with the working electrode. The objects may be polymers capable of carrying ionic currents from the counter electrode to the working electrode. The objects may be water-swollen polymers capable of carrying an ionic current from the counter electrode to the working electrode.

A transparent support containing one or more binding domains is brought into contact with a carbon electrode, e.g. a fibril mat electrode or an electrode comprised of carbon black or carbon felt. Reagents may be flowed either between the support/binding domains and the fibril mat, or through the mat to the binding domains. Light may pass from the binding domains, through the transparent support to a detector.

In another preferred embodiment, an electrode is coated with an optically translucent or transparent layer of carbon (e.g. fibrils) so as to increase the effective surface area of the electrode.

Advantageously, the PMAMS supports and/or cassettes of the invention may be packaged as kits. The kit comprises one or more PMAMS supports prepared according to the invention for conducting ECL reactions including assays, controls and the like. Reagents may be optionally included in the kit, including control reagents, ECL assay and calibration reagents and the like. A reagent mixture may be included which contains a plurality of binding reagents specific for a plurality of different analytes.

5.9. Apparatus For Conducting ECL Reactions

In one embodiment, the PMAMS on supports, and cassettes containing the same, are designed to be inserted into an apparatus, that contains means for applying one or more test samples onto the PMAMS binding domains and initiating a plurality of ECL reactions. Such apparatus may be derived from conventional apparatus suitably modified according to the invention to conduct a plurality of ECL assays based on a support or cassette. The invention provides various apparatus adapted to carry out ECL assays using each of the specific embodiments of PMAMS described in the Sections hereinabove. An apparatus for conducting ECL reactions is disclosed by Zoski et al. (U.S. Pat. No. 5,061,445). Modifications required include the provision for support and/or cassette handling, multiple sample delivery, multiple electrode addressing by a source for a voltage waveform and multiple ECL signal acquisition and processing.

Elements of illustrative apparatus in accordance with the invention are shown in FIG. 6A. Such apparatus 700 comprises upper and lower supports 702, 704 and an electrode guard 710. The upper support bears a plurality of electrode/counterelectrode pairs (not illustrated). The lower support bears the binding domains 706. The apparatus is capable of removing the electrode guard from the cassette and positioning the electrode/counterelectrodes to contact the analyte bound to the binding domains. A reagent or fluid flow space 708 is adjacent to the support bearing the binding domains. The apparatus is also capable of simultaneously or sequentially sending an identical or individually determined voltage wave to each of the plurality of electrode/counterelectrode pairs to trigger ECL reactions in the cassette and then measuring the emitted ECL radiation, by a photon detector, e.g., light detector means. The apparatus can further comprise temperature control means for maintaining the temperature of the support and/or cassette, or the environment thereon and adjusting the temperature as needed to optimize ECL reaction conditions. Temperature control means are preferably heating and cooling means, e.g., electrical resistive heating elements, cooling fans, refrigeration means, and any other suitable source of heating or cooling. Temperature control means also includes temperature sensors, e.g., a thermostat or thermocouple device, and means to turn the heating or cooling means on or off in response to detected temperature changes.

The apparatus also provides means to hold, move and manipulate one or more supports or cassettes to conduct ECL reactions. The apparatus may further comprise a stationary or moveable sample delivery means for placing a sample onto the PMAMS binding domains, as described for cassettes hereinabove.

The apparatus also comprises an electrode contact means able to electrically connect the array of separately addressable electrode connections of the cassette to an electronic-voltage waveform generator means, e.g., potentiostat (see e.g., FIG. 5 of U.S. Pat. No. 5,068,088). The waveform generator means delivers signals sequentially or simultaneously to independently trigger a plurality of ECL reactions in the cassette.

During an ECL assay, ionic current between working and counter electrodes may flow through tonically conducted liquid (for example water containing ionic salts), through a thin film of such liquid, and/or through an ionically conducting solid matrix.

Thus, an apparatus for measuring electrochemiluminescence in a sample can comprise a plurality of cells for holding at least one sample, wherein a cell may be formed from one or more electrodes and one or more counterelectrodes and a first support that comprises a plurality of discrete binding domains. The electrodes and counterelectrodes can be provided on the surface of the first support or on the surface of a second support wherein the second support is in close proximity to the binding domains on the first support. The electrodes and counterelectrodes may occur in pairs. The cell may further comprise a plurality of sensing electrodes to sense the voltage adjacent to the working electrode. The cassette may further comprise a cell containing a reference electrode.

The apparatus further comprises light detection means able to detect ECL reactions conducted in the cassette, e.g., by one or multiple detector means. Such detector means include, simply by way of example, an array of fiberoptic channels in register with the electrode array and positioned adjacent thereto, connected to an array of photodetector means, or to a single light detector means able to scan the array of ECL signals as emitted.

The apparatus optionally comprises a digital computer or microprocessor to control the functions of the various components of the apparatus.

The apparatus also comprises signal processing means. In one embodiment, and simply by way of example, the signal processing means comprises a digital computer for transferring, recording, analyzing and/or displaying the results of each ECL assay.

Alternatively, the apparatus comprises electrode translation means, for example, to scan one or more electrode/counterelectrode pairs across the binding surface to sequentially trigger ECL.

Size exclusion filters may be used in a parallel array of PMAMS.

5.10. ECL Assays That May Be Conducted

ECL labels for use according to the present invention can be selected from among ECL labels known in the art (see Section 2.2, above, and U.S. Pat. No. 5,310,687). The ECL label may comprise, for example, a metal-containing organic compound wherein the metal is selected from the group consisting of ruthenium, osmium, rhenium, iridium, rhodium, platinum, palladium, molybdenum, technetium and tungsten. Suitable linking chemistry for preparing ECL TAG reagents is well known and disclosed, for example, by Bard et al. (U.S. Pat. Nos. 5,310,687 and 5,221,605). The means of attachment of the ECL label to a binding reagent may be covalent and/or noncovalent. An ECL label may bind non-covalently to a binding reagent (e.g., through hydrophobic effects or ionic interactions). In other examples of non covalent attachment, ECL label(s) are bound (covalently or non-covalently) to a complex which in turn is non-covalently linked to a binding reagent. A more specific example would be covalent attachment of Ru(bpy)3 through a linker to a Ni(II)-trinitrilotriacetic acid complex. This molecule will attach to binding reagents which include a peptide sequence containing a plurality of histidines. Other receptor ligand pairs are known in the art which can be used in a similar fashion (Sassenfeld, 1990, TIBTECH 8:88–93).

Furthermore, an ECL label can be used that contains a multiplicity of organometallic compounds (e.g., Ru-containing) configured as a branched network (e.g., through a network of hydrocarbon linkers). Such branched networks containing a multiplicity of organometallic moieties capable of ECL may be attached once or attached at a plurality of positions on a molecule to be ECL labeled. In another embodiment, the ECL label containing a multiplicity of organometallic compounds is a linear polymer with the organometallic groups attached at a plurality of positions along the length of the polymer chain (e.g., linear, branched or cyclic polymers).

A plurality of binding domains may be used in a variety of additional ECL assay formats well known to the art. In quantitative assays, a known amount of ECL labeled reagent is used and the amount of ECL measured is correlated to known standards to calculate the amount of analyte present. Forward, reverse, competitive and sandwich assays can be performed by methods well known to the skilled worker. In competitive assays, for example, a method for quantitatively determining the amount of an analyte of interest in a volume of multicomponent, liquid sample is performed as follows. The binding surface is contacted concurrently with (a) a known amount of an ECL labeled ligand that is capable of competing with the analyte of interest in binding to a binding reagent present on the binding domains, and (b) sample suspected of containing the analyte of interest; the contacting being effected under appropriate conditions such that the analyte of interest and the ligand competitively bind to the binding reagent. The presence of the analyte in the sample will reduce the amount of competing ECL-labeled ligand that binds to the binding domain, thus reducing (relative to when no analyte is present in the sample) the resulting amount of ECL. ECL in the resulting binding domain is triggered and the amount of light emitted is quantitatively determined, thereby quantitatively determining the amount of the analyte of interest present in the sample. Alternatively, the sample may be contacted with the binding surface prior to contacting the binding surface with the ECL labeled ligand; the ECL labeled ligand will then compete with the previously bound analyte from the sample on the PMAMS surface and displace some of the previously bound analyte. In an alternative embodiment, the sample can be treated so as to contain substances/molecules that are ECL-labeled, and a standard amount of unlabeled analyte of interest can be contacted with the binding surface prior to or concurrently with contacting of the binding surface with the sample in order to carry out a competition assay.

In a sandwich assay, the ECL labeled ligand is a binding partner that specifically binds to a second binding moiety on the analyte of interest. Thus, when analyte that specifically binds to a binding reagent in a binding domain of a PMAMS is present in a sample, a "sandwich" is thus formed, consisting of the binding reagent on the binding domain, bound to analyte from the sample, bound to the ECL labeled binding partner. In another competitive sandwich assay, copies of the analyte itself are attached to the binding domains of the multi-array binding surface prior to exposure to the sample. Sample is then contacted with the binding surface. An ECL labeled binding partner (which can specifically bind to the analyte) will bind the analyte in the absence of free analyte (from sample) in the assay solution, but will be competitively inhibited in the presence of free analyte (from sample) in the assay solution.

In alternative embodiments, sequential labeling is performed. For example, in a particular embodiment of a sandwich assay, the analyte bound to the binding domain is contacted sequentially with a plurality of ECL labeled binding partners of the analyte. ECL measurements and optional washing steps are conducted in between contacting with each different binding partner. In this way an ECL measurement of a plurality of different binding moieties of an analyte may be performed (e.g., CD8$^+$, a, b T cell antigen receptor positive T cell). Additionally, multiple ECL labels, each emitting light at a distinguishable wavelength, may each be linked to a different binding reagent specific for a different moiety on an analyte. Further, a plurality of distinguishable reporter means (e.g., ECL label, fluorescent label and enzyme linked label) each attached to a different binding reagent specific for a different binding moiety of an analyte may be used, for example, to distinguish a CD4$^+$, a, b T cell antigen receptor-positive cell from a CD8$^+$ a, b T cell antigen receptor-positive cell.

In preferred embodiments the binding domains contain labelled proteins and/or nucleic acids and/or cells and/or chemical species. Such labelled components (e.g., ECL labels) may be added to the binding domain during fabrication, prior to the start of an assay, during an assay and/or at the end of an assay. For example, multiple labelled components may be added at various times and sequential readings may be taken. Such readings may provide cumulative information. In another embodiment, the binding domains of the PMAMS may be reused a multiplicity of times. After a given assay is performed, the surface may be washed under conditions which rejuvenates the activity of one or more binding domains of the PMAMS surface. By way of example, some binding reactions may be reversed by changing the ionic strength of the reaction solution.

Alternatively, heat may be used to disassociate binding complexes. Some, binding domains may be inherently self-renewing. Binding domains which contain catalytic (e.g., enzymatic) functionalities may be utilized more than once. The binding domains are utilized continuously, and thus can be used in biosensor applications.

Additionally, the assay may be formatted so that the binding reagent attached to the multi-array multi-specific patterned surface is ECL labeled. Upon binding to certain analytes of interest in a sample, the ECL signal will be quantitatively modulated. For example, the ECL labeled binding reagent attached to the surface may be specific for an analyte on a cell surface e.g., antigens such as alpha and beta T cell antigen receptor antigens, or CD4 or CD8 antigens. Upon exposure to a mixture of cells, cells bound to the surface will sterically hinder the ability of an electrode surface, brought into proximity with the multi-array multi-specific surface, from exciting the ECL labeled binding reagent thus down-modulating the ECL signal.

Homogeneous and heterogenous assays may be conducted. In heterogeneous assays, unbound labeled reagent is separated from bound labeled reagent (e.g., by a washing step) prior to exposure of the bound or unbound labeled reagent to an electrical potential. In homogeneous assays, unbound labeled reagent and bound labeled reagent are exposed to an electrical potential together. In homogeneous assays, the intensity or spectral characteristics of the signal emitted by the bound labeled reagent is either greater than or less than the intensity of the signal emitted by the unbound labeled reagent. The presence or absence of the respective bound and unbound components can be determined by measuring the difference in intensity.

Once the desired steps of contacting the binding reagents with analyte or competitor thereof and any binding partners thereto, have been completed, one then ensures that the ECL label is subjected to an environment conducive to ECL. Suitable ECL assay medium are known in the art. Such an assay medium advantageously includes a molecule that promotes ECL of an ECL label, including but not limited to oxalate, NADH, and most preferably tripropylamine. Such a "promoter" molecule can be provided free in solution, or can be provided by prior linkage to or by production at (e.g., as a product of a chemical reaction) the PMAMS surface, a monolayer on the surface, the binding domain, the electrode surface, a binding reagent, and/or an ECL label, etc. If the medium surrounding the ECL label bound to the binding domains resulting from the contacting steps is conducive to ECL, no changes to the medium need be made. Alternatively, the medium can be adjusted or replaced to provide a medium conducive to ECL. An electrode and counterelectrode is already proximate to the binding domain, or is brought near or in contact with the binding domain, a voltage waveform is applied, and ECL is detected or measured.

In a preferred embodiment of the invention, the above-described steps of contacting the binding reagents with analyte or competitor thereof and any binding partners thereto, are carried out in the absence of electrodes and counterelectrodes, i.e., such that the sample does not contact the electrode or counterelectrode. Subsequent to these contacting steps, electrodes and counterelectrodes are brought sufficiently close to the ECL label bound to the binding domain, to trigger an ECL reaction.

A support having a PMAMS may be used for sequencing of nucleic acid strands. For example, a PMAMS with a plurality of binding domains is prepared with different oligonucleotide probes of known nucleotide sequence as the binding reagents in different binding domains. That is, different binding domains will contain binding reagents of different known nucleotide sequence. The oligonucleotide chain or fragments of the oligonucleotide chain to be sequenced are then allowed to bind (hybridize) to the PMAMS binding domains. The nucleic acids to be sequenced are ECL labeled. Binding assays are conducted on the PMAMS and the distribution of ECL signals from the discrete binding domains on the PMAMS is used to sequence the oligonucleotide chain.

The above-described method is based on the ability of short oligonucleotides to hybridize to their complementary or substantially complementary sequence in another nucleic acid molecule (see, e.g., Strezoska et al., 1991, *Proc. Natl. Acad. Sci. USA* 88: 1089–1093; Bains, 1992, *Bio/Technology* 10: 757–58, which are incorporated herein by reference). Conditions can be selected such that the desired degree of sequence complementarity is necessary for successful hybridization. Hybridization of a DNA molecule of unknown sequence to a probe of predetermined sequence detects the presence of the complementary sequence in the DNA molecule. The method is preferably practiced such that the hybridization reaction is carried out with the oligonucleotide probes bound to the binding domains and the sample DNA in solution.

A PMAMS may also be utilized to isolate, screen and/or select a novel molecule or complex of desired function (e.g. binding or catalysis). A PMAMS may be used to isolate compounds and/or lead compounds for therapeutic uses. A PMAMS containing a plurality of peptides, nucleic acids, viral vectors, or polymers, synthesized by a variety of combinatorial chemistries, can be made using the methods of the invention. A wide variety of such PMAMS treated supports may be used to rapidly screen for binding to, for example, an ECL labeled cellular receptor. In one method a first PMAMS with a large diversity of unrelated peptide sequences is used in order to isolate lead binding peptide sequences. Then a PMAMS with peptides of related sequences to those which showed binding to the molecule of interest (e.g., a cellular receptor) on the first PMAMS are then used. The process is repeated until a peptide with the desired binding characteristics are found.

An analyte of interest may be, e.g., a whole cell, a subcellular particle, virus, prion, viroid, nucleic acid, protein, antigen, lipoprotein, lipopolysaccharide, lipid, glycoprotein, carbohydrate moiety, cellulose derivative, antibody or fragment thereof, peptide, hormone, pharmacological agent, cell or cellular components, organic compounds, non-biological polymer, synthetic organic molecule, organo-metallic compounds or an inorganic molecule present in the sample.

The sample may be derived from, for example, a solid, emulsion, suspension, liquid or gas. Furthermore, the sample may be derived from, for example, body fluids or tissues, water, food, blood, serum, plasma, urine, feces, tissue, saliva, oils, organic solvents or air. The sample may comprise a reducing agent or an oxidizing agent.

Assays to detect or measure the following substances may be conducted by the present invention, by incorporation of a binding reagent specific to said substances into the binding domains of the binding surfaces of the invention: albumin, alkaline phosphatase, alt/SGPT, ammonia, amylase, AST/SGOT, bilirubin-total, blood used nitrogen, calcium, carbon dioxide, chloride, cholesterol-total, creatinine, GGT, glucose, HDL cholesterol, iron, LDH, magnesium, phosphorus, potassium, protein-total, sodium, triglycerides, uric acid, drugs of abuse, hormones, cardiovascular system modulators, tumor markers, infectious disease antigens, allergy provoking antigens, immunoproteins, cytokines anemia/metabolic markers, carbamazepine, digoxin, gentamicin, lithium, phenobarbital, phenytoin, procainamide, quinidine, theophylline, tobramycin, valproic acid, vancomycin, amphetamines, antidepressants, barbiturates, benzodiazepines, cannabinoids, cocaine, LSD, methadone, methaqualone, opiates, pheneylindine, phropoxyphene, ethanol, salicylate, acetaminophen, estradiol, progesterone, testosterone, hCG/bhCG, follicle stimulating hormone, luteinizing hormone, prolactin, thyroid hormones such as thyroid stimulating hormone, T4, TUP, total-T3, free-T4, free-T3, cortisol, creatinine kinase-MB, total-creatinine kinase, PT, APTT/PTT, LD ISOs, creatinine kinase ISOS, myoglobin, myo light chain, troponin 1, troponin T, chlamydia, gonorrhea, herpes virus, Lyme disease, Epstein Barr virus, IgE, Rubella-G, Rubella-M, CMV-G, CMV-M, toxo-G, toxo-M, HBsAg (hepatitis B virus surface antigen), HIV 1, HIV 2, anti-HBc, anti-HBs, HCV, anti-HAV IgM, anti-HBc IgM, anti-HAV, HBeAg, anti-HBeAg, TB, prostate specific antigen, CEA, AFP, PAP, CA125, CA15-3, CA19-9, b2-microglobulin, hemoglobin, red blood cells, HBcAb, HTLV, ALT, STS-syphilis, ABO blood type antigens and other blood typing antigens, cytomegalovirus, ferritin, B-12, folate, glycalated hemoglobin, amphetamines, antidepressants and other psychotropic pharmaceuticals.

Measurements of ECL at different binding domains can be done sequentially or simultaneously.

A PMAMS specific for an analyte of interest that is a cell-surface protein is first exposed to a sample containing cells, in which it is desired to count the cells in the sample. In a preferred embodiment, a known sample volume and/or diluted sample is exposed to a PMAMS which has a multiplicity of binding domains specific for at least one cell surface antigen. Bound cells can then be quantified by attachment of a secondary binding group linked to an ECL tag. This is a group capable of interacting with a broad range of cell types, for example an ECL-TAG linked to a hydrophobic group capable of inserting into a cell membrane or to a lectin directed against cell surface sugars. The ECL-TAG is linked to a secondary antibody directed against a cell surface antibody. In a more specific embodiment, several cell types bound to the same domain can be distinguished by the use of multiple ECL-TAG labeled secondary antibodies. One preferably ensures that the number of discrete binding domains specific for a given analyte on the surface of a cell exceeds the average number of cells that will bind that are present in the sample. Statistical techniques can then be utilized to determine the number of cells per sample volume. This technique can also be used, e.g., to count other particles such as viruses, where the binding reagent recognizes an antigen on the virus. The domains can be small compared to the size of a cell so that only one cell can bind per domain, thus leading to a digital signal for each domain which can then be analyzed over the sum of the domains using statistical methods. The domains are large compared to the size of a cell so that multiple cells can bind to a domain. In this case, the level of signal from each domain can be calibrated to give the number of cells per volume of sample. Image analysis using an array of light detectors (e.g., a CCD camera or avalanche photodiode array) could be used to count cells and determine cell morphologies.

The invention preferably also provides for methods for conducting ECL reactions, e.g., assays, at a rate of to 1000 ECL reactions in from 5 to 15 minutes.

5.11. PMAMS For Use With Other Analytic Methods And/Or ECL

The techniques described above for ECL based detection can be used in conjunction with other assay techniques, e.g., as domains in which catalyses and other chemical reactions can occur. Discrete binding domains according to the invention may be used in other assay techniques such as, clinical chemical chemistry assays, e.g., electrolyte determinations, clinical enzyme determinations, blood protein determinations, glucose, urea and creatinine determinations, and the like. Other assay techniques that may be combined with ECL assays and/or used alone with the PMAMS of the invention include chemiluminescent based label, fluorescent based assays, enzyme-linked assay systems, electrochemical assays (see, e.g., Hickman et al., 1991, Science 252:688–691) and/or resonance detection (e.g., surface plasmon and acoustic techniques) assay systems.

PMAS supports with drops may be utilized in which there is a plurality of different chemistries within the array of drops. Each drop may contain different binding reagents and/or different chemical assays (i.e., reaction medium for the same). For example, the drops may be hydrophilic, resting on hydrophilic surface binding domains which are surrounded by hydrophobic surface regions. The drops are protected by a hydrophobic solution covering the surface. The hydrophilic solution to be assayed is deposited on a second PMAMS with hydrophilic binding domains surrounded by hydrophobic regions. The two surfaces are brought into registered proximity so as to bring into contact the hydrophilic domains on the opposite surfaces and a spectral analysis is performed to detect reaction products of the chemical assays.

The fibril mats may be patterned such that there are a plurality of discrete hydrophobic and/or hydrophilic domains surrounded by hydrophilic and/or hydrophobic domains. Drops of aqueous solutions containing binding reagents may rest on hydrophilic regions and be confined by surrounding hydrophobic regions. These drops may contain, for example, fibrils, aggregates of fibrils, binding reagents, ECL reagents, reagents for assays, surfactants, PEGs, detergents, a plurality of biological molecules mentioned above by example, and/or combinations thereof.

The hydrophobic solution covering the first PMAMS is controllably removed (e.g., evaporated, wicked) so as to expose only a portion of the hydrophilic drops at the tops to the environment. A hydrophilic solution to be assayed for an optical chemical reaction is then exposed to the PMAMS surface—the hydrophilic micro-drops and the solution to be assayed mix and analysis (e.g., spectral) is performed.

PMAMS binding domains may also be used as a pre-filter or filter. For instance, a cellular specific PMAMS can be used in certain instances alone as a filter for certain cell types as well as in conjunction with a size exclusion filter. The resulting analyte solution is then exposed to a PMAMS specific for subcellular particulate matter (e.g., viruses). The particulate subcellular PMAMS and/or a size exclusion filter is used to generate a small molecule (e.g., protein, small chemical entities) analyte solution. By utilizing a serial PMAMS assay system the analyte solution may be sequentially purified in order to decrease non-specific analyte interactions.

The optical opacity of a material used for a support, electrode and/or binding domain may be varied to achieve desired properties. Such a material may be translucent, transparent or substantially opaque, depending on the thickness, compositing and/or optical density of the material.

The optical opacity of fibril mats increases with increasing thickness of the mat. Very thin mats are optically translucent. Thicker mats can be substantially opaque. In some examples, mats that range in thickness from 0.01 $\mu$m to 0.5 $\mu$m are substantially translucent. In other examples, mats with a thickness greater than 20 $\mu$m are substantially opaque. Mats with a thickness between 0.5 $\mu$m and 20 $\mu$m have intermediate opacity, which increases with increasing thickness of the fibril mat. The optical opacity of a particular thickness of a mat may depend on the composition, density, derivatization, number of layers, types and quantities of materials dispersed in the mat, and/or a combination thereof. It may also depend on the wavelength of the light used.

If a material is substantially translucent at a given thickness and substantially opaque for another thickness, light emitted from a certain depth in the material may pass out of the material while light emitted from another (e.g. greater) depth may be substantially absorbed or scattered by the material. In one example, the variable opacity of a material allows the material to be used as an optical filter.

Light emitted from a certain depth in a fibril mat may pass substantially through the mat and be observed with a detector placed on or in proximity to a surface of the fibril mat. Light emitted from another depth may be substantially absorbed and/or scattered by the mat and not be observed by a detector placed on or in proximity to the surface of the mat. This property of a fibril mat (and/or optically similar materials) may be used to distinguish between bound and unbound reagents in ECL assay.

Certain reagents can diffuse (actively or passively), be pulled (e.g., by suction filtration and/or by capillary action), wicked, or pushed by pressure to a sufficient depth in a porous material that emission of light from these reagents is substantially or entirely absorbed or scattered by the mat. In one example, a fibril mat acts as both a physical and an optical filter though which certain reagents are passed, certain reagents are entrained, and/or certain reagents bind to a very thin layer either at or in proximity to the surface of the mat. Reagent bound to one or more binding domains and/or species bound to species bound to one or more binding domains (these domains being located either on the surface of the fibril mat or in a very thin layer near the surface of the mat on the PMAMS) are prevented from diffusing, being pulled, etc. into or through the mat. Reagents and/or other solutions are flowed or suspended on and/or over the surface of the fibril mat such that reagents bind only to a very thin layer on the surface of the mat. Reagents can be washed through the mats, once or many times, in one or more directions. Reagents may bind to the fibril mat, one or more binding domains, other or the same reagents bound to one or more binding domains, be entrained inside the mat, pass through the mat, or a combination thereof.

Porous materials used in supports and/or electrodes may have more than one layer in which the upper layer has binding domains and other layers within the mat do not have binding domains. In one example, a fibril mat, (illustrated schematically in FIG. 29), the upper layer 2900 is thick enough to prevent passage of light that originates in layer(s) 2901, 2902 from the mat below this layer. Light 2903 that originates from sources 2904, 2905 bound to this upper layer can be detected by a detector 2906 located at or in proximity to the surface of the mat. Light originating from sources 2907, 2908, 2909 in lower layers 2901, 2902 is absorbed and/or scattered by either or all layers and cannot be detected by the detectors 2906, 2910.

A pre-filtration step may be used to select particular sizes, types, derivatives of fibrils and/or fibril aggregates before the mat is fabricated. The filter agent used to filter a suspension of fibrils is a mat of fibrils of a certain or many porosities.

A porous material (e.g. a fibril mat) may act as the support for the binding domains, an electrode which may be used for ECL or other electrochemical applications, a filter that can be used to control delivery of reagents, and/or an optical filter that can transmit, absorb and/or scatter light to varying degrees.

5.12. Electrochromic ECL Display Panels

The invention also provides for the production of isolated electrochemical pixels for use in flat panel displays. Lithographic techniques have been proposed for use in electrochromic and electrochemiluminescence based flat panel displays to create pixels which when electronically addressed have limited effect on neighboring pixels (i.e., limited cross-talk) (see U.S. Pat. No. 5,189,549). A limitation of the lithographic technique for reducing such cross-talk is that the electrolyte material must be capable of changing its conductivity upon exposure to light. It is a feature of the current invention to reduce cross-talk between pixels without the necessity of using materials capable of photo-induced conductivity modulation thereby allowing the use of a wide range of different solutions, gels or films.

The two electrode surfaces which are the active region of the pixel are on two surfaces facing each other in a sandwich configuration. The electrode surfaces are coated with, for example, complementary electrochromic materials. To reduce cross-talk a conductive electrolytic film is placed between the electrode surfaces with non-conductive regions between different electrode pairs (i.e., between pixel elements). If the coated electrode surfaces are hydrophilic then the areas of the surface around the electrodes are made to be hydrophobic (e.g., by means of stamping or deposition through a mask) and hydrophilic conductive droplets are placed on the electrode on the first surface (e.g., by means of a fluidics array) and then the second surface is robotically aligned and brought into contact with the first surface so that the electrodes are in register. The electrolytic droplets can thus be constrained to the area within one pixel without any conductive material between pixels. The electrode pairs of a pixel are side by side in close proximity on the same surface. If the coated electrode pairs are hydrophilic the area encompassing both electrodes is made to be hydrophilic with a hydrophobic ring around the hydrophilic electrode area (e.g., by means of stamping or deposition through a mask). The droplets described in the two embodiments above are stabilized using hydrophobic solutions. The viscosity of the solutions may be increased to increase the stability of the droplet arrays. The hydrophilicity and hydrophobicity may be reversed. In other embodiments the droplets may contain solutions capable of polymerizing to increase the stability and/or conductivity (e.g., conducting polymers) of the film between or above the electrode pairs. Additionally, structural features may be utilized to limit cross-talk between pixels. For example, an elastomeric stamp (e.g., poly (dimethylsiloxane)) with ring shaped stamp protrusion features capable of circumscribing side by side electrode pixel pairs on a surface may be used to isolate electrolytic solutions, gels, or films between pixels. Alternatively, side by side electrode pixel pairs may be placed in electrically insulating well-like structures on a surface, electrolytic solutions, gels or films placed in the wells above the electrodes, and the entire surface covered or coated to isolate and contain the electrolytic components of each pixel.

5.13. PMAMS For Use In Other Chemical Reactions

The PMAMS of the invention can also be used to conduct chemical reactions not in combination with ECL. For example, all the techniques and non-ECL assays discussed in Section 5.11 above can be used.

A cassette is provided for detecting or measuring an analyte of interest in a sample, comprising: (a) a first support having a plurality of discrete binding domains on the surface thereof to form at least one binding surface, at least some of the discrete binding domains being of different binding specificities than other binding domains, each of the plurality of discrete binding domains being hydrophilic and surrounded by hydrophobic regions, and (b) a second support having a plurality of hydrophilic domains comprising reaction media suitable for conducting a chemical assay thereon to form an assay surface, in which the plurality of discrete binding domains and the plurality of reaction media is capable of being brought into contact so that a sample to be analyzed present on each binding domain is contacted with a reaction medium to detect or measure an analyte of interest. Alternatively, the binding domains can be hydrophobic, and the second support has a plurality of hydrophobic domains containing reaction medium.

The invention also provides a method for detecting or measuring analytes of interest in a sample, comprising: (a) placing drops of a sample containing an analyte to be detected or measured on a plurality of discrete binding domains on a support surface, in which the plurality of discrete binding domains comprises at least one binding domain that contains binding reagents that are identical to each other and that differ in specificity from the binding reagents contained within other binding domains, each of the discrete binding domains being characterized as either hydrophobic or hydrophilic, with the proviso that the region of the support surface surrounding each binding domain is (i) hydrophobic if the binding domain is hydrophilic, and (ii) hydrophilic if the binding domain is hydrophobic, so as to allow one or more analytes of interest in the sample to bind to the binding domains, and (b) contacting the drops on the first support with a surface of a second support having a plurality of discrete hydrophilic domains comprising reaction media suitable for conducting a chemical assay thereon, and (c) determining the presence of the analytes of interest that are bound to the binding domain.

Also provided is a method for detecting or measuring analytes of interest in a sample, comprising (a) placing drops of a sample containing an analyte to be detected or measured on a plurality of discrete binding domains on a support surface in which the plurality of discrete binding domains comprises at least one binding domain that contains binding reagents that are identical to each other and that differ in specificity from the binding reagents contained within other binding domains, each of the discrete binding domains being characterized as either hydrophobic or hydrophilic, with the proviso that the region of the support surface surrounding each of the binding domains is (i) hydrophobic if the binding domain is hydrophilic, and (ii) hydrophilic if the binding domain is hydrophobic, so as to allow one or more analytes of interest in the sample to bind to the binding domains, and (b) placing drops of a reaction medium on the drops of sample; and (c) determining the presence of analytes of interest that are bound to the binding domain.

In a particular example of this aspect of the invention, binding domains, each of which have incorporated a different enzyme that utilizes as a substrate a sequential intermediate in a chemical reaction are situated on a PMAMS surface, such that the product of a given enzymatic reaction, which is the reactant for a subsequent enzyme, flows to the next enzyme in the reaction pathway. The invention also provides for bulk immobilization of enzymes on self-assembling monolayers, e.g., for industrial application, using methods as described above.

For example, sheets with such immobilized enzymes on one or both sides may be stacked to achieve high surface area to solution volume ratios. Alternatively, such immobilized enzymes may be attached to porous materials. Additionally, such immobilized enzymes may be on dipsticks, stirring agents, on the walls of tubes or capillaries, or on the walls of containers such as an incubator chamber.

In an alternative aspect of the invention, non-ECL assays such as described above can be carried out on PMAMS analogs, said PMAMS analogs differing from PMAMS as described above in that the PMAMS analogs contain discrete domains for carrying out non-ECL reactions, the discrete domains not necessarily having incorporated a binding reagent and therefore not necessarily being binding domains. Such PMAMS analogs have discrete domains for carrying out reactions and are prepared so as to inhibit spreading and/or diffusion of fluid applied to the discrete domains. In one embodiment, the domains are either hydrophobic or hydrophilic relative to the surrounding regions on the support surface, in order to aid in confining the reaction medium and/or sample to the discrete domains. The use of wells, deposition of reaction medium or sample on felts or porous materials, deposition and drying of reaction medium or sample on gels, films, etc., can be used to inhibit spreading or diffusion. Each of such discrete domains is less than 1 mm in diameter or width, preferably in the range of 50 nm to 1 mm, most preferably in the range of 1 micron to 1 mm. The same or different reaction medium can be deposited on each of the discrete domains prior to sample application, or sample application can precede deposition of reaction medium.

In a preferred aspect of the use of PMAMS analogs to conduct non-ECL assays, drops of reaction medium are placed on a plurality of discrete domains, preferably delivered concurrently from an array of microfluidic guides; and then, optionally, to enhance stability and/or protect the drop, a more viscous solution (e.g., oil) is placed on top of the reaction medium or, alternatively, in between the discrete domain; and then sample containing an analyte to be detected or measured is applied to each domain, either by discrete application to each discrete domain or, in bulk, by exposing the entire surface of the PMAMS analog containing the domains to a fluid sample. Any resulting reaction in the binding domains is allowed to proceed, and the results are observed by use of a reporter and detection system selected from among those known in the art.

5.14. ECL Assays Employing The Capture Of Particles On Porous Electrodes

The invention includes a method for performing an electrochemiluminescence binding assay in which a complex is formed. The complex includes, at least, a particle and a label compound capable of electrochemiluminescence. The complex may also include ligands used in electrochemiluminescence assays as disclosed for example in Yang H. J. et al., BioTechnology, 12, (1994), 193–194. The method includes the steps of (a) forming the complex; (b) collecting the complex by filtration on a porous, conductive electrode; (c) inducing the label compound in the collected complex to luminesce by imposing a voltage on the electrode; and (d) detecting the emitted luminescence from the electrode.

In another method for performing an electrochemiluminescence binding assay, the particle capable of complexing with a component of an electrochemiluminescence assay is first collected on a porous conductive electrode. Then the sample containing the analyte of interest is passed through the porous, conductive electrode and forms complex on the particle theretofore collected on the electrode. Then the label compound is induced to luminesce by imposing a voltage on the electrode and the emitted luminescence is detected to measure the presence of the analyte of interest. In a preferred embodiment the porous, conductive electrode will be preprepared with particles incorporated therein and upon use the sample containing analyte of interest will be passed through the electrode to form the complex.

The invention can be adapted to methods for performing a plurality of electrochemiluminescence binding assays for a plurality of analytes of interest. In such assays a plurality of complexes are formed, each of the complexes including at least a particle and a label compound and these are collected on a plurality of discrete domains, each of the domains including a porous conductive electrode. As described, the particles of the label compound and optionally other assay components may be complexed in solution then collected on the domains or the domains may contain the particles in the first instance and be complexed with the label compound and optionally other assay components by passing the sample through the electrode.

The invention can be adapted for use in standard formats for high-throughput assay processing e.g., 96-well on 384-well plates.

In certain preferred embodiments the particles may contain a luminescence species capable of acting as an internal standard in the assay. The luminescence thereof can be measured to calibrate the assay.

The invention includes binding assays in which particles are used as solid-phase supports for binding reagents. The term particle implies no restrictions on the size, shape or composition. The particles are captured on a porous electrode by filtration and the presence of analyte is detected by the excitation of ECL from ECL-labels present in the binding complexes on the particles.

Particle-based assays have been used in ECL assays (see for example PCT published applications WO90/05301 and WO92/14139) assays because they have a high binding capacity. They also allow the binding event to occur with kinetic rates approaching those observed for binding events in solution.

Highly sensitive and precise assays have been conducted using a system that employs a magnetic field to capture magnetic particles on a metal surface (see PCT published application WO92/14139; Deaver, D. R., Nature 377, (1995) 758–760; Yang, H. J. et al., BioTechnology 12, (1994) 193–194). This capture process places the particles in close proximity to an electrode so that excitation of labeled particles can be effected. This technology has been highly successful in many areas. It does, however, have some limitations (primarily cost and complexity) that restrict its use in low cost assays employing disposable cartridges.

A system that captures particles by filtration through porous electrodes takes advantage of the high binding capacity and favorable kinetics of particle-based assays. It also simplifies the fluidics, may employ a large variety of inexpensive, non-magnetic, commercially available particles, and can use inexpensive, porous, carbon-based electrodes. It can also improve the efficiency of ECL excitation of labels bound to particles. A porous electrode may have a significantly higher effective surface area than a non-porous electrode e.g., a metal film. If the electrode is a fibril mat, which is both porous and comprised of fibrous materials, the fibrils may contact, e.g. by wrapping around or laying across, a substantial fraction of the particle.

The invention includes a cassette containing a porous electrode that captures particles for the detection of analytes by ECL. The cassette may contain a working electrode comprising a thin ECL-active layer of carbon fibrils supported on an ECL-inactive filter (see Sec. 5.1 and the references cited therein for a detailed description of carbon fibrils. See Sec. 5.7 for a detailed description of fibril mats). A separate chamber in the cassette contains streptavidin-coated particles and dried binding reagents, e.g. a biotin-labeled capture reagent and an ECL-tag labeled detection reagent. The cassette also provides a means for introducing a liquid sample to the chamber containing the particles, means for capturing the particles on the working electrode by filtration, a counter electrode and a reference electrode. The invention also includes associated systems for conducting ECL assays with the cassette, e.g. a housing, electrical connections to the electrodes in the cassette, a waveform generator or potentiostat, a charge coupled device (CCD) for imaging the ECL emitted from the PMAMS, and a microcomputer for controlling the waveform generator and analyzing the image received by the camera.

There are several desirable embodiments of the working electrode for particle-based assays in which the particles are captured by filtration. The material of which the electrode is formed must be capable of exciting ECL from an ECL label in close proximity to it when an appropriate electrochemical potential is applied. If the electrode is porous, the size of the pores must be large enough to allow filtration of unbound reagents into or through the electrode but is sufficiently small to capture the particles.

Preferably, the working electrode is comprised of a conducting filter. Conducting filters may be formed, for example, from porous carbon, aggregate of particulate carbon, from mats of graphitic fibers, carbon fibrils and/or porous metals that are capable exciting ECL. The electrode may be composed of a non-conducting porous material, e.g., a commercially available polymer-based filtration membrane, coated with an ECL-active material such as gold, platinum and/or a mat of graphitic fibers). The electrode may have multiple layers. In one embodiment, a thin layer of an ECL-active electrode material is deposited on a thicker ECL-inactive (but electrically conducting) material. The terms "active" and "inactive" refer to the relative efficacy of the electrode for exciting ECL from an ECL label, this characteristic being dependent on both the structure of the ECL label and the conditions used to trigger ECL in a specific application. The conductive, ECL-inactive layer ensures good electrical contact along the entire surface of the active layer, but prevents the excitation of ECL from unbound ECL-tag labeled reagents that have filtered through the active layer. In a preferred embodiment, the ECL-active layer is a thin mat of carbon fibrils and the ECL-inactive support is stainless steel filter paper.

Many techniques for immobilization of binding reagents on particles by either non-covalent and/or covalent coupling reactions are known in the art. For example, the particles may be coated with streptavidin and specific binding reagents are then captured using a streptavidin-biotin interaction.

A wide variety of particles suitable for use in the invention are commercially available. These include beads commonly used in other types of particle-based assays e.g., magnetic, polypropylene, and latex particles, particles typically used in solid-phase synthesis e.g., polystyrene and polyacrylamide particles, and particles typically used in chromatographic applications e.g., silica, alumina, polyacrylamide, polystyrene. The particle may also be a fiber such as a carbon fibril.

Materials are available with a variety of functional groups on their surface. This allows for the use of a wide spectrum of immobilization chemistries. In some assays, the analyte itself may act as a particle. For example, an assay for cells with a specific cell-surface antigen (or an assay to quantify the amount of a cell-surface marker in a population of cells) may be carried out by treating the cells with an ECL-tag labeled antibody against the antigen followed by filtration of the cells onto the porous electrode.

This invention may be used to conduct many different binding assays including those described in section 5.10. These include immunoassays and nucleic acid hybridization assays in both competitive and sandwich formats. Many of these assays detect a labeled analyte or binding reagent in proximity to an electrode. Conducting the binding reactions on particles in suspension using gentle mixing if necessary is advantageous because the kinetics of the binding reactions are particularly favorable (they can approach those of a homogeneous reaction).

Alternatively, the particles can be deposited on an electrode and the binding reactions carried out by flowing samples past the trapped particles. Particles bearing binding domains can be deposited on the electrode in a patterned array, i.e. a PMAMS, by a variety of methods disclosed in Sec. 5.1.

In one embodiment, the particles are deposited on an electrode in an array that corresponds to the pattern of a 96-well plate. This particle/electrode fixture can form the basis of a kit used for high-throughput ECL assays. A mask with holes in a 96-well pattern is pressed against the electrode such that the holes in the mask are aligned with the pattern of deposited particles. The walls of the holes define the walls of the wells; the electrode and particles define the bottom of the wells and the binding regions. Preferred kits may contain any number of holes that meet industry standards, (e.g. 96 or 384 holes for high throughput screening).

Particles bearing binding reagents may be deposited in a plurality of zones on an electrode. There may be two or more zones with particles bearing the same binding reagents. There may be two or more zones with particles bearing different binding reagents.

A sample may be delivered to one or more zone by fluidic guides or it may be flushed through all zones in a single step.

Alternatively, the particles may be deposited uniformly on the surface of the electrode, (i.e. not in a patterned array) and a fixture with holes may be pressed against the electrode to define the active area of the electrode.

It is often desirable to include one or more internal standards. Comparing a signal to one generated by an internal standard can compensate for variations in the manufacture of an assay cassette or in the execution of the assay. Dyes may be incorporated into particles as internal standards. Particles that incorporate fluorescent dyes are commercially available; some of these dyes can be induced to emit ECL. A dye that differs from a specific ECL-label (for example, by its spectral properties, by the electrochemical potential at which ECL is emitted from it and/or its ECL lifetime) allows for the simultaneous measurement of ECL from the specific ECL label and the internal standard. ECL emissions with different spectral properties can be distinguished by the use of filters, gratings, and/or other techniques known in the art for measuring light within a defined spectral window.

Particles can be used to prepare a PMAMS for the simultaneous execution of one or more assays for one or more analytes. By way of example, a plurality of suspensions of particles can be prepared wherein each suspension comprises particles bearing immobilized capture reagents. A PMAMS is formed by applying microdrops of the suspensions, e.g by methods disclosed in Sec. 5.1 to defined regions on the working electrode.

A cassette may contain only one binding domain for conducting one ECL assay. In this case, the intensity of the ECL may be quantified using a single light detector. Comparison of the light intensity to that obtained from known concentrations of the analyte allows for quantification of the analyte. Light detection devices that may be used include photo diodes, photomultiplier tubes and avalanche photo diodes.

The cassette may contain a plurality of binding domains. The emitted light can be imaged to resolve the signals generated at each binding domain. Imaging may be achieved with an array of light detectors such as a CCD camera (see Sec. 5.5). Cross talk between closely packed binding domains can be eliminated by positioning an array of lenses over the array of binding domains. Alternatively, mathematical analysis of the intensities measured at the array of detectors can compensate for such cross talk.

5.15. ECL Assays Employing PMAMS On Electrodes

The invention includes a cassette containing a PMAMS formed directly on the surface of an electrode. The cassette contains a working electrode comprising a thin metal film on a support material. A plurality of binding domains, i.e. a PMAMS, are present on the surface of the metal film. The cassette also includes a means for introducing fluid samples and reagents over the surface of the electrode, and a counter electrode to allow for electrochemical excitation of ECL at the working electrode. A reference electrode may also be included for better control of the electrochemical potential at the working electrode. An apparatus for conducting ECL assays including a cassette which may comprise a housing, electrical connections to the electrodes in the cassette, a waveform generator or potentiostat, a CCD camera for imaging the ECL emitted from the PMAMS, and a microcomputer for controlling the waveform generator and analyzing the image received by the camera.

The formation of PMAMS directly on the working electrode has several advantages over previous ECL systems: The combination of the working electrode and the solid phase support for the binding assays into one unit greatly simplifies the manufacture and execution of ECL assays in a disposable format, allowing disposable assays to be produced at lower cost. A plurality of assays can be performed without the use of multiple ECL labels. The excitation of ECL from each of a plurality of assays can be conducted simultaneously by applying a potential to one working/counter electrode pair, all of the binding domains being located on the surface of the same working electrode). The use of the surface of a metal as the support for the PMAMS allows the use of well developed technology—e.g., the formation and patterning of self-assembled monolayers (SAMs) on metals—for the formation of the PMAMS.

The working electrode may be made of a wide range of materials including metals (e.g., gold and platinum), metal oxide conductors and semiconductors (e.g., ITO), carbon (e.g., graphite, carbon black, carbon fibrils), and conducting organic polymers (e.g., polythiophene). The electrode may comprise a composite of different materials.

In one embodiment, the working electrode is a thin (5 nm–10,000 nm) film on a substrate. The preparation of such films by techniques including evaporation, polymerization, sputtering, chemical vapor deposition, and plating is known in the art. In a preferred embodiment, the working electrode is a thin film of gold evaporated on a substrate. The properties of the substrates for the thin film electrodes can be chosen according to the requirements of the assay system. The substrate may be solid, or if filtration of samples through the electrode or wicking of samples along the electrode is desired, the substrate may be a porous material e.g., a filtration membrane.

Binding reagents may be immobilized by non-specific adsorption directly to the electrode surface or by covalent attachment to a chemical functional groups on the surface of the electrode. One approach to the introduction of chemical functional groups on the surface of an electrode is electrodeposition or electropolymerization of thin films. Another approach is the preparation of self-assembled monolayers (SAMs). Examples of SAMs that can be prepared on electrode materials include monolayers of organic thiols on gold, and organic silanes on ITO (see Sec. 5.1). As shown in FIG. 50, a SAM may be prepared by the reaction of a molecule A-L-B 5032 with the surface of the electrode 5033, where A is the functional group responsible for the attachment of the molecule to the electrode, L is a linking chain, and B is a functional group which can be used for the attachment of binding reagents 5034 to the surface. Alternatively, B may be a binding reagent.

In a preferred embodiment, the SAM is formed by the reaction of terminally functionalized alkane thiols (HS-$(CH_2)_n$-B) with thin films of gold deposited on a substrate. Alkane thiols with a variety of functional groups (B) can be prepared, allowing for the use of a variety of immobilization chemistries. For example, if group B includes a carboxylate group, binding reagents which include an amino group can be immobilized by reaction with the SAM after activation of the SAM with ethyl-3-diaminopropylcarbodiimide (EDC) in the presence of (N-hydroxysuccinimide (NHS). Alternatively, functional group B may be a methyl group, binding reagents may be immobilized by non-specific hydrophobic interactions or if functional group B contains a biotin moiety, streptavidin or other reagents linked to streptavidin either covalently or through a biotin-streptavidin interaction) may be immobilized on the surface.

Many other chemistries for the immobilization of binding reagents are known in the art and can be employed. In some cases it may be desirable to control the density of functional groups B on the surface of the electrode in order to control the density of binding reagents immobilized on the surface or to maintain some desirable property of the surface, e.g. resistance to non-specific binding. The control of the surface density of the functional group B can be achieved by treating the electrode surface with a mixture containing the monomers A-L-B and A-L-C in a ratio determined to produce a mixed SAM with the desired concentration of B on the surface. The functional group C is chosen to be resistant to the immobilization chemistry used to couple binding reagents to B and may have other desirable properties such as producing surfaces with reduced non-specific binding.

The formation of PMAMS on the surface of an electrode can be achieved by a variety of methods including: (i) photolithographic immobilization; (ii) microcontact printing; and (iii) the controlled application of drops of binding reagents to the surface through the use of microcapillary arrays or ink-jet printing (see discussion in Sec. 5.1). Patterned SAMs can be used to better define the areas on the surface which are modified with binding domains. For example, microcontact printing can be used to pattern an area of circles on a gold surface presenting a hydrophilic SAM formed from a carboxylic acid terminated alkane thiol. The remaining gold surface can then be reacted with a methyl terminated alkane thiol to give a hydrophobic SAM. After activation of the surface with EDC in the presence of NHS, drops, each containing a different antibody, are applied to the hydrophilic circles. The drops will be confined to the hydrophobic regions due to the hydrophobic nature of the surface outside the circles, thus allowing careful control of the area of the immobilized binding domains.

The types of assays which can be conducted using PMAMS immobilized on a electrode include those described in Sec. 5.10. Many of these assays (for example, immunoassays and nucleic acid hybridization assays in both competitive and sandwich formats) rely on the detection of the binding to the electrode surface of a binding reagent or analyte that has been labeled with an ECL-active group (tag). The intensity of the signal emitted from a tag-labeled reagent on the surface of SAM can be strongly influenced by the nature of the potential waveform used to excite ECL. For example, SAMs of alkanethiolates on gold are good electrical insulators but highly oxidizing or reducing potentials at the electrode surface may reduce the insulating properties of the film by introducing disorder in the monolayer. Excitation of ECL at potentials which do not introduce disorder into the SAM requires the transfer of electrons through the monolayer by tunneling. Much higher intensity signals can be achieved by applying potentials that introduce disorder into the SAM, thus allowing less hindered flow of current to the electrode. These potentials can be applied prior to or during the excitation of ECL. Alternatively, the SAMs could be formed using conditions known in the art to give disordered monolayers. The conductivity of monolayers can also be increased by including a constituent in the monolayer which facilitates the transfer of electrons (for example, by the introduction of a pi-conjugated system into the linking group L). The formation of SAMs with high conductivity is discussed in more detail in section 5.7.

In some cases the use of potentials which do not introduce disorder into the SAMs is advantageous. Under these conditions, the discrimination of bound tag-labeled reagents from unbound tag-labeled reagents in solution will be maximized due to the strong dependence of electron tunneling on distance, thus, eliminating the need for a wash step. An ECL label on the surface will give a much stronger ECL signal than an ECL label in solution) ECL can be modulated by changes in conductivity between the SAM and the ECL label that result from a binding event. The use of this approach to conduct nucleic acid hybridization assays is described in Sec. 5.7.

A cassette of the invention may contain only one binding domain for conducting one ECL assay. The intensity of the ECL may be quantified using a single light detector. Comparison of the light intensity to that obtained from known concentrations of the analyte allows for quantification of the analyte. Light detection devices which may be used include photo diodes, photomultiplier tubes and avalanche photo diodes. A cassette may also contain a plurality of binding domains. The emitted light from such cassette must be imaged to separate the signals generated at each binding domain. Imaging may be achieved by an array of light detectors such as a CCD camera (see Sec. 5.5). Cross talk between closely packed binding domains can be eliminated by positioning an array of lenses over the array of binding domains or by mathematical analysis of the intensities of the signals from the several binding domains.

5.16. ECL Assays Employing PMAMS On A Porous Substrate

FIG. 37 shows a cassette where binding domains 3702 in and/or on a matrix 3703 are presented on a surface 3701. After completion of binding reactions on the binding domains, a second surface 3700 supporting a working electrode 3704 and a counter electrode 3705 is positioned so that the binding domains are in close proximity to the working electrode. Luminescence from an ECL label bound to the binding domains may be detected from either or both surfaces. We refer to this configuration for ECL as the "Two Surface" ECL assay.

FIG. 38 shows a cassette where binding domains 3805, 3806, 3807 are presented on the surfaces of matrices supported on a counter electrode 3800. After completion of binding reactions on the binding domains, a working electrode 3801 is positioned in close proximity to the surface of the matrices. Luminescence from an ECL label bound to a binding domain may be detected through either or both of the electrodes if either or both of the electrodes is transparent or semi-transparent and/or from the side.

The invention also includes an apparatus for conducting ECL assays using cassettes containing a PMAMS. An apparatus for conducting ECL assays using the cassette described in FIG. 38 includes means for making electrical connections to the electrodes, means for controlling the potential at the electrodes, means for moving the matrix into close proximity with the working electrode and means for imaging the light emitted during excitation of ECL.

The Two Surface method has several advantages over previous ECL methods. A plurality of assays can be performed conveniently without the use of multiple ECL labels. The excitation of ECL from each of a plurality of assays can be conducted simultaneously by applying a potential to one working/counter electrode pair, all the binding domains being placed in proximity to the same working electrode. The working electrode can be protected during the binding reaction from the sample by a physical barrier that is removed prior to the excitation of ECL, thus, preventing contamination of the electrode surface which could result in a change in its electrochemical performance. As illustrated in FIG. 55 for the case of a sandwich immunoassay, the binding of ECL-tag labeled reagent 5203 to analyte 5202 bound to primary antibody 5201 immobilized on the matrix 5200 results in the optimal presentation of the tag 5204 to the electrode surface 5205, (i.e. with a minimum of organic material—such as protein, nucleic acid, or linking groups—between the tag and the surface of the electrode. The matrix may be used for the concentration and/or separation of components of a sample, for example, by electrophoresis and/or filtration through the matrix. The matrix may be used as a medium for the storage of assay reagents in dried or partially hydrated form. The surface of the matrix can be placed in conformal contact with the working electrode.

The PMAMS are preferably formed in and/or on a matrix with one or both of the following characteristics. The matrix is capable of carrying ionic currents between the working and counter electrodes, and therefore, can complete the electrochemical circuit. The matrix is preferably capable of making intimate contact with the working electrode e.g. it is elastomeric and/or compliant. Materials with these characteristics are known in the art and include porous materials such as filtration membranes and water-swollen polymeric gels. In some embodiments of the invention, e.g. if light excited at the working electrode is detected through the matrix, it is advantageous for the matrix to be transparent.

PMAMS can be generated on porous materials (e.g., gels) with varying pore size and solvent content. For example, polyacrylamide gels varying in pore size can be made by varying the concentration of acrylamide and the degree of crosslinking.

On such matrices with pore sizes smaller than the analyte, binding reactions will occur substantially on the surface of the gel. In this case, filtration and/or electrophoresis through the gel can be used to concentrate analytes at the surface of the gel and modulate the kinetics, e.g., increase the rate, of the binding reaction. Faster kinetics are advantageous in rapid assays and may generate increased sensitivity in a shorter time period.

On matrices with pore sizes larger than the analyte, binding reactions can occur on the surface as well as the bulk of the gel. In this case, filtration and/or electrophoresis can be used to increase the kinetics of binding as well as to remove unbound species from the surface.

PMAMS formed on gels can be stored wet and/or they may be stored in a dried state and reconstituted during the assay. The reagents necessary for ECL assays can be incorporated in the gel before storage, by permeation into the gel or by incorporation during formation of the gel, and/or they can be added during the assay.

The immobilization of binding domains to matrices by covalent and noncovalent linkages is known in the art. Some examples of methods for the immobilization of binding domains to a variety of matrix materials is described in more detail in Sec. 5.1. Sec. 5.1 also describes in detail methods for the patterning of binding domains on a matrix to form a PMAMS. These patterning methods may include the following: i) photolithographic immobilization; ii) patterned application of microdrops of reagents to the surface of a matrix; iii) application of drops or microdrops containing the binding domains in the matrix in liquid form to a substrate followed by solidification and/or gelling of the liquid using known techniques including, crosslinking, polymerization, cooling below the gelling transition, etc., to give distinct drops on the substrate composed of the matrix material, each solidified drop thereby comprising a different binding domain; iv) using matrices to achieve separations, e.g. by electrophoresis in a polyacrylamide slab; and v) Forming a layered structure of matrices each containing one or more binding domains.

The working electrode is preferably made from an electrode material that is capable of exciting ECL from an ECL label in close proximity to the surface when the appropriate electrochemical potential is applied. In some embodiments light is detected from the surface of the PMAMS through the working and/or the counter electrode. In these cases, it is advantageous to use a transparent or semi-transparent electrode material. These electrode materials are known in the art. Examples include films made of indium tin oxide as well as very thin (<30 nm) films of gold. Alternatively, it may be advantageous to protect the working electrode from the sample. A physical barrier on the electrode may protect it during incubation of the sample with the PMAMS. The physical barrier is then removed before placing the PMAMS in close proximity to the electrode.

5.17. ECL Assays Employing PMAMS On Composite Electrodes

In preferred embodiments of the invention the electrode is a composite of a polymer containing a multiplicity of carbon fibrils dispersed therein. Desirably the composite is porous.

A preferred apparatus for conducting an assay comprises as a first element a matrix containing carbon fibrils dispersed therein, and one or more binding domains containing a reagent capable of binding a component of an assay.

An apparatus for detection of an analyte by electrochemiluminescence may comprise an electrode comprised of a composite of a matrix having a multiplicity of conducting particles dispersed therein and a binding domain containing a reagent capable of binding a component of an electrochemiluminescence assay. Desirably the matrix is a polymer and the conducting particles are carbon. The conducting particles are desirably are carbon fibers and best results obtained were the carbon fibers or carbon fibrils.

Apparatus for use in the detection of a plurality of analytes are also included in the invention. In such apparatus the electrode is comprised of a matrix containing a multiplicity of conducting particles dispersed therein and the plurality of binding domains supported on a surface of the electrode, each of those domains containing the reagent capable of binding a component of an electrochemiluminescence assay.

The properties of electrodes comprising a polymer and dispersed carbon fibrils may be modified by a subjecting the composite to various chemical and physical steps such as oxidation, exposure to a plasma and exposure to a reagent capable of derivatizing the electrode by addition of one or more functional groups. In the latter method the polymer can be derivatized or the fibrils contained therein can be derivatized or both can be derivatized. Desirably the composite is subjected to a chemical or physical treatment to affect the modification for a time sufficient to alter the electrical potential at which electrochemiluminescence occurs in an electrochemiluminescent compound situated at said composite. It is also within the invention to modify the properties of any electrode comprising a polymer and multiplicity of carbon fibrils dispersed therein by modifying the electrode to expose a desired functional group thereupon. The invention also includes electrodes which have been modified by chemical or physical treatment to alter the electrical potential at which electrochemiluminescence occurs.

The invention includes a cassette containing a PMAMS formed directly on the surface of an electrode comprised of more than one material, i.e. a composite electrode. The several components of such a cassette are described above.

The composite electrode may be comprised of conductive and/or electrochemically active particles impregnated in a support matrix. For example, the matrix may be comprised of oils, waxes, paraffins, plastics, ceramics, teflon, polymers, elastomers, gels and/or combinations thereof. Some examples of commercial polymers that can be used in the manufacture of composite electrodes include, but are not limited to, EVA, polyethylene (PE), polystyrene (PS), and ABS.

The matrix can be chosen to meet design requirements for a given application. The material may be appropriate for a specific type of immobilization chemistry, it may give high specific signal and/or low background signals in a particular type of assay, and/or because the material has desirable physical properties, e.g., flexibility, strength, chemical resistance.

A composite electrode can be formed using any particles that when combined in a matrix provides an electrically conductive composite. The particles may be carbon, e.g. particulate carbon, carbon black, carbon fibers, carbon felts and preferably are carbon fibrils (Secs. 5.1 and 5.7).

Composites that contain more than one type of particle and/or more than one type of material for the matrix can be used. For example; a composite electrode may include one type of particle to impart electrical conductivity and ECL-activity and another type of particle as a support for binding domains.

In a preferred embodiment, a composite electrode is comprised of a blend of carbon particles and a matrix. In a particularly preferred embodiment, a composite electrode is comprised of carbon fibrils and a polymer. U.S. Pat. Nos. 5,304,326 and 5,098,771 describe polymer composites impregnated with fibrils.

Fibril-polymer composite electrodes can be produced by techniques known in the art of manufacturing plastic materials and parts. For example, flat electrodes can be cut from pressed sheets or extruded films of a fibril composite. Electrodes with complicated shapes or surface features such as grooves or channels for the movement of fluid or wells for reaction chambers can be formed by injection molding.

The composite electrode may be a solid or may be porous. Porous composites may be formed by using techniques for producing porous plastic materials, e.g., filtration membranes. Filtration through a porous composite electrode can improve the kinetics of binding reactions to binding domains immobilized on the surface of the electrode.

Binding reagents may be immobilized on unmodified composite electrodes. For example, binding reagents may be immobilized by non-specific adsorption onto the matrix and/or onto the conductive particles. Functional groups present on the matrix and/or the conductive particle can be used for immobilization of reagents. These reagents can serve as binding reagents and/or as reagents that change the properties of the surface e.g. wettability or resistance to non-specific binding. Methods for covalent and non-covalent immobilization of reagents on materials that can be used as matrices are known in the art (see Sec. 5.1).

The composite electrode may be modified by chemical or mechanical treatment to improve the immobilization of binding reagents. The surface may be treated to introduce functional groups for immobilization of reagents. Techniques that may be used include exposure to electromagnetic radiation, ionizing radiation, plasmas or chemical reagents such as oxidizing agents, electrophiles, nucleophiles, reducing agents, strong acids, and strong bases and/or combinations thereof (see Sec. 5.18).

One particularly interesting embodiment is the modification of such composite electrode, and more broadly a composite material (not limited to an electrode) comprising a matrix (such as a polymer) and one or more fibrils and/or fibril structures dispersed therein, by treatment with a plasma. The treatment is carried out in order to alter the surface characteristics of the fibrils, fibril structures and/or the matrix, which come in contact with the plasma during treatment; by this means the fibril composite treated can be functionalized or otherwise altered as desired. Once equipped with the teaching herein, one of ordinary skill in the art will be able to adapt and utilize well-known plasma treatment technology (without the need for further invention or undue experimentation) to the treatment of such composite materials. Thus, the treatment can be carried out in a suitable reaction vessel at suitable pressures and other conditions and for suitable duration, to generate the plasma, contact it with the composite material, and effect the desired kind and degree of modification. Plasmas such as those based on oxygen, ammonia, helium or other chemically active or inert gases can be utilized. Depending on its properties, the modified composition can be utilized as an electrode (such as described above) or for other applications.

It may be advantageous to immobilize binding reagents on both the matrix and the particles or it may be advantageous to immobilize binding reagents on only one of the components, i.e. the matrix or the particles. By way of example, a composite electrode comprised of fibrils in EVA (a copolymer or ethylene and vinyl acetate) may be treated with a mixture of chromic acid and sulfuric acid to introduce carboxylic acid groups on the electrode. These carboxylic acid groups can then be used to immobilize binding reagents containing amines by formation of an amide bond. Alternatively, a composite of fibrils in EVA can be treated with sodium hydroxide. In this case, the fibrils remain unmodified but hydroxyl groups are exposed on the polymer. These hydroxide groups can then be used to immobilize binding reagents containing a nucleophile.

Modification of composites may lead to other favorable properties. Modification of the matrix and/or the particles may produce a composite electrode with a high binding capacity. The introduction of hydrophilic groups to the composite electrode may hydrate the matrix and lead to the formation of a thin water-swollen gel layer. Reagents can be immobilized within such a gel layer, allowing for the immobilization of more reagents than could occupy a flat, solid, surface with the same geometric surface area. Partial degradation of the matrix can increase the exposed surface area of the conducting particles and lead to high surface-area electrodes for the immobilization of binding reagents directly on the conductive particles, especially when the particles are fibers which can extend into the solution.

Modification of a composite surface may shift the electrochemical potential required to excite ECL. Modification of the composite electrode may reduce or increase the overpotential required for excitation of ECL from an ECL tag, thereby allowing certain signals, e.g. the signal from an analyte and a background signal, to be resolved.

The formation of PMAMS on the surface of a composite electrode can be achieved by a variety of methods including photolithographic immobilization, microcontact printing and/or the controlled application of drops of binding reagents to the surface through the use of microcapillary arrays or ink-jet printing (see Sec. 5.1). Alternatively, the surface of a composite electrode may be divided into distinct regions by placing it in contact with a mask.

The invention includes a disposable multiwell plate for use in ECL assays (hereon referred to as an "ECL Plate"). In one embodiment, an ECL Plate is manufactured by shaping (e.g., pressing, molding, or forming) a conductive composite into the form of a multiwell microtiter plate. In another embodiment, a mask is formed that comprises an array of holes through a sheet of a material. Such a mask is then sealed against an electrode (the electrode is preferably a conducting composite or a fibril mat; the preparation of fibril mats is described in detail in Section 5.7, Section 5.18 and the references therein). The holes through the mask will then define wells with walls comprising the mask and bottom comprising the electrode. The mask and the electrode may be provided to the user as a preassembled disposable cassette, or as individual disposable components of a kit. Alternatively, only the electrode may be disposable. The electrode may be solid and/or porous. In the case of a porous electrode, binding reactions may be carried out by filtering reagents through the electrode (multiwell filtration manifolds for use in binding assays—"dot blots"—are known in the art). In a different embodiment of the ECL Plate, a plurality of holes in a mask (as described in the previous embodiment) is sealed against a plurality of individual electrodes such that the electrodes in individual wells and/or groups of wells can be individually probed.

An ECL plate is preferable shaped in a standard form used for multiwell microtiter plates. These standard formats are known in the art and include, but are not limited to, 24, 96, and 384 well plates. The use of a standard format allows the integration of commercially available equipment for carrying out binding reactions on microtiter plates (e.g., equipment for moving plates, washing plates and/or dispensing samples). The invention includes an apparatus for exciting ECL from the electrode or electrodes of an ECL Plate and quantifying the ECL emitted from each well.

ECL plates may be provided to the end user with immobilized binding reagents for one or more analytes. Alternatively, the user could be provided with a kit comprising an ECL Plate and the reagents necessary for immobilizing binding reagents (when such binding reagents are provided by the user).

Composite electrodes may be used in assays that do not use ECL. They may be used as solid-phase binding supports for assays based on fluorescence, chemiluminescence, or ELISA-type formats. They may be used as electrodes and/or solid phase supports for assays based on amperometric or potentiometric electrochemical detection.

5.18. ECL Assays Employing PMAMS On A Porous Electrode

The electrode of the invention may comprise a mat of a multiplicity of carbon fibrils. Such mats have now been found to perform well as electrodes for use in electrochemiluminescence assays.

The mats broadly comprise a multiplicity of carbon fibrils and at least one domain containing an assay reagent. In one embodiment of the invention the mat may be comprised of two or more layers of different conductivity, two or more layers of derivitized or underivitized carbon fibrils or combinations of derivitized and underivitized fibrils, two or more layers of fibrils of different optical opacity or two or more layers of fibrils of different pore sizes.

Desirably these mats are used in electrodes for electrochemiluminescence assays. The electrode includes a support and a fibril mat comprising a multiplicity of carbon fibrils and means for making electrical contact with the mat. The electrode may contain a binding domain containing a reagent capable of binding a component of an electrochemiluminescence assay.

The invention includes kits for making electrodes for use in such assays. The kits include a support, a fibril mat and means for making electrical contact with the mat. The fibril mat may include a binding domain.

The electrode may be conductive or porous and desirably is conductive and porous and may be, for example, comprised of a metal-coated porous material. The electrode may be stainless steel fiber mesh.

Fibril mats for use as a support for an electrode in an electrochemiluminescence assay may be prepared in several different ways. In one such method the fibrils are produced with a binding reagent immobilized on their surface. These fibrils are dispersed in a medium. They are thereafter filtered from solution to produce a fibril mat.

Alternatively, the fibril mat may be prepared by dispersing the fibrils in a medium, filtering the fibrils from the medium to prepare the mat and finally derivatizing the fibril mat to prepare them for mobilization of a binding reagent thereupon.

The invention broadly includes methods for performing an electrochemiluminescence binding assay for an analyte of interest. The method includes the steps of (a) an electrode comprised of a conductive polymer; and (b) a binding domain containing a reagent capable of binding a component of a binding electrochemiluminescence assay.

The method of the invention can be used to conduct electrochemiluminescence binding assays for a plurality of analytes of interest in a biological sample. This method includes the steps of (a) contacting a sample containing analyte of interest and a label compound capable of electrochemiluminescence, with an electrode comprising a multiplicity of carbon fibrils containing a binding domain containing a reagent capable of binding a component of an electrochemiluminescence assay; (b) inducing the label compound at the electrode to luminesce by imposing a voltage thereupon; and (c) detecting the emitted luminescence.

Alternatively, the method includes (a) contacting a sample containing a plurality of analytes of interest and a label compound capable of electrochemiluminescence with a plurality of electrode zones, each of which comprises a fibril mat containing a domain containing a reagent capable of binding a component of an electrochemiluminescence assay; (b) inducing the label compound collected on said fibril mats to electrochemiluminescence; and (c) measuring the emitted luminescence.

The invention also includes a cassette containing a porous electrode. The cassette contains a working electrode consisting of a porous mat of carbon fibrils supported by a porous material. One or more binding domains are present on the surface of the working electrode.

The porous electrode may be comprised of carbon e.g., graphitic carbon, glassy carbon or carbon fibers and in a particularly preferred embodiment comprises carbon fibrils. The binding domains of the PMAMS may be supported by a fibril mat (see Sec. 5.7). The mats may support a plurality of discrete binding domains, any two or more of which may be identical to each other or all of which may differ from one another. The fibril mat may, alternatively, support one binding domain.

Carbon fibrils may be prepared with chemical functional groups attached covalently or by physical absorption to their surface. These and other chemical functional groups can be used to attach other materials to the surface of fibrils. For example, an antibody that can be used in an ECL assay can be attached to one or more fibrils or a fibril mat.

The fibril mat may be in a single layer containing underivatized fibrils, derivatized fibrils or a mixture of two or more different types of fibrils. The fibril mat may have two or more layers. Successive filtration steps may be used to form mats of fibrils composed of one or more distinct layers that are either in contact with or in close proximity to one or more other layers. For example, a two-layer fibril mat may contain a layer of underivatized fibrils and a layer of fibrils derivatized with a biomolecule. In some multi-layered mats, there may be overlap or mixing between layers.

The ECL signal that originates from a fibril mat can depend on the composition of the mat. For example, different electrochemical potentials may be required to elicit ECL at mats of derivatized fibrils as compared to mats of underivatized fibrils. This differences in electrochemical potential can be specific for or limited to one or more components of an assay. A mat composed of derivatized fibrils may shift the electrochemical potential at which the background ECL signal is observed to a different electrochemical potential than that at which a ECL from a particular species is observed, i.e., the signal from the components of the assay that are desirable to measure, and in doing so, increase resolution between the specific signal and the background signal.

Different types of fibrils may be used to prepare fibril mats with certain capabilities. In mats composed of a layer of underivatized fibrils and a layer of derivatized fibrils, the layer of underivatized fibrils may provide an electrical connection between an electrical conductor and the layer of derivatized fibrils and also provide physical strength. The layer of derivatized fibrils contains one or more of the reactants necessary to conduct an assay. In another embodiment, a mat may contain one or more fibrils derivatized with a molecule that serves as an internal standard for calibration of other signals. A mat may also contain a layer of fibrils that are ECL inactive, the inactive layer providing physical support for a layer of fibrils that are ECL active.

It may be useful to support a fibril mat on another material e.g. on a porous material such as a filter membrane. The fibril mat can be formed on the membrane by filtering a suspension of fibrils through the membrane so as to capture a layer of fibrils on the surface thereof. Multiple-layer mats can be prepared by successive filtering of different types of fibrils.

Electrical connections to fibril mats supported on non-conducting membranes can be made by contacting one or more electrically conducting elements, e.g. a wire, a metal mesh or a metal ring, with a surface of the fibril mat or an electrically conducting element e.g. an array of metal pins, can be inserted into or through the fibril mat.

A filter membrane used to support a fibril mat may be electrically conducting. Examples of conducting filters include metal-coated polymer membranes, conducting polymer membranes, metal meshes, carbon paper, carbon felts, porous metal films, sintered metal filters, metal-fiber filters and/or metal-fiber papers.

Metal-coated polymer membranes can be prepared by coating these with one or more metals by thermal evaporation, electron-beam evaporation, sputtering, chemical vapor deposition or plating. In a preferred embodiment, a polymeric filtration membrane is coated with gold by thermal evaporation.

Where filter membranes do not capture fibrils efficiently by filtration, methods can be used to improve filtration efficiency. The effective pore size of the membrane can be reduced by deposition of metals on the surface and/or interior regions of the filter. The filter membrane can be partially plugged or occluded with a material of appropriate size, i.e. a filter aid can be used. The filter can be treated chemically to induce binding between the fibrils and the filter. Binding may be by means of covalent bonds, van der Waals forces, hydrogen bonding, charge/charge interactions, or by hydrophobic hydrophilic interactions, or by biospecific bonding (protein/ligand, antibody/antigen, etc.). The fibrils may be captured by other mechanisms e.g. deposition on the surface of the filter by evaporation of the liquid in which they are suspended.

A filter that supports a fibril mat can work as an electrode for ECL. Examples include filters composed of, or coated with, gold, platinum, carbon, and/or indium-tin oxide(ITO). In such embodiments, both the support and the fibril mat may contribute to the observed ECL signal. In some embodiments, a filter that supports a fibril mat does not function as an electrode for ECL. Such filters provide support and electrical connectivity for the fibril mat, but do not contribute to the observed ECL signal including the background ECL signal.

Fibril mats can also be supported on non-porous materials. Fibril mats may be supported on a material capable of acting as an ECL electrode such as gold foil, platinum foil, conducting composites or ITO. Fibril mats may be supported on a material that cannot function as an ECL electrode such as stainless steel, nickel or non-conducting materials.

PMAMS can be prepared on fibril mats. The reagents necessary to form the PMAMs are delivered to spatially distinct regions of a previously formed fibril mat by microfluidic guides as described previously. For example, an array of microfluidic guides (G1, G2, . . . Gn) can be used to deliver biotinylated antibodies (A1, A2 . . . An) to spatially distinct regions of a mat composed of streptavidin-coated fibrils. Derivatized fibrils may be delivered to spatially distinct regions of a support by microfluidic guides where they are captured, e.g. by filtration or evaporation. For example, an array of microfluidic guides (G1, G2, . . . Gn) can be used to deliver fibrils (F1, F2, . . . Fn) covalently linked to antibodies (A1, A2 . . . An) to spatially distinct regions of a gold-coated ultrafiltration membrane. In yet another method, a suspension of fibrils may be filtered through a physical mask, e.g. a wire mesh, placed in contact with a filter membrane so that fibrils deposit on the filter wherever the filter is exposed by the spaces between the wires of the mesh.

The types of assays that can be conducted using PMAMS immobilized on fibril mats include those described in section 5.10. Because the fibril mat is porous, it is possible to conduct assays by flowing the reagents through the fibril mat and in some cases the underlying support. Because the size of the pores in a fibril mat may be small (for example, 10–10000 nm), flowing the reagents through the mat mixes the reagents efficiently. This reduces the time required to conduct an immunoassay by improving the rate of mass transfer to the surface of the binding regions. Assays conducted by wicking a sample into or through the mat benefit similarly from increased kinetics. Alternatively, the fibril mat may be soaked in the sample. The fibril mat can also act as a filter to remove unwanted materials from biological samples.

Fibril mat electrodes may be used in assays that do not use ECL. They may be used as solid-phase binding supports for assays based on fluorescence, chemiluminescence, or ELISA-type formats. They may be used as electrodes and/or solid phase supports for assays based on amperometric or potentiometric electrochemical detection.

5.19. Methods For Increasing Signal To Background

It has also now been discovered that two or more signals originating from electrochemiluminescence species in an electrochemiluminescence assay can be resolved by conducting the assay at an electrode having at least two zones which have different electrochemical potentials at which electrochemiluminescence occurs. By this method it is possible to resolve signal from background electrochemiluminescence and thereby significantly improve the performance of the assay.

Another method for resolving two or more signals originating from electrochemiluminescence species in an assay comprises including in the assay a reagent which selectively modulates the electrochemiluminescence of one of the electrochemiluminescence species. For example, a reagent can be included which quenches electrochemiluminescence from one of the species.

Another method for resolving two or more signals from electrochemiluminescence species comprises conducting the assay and an electrode which includes one zone which is inactive for generating electrochemiluminescence from one or more of the species in the assay.

Background signals can be distinguished from a desired signal in an assay by conducting the assay at an electrode which induces electrochemiluminescence for the label and for the background, respectively, at different electrochemical potentials. Likewise, the signals from two or more species labeled with the same electrochemiluminescent compound can be distinguished from one another at an electrode which induces the electrochemiluminescence from each of the labels at different potentials. These improved methods can be carried out on composite electrodes, desirably those comprised of carbon and best results are obtained by those which have been modified by chemical or physical treatment to change the electrochemical potential at which electrochemiluminescence takes place.

The invention includes methods for performing an electrochemiluminescence binding assay for an analyte of interest which comprises the steps of (a) contacting a sample containing analyte of interest and a label compound capable of electrochemiluminescence, with an electrode comprising a multiplicity of carbon fibrils containing a binding domain containing a reagent capable of binding a component of the assay, the carbon fibrils having been modified by chemical or physical treatment to alter the electrochemical potential at which electrochemiluminescence of at least one species in the assay occurs; (b) inducing the label compound at said electrode to luminesce by imposing a voltage thereupon; and (c) detecting the emitted luminescence.

The demands of researchers and clinicians make it imperative to lower detection limits of assays, to increase the sensitivity of those assays and to increase the speed at which these assays are performed.

A critical parameter in meeting these demands is the optimization of the signal to background ratio. Here, the signal to background ratio (S/B) is defined as the ratio of the signal from components of the sample that are desirable to measure, (e.g. an analyte) to the signal from components of a sample that are not desirable to measure (e.g. contaminants). Optimization of the S/B ratio generally involves maximizing the signal from components that are desirable to measure and minimizing the background signal.

Various methods are known in the art for increasing the signal from labeled species. For example, in U.S. Pat. No. 4,652,333 particles labeled with fluorescent, phosphorescent or atoms fluorescent labels can be concentrated by microfiltration before a measurement step is performed.

Various methods are also known in the art for reducing the background signal. Wash steps have been used to remove contaminants, unbound analytes, unbound labeled species, or other components of the sample.

It is advantageous to resolve two or more signals such that detection of one or more signals is optimized.

Figure 58A:
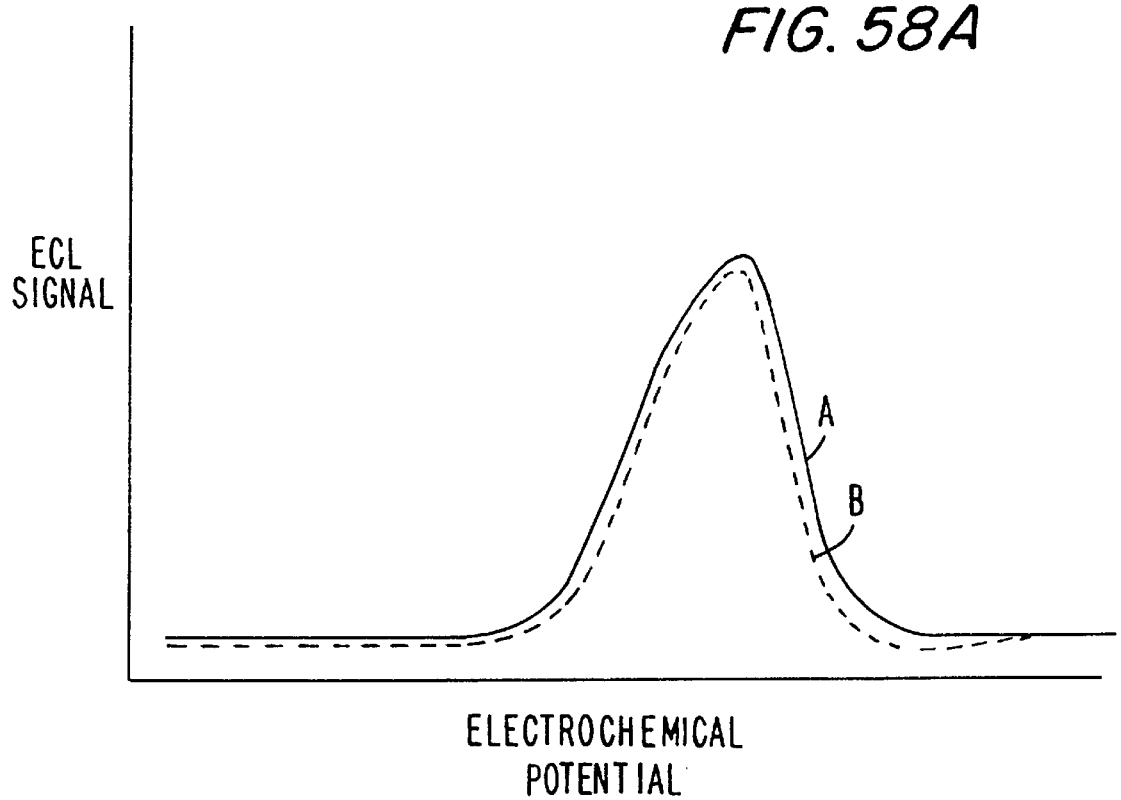
Figure 58B:
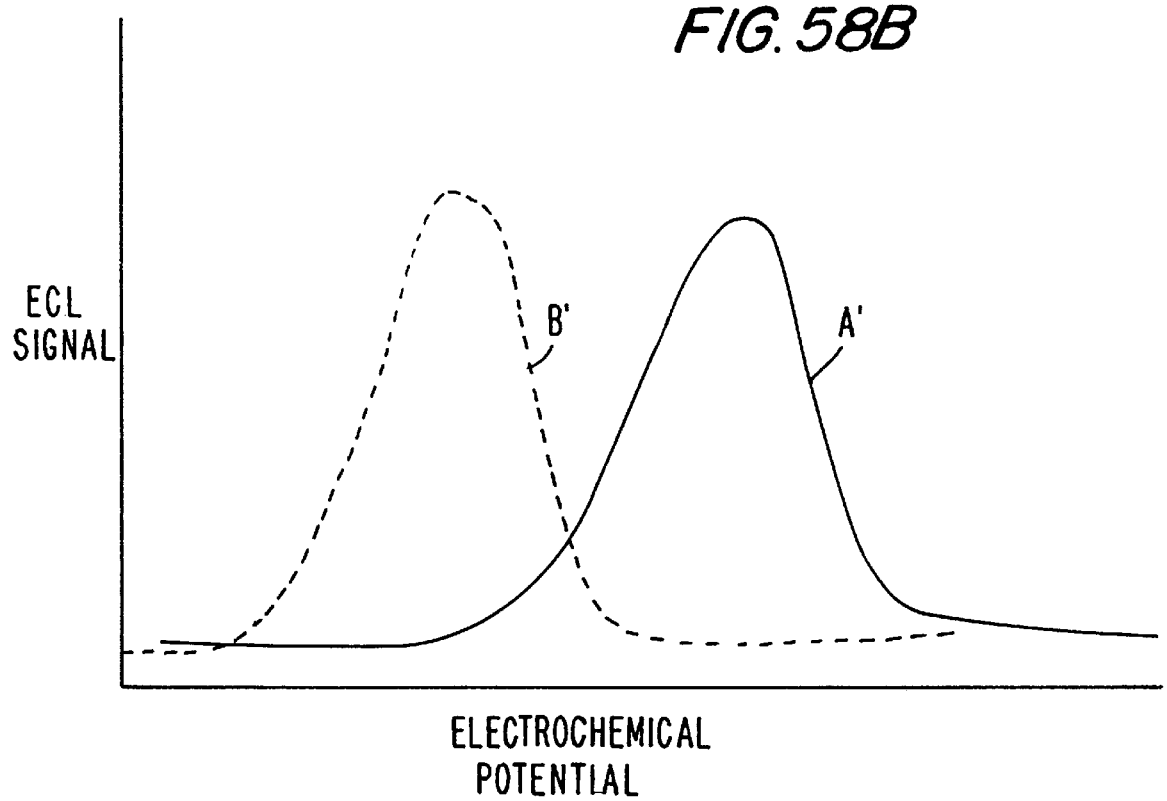

FIG. 58 illustrates a method in which the electrochemical potential of the ECL signal for one or more components is shifted. In FIG. 58A, the ECL signals for two components (A and B) of a sample appear at similar electrochemical potentials. As such, they are difficult to resolve. FIG. 58B shows ECL signals for two components (A' and B') that appear at different electrochemical potentials. The potential of the ECL signal for component B' has shifted to a different potential and the ECL signals for components A' and B' are readily resolved.

The selective shift in electrochemical potential that is illustrated in FIG. 58 can be accomplished by choosing a material for a working electrode according to the electrochemical potentials at which ECL is elicited from one or more labels in proximity to the electrode. Alternatively, a material may be modified by chemical or mechanical treatment so as to change the electrochemical potential of the ECL signal for one or more components of a sample.

The electrode may have two or more regions with different electrochemical properties so that one region of the electrode excites an ECL label at a different electrochemical potential than another region. The electrode may be a two-layered fibril in which layer 1 has been derivatized with a binding reagent that binds one or more analytes from a sample and molecules bearing ECL labels and layer 2, conversely, has not been derivatized. It does not bind the analytes but can interact with other components of the sample that give a background ECL signal. As a consequence of the derivatization, layer 1 has different electrochemical properties than layer 2. The ECL signal from labeled molecules bound to layer 1 appears at a higher electrochemical potential than the background ECL signals that originate from layer 2.

In another embodiment, a compound that changes the electrochemical properties, e.g. the electrochemical potential at which ECL is elicited from a label and/or the intensity of the ECL signal of one or more components in a sample, can be added to the sample.

Figure 59A:
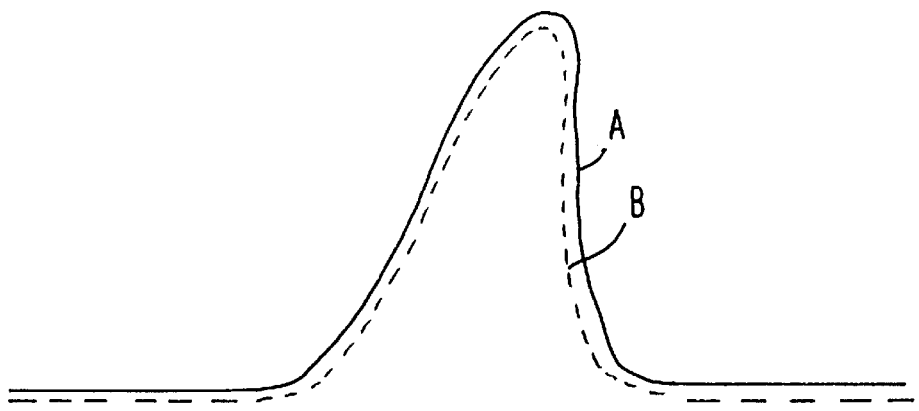
Figure 59B:
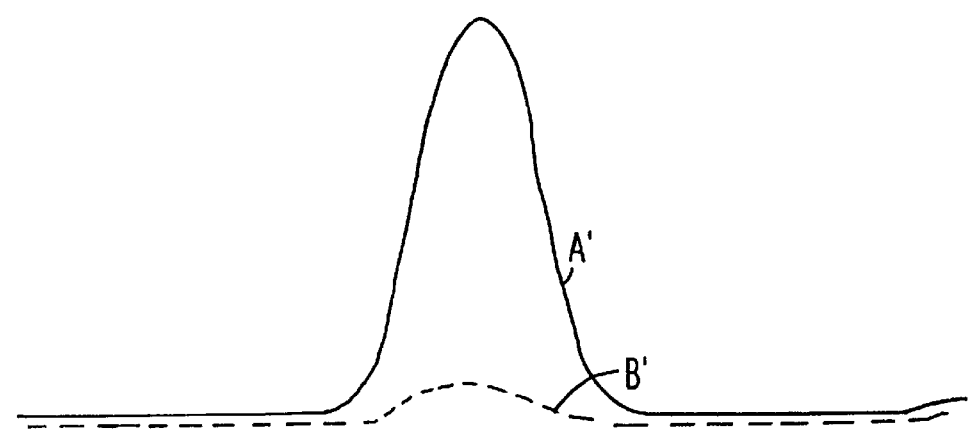

FIG. 59 shows a schematic of another method for resolving two or more signals. The intensity of the ECL signal for one or more components of a sample is reduced relative to the intensity of the ECL signal for other components of the sample. In FIG. 59A, two components (A and B) have ECL signals that appear at similar electrochemical potentials. In FIG. 59B, the value of the intensity of the ECL signal for component B' has become smaller relative to the intensity of the ECL signal of component A'.

The selective change in the intensities of ECL signals illustrated in FIG. 59 can be accomplished by adding a material that quenches the ECL signal for one or more components of a sample. Alternatively, The working electrode may have two or more regions with different electrochemical properties, e.g., an electrode may have one or more regions (R1) that can trigger ECL ("ECL-active") and one or more regions (R2) that cannot trigger ECL ("ECL-inactive"). Components (A1) of a sample bound to regions R1 give an ECL signal in the presence of an appropriate electrochemical potential while the components (B2) of a sample bound to R2 give no ECL signal.

The term "ECL-inactive" can also describe regions of an electrode that produce a non-zero ECL signal that is substantially smaller than the ECL signal from other regions of an electrode or a different electrode. A given material may be ECL-active under some conditions, e.g. in the presence of buffers or certain ECL labels and be ECL-inactive under different conditions.

An electrode can be composed of fibrils, which are ECL active, and a support which is ECL inactive. In this embodiment, the components of the sample that are in electrochemical contact with the fibrils emit an ECL signal when the proper electrochemical potential is applied. In contrast, components of the sample that are in electrochemical contact with the ECL-inactive support and not the fibrils do not give an ECL signal when the electrochemical potential is applied.

The optical opacity of an electrode can be used to selectively prevent detection of ECL signals from one or more components of a sample (see Sec. 5.11 and FIG. 29).

An electrode may be ECL active for one or more components of a sample and ECL inactive for other components.

In another embodiment, one or more components ($A_n$) of a sample can be in electrochemical contact with an ECL active electrode and one or more components ($B_n$) of a sample can be out of electrochemical contact with an ECL electrode, i.e. they are not in sufficient proximity to the electrode. When an appropriate electrochemical potential is applied to the electrode, an ECL signal originates from components $A_n$ and not from components $B_n$. An electrode may consist of a porous, ECL active layer bearing one or more binding domains for analytes $A_n$ and a porous, ECL inactive layer. When a sample is filtered through this electrode, some analytes An bind to the ECL active layer, and unbound components are captured in the ECL-inactive layer. When a potential is applied to the electrode, ECL is triggered for the bound components A, since they are bound to an ECL active layer, but not for the other components, since they are entrained in an ECL inactive layer. The invention is further described in the following examples which are in no way intended to limit the scope of the invention.

6. EXAMPLES

All carbon fibrils used in these examples were CC fibrils obtained from Hyperion Catalysis Incorporated, Lot Number 166-39-1. These fibrils had diameters that ranged approximately from 3.5 nm to 70 nm, with lengths greater than 10 times the diameter, an outer region of multiple layers of carbon atoms and a distinct inner core region.

6.1. Preparation Of An NAB PMAMS Surface By Micro-Stamping

An exposed and developed photoresist master of 1–2 microns thickness is prepared according to well known procedures in a square array pattern. A 10:1 mixture of SYLGARD silicone elastomer 184 (poly(dimethylsiloxane); available from Dow Corning) and the corresponding SYLGARD 184 curing agent is poured over the master and cured. The polymerized SYLGARD 184 is carefully removed from the silicon master. The resulting elastomeric stamp is "inked" by exposure to a hydrophilic OH-terminated alkane thiol, $SH(CH_2)_{11}-(OCH_2CH_2)_6OH$, in an ethanolic solution (1–10 mM), robotically brought into pin registered contact with an aligned gold surface, and removed. The substrate is then washed for a few seconds (e.g., 2–10 seconds) with a solution of a hydrophobic $CH_3$-terminated alkane thiol, $SH(CH_2)_{10}CH_3$ (1–10 mM in ethanol) (Kumar et al., supra and Prime et al., Science 252:1164–7). The resulting surface is then gently dried under a stream of nitrogen. A capillary array containing hydrophilic solutions is then robotically brought into pin registered contact with the aligned surface aligning the capillaries with the $SH(CH_2)_{11}-(OCH_2CH_2)_6OH$ domains. Each capillary in the capillary array contains monoclonal antibodies (MABs), specific for an analyte of interest, capable of covalently binding to the reactive OH groups on the hydrophilic domains through an amide linkage.

6.2. Preparation Of An MAB And Nucleic Acid PMAMS Surface By Micro-Stamping

An exposed and developed photoresist master of 1–2 microns thickness is prepared according to well known procedures in a square array pattern. A 10:1 mixture of SYLGARD silicone elastomer 184 and the corresponding SYLGARD 184 curing agent is poured over the master and cured. The polymerized SYLGARD 184 is carefully removed from the silicon master. The resulting elastomeric stamp is "inked" by exposure to a hydrophilic OH-terminated alkane thiol, $SH(CH_2)_{11}-(OCH_2CH_2)_6OH$, in an ethanolic solution (1–10 mM), robotically brought into pin registered contact with an aligned gold surface, and removed. The substrate is then washed for a few seconds (e.g., 2–10 seconds) with a solution of a hydrophobic $CH_3$-terminated alkane thiol, $SH(CH_2)_{10}CH_3$ (1–10 mM in ethanol) (Kumar et al., supra and Prime et al., Science 252:1164–7). The resulting surface is then gently dried under a stream of nitrogen. A capillary array containing hydrophilic solutions is then robotically brought into pin registered contact with the aligned surface aligning the capillaries with the $SH(CH_2)_{11}-(OCH_2CH_2)_6OH$ domains. Each capillary in the capillary array contains antibodies or modified nucleic acids, specific for an analyte of interest, capable of covalently binding to the reactive OH groups on the hydrophilic domains through amide bond linkages.

6.3. Preparation Of A PMAMS surface By Etching

A clean gold surface is exposed to a hydrophilic OH-terminated alkane thiol, $SH(CH_2)_{11}-(OCH_2CH_2)_6OH$ (Prime et al., Science 252:1164–1167) in an ethanolic solution (1–10 mM). A linear array of fine tipped etching utensils is robotically brought into optically registered contact with an aligned gold surface, and the linear array is used to etch in both the X and Y dimensions of the surface creating a two dimensional grid array of $SH(CH_2)_{11}-(OCH_2CH_2)_6OH$ domains. The substrate is then washed for a few seconds (eg. 2–10 seconds) with a solution of a hydrophobic $SH(CH_2)_{11}-(OCH_2CH_2)_6CH_3$ (1–10 mM in ethanol). The resulting surface is then gently dried under a stream of nitrogen. A capillary array containing hydrophilic solutions is then robotically brought into pin registered contact with the surface aligning the capillaries with the $SH(CH_2)_{11}-(OCH_2CH_2)_6OH$ domains. Each capillary in the capillary array contains antibodies or nucleic acids, specific for an analyte of interest, capable of covalently binding to the reactive OH groups on the hydrophilic domains.

6.4. Sandwich Assay On A PMAMS Surface

A transparent PMAMS surface is made as described above which is substantially transparent with a patterned multi-specific array of primary antibodies linked to the surface. The support, electrode assay, monologues surface use selected to be transparent. The PMAMS surface is then exposed to a solution sample suspected of containing an analyte of interest to be assayed. The sample is then washed away leaving antibody bound analytes on the surface. The PMAMS surface is then exposed to a solution containing secondary ECL-labeled antibodies specific for bound analytes on the surface. This solution is then washed from the PMAMS surface leaving ECL labeled secondary antibodies bound to the domains where analyte is present.

The electrode assay is protected by a removable barrier to prevent premature contact of the sample with the electrode surface in order to avoid contamination effects. The barrier is then removed and the electrode array, that is wetted with assay buffer, is brought into aligned contact with the PMAMS surface. The electrode array is connected to an electronic potential wave form generator, and potential is applied to working electrode/counterelectrode pairs. A CCD then reads the light emitted and the signal is sent to a microprocessor which converts the signal to the desired readout form.

The readout is compared to the readout obtained using controls in the form of known quantities of an analyte of interest to calculate the actual quantity of analyte.

6.5. Assay On A First And Second PMAMS Surface

A transparent PMAMS surface is made as described above with a patterned multi-specific array of primary antibodies linked to the surface. The PMAMS surface is then exposed to a solution sample suspected of containing an analyte of interest to be assayed. The sample is then washed away leaving antibody bound analytes on the surface.

A second PMAMS, under a protective cover, is provided, with an alternating hydrophobic/hydrophilic pattern on which there are patterned micro-drops of a plurality of secondary antibodies labeled with ECL tag.

The barrier protecting the second PMAMS in register with the first PMAMS is removed and the micro-drops are brought into register with the primary antibody binding domains on the first PMAMS. The second PMAMS is lifted off and the electrode array and is brought into aligned contact with the first PMAMS surface. The electrode array is connected to an electrical potential wave form generator, and potential is applied to working electrode/counterelectrode pairs. A photo multiplier tube then reads the light emitted and the signal is sent to a microprocessor which converts the signal to the desired readout form.

The readout is compared to the readout obtained using controls in the form of known quantities of an analyte of interest to calculate the actual quantity of analyte.

6.6. Nucleic Acid Assay On A PMAMS Surface

A transparent PMAMS surface is made as described above with a patterned multi-specific array of single-stranded nucleic acid probes linked to the surface. The probes are complementary to the 5' region of a nucleic acid analyte of interest. The PMAMS surface is then exposed to a solution sample suspected of containing a hybridizable nucleic acid analyte of interest to be assayed, the sample having been previously denatured, i.e., treated to render the analyte of interest single stranded. The sample is then washed away leaving hybridized analytes on the surface. The PMAMS surface is then exposed to a solution containing secondary ECL labeled nucleic acid probes specific for the 3' terminus of the nucleic acid analytes bound on the surface. This solution is then washed from the PMAMS surface leaving ECL labeled nucleic acid probes bound to the domains where analyte is present.

The barrier protecting the second PMAMS in register with the first PMAMS is removed and the micro-drops are brought into register with the primary antibody binding domains on the first PMAMS. The second PMAMS is lifted off and the electrode array and is brought into aligned contact with the first PMAMS surface.

The electrode array is connected to an electronic potential wave form generator, and potential is applied to working electrode/counterelectrode pairs. A CCD then reads the light emitted and the signal is sent to a microprocessor which converts the signal to the desired readout form.

The readout is compared to the readout obtained using controls in the form of known quantities of an analyte of interest to calculate the actual quantity of analyte.

6.7. Competitive Assay On A PMAMS Surface With A Photomultiplier Detector

A transparent PMAMS surface is made as described above with a patterned multi-specific array of primary antibodies, specific for an analyte of interest, linked to the surface. The PMAMS surface is then exposed to a solution sample to be assayed which is a mixture of a sample suspected of containing the analyte of interest and a known amount of an ECL labeled molecule competitive with the analyte of interest for binding to the antibodies. The sample is then washed away leaving antibody bound analytes and/or labelled competitive binders on the surface.

The electrode array is protected by a removable barrier to prevent contact of the sample with the electrode surface in order to avoid contamination effects. The barrier is then removed and the electrode array, that is wetted with assay buffer, is brought into aligned contact with the PMAMS surface. The electrode array is connected to a electronic potential wave form generator, and potential is applied to working electrode/counterelectrode pairs. A photomultiplier tube then reads the light emitted and the signal is sent to a microprocessor which converts the signal to the desired readout form.

The readout is compared to the readout obtained using controls in the form of known quantities of an analyte of interest to calculate the actual quantity of analyte.

6.8. Competitive Assay On A PMAMS Surface With A CCD Detector

A transparent PMAMS surface is made as described above with a patterned multi-specific array of primary antibodies linked to the surface. The PMAMS surface is then exposed to a solution sample suspected of containing the analyte of interest to be assayed. The sample is then washed away leaving antibody bound analytes on the surface.

A second PMAMS, under a protective cover, is provided with an alternating hydrophobic/hydrophilic pattern on which there are patterned micro-drops of a plurality of a known amount of an ECL labeled molecule competitive with an analyte of interest.

The barrier protecting the second PMAMS in register with the first PMAMS is removed and the micro-drops are brought into register with the primary antibody binding domains on the first PMAMS. The second PMAMS is lifted off and the electrode array is brought into aligned contact with the PMAMS surface. The electrode array is connected to a electronic potential wave form generator, and potential is applied to working electrode/counterelectrode pairs. A CCD then reads the light emitted and the signal is sent to a microprocessor which converts the signal to the desired readout form.

The readout is compared to the readout obtained using controls in the form of known quantities of an analyte of interest to calculate the actual quantity of analyte.

6.9. Preparation Of An MAB PMAMS Surface By Micro Stamping With An $SH(CH_2)_{10}CH_3$ Alkane Thiol An exposed and developed photoresist master of 1–2 microns thickness is prepared according to well known procedures in a square array pattern. A 10:1 mixture of SYLGARD silicone elastomer 184 (poly(dimethylsiloxane); available from Dow Corning) and the corresponding SYLGARD 184 curing agent is poured over the master and cured. The polymerized SYLGARD 184 is carefully removed from the silicon master. The resulting elastomeric stamp is "inked" by exposure to a hydrophilic OH-terminated alkane thiol, $SH(CH_2)_{11}OH$, in an ethanolic solution (1–10 mM), robotically brought into pin registered contact with an aligned gold surface, and removed. The substrate is then washed for a few seconds (e.g., 2–10 seconds) with a solution of a hydrophobic $CH_3$-terminated alkane thiol, $SH(CH_2)_{10}CH_3$ (1–10 mm in ethanol) (Kumar et al., supra). The resulting surface is then gently dried under a stream of nitrogen. A capillary array containing hydrophilic solutions is then robotically brought into pin registered contact with the aligned surface aligning the capillaries with the $SH(CH_2)_{11}OH$ domains to place specific antibodies at each domain. Each capillary in the capillary array contains monoclonal antibodies, specific for an analyte of interest, capable of covalently binding to the reactive OH groups on the hydrophilic domains.

6.10. Preparation Of An MAB And Nucleic Acid PHAMS Surface By Micro-Stamping With An $SH(CH_2)_{10}CH_3$ Alkane Thiol An exposed and developed photoresist master of 1–2 microns thickness is prepared according to well known procedures in a square array pattern. A 10:1 mixture of SYLGARD silicone elastomer 184 and the corresponding SYLGARD 184 curing agent is poured over the master and cured. The polymerized SYLGARD 184 is carefully removed from the silicon master. The resulting elastomeric stamp is "inked" by exposure to a hydrophilic OH-terminated alkane thiol, $SH(CH_2)_{11}OH$, in an ethanolic solution (1–10 mM), robotically brought into pin registered contact with an aligned gold surface, and removed. The substrate is then washed for a few seconds (e.g., 2–10 seconds) with a solution of a hydrophobic $CH_3$-terminated alkane thiol, $SH(CH_2)_{10}CH_3$ (1–10 Mm in ethanol) (Kumar et al., supra). The resulting surface is then gently dried under a stream of nitrogen. A capillary array containing hydrophilic solutions is then robotically brought into pin registered contact with the aligned surface aligning the capillaries with the $SH(CH_2)_{11}OH$, domains to place specific antibodies and/or hybridizable nucleic acids at each domain. Each capillary in the capillary array contains antibodies or modified nucleic acids, specific for an analyte of interest, capable of covalently binding to the reactive OH groups on the hydrophilic domains through amide bond linkages.

6.11. Preparation of A PMAMS Surface Using A Streptavidin-Biotin Linker

An exposed and developed photoresist master of 1–2 mm thickness is prepared according to well known procedures in a square array pattern. A 10:1 mixture of SYLGARD silicone elastomer 184 and the corresponding SYLGARD 184 curing agent is poured over the master and cured. The polymerized SYLGARD 184 is carefully removed from the silicon master. The resulting elastomeric stamp is "inked" by exposure to a mixture of mercaptoundecanol and 12-mercapto(8-biotinamide-3,6-dioxaoctyl)dodecanamide where the mole fraction of the biotinylated thiol is 0.1 (see Spinke et al., 1993, Langmuir 9:1821–5 and Spinke et al., 1993, J. Chem. Phys. 99(9): 7012–9). The substrate is then washed for a few seconds (e.g., 2–10 seconds) with a solution of a hydrophobic $CH_3$-terminated alkane thiol, $HS(CH_2)_{10}CH_3$ alkane thiol (1–10 mM in ethanol) (see Kumar et al. supra, Biebuyck, Whitesides). The resulting surface is then gently dried under a stream of nitrogen. A capillary array containing a solution of streptavidin in each capillary is then robotically brought into pin registered contact with the aligned surface. Each capillary in the capillary array is aligned and brought into contact with a biotinylated domain and the capillary array is removed and the surface washed. A second capillary array containing a multiplicity of biotinylated antibodies and biotinylated nucleic acids solutions is then robotically brought into pin registered contact with the aligned surface to place specific antibodies and nucleic acids on each domain.

6.12. Preparation Of An RAB Single Surface

An electrode array of interdigitating working and counterelectrode pairs on a gold on silicon surface is fabricated through methods known in the art (for example see Kumar et al supra). In this example, the electrode array and the discrete binding domain array exist on the same surface of a support. An exposed and developed photoresist master of 1–2 microns thickness is prepared according to well known procedures in the pattern of the working electrodes. A 10:1 mixture of SYLGARD silicone elastomer 184 (poly (dimethylsiloxane(PDMS)); available from Dow Corning) and the corresponding SYLGARD 184 curing agent is poured over the master and cured. The polymerized SYLGARD 184 is carefully removed from the silicon master. The resulting elastomeric stamp is "inked" by exposure to a hydrophilic OH-terminated alkane thiol, $SH(CH_2)_{11}$—$(OCH_2CH_2)_6OH$, in an ethanolic solution (1–10 mM), robotically brought into pin registered contact with the aligned working electrodes on gold electrode array surface, and is then removed. A capillary array containing hydrophilic solutions is then robotically brought into pin registered contact by aligning the capillaries with the $SH(CH_2)_{11}$—$(OCH_2CH_2)_6OH$ domains on the electrode array surface to place specific antibodies on each domain. Each capillary in the capillary array contains monoclonal antibodies, specific for an analyte of interest, capable of covalently binding to the reactive OH groups on the hydrophilic domains through an amide linkage.

6.13. Assay Conducted On An KAB Single Surface

A support as described 6.12, supra, is fabricated. A PDMS stamp is fabricated as previously described from a photoresist master patterned as rings which each independently circumscribe a working electrode/counterelectrode pair. The electrode array surface is then exposed to a sample to be analyzed, washed with a mixture of ECL labelled secondary antibodies, and then washed with an assay buffer solution containing tripropyl amine. The PDMS stamp is then aligned and brought into registered contact aligning the rings of the PDMS stamp so as to circumscribe and define individual volume elements of assay buffer above each electrode pair. An overpotential is applied to the electrode pairs so as to release the monolayer from the surface exposing the working electrode to the ECL labelled secondary antibodies. A photomultiplier tube then reads the light emitted through the transparent PDMS and the signal is sent to a microprocessor which converts the signal to the desired readout form.

The readout is compared to the readout obtained using controls in the form of known quantities of an analyte of interest to calculate the actual quantity of analyte.

6.14. Preparation Of A Single Surface With Working And Counterelectrodes

An electrode array of interdigitating working and counter gold electrode pairs with gold binding domains in between the interdigitating electrodes on a gold on silicon support is fabricated through methods known in the art (for example see Kumar et al. supra). In this example, the electrode array and the discrete binding domain array exist on the same surface. An exposed and developed photoresist master of 1–2 microns thickness is prepared according to well known procedures in the pattern of the binding domains in between the interdigitating electrode pairs. A 10:1 mixture of SYLGARD silicone elastomer 184 (poly(dimethylsiloxane (PDMS)); available from Dow Corning) and the corresponding SYLGARD 184 curing agent is poured over the master and cured. The polymerized SYLGARD 184 is carefully removed from the silicon master. The resulting elastomeric stamp is "inked" by exposure to a hydrophilic OH-terminated alkane thiol, $SH(CH_2)_{11}$—$(OCH_2CH_2)_6OH$, in an ethanolic solution (1–10 mM), robotically brought into pin registered contact with the aligned gold binding domains on the electrode array surface, and is then removed. A capillary array containing hydrophilic solutions is then robotically brought into pin registered contact, aligning the capillaries with the $SH(CH_2)_{11}$—$(OCH_2CH_2)_6OH$ domains on the electrode array surface to place specific antibodies on each domain. Each capillary in the capillary array contains antibodies specific for an analyte of interest, capable of covalently binding to the reactive OH groups on the hydrophilic domains through an amide linkage.

6.15. Assay Conducted On A Single Surface With Working And Counterelectrodes A support surface as described 6.14 supra is fabricated by the described methods. The prepared surface is exposed to a sample to be analyzed, washed with a mixture of ECL labelled secondary antibodies, and then washed with an assay buffer solution containing tripropyl amine. The electrode array is connected to a electronic potential wave form generator, and potential is applied to working electrode/ counterelectrode pairs. A photomultiplier tube then reads the light emitted and the signal is sent to a microprocessor which converts the signal to the desired readout form.

The readout is compared to the readout obtained using controls in the form of known quantities of an analyte of interest to calculate the actual quantity of analyte.

6.16. Preparation Of A Surface With Counterelectrodes

An exposed and developed photoresist master of 1–2 microns thickness is prepared according to well known procedures in a square array pattern. A 10:1 mixture of SYLGARD silicone elastomer 184 and the corresponding SYLGARD 184 curing agent is poured over the master and cured. The polymerized SYLGARD 184 is carefully removed from the silicon master. The resulting elastomeric stamp is "inked" by exposure to a hydrophilic OH-terminated alkane thiol, $SH(CH_2)_{11}$—$(OCH_2CH_2)_6OH$, in an ethanolic solution (1–10 mM), robotically brought into pin registered contact with an aligned patterned counterelectrode and square binding domain on a gold surface, and removed. The patterned gold surface consists of addressable ring counterelectrodes circumscribing the binding domains where the $SH(CH_2)_{11}$—$(OCH_2CH_2)_6OH$ has been stamped. A gap or separation space exists between each gold counterelectrode and each square gold substrate for each monolayer binding domain. A capillary array containing binding reagent solutions is then robotically brought into pin registered contact with the aligned surface registering the capillaries with the $SH(CH_2)_{11}$—$(OCH_2CH_2)_6OH$ domains to place specific antibodies or nucleic acids on each domain. Each capillary in the capillary array contains antibodies or nucleic acids, specific for an analyte of interest, capable of covalently binding to the reactive OH groups on the hydrophilic domains.

6.17. Assay Conducted On A Single Surface With The Working And Counterelectrodes On Different Surfaces The support surface described above in example 6.16 is exposed to a sample solution to be analyzed. The support surface is then washed and exposed to a solution containing a plurality of ECL labelled monoclonal antibodies or ECL labelled nucleic acids of differing specificity and then washed with assay buffer containing tripropyl amine. A transparent addressable working electrode array is fabricated with each working electrode in the array corresponding to a discrete binding domain/counterelectrode region on the support as described above in Section 6.16. The two supports are wetted with the assay buffer and robotically brought into registered aligned conformal contact. The electrode arrays are connected to an electronic potential wave form generator, and potential is applied to the aligned working electrode/counterelectrode pairs creating a potential field between the two supports. A CCD then reads the light emitted through the transparent working electrode and the signal is sent to a microprocessor which converts the signal to the desired readout form.

The readout is compared to the readout obtained using controls in the form of known quantities of an analyte of interest to calculate the actual quantity of analyte.

6.18. Fabrication Of A CC (Dispersed) Fibril MAT By Vacuum Filtration

An aqueous slurry of CC fibrils, with 1 mg fibrils/mL solution was prepared by mixing 0.1% w/w CC fibrils/ deionized water. The CC fibrils were dispersed (the larger, micron-scale aggregates were dispersed into small aggregates or individual fibers) in the slurry by immersing a 400 watt sonication horn in the slurry for between 10 minutes and 1 hour. The extent of dispersion was monitored by optical microscopy.

A nylon filter membrane (0.47 µm pore size, 25 mm diameter) was placed in a 25 mm diameter glass fritted filter. The dispersed fibril slurry was filtered through the membrane/filter set-up by suction filtration (FIG. 23A). Aliquots of the slurry (5 ml) were diluted with 20 ml deionized water, then filtered through the membrane/filter set-up. For an average mat of approximately 0.25–0.3 gram/ cc, a mat of approximately 100 µm required 6 aliquots.

Suction filtration was continued until all of the water from the dispersion was removed from the mat (by visual inspection). The mat was peeled (by hand) directly from the filter membrane.

The mat was dried in an oven for approximately 10–15 minutes at 60° C. The mat was cut, punched or otherwise sectioned for use.

6.19. Fabrication Of A Fibril Mat On A Metal Mesh Support By Evaporation

An aqueous slurry of CC fibrils, with 1 mg fibrils/mL solution was prepared by mixing 0.1% w/w CC fibrils/ deionized water. The CC fibrils were dispersed (the larger, micron-scale aggregates were dispersed into small aggregates or individual fibers) in the slurry by immersing a 400 watt sonication horn in the slurry for between 10 minutes and 1 hour. The extent of dispersion was monitored by optical microscopy.

A 1 $cm^2$ section of stainless steel mesh (400 count) was placed on a 25 mm diameter paper filter. A 5 ml aliquot of the slurry was pipetted onto the surface of the screen/filter paper ensemble. The water in the slurry was allowed to evaporate, either at room temperature and pressure, or in a heated oven.

Once the fibril mat was dry, additional aliquots were added. The fibril and screen were peeled as a single unit from the filter paper.

The mat was cut, punched or otherwise sectioned for use.

6.20. Immobilization Of Avidin On Fibrils Bearing NHS-Ester Functional Groups Fibrils derivatized with COOH (provided by Hyperion Catalysts Inc.) were suspended in anhydrous dioxane at −10 mg/ml with constant stirring. A 20-fold molar excess of N-hydroxysuccinimide was added and allowed to dissolve. Next, a 20-fold molar excess of ethyl-diamino-propyl-carbodiimide (EDAC) was added, and the mixture was stirred for 2 hours at room temperature.

After stirring, the supernatant was aspirated and the solids were washed three times with anhydrous dioxane, one time with anhydrous methanol, and filtered on a 0.45 µm polysulfone membrane. The filtrate was washed with additional methanol and the placed in a glass vial under vacuum until no further reduction in weight was observed.

10.4 mg of NHS-ester fibrils were washed with PBS-1 (−70 mM phosphate, 150 mM NaCl) (ORIGEN reagent 402-130-01, pH 7.8, IGEN, Inc.). The washed fibrils were suspended in 2.3 ml solution of avidin (8.3 mg avidin/ml PBS-1).

The suspension was allowed to sit at room temperature for 1.5 hours, with constant rotation of the flask to provide agitation.

After 1.5 hours, the suspension was stored for 16 hours at 4° C., then brought to room temperature and washed with PBS-1 and stored at 4° C. as a suspension in PBS-1.

6.21. Immobilization Of Monoclonal Antibody (Anti-AFP) On Carbon Fibrils

Carbon fibrils functionalized with NHS esters were prepared as described in Example 6.20.

14 mg of fibril-NHS ester was mixed with 500 ml PBS-1 buffer. The mixture was sonicated for 20 min, until it became a viscous slurry. An additional 500 ml of PBS-1 buffer was added.

A total of 1.6 mg anti-AFP (alpha-fetal protein) antibody in 80 ml PBS-1 was added to the above slurry. The reaction was allowed to sit at room temperature for 2.5 hours.

6 ml PBS-1 buffer was added and the reaction mixture was centrifuged at 4° C. for 5 minutes. The supernatant was removed by pipette. This procedure was repeated 9 times.

After the final wash, the supernatant was removed, and the fibril-antiAFP product was stored at 4° C.

6.22. Cyclic Voltammograms Of Fibril Mats: Comparison Of Fibril Mat With Gold Foil Electrode Cyclic voltammograms of 6 mM $Fe^{3+/2+}(CN)_6$ in 0.5 M $K_2SO_4$ were measured. In FIG. 30A, the CV for a plain fibril mat of CC(dispersed) was measured at 0.10 mA/cm at 10, 25 and 50 mV/sec. The mat was fabricated as described in Example 6.18. In FIG. 30B, the CV was measured for a gold foil electrode at 0.05 mA/cm at 10, 25 and 50 mV/sec. All potentials are in Volts vs. Ag/AgCl.

6.23. Electrochemical Properties Of Fibril Mat Electrodes: Comparison Of Anodic Peak Current With Thickness of The Mat Cyclic voltammograms of 6 mM $Fe^{3+/2+}(CN)_6$ in 0.5 M $K_2SO_4$ were measured for fibril mats of the same geometric area (0.20 cm$^2$), but different thicknesses. The anodic peak current (FIG. 31) increased with increasing thickness of mat for thicknesses that ranged from 24 μm to 425 μm. For each thickness, the anodic peak current also increased with increasing scan rates (for rates that ranged from 10 mV/sec to 150 mV/sec). The rate of increase of the anodic peak current, as a function of thickness, also increased with increasing thickness. Fibril mats that were 24 μm thick behaved comparably to gold foil electrodes.

6.24. Non-Specific Binding Of Proteins To Fibrils

Non-specific binding of proteins to carbon fibrils (cc) was measured as follows: i) a solution of $Ru(bipy)_3^{2+}$ ("TAG1") labeled proteins was exposed to a known quantity of carbon fibrils until equilibrium was reached; ii) the labeled-protein/fibril solution was centrifuged, and the supernatant was collected, and iii) the amount of labeled-protein remaining in the supernatant was assayed using electrochemiluminescence (ECL).

To generate the curve shown in FIG. 32, anti-CEA antibody attached to derivatized TAG1 (antibody to carcinoembryonic antigen attached to a derivatized TAG1 ECL label) at 3 μg/mL, was added to serial dilutions of CC(plain) fibrils in 0.1 M potassium phosphate buffer at pH 7. Fibrils were removed by centrifugation after vortexing for 20 minutes. ECL assays that measured the amount of protein (unbound) remaining in the supernatant were run in an ORIGEN 1.5 (IGEN, Inc.) analyzer on aliquots of the reaction mixture supernatant diluted 5 times with ORIGEN assay buffer. A decrease in the ECL signal (relative to the ECL signal for an object of the reaction mixture that had not been exposed to fibrils) resulted from increased binding of protein labelled with a derivatized TAG1when a higher concentration of carbon fibrils were present.

6.25. Reduction Of Non-Specific Binding Of Proteins To Fibrils With Detergents/Surfactants Using the method described in Example 6.2.4, the effect of surfactant on protein binding to fibrils was analyzed. Triton X-100 was added to the anti-CEA attached to derivatized TAG1/fibril mixture, the solution was incubated for 20 minutes, the tubes were centrifuged, and aliquots of the supernatant, diluted 5 times with ORIGEN assay buffer, were analyzed by ECL. The results are shown in the Table below and in FIG. 33.

| Tube Number | [T-X100], ppm | Peak Intensity | Prot-TAG1 μg/ml | [GF], ppm |
|---|---|---|---|---|
| 19 | 1674 | 1611 | 2.65 | 52 |
| 18 | 837 | 1634 | 2.65 | 52 |
| 17 | 418 | 1697 | 2.65 | 52 |
| 16 | 209 | 1583 | 2.65 | 52 |
| 15 | 105 | 1772 | 2.65 | 52 |
| 14 | 52 | 1463 | 2.65 | 52 |
| 13 | 26 | 627 | 2.65 | 52 |
| 12 | 13 | 23 | 2.65 | 52 |

A curve that results from plotting the ECL intensity of a protein labelled with a derivatized TAG1 in solution vs. Triton X-100 concentration is shown in FIG. 33. A higher ECL signal corresponds to more derivatized-TAG1-labeled protein in the supernatant, which corresponds to less derivatized-TAG1-labeled protein bound to the fibrils. Concentrations of Triton x-100 that ranged from 10 ppm to 100 ppm reduced the extent of binding; the concentration from 100 to 2000 ppm did not further extent of binding.

6.26. ECL Of Free TAG In Solution With Fibril Mat Electrode

A fibril mat prepared as in Example 6.18 was installed in the mounting area 3403 of the working electrode holder 3401 of the "Fibril Cell" fixture shown in FIG. 34. The holder 3401 was slipped into the bottom of the electrochemical cell compartment 3400. The 3 M Ag/AgCl reference electrode (Cyprus # EE008) was installed into the electrochemical cell compartment through the reference cell hole 3402. The cell was filled with Assay Buffer (IGEN # 402-005-01 lot# 5298) and attached to the PMT holder 3404. Using a EG&G PARC model 175 universal programmer and an EG&G model 175 Potentiostat/Galvanostat the potential was swept from 0 V to +3 V vs. Ag/AgCl at 100 mV/s. The ECL was measured by a Hamamatsu R5600U-01 which was powered at 900V by a Pacific Instruments model 126 Photometer. The analog data was digitized at 10 Hz by a CIO-DAS-1601 A/D board driven by HEM Snap-Master. The Fibril Cell was drained, flushed with 1000 pM TAG1 (IGEN # 402-004-C lot# 4297), and filled with 1000 pM TAG1. The potential was swept as with Assay Buffer. Shown in FIG. 35 are the ECL traces (measured at 24.0±0.2 C) for Assay Buffer 3501 and 1000 pM TAG1 3502. The dark corrected ECL peak area was 22.10 nAs for Assay Buffer and 46.40 nAs for 1000 pM TAGl.

6.27. ECL Of Adsorbed Labeled Antibody With Fibril Mat Electrode

Fibril mats were made to a thickness of 0.0035 inches from plain cc-dispersed fibrils in the manner described in Example 6.18. The dried mats were then punched into 3 mm disks and mounted onto supports. The supports used in this experiment were fabricated from 0.030 inches polyester sheet patterned by screen printed conductive gold ink. This conductive gold ink formed the counter electrode, reference electrode, and provided leads for the working and other electrodes. Two fibril mat disks were mounted to each patterned support using two sided carbon containing conductive tape (Adhesives Research). After mounting, the disks were spotted with 0.5 µl of 10 µg/ml anti-TSH antibody attached to derivatized TAG1 in deionized water (Ru-TSH mono 1:2 Jun. 2, 1995, IGEN, Inc.) or 0.5 µl of 10 µg/ml anti-TSH unTAG1'ed capture antibody in deionized water (TSH poly Jun. 25, 1995, IGEN, Inc.) and allowed to dry. After drying, the mats were flooded with IGEN assay buffer. Flooded mats on supports were loaded into an IGEN Origen 1.5 based instrument and ECL was read using a scan rate of 500 mV/s from 0 to 4500 mV. FIG. 43 compares the peak ECL signals from TAG1-antibody containing mats 4301 and unTAG1'ed capture antibody containing mats 4302.

6.28. ECL Using Fibril Mat Electrode For Sandwich Assay

Anti-AFP capture antibody was immobilized on fibrils as described above. Anti-AFP fibrils were washed into deionized water (dI) and resuspended at a density of 1 mg/ml. A four layer fibril mat was produced using vacuum filtration as described in Example 6.18. Two milligrams of anti-AFP fibrils were added to 3 mg of plain CC dispersed fibrils and the mixture diluted to a total volume of 20 ml in dI. The diluted mixture was filtered onto a 0.45 µm nylon filter. This initial mat layer was then followed by two core layers, each consisting of 5 mg of plain CC dispersed fibrils. The mat core was then topped with a mixed fibril layer identical to the initial layer. This resulted in a fibril mat that was ~40% anti-AFP fibrils on the top and bottom surface and ~100% plain fibrils in the core. This mixed mat was air dried under vacuum and punched into 3 mm disks. These disks were then mounted onto supports as described in Example 6.27. Dry, supported, anti-AFP mats were flooded with AFP calibrators A, C, and F (IGEN, Inc.) and allowed to incubate for 15 minutes at room temperature on the bench top. After incubation, supported electrodes were washed with a dI stream for 10 seconds and then blotted dry with a lint free wipe. Fibril mats were then flooded with anti-AFP attached to antibody labelled with derivatized TAG1 (IGEN, Inc.) and allowed to incubate for 15 minutes at room temperature on the bench top. After incubation the supported electrodes were washed with dI and dried with a wipe. Fibril mats were then flooded with IGEN assay buffer and read as described in Example 6.27.

6.29. ECL Detection Of TAG1-Labeled Avidin On A Polyacrylamide Surface

A cross-linked polyacrylamide gel containing covalently bound biotin was prepared by copolymerization of acrylamide, bis-acrylamide, and N-Acryloyl-N'-biotinyl-3,6-dioxaoctane-1,9-diamine (biotin linked to an acrylamide moiety through a tri(ethylene glycol) linker) using well known conditions (initiation with ammonium persulfate and TEMED). In this experiment, the concentrations of the three monomeric species were 2.6 M, 0.065 N, and 0.023 a respectively (these concentrations of acrylamide and bis-acrylamide are reported to result in gels with pore sizes smaller than most proteins). Polymerization of the solution containing the monomers between two glass plates held apart to a distance of approximately 0.7 mm led to the formation of a slab gel with the same thickness. After the polymerization reaction was complete, any unincorporated biotin was washed out by soaking the gel in four changes of PBS. Avidin labeled with a derivatized TAG1 (where Avidin refers to NeutrAvidin, a modified avidin designed to exhibit reduced NSB, was used in this experiment) was bound to the surface of the gel by soaking the gel in a solution containing the protein at a concentration of 50 µg/mL in PBS for 20 min. Excess TAG1-labeled avidin was then washed away by soaking the gel in four changes of ECL assay buffer (200 mM sodium phosphate, 100 mM tripropylamine, 0.02% (w/v) Tween-20, pH 7.2). As shown in FIG. 39, the gel (3900) was then placed in contact with gold working (3901) and counter (3902) electrodes patterned on a glass support (3903). Ramping the potential across the two electrodes from 0.0 to 3.0 V and back to 0.0 V at a rate of 500 mV/s led to an ECL light signal as measured from a PMT (3904) placed above the gel (FIG. 40). A gel prepared without inclusion of the biotin containing acrylamide derivative gave no ECL signal (FIG. 41). This signal obtained for the biotin-containing polymer was indicative of close to a full monolayer of protein is present on the surface of the gel.

6.30. ECL Sandwich Immunoassay On A Polyacrylamide Surface

A cross-linked polyacrylamide gel containing covalently bound biotin is prepared as described in Example 6.29. Streptavidin is adsorbed on the surface of the gel to form a binding domain capable of capturing biotin labeled species. The surface is treated with a solution containing tripropylamine, an unknown concentration of an analyte, a biotin-labeled antibody against the analyte, and a different ECL TAG1-labeled antibody against the analyte. The presence of the analyte causes the formation of a complex of the analyte and the two antibodies which is then captured on the streptavidin surface. ECL tag bound to secondary antibody present on the surface is measured as described in example 6.29

6.31. Multiple ECL Sandwich Immunoassays On Polyacrylamide Surfaces Supported On An Electrode An exposed and developed photoresist master of 1–2 microns thickness is prepared according to well known procedures to give a pattern of circular depressions arranged in an array. A 10:1 mixture of SYLGARD silicone elastomer 184 and the corresponding SYLGARD 184 curing agent is poured over the master and cured. The polymerized SYLGARD is carefully removed from the silicon master. The resulting elastomeric stamp is "inked" by exposure to a solution containing the hydroxyl terminated thiol $HS\text{-}(CH_2)_{11}\text{-}(OCH_2CH_2)_3\text{-}OH$ (1–10 mM) in ethanol, brought into contact with an aligned gold substrate and removed. The substrate is washed for several seconds with a solution containing the thiol $HS\text{-}(CH_2)_{10}\text{-}CH_3$ (1–10 mM in ethanol). The resulting surface is then rinsed with ethanol and dried under a stream of nitrogen. Treatment of the surface with a solution containing acryloyl chloride and triethylamine in dioxane leads to functionalization of the hydroxyl terminated domains with acrylate groups. A capillary array containing mixtures of acrylamide, bis-acrylamide, N-acryloylsuccinimide, azo-bis-cyanovaleric acid, and antibodies presenting amino groups is then brought into contact with the aligned surface aligning the capillaries with the acrylate terminated domains to place prepolymer solutions containing specific antibodies at each domain. Each capillary in the capillary array contains antibodies specific for a different analyte of interest. Exposure of the patterned prepolymer droplets to UV light leads to the formation of cross-linked gels on the substrate each presenting a binding domain at the surface. The assay is carried out by treatment of the substrate with a mixture of analytes capable of binding at one or more of the binding domains presented on the gel surfaces in a buffered solution containing tripropylamine and ECL-TAG1 labeled secondary antibodies. The binding domains (4200, 4201, 4202) (on polyacrylamide drops (4203) on a gold electrode (4232) are then placed in close proximity to an ITO working electrode (4204) as shown in FIGS. 42A–B. Light emitted from each of the binding domains is quantified using a CCD camera (4205) and compared to binding domains for internal standards included in the sample solution.

6.32. Multiple ECL Competitive Immunoassays On Polyacrylamide Surfaces Supported on An Electrode An exposed and developed photoresist master of 1–2 microns thickness is prepared according to well known procedures to give a pattern of circular depression arranged in an array. A 10:1 mixture of SYLGARD silicone elastomer 184 and the corresponding SYLGARD 184 curing agent is poured over the master and cured. The polymerized SYLGARD is carefully removed from the silicon master. The resulting elastomeric stamp is "inked" by exposure to a solution containing the hydroxyl terminated thiol HS-$(CH_2)_{11}$—$(OCH_2CH_2)_3$—OH (1–10 mM) in ethanol, brought into contact with an aligned gold substrate and removed. The substrate is washed for several seconds with a solution containing the thiol HS-$(CH_2)_{10}$—$CH_3$ (1–10 mM in ethanol). The resulting surface is then rinsed with ethanol and dried under a stream of nitrogen. Treatment of the surface with a solution containing acryloyl chloride and triethylamine in dioxane leads to functionalization of the hydroxyl terminated domains with acrylate groups. A capillary array containing mixtures of acrylamide, bis-acrylamide, N-acryloylsuccinimide, azo-bis-cyanovaleric acid, and antibodies is then brought into contact with the aligned surface aligning the capillaries with the acrylate terminated domains to place prepolymer solutions containing specific antibodies at each domain. Capillaries in the capillary array contain antibodies specific for different analytes of interest. Exposure of the patterned prepolymer droplets to UV light leads to the formation of cross-linked gels on the substrate each presenting a binding domain at the surface. The assay is carried out by treatment of the substrate with a mixture of analytes capable of binding at one or more of the binding domains presented on the gel surfaces in a buffered solution containing tripropylamine and ECL-TAG1 labeled analogues of the analytes (i.e., setting up a competition of ECL-TAG1 labeled and unlabeled analytes for binding to the binding domains). The binding domains (4200, 4201 and 4202) (on polyacrylamide drops (4203) on a gold electrode (4232)) are then placed in close proximity to an ITO working electrode (4204) as shown in FIG. 42. Light emitted from each of the binding domains is quantified using a CCD camera (4205) and compared to binding domains for internal standards included in the sample solution.

6.33. Multiple ECL Assays For Binding Of Cells On Polyacrylamide Surfaces Supported On An Electrode An exposed and developed photoresist master of 1–2 microns thickness is prepared according to well known procedures to give a pattern of circular depressions arranged in an array. A 10:1 mixture of SYLGARD silicone elastomer 184 and the corresponding SYLGARD 184 curing agent is poured over the master and cured. The polymerized SYLGARD is carefully removed from the silicon master. The resulting elastomeric stamp is "inked" by exposure to a solution containing the hydroxyl terminated thiol HS-$(CH_2)_{11}$—$(OCH_2CH_2)_3$—OH (1–10 mM) in ethanol, brought into contact with an aligned gold substrate and removed. The substrate is washed for several seconds with a solution containing the thiol HS-$(CH_2)_{10}$—$CH_3$ (1–10 mM in ethanol). The resulting surface is then rinsed with ethanol and dried under a stream of nitrogen. Treatment of the surface with a solution containing acryloyl chloride and triethylamine in dioxane leads to functionalization of the hydroxyl terminated domains with acrylate groups. A capillary array containing mixtures of acrylamide, bis-acrylamide, N-acryloylsuccinimide, azo-bis-cyanovaleric acid, and antibodies directed against cell surfaces is then brought into contact with the aligned surface aligning the capillaries with the acrylate terminated domains to place prepolymer solutions at each domain. Exposure of the patterned prepolymer droplets to UV light leads to the formation of cross-linked gels on the substrate each presenting a binding domain at the surface. The assay is carried out by treatment of the binding domains first with a suspension of cells, then with a mixture of binding reagents capable of binding one or more of the cells bound to the gel surfaces in a buffered solution containing tripropylamine and ECL-TAG1 labeled secondary antibodies and/or other binding reagents specific for the analytes. The binding domains (4200, 4201, and 4202) (on polyacrylamide drops (4203) on a gold electrode (4232) are then placed in close proximity to an ITO working electrode (4204) as shown in FIG. 42. Light emitted from each of the binding domains is quantified using a CCD camera (4205) and compared to binding domains for internal standards included in the sample solution.

6.34. Multiple ECL Assays For Binding Of Analytes To Cells On Polyacrylamide Surfaces Supported On An Electrode An exposed and developed photoresist master of 1–2 microns thickness is prepared according to well known procedures to give a pattern of circular depressions arranged in an array. A 10:1 mixture of SYLGARD silicone elastomer 184 and the corresponding SYLGARD 184 curing agent is poured over the master and cured. The polymerized SYLGARD is carefully removed from the silicon master. The resulting elastomeric stamp is "inked" by exposure to a solution containing the hydroxyl terminated thiol HS-$(CH_2)_{11}$—$(OCH_2CH_2)_3$—OH (1–10 mM) in ethanol, brought into contact with an aligned gold substrate and removed. The substrate is washed for several seconds with a solution containing the thiol HS-$(CH_2)_{10}$—$CH_3$ (1–10 mM in ethanol). The resulting surface is then rinsed with ethanol and dried under a stream of nitrogen. Treatment of the surface with a solution containing acryloyl chloride and triethylamine in dioxane leads to functionalization of the hydroxyl terminated domains with acrylate groups. A capillary array containing mixtures of acrylamide, bis-acrylamide, N-acryloylsuccinimide, azo-bis-cyanovaleric acid, and cells is then brought into contact with the aligned surface aligning the capillaries with the acrylate terminated domains to place prepolymer solutions containing specific cell types at each domain. Capillaries in the capillary array contain cells with different surface structures that bind different analytes. Exposure of the patterned prepolymer droplets to UV light leads to the formation of cross-linked gels on the substrate each presenting a binding domain at the surface. The assay is carried out by treatment of the gels with a sample containing a mixture of analytes capable of binding at one or more of the binding domains presented on the gel surfaces in a buffered solution containing tripropylamine and ECL-TAG labeled antibodies and/or other binding reagents specific for the analytes. The binding domains (4200, 4201 and 4202) (on polyacrylamide drops (4203) on a gold electrode (4232) are then placed in close proximity to an ITO working electrode (4204) as shown in FIG. 42. Light emitted from each of the binding domains is quantified using a CCD camera (4205) and compared to binding domains for internal standards included in the sample solution.

6.35. Multiple ECL Competitive Hybridization Assays on Polyacrylamide Surfaces Supported On An Electrode An exposed and developed photoresist master of 1–2 microns thickness is prepared according to well known procedures to give a pattern of circular depression arranged in an array. A 10:1 mixture of SYLGARD silicone elastomer 184 and the corresponding SYLGARD 184 curing agent is poured over the master and cured. The polymerized SYLGARD is carefully removed from the silicon master. The resulting elastomeric stamp is "inked" by exposure to a solution containing the hydroxyl terminated thiol HS-$(CH_2)_{11}$—$(OCH_2CH_2)_3$—OH (1–10 mM) in ethanol, brought into contact with an aligned gold substrate and removed. The substrate is washed for several seconds with a solution containing the thiol HS-$(CH_2)_{10}$—$CH_3$ (1–10 mM in ethanol). The resulting surface is then rinsed with ethanol and dried under a stream of nitrogen. Treatment of the surface with a solution containing acryloyl chloride and triethylamine in dioxane leads to functionalization of the hydroxyl terminated domains with acrylate groups. A capillary array containing mixtures of acrylamide, bis-acrylamide, N-acryloylsuccinimide, azo-bis-cyanovaleric acid, and nucleic acid probes functionalized with amino groups is then brought into contact with the aligned surface, aligning the capillaries with the acrylate terminated domains to place prepolymer solutions containing specific probes at each domain. Capillaries in the capillary array contain probes specific for a nucleic acid sequence of interest. Exposure of the patterned prepolymer droplets to UV light leads to the formation of cross-linked gels on the substrate, each presenting a binding domain at the surface. The assay is carried out by treatment of the substrate with a sample mixture that may contain sequences capable of binding at one or more of the binding domains presented on the gel surfaces in a buffered solution containing tripropylamine and ECL-TAG1 labeled sequences which can compete with the analytes of interest for binding to the surface. The binding domains (4200, 4201, and 4202) (on polyacrylamide drops (4203) on a gold electrode (4232) are then placed in close proximity to an ITO working electrode (4204) as shown in FIG. 42. Light emitted from each of the binding domains is quantified using a CCD camera (4205) and compared to binding domains for internal standards included in the sample solution.

6.36. Multiple ECL Hybridization Sandwich Assays On Polyacrylamide Surfaces Supported On An Electrode An exposed and developed photoresist master of 1–2 microns thickness is prepared according to well known procedures to give a pattern of circular depression arranged in an array. A 10:1 mixture of SYLGARD silicone elastomer 184 and the corresponding SYLGARD 184 curing agent is poured over the master and cured. The polymerized SYLGARD is carefully removed from the silicon master. The resulting elastomeric stamp is "inked" by exposure to a solution containing the hydroxyl-terminated thiol HS-$(CH_2)_{11}$—$(OCH_2CH_2)_3$—OH (1–10 mM) in ethanol, brought into contact with an aligned gold substrate and removed. The substrate is washed for several seconds with a solution containing the thiol HS-$(CH_2)_{10}$—$CH_3$ (1–10 mM in ethanol). The resulting surface is then rinsed with ethanol and dried under a stream of nitrogen. Treatment of the surface with a solution containing acryloyl chloride and triethylamine in dioxane leads to functionalization of the hydroxyl terminated domains with acrylate groups. A capillary array containing mixtures of acrylamide, bis-acrylamide, N-acryloylsuccinimide, azo-bis-cyanovaleric acid, and nucleic acid probes functionalized with amino groups is then brought into contact with the aligned surface, aligning the capillaries with the acrylate terminated domains to place prepolymer solutions containing specific probes at each domain. Capillaries in the capillary array contain probes specific for a nucleic acid sequence of interest. Exposure of the patterned prepolymer droplets to UV light leads to the formation of cross-linked gels on the substrate, each presenting a binding domain at the surface. The assay is carried out by treatment of the substrate with a sample mixture that may contain sequences capable of binding at one or more of the binding domains presented on the gel surfaces in a buffered solution containing tripropylamine and ECL-TAG1 labeled sequences which can bind the analytes at sequences not complementary to the surface-bound probes. The binding domains (4200, 4201, and 4202) (on polyacrylamide drops (4203) on a gold electrode (4232) are then placed in close proximity to an ITO working electrode (4204) as shown in FIG. 42. Light emitted from each of the binding domains is quantified using a CCD camera (4205) and compared to binding domains for internal standards included in the sample solution.

6.37. Multiple Assays Of Different Types On A Polyacrylamide Surfaces Supported On An Electrode An exposed and developed photoresist master of 1–2 microns thickness is prepared according to well known procedures to give a pattern of circular depressions arranged in an array. A 10:1 mixture of SYLGARD silicone elastomer 184 and the corresponding SYLGARD 184 curing agent is poured over the master and cured. The polymerized SYLGARD is carefully removed from the silicon master. The resulting elastomeric stamp is "inked" by exposure to a solution containing the hydroxyl terminated thiol HS-$(CH_2)_{11}$—$(OCH_2CH_2)_3$—OH (1–10 mM) in ethanol, brought into contact with an aligned gold substrate and removed. The substrate is washed for several seconds with a solution containing the thiol HS-$(CH_2)_{10}$—$CH_3$ (1–10 mM in ethanol). The resulting surface is then rinsed with ethanol and dried under a stream of nitrogen. Treatment of the surface with a solution containing acryloyl chloride and triethylamine in dioxane leads to functionalization of the hydroxyl terminated domains with acrylate groups. A capillary array containing mixtures of acrylamide, bis-acrylamide, N-acryloylsuccinimide, azo-bis-cyanovaleric acid, and any of the binding reagents described in Examples 6.31–6.36 is then brought into contact with the aligned surface aligning the capillaries with the acrylate terminated domains to place prepolymer solutions containing specific probes at each domain. Each capillary in the capillary array contains binding domains specific for analytes of interest. Exposure of the patterned prepolymer droplets to UV light leads to the formation of cross-linked gels on the substrate each presenting a binding domain at the surface. The assay is carried out by treatment of the substrate with a sample mixture that may contain analytes capable of binding at one or more of the binding domains presented on the gel surfaces in a buffered solution containing tripropylamine and either ECL-TAG1 labeled analogues of analytes which compete with analytes for binding to the binding domains and/or ECL-TAG1 labeled secondary binding reagents to the analytes of interest. The binding domains (4200, 4201, and 4202) (on polyacrylamide drops (4203) on a gold electrode (4232) are then placed in close proximity to an ITO working electrode (4204) as shown in FIG. 42. Light emitted from each of the binding domains is quantified using a CCD camera (4205) and compared to binding domains for internal standards included in the sample solution.

6.38. Highly Reversible ECL

Polycrystalline gold electrodes (purchased from Bio-Analytical Services, 2 mm$^2$) were cleaned by hand polishing sequentially with 0.5 μm and 0.03 μm alumina slurry, followed by chemical etching in 1:3 $H_2O_2/H_2SO_4$ and electrochemical cycling in dilute $H_2SO_4$ between −0.2 V and 1.7 V vs. Ag/AgCl. The clean electrodes were then immersed overnight in a dilute solution of octylthiol ($C_8SH$) dissolved in ethanol. Protein adsorption was carried out by covering $C_8SH$-modified electrodes with 20 μl of TAG1-labeled bovine serum albumin (BSA) dissolved in phosphate buffer saline (PBS, 0.15 M NaCl/0.1 M NaPi, pH 7.2) and washing the surface extensively with the same buffer after ten minute incubation.

ECL was done in a three-electrode cell with a Ag/AgCl reference electrode, platinum wire counter electrode and an EG&G 283 potentiostat. The light intensity was measured with a Pacific Instruments photometer and a Hamamatsu photo-multiplier tube placing at the bottom of the electrochemistry cell. The protein-adsorbed electrode was immersed in a solution of 0.1 M TPA and 0.2 M phosphate, pH 7.2. Highly reversible ECL response (substantially similar intensity on the forward and backward scans) was observed when the electrode potential was cycled between 0.0 V and 1.2 V, as shown in FIG. 44A, indicating the reversible nature of the ECL process and stability of the thiol and protein layers on the electrode.

Cyclic voltammetric experiments were conducted on the same instruments as for ECL, without the use of PMT and photometer. In the experiment, a $C_8SH$-covered electrode (no protein) was placed in a solution of 1 mM potassium ferricyanide (in PBS) and the electrode was scanned from +0.5 V to 1.2 V and back, followed by another cycle between +0.5 V and −0.3 V. It is indicative that the monolayer is still intact and not desorbing at 1.2 V, since there was only capacitive current in the voltammogram between +0.5 V and −0.3 V and no faradaic current of ferricyanide (FIG. 44B).

6.39. Quasi-Reversible ECL

Electrode modification and protein adsorption were done in the same way as described above. In the ECL experiments, the potential was scanned between 0.0 V and 1.5 V, and the corresponding light intensity was recorded. As illustrated in FIG. 45A, there was some loss of ECL between the forward and backward scans of the same cycle, as well as between different cycles. Cyclic voltammograms of the thiol/Au in ferricyanide after oxidizing at 1.5 V showed a significant amount of faradaic current, indicative of at least partial desorption of the thiol monolayer at 1.5 V (FIG. 45B).

6.40. Irreversible ECL

In these experiments, electrode modification and protein adsorption were conducted in the same way as in Example 6.38. To measure ECL, the electrode potential was scanned all the way up to 2.0 V and back to 0.0 V. Intense light was observed on the forward scan (more light than was observed under reversible conditions in Example 6.38), but it dropped to the background on the reverse scan, as shown in FIG. 46A. Cyclic voltammograms of the modified electrode in ferricyanide after oxidizing at 2.0 V indicated most of the thiol monolayer was desorbed (FIG. 46B).

6.41. An ECL Sandwich Immunoassay Using A Primary Antibody Immobilized on A Patterned Gold Electrode In this example an antibody against prostrate specific antigen (PSA) is immobilized on a patterned gold electrode for use in an immunoassay for PSA.

An exposed and developed photoresist master of one to two microns thickness is prepared according to well known procedures to give a layer of photoresist on a silicon support with a 1 mm×1 mm square patch where photoresist is removed. A 10:1 mixture of SYLGARD silicone elastomer 184 and the corresponding curing agent is poured over the master and cured. The polymerized-SYLGARD is carefully removed from the silicon master. The resulting elastomeric "stamp" is "inked" by exposing it to a solution containing the hydroxyl-terminated thiol $HS$-$(CH_2)_{11}(OCH_2CH_2)_3$—OH and the nitrilotriacetic acid (NTA) terminated-thiol $HS$-$(CH_2)_{11}(OCH_2CH_2)_3OC(O)NH(CH_2)_4CH(CO_2H)N(CH_2CO_2H)_2$ in ethanol. The "inked" stamp is brought into contact with a gold substrate and removed to form a 1 mm×1 mm SAM. The substrate is washed for several seconds with a solution containing only the hydroxl-terminated thiol in ethanol, to prevent non-specific binding of proteins to the regions outside the stamped feature. The resulting surface is then rinsed with ethanol and dried under a stream of nitrogen. Treatment of the surface with a solution of $NiCl_2$ followed by treatment with a solution containing a fusion protein presenting the binding sites of an anti-PSA mouse monoclonal and the peptide (His)$_6$, leads to immobilization of the fusion protein on the surface in a controlled manner. This process yields a reproducible and predetermined amount of immobilized protein on the surface. The orientation of the protein on the surface is controlled by the location of the (His)$_6$ sequence in the primary structure of the fusion protein. The absolute amount of immobilized protein is controlled by the ratio of NEA terminated-thiol to hydroxy-terminated thiol in the stamped SAM and by the surface area of the stamped feature. A calibration curve for PSA is determined by preparing solutions containing known concentrations of PSA in serum (at concentrations ranging from 1 fM to 1 uM. A number of surfaces prepared as described above are treated with the PSA calibration standards and then with a solution containing a secondary antibody against PSA (labeled with a derivative of TAG1) at an optimized concentration. A calibration curve is determined by immersing the surfaces in a solution containing 0.1 M TPA and 0.2 M phosphate (pH 7.2), and measuring the peak intensity of light emitted when the electrical potential at the gold surface is cycled between 0.0 and 2.0 V at a scan rate of 0.5V/sec. The determination of unknown concentrations of PSA in serum in a sample is conducted by the same procedure except that the concentration of PSA is calculated from the peak ECL signal by reference to the calibration curve.

6.42. Preparation Of Aerosil-200 Silica Particles Coated With Streptavidin

Aerosil-200 (Degussa Corporation, Akron, Ohio, USA), a fumed silica with a particle size of 12 nm and an active surface area of 175–220 m²/g, was chemically modified to introduce NHS ester groups. The modification involved three steps: i) amino groups were introduced to the surface of the particles by reaction with 3-aminopropyltrimethoxysilane. The Aerosil-200 (155.5 mg) was combined with 3-aminopropyltrimethoxysilane (513 mg) in 5 mL of toluene and refluxed for 1 hour. The silica particles were washed two times with 4 mL of toluene, three times with 4 mL of methanol and three times with 4 mL of dichloromethane. Each wash consisted of centrifugation of the suspension followed by resuspension of the pellet in fresh solvent; ii) the amino groups were reacted with succinic anhydride to introduce carboxylic acid groups to the surface. The 55.2 mg of washed particles were resuspended in 3 mL of anhydrous DMF. Succinic anhydride (102 mg) and triethylamine (0.025 mL) were added and the suspension stirred for 16 h. Additional succinic anhydride (50 mg) was added and the reaction was allowed to proceed for another 3 hours. Excess reagent was removed by washing the particles two times with DMF, once with methanol, and two times with dichloromethane; and iii) the carboxylic acid groups on the surface were activated as N-hydroxysuccinimide (NHS) esters by reaction with NHS and ethyl-3-diaminopropylcarbodiimide (EDC). The particles (25.1 mg were resuspended in 3 mL of methylene chloride. NHS (64 mg) and EDC (110 mg) were added and the suspension was then stirred for 3 hours. The particles were then washed three times with dichloromethane and dried under vacuum.

The activated silica particles were coated with streptavidin by the reaction of the protein with the NHS esters on the surface of the activated particles. The particles (~1.5 mg) were added to solution containing 0.750 mg of streptavidin in phosphate buffered saline (PBS), pH 7.85. The reaction was allowed to proceed for 16 hours. The particles were then washed with PBS and water and resuspended in PBS to give a stock suspension containing particles at a concentration of 0.1 mg/mL.

6.43. Formation Of A Fibril Mat On A Support Of Stainless Steel Filter Paper For Use In Particle-based ECL Assays A fibril ink was formed by the sonication of a suspension of CC fibrils (0.1 mg/mL in 0.2% triton X-100 in water) for 15 minutes using a probe sonicator (Branson Ultrasonic Corp., Danbury, Conn., USA). The suspension was filtered using gentle suction onto an ⅛" diameter circular region on a disc of stainless steel filter paper (GA-4, Baekart Fibre Technologies). The thickness of mats formed by this method was approximately 1 μm/mL of added fibril ink.

6.44. A Particle-based ECL Assay For AFP Using Streptavidin-Coated Beads Captured On A Fibril Mat An AFP assay was run using the following steps: i) formation of a sandwich immune complex on the surface of beads in suspension; ii) filtration of the beads onto a fibril mat supported on stainless steel filter paper; and iii) detection of ECL from TAG1-labeled antibodies in the immune complexes by scanning the fibril electrode to an oxidizing potential. The assay was run using an AFP assay kit (Boehringer-Mannheim). This assay kit is designed for ECL-based assays using the Elecsys System (Boehringer-Mannheim); a system which captures magnetic beads on a platinum electrode by the application of a magnetic field. The assay kit included the following stock solutions: a suspension containing streptavidin-coated magnetic beads (M-280, Dynal Inc.), a biotin-labeled capture antibody (R-1), a TAG1-labeled secondary antibody (R-2), and a series of calibrators containing AFP dissolved in a matrix designed to simulate serum.

To determine a calibration curve for the assay, the stock suspension of streptavidin-coated beads (0.017 mL containing ~0.012 mg of beads) was combined in a plastic tube with the stock solutions containing R-1 (0.017 mL), R-2 (0.017 mL), and an AFP calibrator (0.010 mL). The tube was vortexed and then gently shaken for 30 minutes at room temperature. The suspension was then filtered using gentle suction onto a fibril mat (mat thickness=0.030 mm) formed as described in Example 6.43. The mat was washed with ECL Assay Buffer (IGEN, Inc.). The ECL was then measured as described in Example 6.26. Each calibrator was run in triplicate. FIG. 48 shows the background corrected ECL signal as a function of the concentration of AFP.

6.45. A Particle-based ECL Assay For AFP Using Streptavidin-Coated Silica Beads Captured On A Fibril Mat An AFP assay was run as described in Example 6.44 except that streptavidin-coated silica particles (Aerosil-200, prepared as described in Example 6.42) were used instead of the magnetic beads supplied with the AFP assay kit. To determine a calibration curve for the assay, the stock suspension of streptavidin-coated Aerosil-200 (0.010 mL containing 0.001 mg of particles) was combined in a plastic tube with the stock solutions containing R-1 (0.017 mL), R-2 (0.017 mL), and an AFP calibrator (0.010 mL). The tube was vortexed and then gently shaken for 30 minutes at room temperature. The suspension was then filtered using gentle suction onto a fibril mat (mat thickness=40 mm) formed as described in Example 6.43. The mat was washed with ECL Assay Buffer (IGEN, Inc.). The ECL was then measured as described in Example 6.26. Each calibrator was run in triplicate. FIG. 49 shows the background corrected ECL signal as a function of the concentration of AFP.

6.46. ECL Emitted From Fluorescent Dye-Labeled Latex Beads Captured on A Fibril Mat Electrode This example describes an experiment showing that fluorescent dyes incorporated into beads could be used as internal standards in bead-based ECL assays. Three types of fluorescent beads were purchased from Polysciences Inc. The beads differed in the excitation and emission wavelengths of the incorporated dyes: i) Catalog # 17685 ($l_{ex}$=273 nm, $l_{ex}$=340 nm). ii) Catalog # 19392 ($l_{ex}$=530 nm, l=590 nm). iii) Catalog # 17797 ($l_{ex}$=641 nm, $l_{em}$=740 nm). Fibril mats were prepared as described in Example 6.43. The fluorescent beads (0.010 mg) were filtered on to the mats using gentle suction. The mats were washed with ECL Assay Buffer (IGEN, Inc.) and the ECL measured as described in Example 6.26. Each bead was tested in triplicate. All three beads emitted ECL under these conditions. The average integrated ECL signals measured for Polyscience catalog # 17685, 19392, and 17797 beads were 0.7 nA•s, 6.0 nA•s, and 2.3 nA•s, respectively.

6.47. An ECL Sandwich Immunoassay For AFP Using Biotin-Streptavidin Capture To Immobilize A Capture Antibody on A Gold Electrode In this example, an antibody against alpha-fetoprotein (AFP) is immobilized on a gold electrode for use in an immunoassay.

Glass slides (1 cm×1 cm×0.06 cm) were coated on one side with a thin gold film by thermal evaporation. The gold film was formed by the evaporation of 3 nm of Ti as an adhesion layer followed by 100 nm of Au (99.99%). A self-assembed monolayer (SAM) was formed on the gold films by incubation of the slides in an ethanolic solution containing mercaptoundecanoic acid at a concentration of 1 mM for a period of approximately 10 hours. The carboxylic acid groups presented at the surface of the SAM were activated by treatment for 10 minutes with 0.05 mL of an aqueous solution containing 1-ethyl-3-(3-dimethylaminopropyl)carbodiimide (EDC) and N-hydroxysuccinimide (NHS) at concentrations of 0.2 M and 50 mM respectively. The surface was then washed briefly with water. Streptavidin was immobilized on the activated surface by treatment of the surface for 60 minutes with 0.05 mL of a solution containing streptavidin at a concentration of 0.3 mg/mL in phosphate buffered saline (PBS). The surface was blocked by adding 0.08 mL of an aqueous solution containing 1 M ethanolamine, pH 8.5. After incubating for 30 minutes the chip was washed with HBS/p20 (10 mM HEPES, 0.15 M NaCl, 0.005% Tween 20, pH 7.4).

The AFP assay kit (Boehringer-Mannheim) consists of a stock solution of biotin labeled primary antibody (0.007 mg/mL), a stock solution of TAG1-labeled secondary antibody (0.012 mg/mL), and five calibrator solutions in an artificial matrix designed to simulate human serum. The assay conditions were not optimized for these reagents. To conduct an AFP assay, 0.020 ml of the primary antibody stock, 0.020 ml of the secondary antibody stock, and 0.020 ml of a calibrator solution were combined and applied to a slide that had been coated with streptavidin. The solution was incubated on the surface for 20 minutes. The surface was then washed with HBS/p20 (10 mM HEPES, 0.15 M NaCl, 0.005% Tween 20, pH 7.4).

ECL was measured on the surface of a slide by the following procedure: The slide was placed in an electrochemical cell. The cell contained an O-ring which defined the area of the gold surface which was electrochemically excited (0.13 cm$^2$). The cell also contained a Pt counter electrode and a Ag/AgCl reference electrode as well as a means to make electrical contact to the gold film. The cell was held in a defined position under a photomultiplier tube (PMT) to allow for reproducible detection of ECL emission. To excite ECL, the electrodes were immersed in assay buffer (0.1 M tripropylamine, 0.2 M sodium phosphate, 0.02% (w/v) Tween-20, pH 7.2) and the electrical potential at the gold surface ramped from 0 V to 2 V (vs. Ag/AgCl) at a rate of 0.2 V/s. The photocurrent generated at the PMT was integrated over the duration of the scan to give an ECL signal in units of nAes.

FIG. 51 shows a plot of the ECL signal vs. the concentration of AFP in solution.

6.48. The Detection Of Nucleic Acid Hybridization To A Probe Immobilized On A Gold Electrode The oligonucleotides used in this example are defined as follows:

SC1.2: 5' ca gtt gtg tgc cac cta caa 3' C6 Disulfide modifier
SC2.3: 5' ttg tag gtg gca cac aac tg 3' C3 Amino Modifier
SC4.1: 5' TAG1-gaa-aat-gtg-ctg-acc-gga-cat-gaa-aat-gag 3'

The oligonucleotides were purchased from Oligos Etc. Inc. SC2.3 was labeled with the TAG1 by reaction with a derivative of TAG1 presenting an NHS ester (NHS-TAG, IGEN Inc.). SC2.3 (130 nmole) in 0.100 ml of PBS pH 7.4 was combined with 0.400 ml of DMSO in a 0.5 mg vial of TAG-NHS-ester. The solution was mixed and incubated overnight in the dark at room temperature. Following the overnight incubation the labeling reaction was diluted with 1.380 ml of deionized water. An aqueous solution containing sodium chloride at a concentration of 5 M (0.120 mL) was added followed by 0.120 mL of absolute ethanol. This solution was then incubated at −70° C. for at least 1 hour to precipitate the product. The labeled oligonucleotide was centrifuged at 5000×g for 10 minutes at 10° C. The resulting pellet was washed twice with 0.5 mL of a 70% (v/v) solution of ethanol in water. The washed pellet was dried under vacuum and stored in the dark at −20° C. The manufacturer of the SC4.1 oligonucleotide labeled the probe with TAG1 during the oligonucleotide synthesis by reaction with a phosphoramidite derivative of TAG1 (IGEN, Inc.).

Glass slides (1 cm×1 cm×0.06 cm) were coated on one side with a thin gold film by thermal evaporation. The gold films were formed by the evaporation of 4 nm of Ti as an adhesion layer followed by 200 nm of Au (99.99%). Wells were formed above the gold films by sealing the slides, with O-rings, against holes drilled through a block of plastic. The O-rings defined the area of the gold films in contact with solution (0.25 cm$^2$). The oligonucleotide SC1.2 was immobilized on the surface of the gold films by adding 0.050 mL of a solution containing 0.010 mg of the oligonucleotide (in 10 mM ammonium acetate, pH 6.0) to each well. The immobilization was allowed to proceed overnight in a dark desiccator, during which time the solution containing the oligonucleotide evaporated to dryness. Excess reagents were then removed by several washes with deionized water.

Prehybridization of the oligonucleotides on the surface of the gold slide was accomplished by the addition of 0.050 mL of a solution containing the components of SSC solution (1×), the components of Denhardts Solution(1×), yeast tRNA (0.100 mg/mL), and sonicated herring sperm DNA (0.050 mg/mL). The slides were then shaken vigorously for 30 minutes at room temperature. Following the prehybridization step, the slides were washed with SSC and hybridized with calibration solutions containing (1×10$^{12}$) molecules of TAG1-labeled SC2.3 (an oligonucleotide complementary to the sequence immobilized on the surface), or TAG1-labeled SC4.1 (a non-complementary probe used as a negative control to test for non-specific binding). The TAG1-labeled probes were applied as solutions in 0.050 ml of the solution used for prehybridization. The hybridization was allowed to proceed for 2 hours at room temperature with vigorous shaking. The gold slides were then washed three times with 1×SSC containing 0.1% (w/v) SDS, incubated with the same buffer for 30 minutes at room temperature and rinsed with ECL assay buffer (IGEN, Inc.). ECL was excited from the surface of the gold film as described in Example 6.47. ECL was also excited from a surface that was not exposed to a TAG1-labeled probe in order to measure the magnitude of the background signal. The value of the background corrected signal from the complementary probe was 3.3×10$^3$ nA•s, showing that the TAG1-labeled probe hybridized to the surface and could be detected by ECL. The value of the background corrected signal from the non-complementary probe was −2.2×10$^1$ nA•s, showing that the binding of the non-complementary probe was specific and that the non-specific binding was low.

6.49. Preparation Of Sheets Of A Composite Electrode Containing Fibrils And EVA A composite electrode was prepared by compounding fibrils with a polymer and compression molding the compounded material into a sheet. Fibrils were compounded into EVA by using a Brabender Plasticorder with a twin screw metering head at a temperature of 180 degrees centigrade and a speed of 100 r.p.m. 9.45 grams of fibrils were dry blended with 25.55 grams of EVA (Quantum Chemical, Microthene, FS-532). The blended materials were added to the mixing head over a period of 1 minute to allow the material to melt. Mixing was continued for an additional 5 minutes and then the composite was removed from the mixing head and allowed to cool. To prepare sheets of the composite for use as an electrode, a 2 gram piece of the compounded material was assembled into a sandwich between two polished stainless steel plates (triple plated ferrotype plates, Testrite Company) and the assembly was placed between heated platens set at 180 degrees Centigrade in a hydraulic press (Carver). After allowing time for the material to be heated, the composite was pressed into a flat sheet at 10000 pounds total pressure. The assembly was then removed from the press and allowed to cool to room temperature. The assembly was separated and a flat disk with nominal thickness of 20 mils was removed.

6.50. Oxidation of Fibril-Polymer Composites By Chromic Acid

Composites of carbon fibrils (27% by weight) with ethyl vinylacetate (fibril-EVA) and carbon fibrils with polyethylene (fibril-PE) were used. The composites were obtained as 3" disks that were approximately 1 mm thick. Both fibril-EVA and fibril-PE composites were oxidized by floating the disks on a solution containing chromic acid ($CrO_3$, $H_2O$ and $H_2SO_4$ (29/42/29; w/w/w)), at room temperature for 1 hour. After reaction with the chromic acid solution, the oxidized composites were then washed 4–5 times with deionized water, soaked for at least 5 minutes in deionized water and dried in air for 1 hour.

6.51. Derivatization Of A Fibril-Polymer Composite With A Mixture Of Sulfuric And Nitric Acids A composite of EVA and carbon fibrils (in the form of a 3" diameter flat disk) was treated with a mixture of sulfuric acid and nitric acid with 1:1 ratio (12 mL) for 3 hours. The treated composite was washed with water. To the treated composite in a mixture of water (150 mL) and ammonium hydroxide (30%, 150 mL) was added sodium dithionite (10 grams). The reaction mixture was refluxed for 2 hours. The composite was washed extensively with water.

6.52. Preparation Of A Fibril Composite Electrode With Exposed Hydroxyl Groups Hydroxyl groups were exposed on fibril-EVA composites by hydrolysis of acetate groups at and near the surface of the composite. Discs (3" diameter, 0.01" thickness) of the composite material (27% CC fibrils in EVA, by weight) were immersed in 100 mL of a 2 M solution of NaOH for 17–20 hours at room temperature. This treatment leads to the exposure of hydroxyl groups on both sides of the composite. The composite was washed with water and methanol and then allowed to dry in air.

6.53. Immobilization Of streptavidin On Oxidized Fibril-Polymer Composites

EVA-fibril composites were oxidized as described in example 6.50 or by exposure to an oxygen plasma. The oxidized 3" disc composites were dried under vacuum pump for 1 hour and soaked overnight (with shaking) in 25 ml of dichloromethane containing 0.1 M EDC (1-ethyl-3-(3-dimethylaminopropyl(carbodiimide) and 0.1 M N-hydroxysuccinamide. The NHS activated composites were washed with dichloromethane, methanol, deionized water and methanol, then allowed to dry at room temperature.

For immobilization of streptavidin, the NHS activated composites were rinsed with deionized water and floated on 6 mL of streptavidin solution so that the NHS-ester activated surface faced down. The streptavidin solution was prepared in PBS-1 (0.1 M sodium phosphate, 0.15 M sodium chloride, pH=7.8) in a concentration of 0.7 mg/ml. The composite was shaken for 3 hours in the streptavidin solution and washed by shaking in 20 ml of PBS-1 containing 0.1% Triton for 30 minutes (one time) and in 20 ml of PBS-1 for 30 minutes (5 times). The streptavidin loaded EVA composites were stored in PBS-1 at 4° C.

6.54. Immobilization Of Proteins On Fibril-Polymer Composites Via SMCC Activation A 3" diameter disc of EVA-fibril composite that had been treated with a mixture of nitric and sulfuric acids (as in Example 6.51) was placed in 15 mL of sodium phosphate buffer (0.1 M, pH 7.5). Sulfosuccinimididyl-4-(N-maleimidomethyl)-cyclohexane-1-carboxylate (sulfo-SMCC, 10 mg) was added and the reaction mixture was incubated for 3 hours at room temperature. The reaction was stopped and the composite was washed with sodium phosphate buffer. To a solution of streptavidin (4.5 mg) in 0.1 M sodium phosphate, 20 mM EDTA, pH 7.5 (300 mL), was added Traut's reagent (19.8 mL, 2.8 mg/mL). The reaction mixture was incubated at room temperature for 1 hour and 30 minutes. The sulfhydryl-labeled Streptavidin was purified using a PD-10 (Pharmacia) disposable size exclusion column (collected in a 3.5 mL fraction). The SMCC-treated composite (1 inch, derived via nitration/reduction of EVA CC composite) was placed in the solution containing sulfhydryl-labeled streptavidin (3.5 mL) and incubated with shaking for overnight at 4° C. The resulting streptavidin-coated composite was washed (5×20 minutes) by shaking in 0.1 M sodium phosphate, pH 7.5, containing 1% Triton X-100.

6.55. Immobilization Of Streptavidin On A Composite Electrode Presenting Exposed Hydroxyl Groups Streptavidin was immobilized on a fibril-EVA composite that presented hydroxyl groups at and near the surface. The protein was immobilized after activation of the hydroxyl groups with carbonyldiimidazole (CDI). Fibril-EVA composite electrodes that had been treated with NaOH to expose hydroxyl groups (by the procedure described in Example 6.52) were dried under vacuum. The dry composite was immersed in 50 mL of anhydrous methylene chloride in a dry glass jar. To the solution was added 100 mg (0.6 mmol) of 1,1'-carbonyldiimidazole (CDI) and the jar was gently rocked for 1 h at room temperature. The composite was then washed with methylene chloride and methanol and then allowed to dry in air. The CDI activated composite was cut (using a punch) into ³⁄₁₆" discs (96 total). Each disc was placed at the bottom of the well of a 96 well microtiter plate. Streptavidin (100 mL of a 0.1 mg/mL solution in 0.2 M sodium bicarbonate, pH 8.5) was then added to each well. The immobilization was allowed to proceed for 18–20 h at 4° C. The discs were washed three times by soaking in 100 ml portions of 50 mM sodium phosphate, pH 7.5 and stored in 100 mL of 50 mM sodium phosphate, pH 7.2 until used.

6.56. Assay For AFP On A Composite Electrode Of EVA And Fibrils

The AFP assay was performed using an EVA-fibril composite electrode with streptavidin immobilized on it (prepared as described in Example 6.53). The assay was carried out in a ninety-six well plate that was preblocked with 1% BSA solution (1% BSA and 0.3% Tween 20 in 0.1 M sodium phosphate, pH=6.8) and rinsed once with 0.3% Tween 20 in 0.1 M sodium phosphate, pH=6.8, prior to the assay. Forty eight discs with diameters of 3/16" were punched from a 3" diameter EVA-SA composite and placed in the ninety-six well plate with the treated surfaces up. Fifty microliters of biotinylated AFP antibody were added to the wells that contained composites. The plate was then shaken at room temperature for 30 minutes. The composites were rinsed twice with 0.1 mL of PBS-1 and shaken for 1 hour at room temperature with the mixture of 0.05 mL of calibrators and 0.05 mL of TAG1 labeled antibody. At the end of the reaction, composites were rinsed with 0.150 mL of ECL assay buffer and stored in protein buffer (3% BSA, 3% Tween 20, 25 mM sodium chloride and 0.1 M sodium phosphate, pH=7.3) until the ECL was measured. We used eight AFP calibrators ranging from 0.56 to 7950 IU/ml. Each calibrator was assayed in six replicates. FIG. 53 shows the results.

6.57. ECL Assay For TSH Using A Composite Electrode Of EVA And Fibrils

The assay was conducted using 3/16 diameter streptavidin-coated discs of EVA-fibril composite (prepared as described in Example 6.55). The assay reagents were part of a TSH assay kit (IGEN, Inc.) and included a biotin-labeled anti-TSH antibody and a TAG1-labeled anti-TSH antibody, each dissolved in a buffer (TSH Assay Diluent). The discs were placed into individual wells of a 96-well microtiter plate. The biotin-labeled antibody (0.05 mg, 0.012 mg/mL) was added to each well and the plate was gently shaken for 30 minutes at 37° C. After washing the discs with TSH Assay Diluent, solutions containing the TAG1-labeled antibody (0.025 mL, 600 ng/mL) and varying amounts of TSH were added and the plate shaken another 60 minutes at 37° C. The discs were washed with and stored in TSH Assay Diluent until their analysis by ECL.

6.58. DNA Hybridization Assay On A Fibril-Polymer Composite

This example describes an assay for a sequence of DNA. The assay involves the formation of a sandwich complex on a streptavidin-coated composite electrode which includes a biotin-labeled capture probe (SC5), an analyte (SC3.1) and a TAG1-labeled probe (SC4.1). SC3.1 and SC4.1 are described in Example 6.48. SC5 was purchased from Oligos, Etc., Inc. and has the sequence 5'-ca gtt gtg tgc cac cta caa gca tta cgg act agt cat ggt tca cag agg-3'-biotin. oxidized fibril-EVA composites were activated with EDC and NHS as described in Example 6.53. Wells were defined above 3/8" discs of the composite by sealing the discs, with O-rings, against holes drilled through a block of plastic. The O-rings defined the area of the composite (0.25 cm$^2$) in contact with solution placed in the wells. Streptavidin was immobilized on the discs by adding 0.05 mL of a 0.5 mg/mL solution of Streptavidin (in PBS) to each well. The reaction was allowed to proceed for 3 hours at room temperature while shaking the apparatus. The discs were washed twice with PBS, once with PBS containing 0.10% (w/v) Triton x-100 and twice more with PBS.

To capture the biotin labeled oligo we added $10^{13}$ molecules of SC5 in 0.05 mL of ECL Assay Buffer (IGEN, Inc.) and incubated for 2 hours at room temperature with vigorous shaking. Excess SC5 was removed by washing with PBS, PBS containing 0.10% (w/v) Triton x-100, and ECL Assay Buffer. SC4.1 ($10^{12}$ molecules in 0.025 mL) and SC3.1 (varying amounts in 0.025 mL) in ECL Assay Buffer were then added. The hybridization reactions were allowed to proceed for 4 hours. Excess reagents were then removed by washing with PBS, PBS containing 0.10% (w/v) Triton X-100 and ECL Assay Buffer. The discs were then placed in an ECL apparatus and the ECL signal was measured. FIG. 54 shows the ECL signal as a function of the amount of SC3.1.

6.59. Measurement Of The Surface Area Of A Fibril-Composite Electrode

The amount of fibrils protruding from the surface of a composite electrode can be estimated from measurements of the double layer capacitance. Electrodes were prepared by punching out 0.25 inch diameter disks of composite and making electrical contact to one surface by attaching a copper wire with electrical paint. Any exposed copper wire was sealed in epoxy. The electrodes were used to record cyclic voltammograms in argon-purged 0.5M $K_2SO_4$ at several potential scan rates (e.g. 5, 10 and 25 mV/second) between −0.2V vs, Ag/AgCl and +0.8V vs. Ag/AgCl. The double layer charging current, $I_{d1}$, was measured in the broad, flat region of the cyclic voltammograms, typically at +0.25V vs. Ag/AgCl. The slope of plots at $I_{d1}$ vs. scan rate is taken as the double layer capacitance $C_{d1}$. Using an average value of $10\,\mu F/cm^2$ of fibril surface area, and a fibril surface area of 200 M$^2$/gram, the amount of fibrils exposed to the electrolyte can be estimated.

6.60. Preparation Of NHS Ester-Functionalized Fibrils

N-Hydroxysuccinimide (NHS) (0.35 g) and 1-ethyl-3-(3-dimethylaminopropyl) cardodiimide (EDC) (0.60 mg) were added to a suspension containing 220 mg of carboxylated fibrils (provided by Hyperion Catalysts Inc.) in 25 mL of dioxane and the mixture was sonified (Sonifier 250, Branson Ultrasonics) for 5 minutes and stirred at room temperature overnight. The reaction was stopped by vacuum filtration of the reactants from the fibrils in a sintered glass funnel. The fibrils were washed with dioxane (3×15 mL) and methanol (extensively) then dried under vacuum to yield 220 mg NHS ester-activated fibrils.

6.61. Conjugation Of Streptavidin To NHS Ester Fibrils

NHS Ester-modified fibrils (2.1 mg, prepared as described in Example 6.60) were sonified (Sonifier 250, Branson Ultrasonics) in 400 µL PBS-1 buffer (0.1 M sodium phosphate, 0.15 M sodium chloride, pH=7.8) for 5 minutes at the lowest power setting. A solution of streptavidin (2.4 mg in 150 µL PBS-1) was mixed with the dispersed fibril suspension and the mixture (650 µL) was gently shaken for 3 hours at room temperature. The fibrils were washed by multiple cycles of repetitive centrifugation, and resuspension using the following buffers in series: 0.1 M sodium phosphate containing 1% Triton X-100 (1 time), PBS-1 (two times), 0.1 M sodium phosphate containing 0.1% Triton X-100 (1 time), and PBS-1 (4 times). Streptavidin loaded fibrils were stored at 4° C. in PBS-1.

6.62. Fabrication Of A Ultra Thin Fibril Mat (UTFM) On A Nylon Membrane Filter An aqueous suspension containing CC fibrils at a concentration of 0.1 mg/mL was prepared by diluting a stock suspension of the CC fibrils (1 mg/mL in water) into an aqueous solution of Triton X-100 (0.2% (w/v)). The CC fibrils were finely dispersed with a probe sonicator (Sonifier 250, Branson Ultrasonics) by sonicating for 5 min using a duty cycle of 30% and setting the output control to a value of 3. A further dilution of the sonified suspension to a concentration of 0.01 mg/mL was then carried out by diluting 4 mL of the suspension up to a volume of 40 mL with the aqueous solution of Triton X-100.

A UTFM was prepared on a nylon membrane (0.45 mm pore size, 47 mm diameter) by vacuum filtration (see FIG. 24 for an example of an apparatus for filtration of fibril mats). The finely dispersed fibrils were filtered onto the nylon membrane in four aliquots of 4 mL each using a vacuum of approximately 26 in. of Hg. Vacuum filtration was continued until only a trace of liquid remained unfiltered above the membrane (by visual observation). The mat was then removed from the filtration apparatus, compressed between two pieces of clean, dry filter paper, and allowed to dry flat in an oven for approximately 10–15 minutes at 60° C.

The volumes used could be scaled accordingly for electrodes of different areas and/or thickness.

6.63. A Nucleic Acid Hybridization Assay On A Bilayer Ultra Thin Fibril Mat Electrode Streptavidin was covalently immobilized on dispersed CC carbon fibrils as described in Example 6.61. A total of 100 $\mu$g of these fibrils were suspended in a solution containing BSA at a concentration of 1 mg/mL (w/v) to block unoccupied sites on the fibrils. The blocked fibrils were then centrifuged and resuspended in 1 mL of deionized water. This suspension was redispersed by sonification (Sonifier 250, Branson Ultrasonics) for 5 minutes.

An ultra-thin fibril mat (UTFM) was prepared as described in Example 6.62. After the UTFM was prepared, the second layer was formed by the filtration of 17 $\mu$L of the suspension of streptavidin-fibrils onto the first layer under the same conditions as used in Example 6.62.

To conduct the DNA hybridization assay, we used a "capture" oligonucleotide (28 base pairs, biotinylated at the 5' position) that was allowed to hybridize to a complementary "TAGged" oligonucleotide (28 base pairs, end labeled with TAG1-NHS Ester). The assay was prepared by the following steps: i) calibration solutions were prepared that contained variable concentrations of the biotin-labeled oligo and a constant excess ($10^{12}$ molecules) of the TAG1-labeled oligo; ii) the calibration solutions (50 $\mu$L) were filtered through ultra-thin fibril mats (one UTFM per solution) at a flow velocity of 50 $\mu$m/sec to allow capture of the biotinylated complex onto the streptavidin-coated fibrils in the fibril mat; iii) the UTFM was washed with 50 $\mu$L of ECL Assay Buffer (IGEN, Inc.) to remove unbound reagents, and iv) the UTFMs (and the attached oligonucleotide complexes) were transferred to a measurement cell (FIG. 34) and ECL was measured. FIG. 55 shows that the assay measured the TAG1-labeled oligonucleotide with high sensitivity and produced a linear response over a wide dynamic range.

6.64. A Sandwich Immunoassay For AFP On A Bilayer Ultra Thin Fibril Mat Electrode A suspension of streptavidin-coated (and BSA-blocked) fibrils was prepared as described in Example 6.61. The suspension was diluted in ECL Assay Buffer (IGEN, Inc.) to give a stock suspension with a concentration of fibrils of 7 mg/mL. The solution was placed in an ice water bath (to prevent denaturing of the streptavidin) and the fibrils were redispersed by sonication (Sonifier 250, Branson Ultrasonics) for 5 minutes using a duty cycle of 20% and setting the output control to a value of 1.5.

A vacuum filtration apparatus was used to prepare bilayer UTFM electrodes on nylon filter membranes (0.45 mm pore size). The filtration apparatus defined a ⅛" diameter area on the membrane through which filtration occurred. A layer of underivatized fibrils was formed by filtering (using suction) 87.5 $\mu$L of a finely dispersed suspension containing underivatized fibrils at a concentration of 0.01 mg/mL (prepared as described in Example 6.62). A second layer was formed by filtering 50 $\mu$L of the stock suspension of streptavidin-coated fibrils onto the layer of underivatized fibrils.

The AFP assay reagents (Elecsys, Boehringer-Mannheim) were pre-mixed prior to filtration by combining 50 $\mu$L of the stock solution of the biotinylated AFP antibody, 50 $\mu$L of the stock solution of the TAG1-labeled AFP antibody, and 10 $\mu$L of one of several stock solutions containing known concentrations of AFP. The combined solutions were then filtered by suction at a controlled flow velocity using a vacuum pressure of 5 in. of Hg. Each sample took between 30–50 minutes to filter. The mats were then washed with 150 $\mu$L of ECL Assay Buffer (IGEN, Inc.), removed and allowed to dry. The mats were transferred to a measurement cell (FIG. 34) and ECL was measured. FIG. 56 shows the ECL signal as a function of the concentration of AFP in the calibration solution.

6.65. Forming Conductive Films Of Gold On Non-conductive Filter Membranes

Nylon membrane filters from Whatman (0.45 $\mu$m pore size) were coated with sputtered gold using a Balzers MED 010 Minideposition System. The deposition was carried out using an argon plasma (at a pressure of $5 \times 10^{-2}$ mbar) and a discharge current of 100 mA.

6.66. A Sandwich Immunoassay For AFP On An Ultra Thin Fibril Mat Electrode Formed On A Gold-Coated Nylon Filter Membrane A suspension of streptavidin-coated (and BSA-blocked) fibrils was prepared as described in Example 6.61. The suspension was diluted in ECL Assay Buffer (IGEN, Inc.) to give a stock suspension with a concentration of fibrils of 28 mg/mL. The solution was placed in an ice water bath (to prevent denaturing of the streptavidin) and the fibrils were redispersed by sonication (Sonifier 250, Branson Ultrasonics) for 5 minutes using a duty cycle of 20% and setting the output control to a value of 1.5.

A total of thirty-six ⁵⁄₁₆" diameter disks were punched out of A conductive Au-coated nylon filter membranes (100 nm gold film, prepared as described in Example 6.65) was cut (using a hole punch) to form 3/16" diameter discs. The disks were placed into the wells of a multiple sample filtration apparatus, which allows for as many as ninety-six samples at a time to be filtered under a controlled vacuum pressure. This apparatus filters samples onto a 3/16" diameter circular region on each disc. Single layer UTFMs were formed by filtering (using a vacuum of 26 in. of Hg) 82.5 µL of the stock solution of streptavidin-coated fibrils onto the discs. The AFP assay reagents (Elecsys, Boehringer-Mannheim) were pre-mixed prior to filtration by combining 50 µL of the stock solution of the biotinylated AFP antibody, 50 µL of the stock solution of the TAG1-labeled AFP antibody, and 10 µL of one of several stock solutions containing known concentrations of AFP. The combined solutions were then filtered by suction at a controlled flow velocity using a vacuum pressure of 5 in. of Hg. Each sample took between 30 minutes to filter. Each mat was then washed with 150 µL of assay buffer, then removed and stored in a protein buffer which contains 3.0% BSA, 3.0% Tween-20, 25 mM NaCl, and 100 mM $NaH_2PO_4$. The mats were transferred to a measurement cell (FIG. 34) and ECL was measured. FIG. 57 shows the ECL signal as a function of the concentration of AFP in the calibration solution.

6.67. AFP Assay On Two Different Electrodes: Voltammetric Resolution Of Signal And Background The AFP assay was developed on two composite electrodes. Both electrodes were prepared from an ethylene vinyl acetate (EVA) copolymer containing 27% CC-fibrils by weight. One electrode (the "hydrolyzed EVA" electrode) was treated with potassium hydroxide, activated with CDI, and exposed to streptavidin (as in Example 6.55). The other electrode (the "chromic acid EVA" electrode) was treated with chromic acid, treated with NHS and EDC and exposed to streptavidin (as in Example 6.53).

Sandwich complexes containing a biotin-labeled anti-AFP antibody, a TAG1-labeled anti-AFP antibody and AFP were captured on 3/16" discs of the two electrodes by the procedures described in Example 6.56.

Each electrode was installed in an ECL test cell (FIG. 34) with a gasket (1/8" id., 7/8" od., and 0.017" thick) which defined the active area of the electrode (1/8" diameter). The test cell consisted of a black Delrin body that contained a three electrode electrochemical cell and an optical window parallel with the working electrode. The electrodes were a 3M Ag/AgCl reference electrode, a platinum mesh counter electrode, and the fibril-EVA composite as working electrode. The test cell was filled with ca. 1 mL of Assay Buffer and placed in a light-tight box that was heated to ca. 33° C. with a prototype electrical heater. The test cell optical window was placed in front of a PMT and the box was closed. The PMT was powered at 900 V with a Pacific Instruments Model 126 Photometer running in analog mode with a 1 second time constant filter using several of the photocurrent ranges (i.e. 10 nA/V, 30 nA/V, 100 nA/V, 300 nA/V, and 1000 nA/V). The electrochemical cell was controlled by an EG&G PARC Model 175 Universal Programmer and an EG&G PAR Model 173 Potentiostat/Galvanostat. Following a 100 s delay at 0 V vs. 3M Ag/AgCl the potential was swept at 100 mV/s from 0 V ($E_0$), to a lower limit of −0.8 V ($E_1$), an upper limit of 2.3 V ($E_2$) and an ending potential of 0 V ($E_3$). The current range was set at 1 mA/V. The air temperature around the test cell was measured with a Cole Parmer Thermistor Thermometer and probe. All analog data (temperature, light, applied potential, and current) was digitized at 10 Hz with a Computer Boards Inc. CIO-DAS1602/16 A/D board controlled by HEM Data Corp. Snap-Master for Windows J in a Pyramid 100 MHz Pentium computer. From the raw data, plots of ECL and voltammetric current vs. applied potential were prepared and several data were calculated including: maximum anodic current, ECL peak potential (applied potential at the ECL peak), mean ECL dark current (mean light between starting potential and 0.5 V), and dark corrected integrated ECL (the difference between the average ECL over a given potential range and the mean dark all of which was then multiplied by the duration in seconds of the given potential range).

The voltammetry from the AFP assays are dependent upon the electrode used. The voltammograms for the AFP assay on hydrolyzed EVA consist of an irreversible oxidative wave starting at 1.4 V and having an anodic peak at ca. 1.8 V. The maximum anodic current occurs at 2.3 V. Little current is passed between −0.8 V and 1.4 V. The voltammograms from chromic acid treated EVA consist of a very broad irreversible oxidative wave starting at 0.7 V and having several undefined anodic peaks (ca. 1.1, 1.5, and 2.0 V) and a maximum anodic current at 2.3 V. Little current was passed between −0.8 and 0.7 V.

The hydrolyzed EVA yielded ECL traces consisting of a peak at with a small amount of tailing to the high potential side. The peak potentials shifted slightly from 1.85 V for blank signals to 1.75 V for analyte signals. The chromic acid treated EVA yielded two closely spaced peaks, both of which scaled with analyte concentration. These peaks were at ca. 1.6 V and ca. 1.25 V. At low analyte concentrations the peak at 1.6 V was dominant while at higher analyte concentrations the peak at 1.25 V was dominant. The chromic acid treatment increased the peak-to-peak resolution from ca. 100 mV (hydrolyzed EVA) to ca. 350 mV. This peak shift was sufficient to allow the analysis of the first peak which has been shown to be more sensitive to analyte and to reduce the amount of the blank signal used in the analysis.

In similar experiments, we compared the ECL traces for AFP calibrator 1 (predominantly ECL assay buffer, FIG. 60) and AFP calibrator 3 (FIG. 61). In FIG. 60, the ECL signal corresponding to assay buffer appears as a peak with a maximum at 1.5V. In FIG. 61, the ECL signal for assay buffer is also at 1.5V; the additional peak at 1.0V corresponds to the signal from the analyte in a sandwich complex that includes a TAG1-labeled complementary antibody.

7. INCORPORATION OF REFERENCES

The present invention is not to be limited in scope by the specific embodiments described herein. Indeed, various modifications of the invention in addition to those described herein will become apparent to those skilled in the art from the forgoing description and accompanying figures. Such modifications are intended to fall within the scope of the claims. Various publications are cited herein, the disclosures of which are incorporated by reference in their entireties.

What is claimed is:

1. A kit for conducting an electrochemiluminescence assay comprising:
    (a) a porous electrode comprising a plurality of particles, said particles having immobilized thereon binding reagents capable of forming complexes with a component of said electrochemiluminescence assay, wherein said binding reagents are distributed so as to form a plurality of distinct binding domains on said electrode and wherein at least two of said binding domains differ in their specificity for analytes of interest; and (b) an additional binding reagent comprising an electrochemiluminescent label.

2. An apparatus for conducting an assay comprising:
(a) an element comprising
 i) a matrix; and
 ii) one or more carbon fibrils dispersed therein; and
(b) binding reagents immobilized on said element to form one or more binding domains capable of binding a component of a binding assay.

3. An apparatus for use in the detection of an analyte by electrochemiluminescence comprising:
(a) an electrode comprising
 i) a matrix; and
 ii) one or more carbon fibrils dispersed therein; and
(b) binding reagents immobilized on said electrode to form one or more binding domains containing a reagent capable of binding a component of an electrochemiluminescence assay.

4. The apparatus of claim 3, wherein said binding domains are immobilized on said fibrils.

5. The apparatus of claim 3, wherein said binding domains are immobilized on said matrix.

6. An apparatus for use in the detection of a plurality of analytes by electrochemiluminescence comprising:
(a) an electrode comprised of a matrix and a multiplicity of conducting particles dispersed therein; and
(b) a plurality of distinct binding domains supported on said electrode, each domain containing a reagent capable of binding a component of a binding electrochemiluminescence assay, wherein at least two of said binding domains differ in their specificity for analytes of interest.

7. An apparatus as recited in claim 6 wherein said matrix is a polymer.

8. An apparatus as recited in claim 6 wherein said conducting particles are carbon.

9. An apparatus as recited in claim 6 wherein said conducting particle is comprised of carbon fibers.

10. An apparatus as recited in claim 6 wherein said conducting particle is comprised of carbon fibrils.

11. The apparatus of claim 6, wherein said binding domains are immobilized on said particles.

12. The apparatus of claim 6, wherein said binding domains are immobilized on said matrix.

13. The apparatus of claim 6, further comprising a light detector capable of independently measuring electrochemiluminescence generated from at least two of said binding domains.

* * * * *